United States Patent
Alter

(10) Patent No.: US 10,202,643 B2
(45) Date of Patent: Feb. 12, 2019

(54) GENETIC ALTERATIONS IN GLIOMA

(71) Applicant: UNIVERSITY OF UTAH RESARCH FOUNDATION, Salt Lake City, UT (US)

(72) Inventor: Orly Alter, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 0 days.

(21) Appl. No.: 14/354,543

(22) PCT Filed: Oct. 31, 2012

(86) PCT No.: PCT/US2012/062855
§ 371 (c)(1),
(2) Date: Apr. 25, 2014

(87) PCT Pub. No.: WO2013/067050
PCT Pub. Date: May 10, 2013

(65) Prior Publication Data
US 2014/0303029 A1    Oct. 9, 2014

Related U.S. Application Data

(60) Provisional application No. 61/553,840, filed on Oct. 31, 2011, provisional application No. 61/553,870, filed on Oct. 31, 2011.

(51) Int. Cl.
*C12Q 1/6886* (2018.01)
*C12Q 1/6874* (2018.01)
(Continued)

(52) U.S. Cl.
CPC ........ *C12Q 1/6874* (2013.01); *C12N 15/1137* (2013.01); *C12Q 1/6809* (2013.01);
(Continued)

(58) Field of Classification Search
None
See application file for complete search history.

(56) References Cited

U.S. PATENT DOCUMENTS

| 4,816,397 A | 3/1989 | Boss et al. |
| 6,249,692 B1 | 6/2001 | Cowin |

(Continued)

FOREIGN PATENT DOCUMENTS

| EP | 2754077 A1 | 7/2014 |
| EP | 2773777 A1 | 9/2014 |

(Continued)

OTHER PUBLICATIONS

Lee et al. Abstract, 60th Annual American Society of Human Genetics Meeting. Nov. 2-6, 2010, Washington, DC.*

(Continued)

*Primary Examiner* — Joseph G. Dauner
(74) *Attorney, Agent, or Firm* — Ballard Spahr LLP

(57) ABSTRACT

Methods and genetic sequences are described for use in determining the diagnosis, subtype, prognosis, and disease course of high-grade gliomas, such as glioblastoma multiforme. One such method includes determining increased expression of at least one gene on a chromosome segment in cells of the glioma, the segment being 17:57,851,812-17:57,973,757; 7:127,892,509-7:127,947,649; 12:33,854-12:264,310; or 19:33,329,393-19:35,322,055; and estimating, based on the expression, a predicted length of survival, a probability of survival, or a predicted response to a therapy for the glioma.

6 Claims, 58 Drawing Sheets

Specification includes a Sequence Listing.

(51) Int. Cl.
*C12N 15/113* (2010.01)
*C12Q 1/6809* (2018.01)
*G16H 50/30* (2018.01)
*G06F 19/00* (2018.01)

(52) U.S. Cl.
CPC .......... *C12Q 1/6886* (2013.01); *C12Y 201/01* (2013.01); *C12Y 207/11001* (2013.01); *G06F 19/00* (2013.01); *G16H 50/30* (2018.01); *C12N 2310/14* (2013.01); *C12Q 2600/106* (2013.01); *C12Q 2600/158* (2013.01); *Y02A 90/26* (2018.01)

(56) References Cited

U.S. PATENT DOCUMENTS

| | | |
|---|---|---|
| 6,268,490 B1 | 7/2001 | Imanishi et al. |
| 6,670,461 B1 | 12/2003 | Wengel et al. |
| 6,745,173 B1 | 6/2004 | Amundsen |
| 6,794,499 B2 | 9/2004 | Wengel et al. |
| 6,998,484 B2 | 2/2006 | Koch et al. |
| 7,053,207 B2 | 5/2006 | Wengel |
| 7,084,125 B2 | 8/2006 | Wengel |
| 7,399,845 B2 | 7/2008 | Seth et al. |
| 2003/0044775 A1 | 3/2003 | Gulati |
| 2005/0059005 A1 | 3/2005 | Tuschl et al. |
| 2005/0119534 A1 | 6/2005 | Trost et al. |
| 2005/0182005 A1 | 8/2005 | Tuschl et al. |
| 2005/0221293 A1 | 10/2005 | Tuschl et al. |
| 2005/0221490 A1 | 10/2005 | Tuschl et al. |
| 2005/0222067 A1 | 10/2005 | Pfeffer et al. |
| 2005/0227934 A1 | 10/2005 | Stoffel et al. |
| 2005/0239728 A1 | 10/2005 | Pachuk et al. |
| 2005/0261218 A1 | 11/2005 | Esau et al. |
| 2006/0035344 A1 | 2/2006 | Pachuk et al. |
| 2006/0166910 A1 | 7/2006 | Tuschl et al. |
| 2006/0212950 A1 | 9/2006 | Tuschl et al. |
| 2007/0049547 A1 | 3/2007 | Esau et al. |
| 2007/0287179 A1 | 12/2007 | Tuschl et al. |
| 2009/0043082 A1 | 2/2009 | Stoffel et al. |
| 2009/0062228 A1 | 3/2009 | Hannon et al. |
| 2009/0149389 A1 | 6/2009 | Panitch et al. |
| 2009/0203893 A1 | 8/2009 | Esau et al. |
| 2009/0221685 A1 | 9/2009 | Esau et al. |
| 2009/0236225 A1 | 9/2009 | Esau et al. |
| 2009/0275729 A1 | 11/2009 | Stoffel et al. |
| 2009/0286969 A1 | 11/2009 | Esau et al. |
| 2009/0291906 A1 | 11/2009 | Esau et al. |
| 2009/0291907 A1 | 11/2009 | Esau et al. |
| 2009/0298174 A1 | 12/2009 | Esau et al. |
| 2009/0299705 A1 | 12/2009 | Chi et al. |
| 2009/0317907 A1 | 12/2009 | Esau et al. |
| 2010/0149214 A1 | 6/2010 | Wiemker et al. |
| 2011/0166409 A1 | 7/2011 | Donovan et al. |
| 2011/0172514 A1 | 7/2011 | Lee et al. |
| 2014/0249762 A1 | 9/2014 | Alter |
| 2014/0303029 A1 | 10/2014 | Alter |

FOREIGN PATENT DOCUMENTS

| | | |
|---|---|---|
| WO | WO-2006/033756 A2 | 3/2006 |
| WO | WO-2009/021137 A2 | 2/2009 |
| WO | WO-2009/046397 A2 | 4/2009 |
| WO | WO-2009/134479 A1 | 11/2009 |
| WO | WO-2009/153774 A2 | 12/2009 |
| WO | WO-2011/005786 A3 | 1/2011 |
| WO | 2011-112678 A1 | 9/2011 |
| WO | WO-2013/036874 A1 | 3/2013 |
| WO | WO-2013/067050 A1 | 5/2013 |
| WO | WO-2013/188860 A1 | 12/2013 |
| WO | WO-2015/023551 A1 | 2/2015 |
| WO | WO-2016/168525 A1 | 10/2016 |
| WO | WO-2016/168526 A1 | 10/2016 |

OTHER PUBLICATIONS

Suzuki et al. Brain Tumor Pathol. 2004. 21:27-34.*
Hui et al. Laboratory Investigation. 2001. 81(5):717-723.*
Taylor et al. PLoS One. 2008. 3(9):e3179.*
Lai et al. Bioinformatics. 2005. 21(19):3763-3770.*
Philips et al. Cancer Cell. 2006. 9:157-173.*
Burton et al. Cancer Research. 2002. 62:6205-6210.*
Verhaak et al. Cancer Cell. 2010. 17:98-110.*
Iwadate et al. Exp Ther Med. Jan.-Feb. 2010 1(1):53-57.*
Florell et al. J. Neurosurg. 1992. 76:179-183.*
Jansen et al. Lancet Neurol. 2010. 9:717-726.*
Clinical Practice Guidelines for management of adult gliomas: astrocytomas and oligodendrogliomas. Aug. 2009.*
Esteller et al. NEJM. 2000. 434(19):1350-1354.*
Chen et al. Journal of Clinical Oncology. 2007. 25(30):4714-4721.*
Iwadate et al. British Journal of Cancer. 2003. 89:1896-1900.*
Watanabe et al. Neurol Med Chir. 2006. 46:387-394.*
Haas-Kogan et al. J Natl Cancer Inst. 2005. 97(12):880-887.*
Cappuzzo et al. J Clin Oncol. 2005. 23(22):5007-18.*
Gorre et al. Science. 2001. 293:876-880.*
Moroni et al. Lancet Oncol. 2005. 6:279-286.*
Takano et al. Journal of Clinical Oncology. 2005. 23(28):6829-6837.*
Innocenti et al. Semin Oncol. 2011 (38(2):186-195.*
Dai et al. BMC Medical Genomics. 2008. I:24.*
Obata et al. Anticancer Research. 2006. 26:2227-2232.*
Kim et al. Cancer Sci. 2010. 101(4):1007-1013.*
Schaich et al. Annals of Oncology. 2009. 20:175-181.*
Colman, et al., "A multigene predictor of outcome in glioblastoma," Neuro-Oncology, Oct. 2009, vol. 12, No. 1, pp. 49-57.
Cooper, et al., "The Proneural Molecular Signature is Enriched in Oligodendrogliomas and Predicts Improved Survival among Diffuse Gliomas," Plos One, Sep. 2010, vol. 5, No. 9, 9 pages.
Heidenblad, et al., "Microarray analyses reveal strong influence of DNA copy numbers alterations on the transcriptional patterns in pancreatic cancer: implications for the interpretation of genomic amplifications," Mar. 2005, Oncogene, vol. 24, No. 10, 1794-1801.
Ronald, et al., "The Expression of Tousled Kinases in CaP Cell Lines and Its Relation to Radiation Response and DSB Repair," The Prostate, Sep. 2011, vol. 71, No. 13, pp. 1367-1373.
Stevens, et al., "Evaluation of associations between common variation in mitotic regulatory pathways and risk of overall and high grade breast cancer," Breast Cancer Res Treat, May 2011, vol. 129, No. 2, pp. 617-622.
Freire et al. 2008. Exploratory Analysis of the Copy Number Alterations in Glioblastoma Multiforme. Plos One, vol. 3, Issue 12, e4076, pp. 1-11, Dec. 30, 2008.
Lee, C.H. et al. 2012. GSVD Comparison of Patient-Matched Normal and Tumor aCGH Profiles Reveals Global Copy-Number Alterations Predicting Glioblastoma Multiforme Survival. PLoS One, vol. 7, No. 1, e30098, pp. 1-11.
International Search Report, dated Mar. 27, 2013, for PCT Application PCT/US2012/062855, entitled "Genetic Alterations in Glioblastoma," filed Oct. 31, 2012.
Ahmed, J. et al., CancerResource: a Comprehensive Database of Cancer-Relevant Proteins and Compound Interactions Supported by Experimental Knowledge. Nucleic Acids Res. 2011; 39(Database Issue):D960-7.
Anglesio, M.S. et al., Mutation of ERBB2 Provides a Novel Alternative Mechanism for the Ubiquitous Activation of RAS-MAPK in Ovarian Serous Low Malignant Potential Tumors. Mol Cancer Res. 2008; 6(11):1678-90.
Alter et al., Generalized singular value decomposition for comparative analysis of genome-scale expression data sets of two different organisms. Proc Natl Acad Sci USA. 2003; 100: 3351-6.
Arnold et al., Specific beta1-adrenergic receptor silencing with small interfering RNA lowers high blood pressure and improves cardiac function in myocardial ischemia. J Hypertens. 2007; 25(1):197-205.
Ashburner, M. et al., Gene Ontology: Tool for the Unification of Biology. Nat Genet. 2000; 25(1):25-9.

(56) References Cited

OTHER PUBLICATIONS

Ayhan, A. et al., Defining the Cut-Point Between Low- and High-Grade Ovarian Serous Carcinomas: a Clinicopathologic and Molecular Genetic Analysis. Am J Surg Pathol. 2009; 33(8):1220-4.

Bai, Z. and Demmel J.W., Computing the Generalized Singular Value Decomposition. SIAM J Sci Comput. 1993; 14(6):1464-86.

Benedetti, The Tousled-Like Kinases as Guardians of Genome Integrity. ISRN Mol Biol. 2012; 2012: 627596 (9 pages).

Berger, J. A. et al., Jointly analyzing gene expression and copy number data in breast cancer using data reduction models. IEEE/ACM Trans Comput Biol Bioinform. 2006; 3:2-16.

Bird et al., Single-chain antigen-binding proteins. Science. 1988; 242:423-6.

Blanco, P. et al., A Novel Poly(A)-binding Protein Gene (PABPC5) Maps to an X-Specific Subinterval in the Xq21.3Np11.2 Homology Block of the Human Sex Chromosomes. Genomics. 2001; 74(1):1-11.

Bourdon, V. et al., Genomic and Expression Analysis of the 12p. 11-p. 12 Amplicon Using EST Arrays Identifies Two Novel Amplified and Overexpressed Genes. Cancer Res. 2002; 62(21):6218-23.

Bulavin, D.V. et al., Phosphorylation of Human p53 by p38 Kinase Coordinates N-terminal Phosphorylation and Apoptosis in Response to UV Radiation. EMBO J. 1999; 18(23):6845-54.

Cancer Genome Atlas Research Network, Comprehensive Genomic Characterization Defines Human Glioblastoma Genes and Core Pathways. Nature. 2008; 455(7216):1061-8.

Cancer Genome Atlas Research Network, Integrated Genomic Analyses of Ovarian Carcinoma. Nature. 2011; 474(7353):609-15.

Chu, I.M. et al., The Cdk Inhibitor p27 in Human Cancer: Prognostic Potential and Relevance to Anticancer Therapy. Nat Rev Cancer. 2008; 8(4):253-67.

ClustalW2, Retrieved from the Internet: <http://www.ebi.ac.uk/Tools/clustalw2/index.html>. Accessed Dec. 28, 2017 (1 page).

Collinson et al., Predicting Response to Bevacizumab in Ovarian Cancer: A Panel of Potential Biomarkers Informing Treatment Selection. Clin Cancer Res. 2013; 19(18):5227-39.

Corpet et al., Asf1b, the necessary Asf1 isoform for proliferation, is predictive of outcome in breast cancer. EMBO J. 2011; 30(3):480-93.

Cox, D.R., Regression Models and Life-Tables. J Roy Statist Soc B. 1972; 34(2):187-220.

Curran, W.J. Jr. et al., Recursive Partitioning Analysis of Prognostic Factors in Three Radiation Therapy Oncology Group Malignant Glioma Trials. J Natl Cancer Inst. 1993; 85(9):704-10.

De Lathauwer, L. et al., A Multilinear Singular Value Decomposition. SIAM J Matrix Anal Appl. 2000; 21(4):1253-78.

Diaz, F. and Bourguignon, L.Y., Selective Down-Regulation of $IP_3$ Receptor Subtypes by Caspases and Calpain During TNFα-induced Apoptosis of Human T-lymphoma Cells. Cell Calcium. 2000; 27:315-28.

Duncan, T.J. et al., Cytoplasmic p27 Expression is an Independent Prognostic Factor in Ovarian Cancer. Int J Gynecol Pathol. 2010; 29(1):8-18.

Eden, E. et al., GOrilla: a Tool for Discovery and Visualization of Enriched GO Terms in Ranked Gene Lists. BMC Bioinformatics. 2009; 10:48.

Elmen et al., Locked nucleic acid (LNA) mediated improvements in siRNA stability and functionality. Nucl Acids Res. 2005; 33(1):439-47.

Engler, D.A. et al., Genome Wide DNA Copy Number Analysis of Serous Type Ovarian Carcinomas Identifies Genetic Markers Predictive of Clinical Outcome. PLoS One. 2012; 7(2):e30996 (13 pages).

Friedland, S., A New Approach to Generalized Singular Value Decomposition. SIAM J Matrix Anal Appl. 2005; 27(2):434-44.

Golub, G.H. and Van Loan, C.F., Matrix Computations. 4th ed. Baltimore, MD: Johns Hopkins University Press; 2012.

Gorlia, T. et al., Nomograms for Predicting Survival of Patients with Newly Diagnosed Glioblastoma: Prognostic Factor Analysis of EORTC and NCIC Trial 26981-22981/Ce.3. Lancet Oncol. 2008; 9(1):29-38.

Grunweller et al., Comparison of different antisense strategies in mammalian cells using locked nucleic acids, 2'-O-methyl RNA, phosphorothioates and small interfering RNA. Nucl Acids Res. 2003; 31(12):3185-93.

Hahn, W.C. et al., Creation of Human Tumour Cells with Defined Genetic Elements. Nature. 1999; 400(6743):464-8.

Hanahan, D. and Weinberg, R.A., Hallmarks of Cancer: the Next Generation. Cell. 2011; 144(5):646-74.

Harries, M. and Gore, M., Part I: Chemotherapy for Epithelial Ovarian Cancer-Treatment at First Diagnosis. Lancet Oncol. 2002; 3:529-36.

Hashimoto et al., PKU-β/TLK1 regulates myosin II activities, and is required for accurate equaled chromosome segregation. Mutat Res. 2008; 657:63-7.

Hopkins, A.L. and Groom, C.R., The Druggable Genome. Nat Rev Drug Discov. 2002; 1(9):727-30.

Horn, R.A. and Johnson, C.R., Matrix Analysis. 2nd ed. Cambridge, UK: Cambridge University Press; 2012.

Huston et al., Protein engineering of antibody binding sites: recovery of specific activity in an anti-digoxin single-chain Fv analogue produced in *Escherichia coli*. Proc Natl Acad Sci USA. 1988; 85(16):5879-83.

Ikeda, T. et al., Identification and Characterization of the Human Long Form of Sox5 (L-SOX5) Gene. Gene. 2002; 298(1):59-68.

Iorio, M.V. et al., MicroRNA Signatures in Human Ovarian Cancer. Cancer Res. 2007; 67(18):8699-707.

Kallioniemi et al., ERBB2 amplification in breast cancer analyzed by fluorescence in situ hybridization. Proc Natl Acad Sci USA. 1992; 89:5321-5.

Kaplan, E.L. and Meier, P., Nonparametric Estimation from Incomplete Observations. J Amer Statist Assn. 1958; 53:457-81.

Karnoub, A.E. and Weinberg, R.A., Ras Oncogenes: Split Personalities. Nat Rev Mol Cell Biol. 2008; 9(7):517-31.

Kent, W.J. et al., The Human Genome Browser at UCSC. Genome Res. 2002; 12(6):996-1006.

Kim et al., Local and systemic delivery of VEGF siRNA using polyelectrolyte complex micelles for effective treatment of cancer. J Control Release. 2008;129(2):107-16.

Klein, H.L., The Consequences of Rad51 Overexpression for Normal and Tumor Cells. DNA Repair. 2008; 7(5):686-93.

Kolda, T. G. & Bader, B. W. Tensor Decompositions and Applications. SIAM Rev. 2008; 51:455-500.

Kumar, G.R. et al., Importin α-Mediated Nuclear Import of Cytoplasmic Poly(A) Binding Protein Occurs as a Direct Consequence of Cytoplasmic mRNA Depletion. Mol Cell Biol. 2011; 31(15):3113-25.

Kwon, Y.H. et al., The Cdk Inhibitor p21 is Required for Necrosis, but It Inhibits Apoptosis Following Toxin-Induced Liver Injury. J Biol Chem. 2003; 278(32):30348-55.

Lee, L.A. et al., *Drosophila* Genome-Scale Screen for PAN GU Kinase Substrates Identifies Mat89Bb as a Cell Cycle Regulator. Dev Cell. 2005; 8(3):435-42.

Li et al., Non-negative matrix and tensor factorization based classification of clinical microarray gene expression data. Bioinform Biomed. 2010 Intl Conf IEEE. 2010; pp. 438-443.

Li et al., Tousled-like kinase in a microbial eukaryote regulates spindle assembly and S-phase progression by interacting with Aurora kinase and chromatin assembly factors. J Cell Sci. 2007; 120:3883-94.

Millour, et al. Gene Expression Profiles Discriminate between Pathological Complete Response and Resistance to Neoadjuvant FEC100 in Breast Cancer. Cancer Genomics Proteomics. 2006; 3:89-96.

Misra, A. et al., Array Comparative Genomic Hybridization Identifies Genetic Subgroups in Grade 4 Human Astrocytoma. Clin Cancer Res. 2005; 11(8):2907-18.

Mo, Q. et al., Pattern Discovery and Cancer Gene Identification in Integrated Cancer Genomic Data. Proc Natl Acad Sci U.S.A. 2013; 110(11):4245-50.

(56) References Cited

OTHER PUBLICATIONS

Mook et al., Evaluation of locked nucleic acid-modified small interfering RNA in vitro and in vivo. Mol Cancer Ther. 2007; 6(3):833-43.
Moynahan, M.E. and Jasin, M., Mitotic Homologous Recombination Maintains Genomic Stability and Suppresses Tumorigenesis. Nat Rev Mol Cell Biol. 2010; 11(3):196-207.
Morup, M., Applications of tensor (multiway array) factorizations and decompositions in data mining. WIREs: Data Mining and Knowledge Discovery. 2011; 1(1): 24-40.
Nagahara, H. et al., Transduction of Full-length TAT-Fusion Proteins into Mammalian Cells: TAT-p27Kip1 Induces Cell Migration. Nat Med. 1998; 4(12):1449-52.
National Human Genome Research Institute (NHGRI) Grant No. R01 HG-004302 (4 pages).
Olshen, A.B. et al., Circular Binary Segmentation for the Analysis of Array-Based DNA Copy Number Data. Biostatistics. 2004; 5(4):557-72.
Omberg, L. et al., A tensor higher-order singular value decomposition for integrative analysis of DNA microarray data from different studies. Proc Natl Acad Sci. 2007; 104(47):18371-6.
Omberg, L. et al., Global Effects of DNA Replication and DNA Replication Origin Activity on Eukaryotic Gene Expression. Mol Syst Biol. 2009; 5:312 (8 pages).
Paige, C.C. and Saunders, M.A., Towards a Generalized Singular Value Decomposition. SIAM J Numer Anal. 1981; 18(3):398-405.
Pellegrini, M. et al., Expression Profile of CREB Knockdown in Myeloid Leukemia Cells. BMC Cancer. 2008; 8:264 (12 pages).
Peng et al., Transcriptional coactivator HCF-1 couples the histone chaperone Asf1 b to HSV-1 DNA replication components. Proc Natl Acad Sci USA. 2010; 107(6):2461-6.
Ponnapalli et al., A Higher-Order Generalized Singular Value Decomposition for Comparison of Global mRNA Expression from Multiple Organisms. PLoS One. 2011; 6(12): e28072 (14 pages).
Ponnapalli et al., Mathematical Framework: HO GSVD. PLoS One. 2011; Supp. App. S1: A1-A11.
Prisco, M.G. et al., Prognostic Role of Metastasis Tumor Antigen 1 in Patients with Ovarian Cancer: a Clinical Study. Hum Pathol. 2012; 43(2):282-8.
Pujade-Lauraine, E. et al., Bevacizumab Combined with Chemotherapy for Platinum-Resistant Recurrent Ovarian Cancer: The AURELIA Open-label Randomized Phase III Trial. J Clin Oncol. 2014; 32:1302-8.
Romanova, L.Y. et al., The Interaction of p53 with Replication Protein A Mediates Suppression of Homologous Recombination. Oncogene. 2004; 23(56):9025-33.
Rutka et al., Establishment and characterization of a cell line from a human gliosarcoma, Cancer Res. 1986; 46(11):5893-902.
Rutka et al., Establishment and characterization of five cell lines derived from human malignant gliomas, Acta Neuropathologica. 1987; 75:92-103.
Sankaranarayanan et al. Tensor GSVD of Patient- and Platform-Matched Tumor and Normal DNA Copy-Number Profiles Uncovers Chromosome Arm-Wide Patterns of Tumor-Exclusive Platform-Consistent Alterations Encoding for Cell Transformation and Predicting Ovarian Cancer Survival. PLoS One. 2015; 10:1-21.
Shen, R. et al., Integrative Clustering of Multiple Genomic Data Types Using a Joint Latent Variable Model with Application to Breast and Lung Cancer Subtype Analysis. Bioinformatics. 2009; 25(22):2906-12.
Sibley, C.R. et al., The Biogenesis and Characterization of Mammalian MicroRNAs of Mirtron Origin. Nucl Acids Res. 2012; 40(1):438-48.
Sillje, H.H. et al., Mammalian Homologues of the Plant Tousled Gene Code for Cell-Cycle-Regulated Kinases with Maximal Activities Linked to Ongoing DNA Replication. EMBO J. 1999; 18(20):5691-702.
Sillje et al., Identification of human Asf1 chromatin assembly factors as substrates of Tousled-like kinases. Curr Biol. 2001; 11:1068-73.
Sorensen et al., Gene silencing by systemic delivery of synthetic siRNAs in adult mice. J Mol Biol. 2003; 327:761-66.
Tatusova, T. et al., BLAST 2 sequences, a new tool for comparing protein and nucleotide sequences. FEMS Microbiol Lett. 1999; 174:187-8.
Taylor, B. S. et al., Functional Copy-Number Alterations in Cancer. PLoS One. 2008; 3(9):e3179 (16 pages).
Van Loan, C.F., Computing the CS and the Generalized Singular Value Decompositions. Numer Math. 1985; 46(4):479-91.
Van Loan, C.F., Generalizing the Singular Value Decomposition. SIAM J Numer Anal. 1976; 13(1):76-83.
Vandewalle, J. et al., The Generalized Higher Order Singular Value Decomposition and the Oriented Signal-to-Signal Ratios of Pairs of Signal Tensors and Their Use in Signal Processing. Proc ECCTD '03—European Conf on Circuit Theory and Design; 2003. pp. I-389-I-392.
Verma et al., Small interfering RNAs directed against beta-catenin inhibit the in vitro and in vivo growth of colon cancer cells. Clin Cancer Res. 2003; 9(4):1291-300.
Vinayagam et al., A directed protein interaction network for investigating intracellular signal transduction. Sci Signal. 2011; 4(189):rs8 (12 pages).
Waldman, T. et al., p21 is Necessary for the p53-mediated G1 Arrest in Human Cancer Cells. Cancer Res. 1995; 55(22):5187-90.
Ward et al., Binding activities of a repertoire of single immunoglobulin variable domains secreted from *Escherichia coli*. Nature. 1989; 341(6242):544-6.
Wiltshire, R.N. et al., Comparative Genetic Patterns of Glioblastoma Multiforme: Potential Diagnostic Tool for Tumor Classification. Neuro Oncol. 2000; 2(3):164-73.
Yang, D. et al., Integrated Analyses Identify a Master MicroRNA Regulatory Network for the Mesenchymal Subtype in Serous Ovarian Cancer. Cancer Cell. 2013; 23(2):186-99.
International Search Report and Written Opinion were dated Oct. 31, 2012 by the International Searching Authority for International Application No. PCT/US2012/054315, which was filed on Sep. 7, 2012 and published as WO 2013/036874 on Mar. 14, 2013 (Applicant—University of Utah Research Foundation).
International Preliminary Report on Patentability was dated Mar. 12, 2014 by the International Searching Authority for International Application No. PCT/US2012/054315, which was filed on Sep. 7, 2012 and published as WO 2013/036874 on Mar. 14, 2013 (Applicant—University of Utah Research Foundation) (5 pages).
European Search Report and Written Opinion was dated May 20, 2015 by the European Patent Office for EP Application No. 12803209. 8, which was filed on Sep. 7, 2012 and published as EP2754077 A1 on Jul. 16, 2014 (Applicant—University of Utah Research Foundation) (9 pages).
Requirement for Restriction/ Election was dated May 9, 2016 by the USPTO for U.S. Appl. No. 14/201,739, filed Mar. 7, 2014 and published as US 2014-0249762 A1 on Sep. 4, 2014 (Applicant—University of Utah Research Foundation; Inventor—Orly Alter) (6 pages).
Response to Requirement for Restriction/ Election was dated Jul. 11, 2016 by the USPTO for U.S. Appl. No. 14/201,739, filed Mar. 7, 2014 and published as US 2014-0249762 A1 on Sep. 4, 2014 (Applicant—University of Utah Research Foundation; Inventor—Orly Alter) (2 pages).
Non Final Rejection was dated Aug. 5, 2016 by the USPTO for U.S. Appl. No. 14/201,739, filed Mar. 7, 2014 and published as US 2014-0249762 A1 on Sep. 4, 2014 (Applicant—University of Utah Research Foundation; Inventor—Orly Alter) (9 pages).
Abandonment was dated Mar. 13, 2017 by the USPTO for U.S. Appl. No. 14/201,739, filed Mar. 7, 2014 and published as US 2014-0249762 A1 on Sep. 4, 2014 (Applicant—University of Utah Research Foundation; Inventor—Orly Alter) (2 pages).
International Preliminary Report on Patentability was dated May 6, 2014 by the International Searching Authority for International Application No. PCT/US2012/062855, which was filed on Oct. 31, 2012 and published as WO 2013/067050 on May 10, 2013 (Applicant—University of Utah Research Foundation) (7 pages).
Partial European Search Report was dated Jun. 24, 2015 by the International Searching Authority for International Application No.

(56) References Cited

OTHER PUBLICATIONS 12846126.6, which was filed on Oct. 31, 2012 and published as EP 2773777 A1 on Sep. 10, 2014 (Applicant—University of Utah Research Foundation) (8 pages).
Supplementary European Search Report and Opinion were dated Oct. 13, 2015 by the International Searching Authority for International Application No. 12846126.6, which was filed on Oct. 31, 2012 and published as EP 2773777 A1 on Sep. 10, 2014 (Applicant—University of Utah Research Foundation) (15 pages).
International Search Report and Written Opinion were dated Sep. 16, 2016 by the International Searching Authority for International Application No. PCT/US2016/027641, which was filed on Apr. 14, 2016 and published as WO/2016/168525 on Oct. 20, 2016 (Applicant—University of Utah Research Foundation) (13 pages).
International Preliminary Report on Patentability dated Oct. 17, 2017 by the International Searching Authority for Patent Application No. PCT/US2016/027641, which was filed on Apr. 14, 2016 and published as WO 2016/168525 on Oct. 20, 2016 (Inventor—Alter et al.; Applicant—Univ. of Utah Research Foundation; (7 pages).
Preliminary Amendment filed on Oct. 13, 2017 with the U.S. Appl. No. 15/566,294, filed Oct. 13, 2017 (Inventor—Alter et al.; Applicant—Univ. of Utah Research Foundation; (3 pages).
International Search Report and Written Opinion were dated Jul. 6, 2016 by the International Searching Authority for International Application No. PCT/US2016/027642, which was filed on Apr. 14, 2016 and published as WO 2016/168526 on Feb. 14, 2017 (Applicant—University of Utah Research Foundation) (15 pages).
International Preliminary Report on Patentability completed on Jun. 7, 2017 by the International Searching Authority for Patent Application No. PCT/US2016/027642, which was filed on Apr. 14, 2016 and published as WO 2016/168526 on Oct. 20, 2016 (Inventor—Orly Alter; Applicant—University of Utah Research Foundation; (129 pages).
Preliminary Amendment filed Oct. 13, 2017 with the U.S. Appl. No. 15/566,298, filed Oct. 13, 2017 (Inventor—Alter et al.; Applicant—Univ. of Utah Research Foundation; (3 pages).

\* cited by examiner

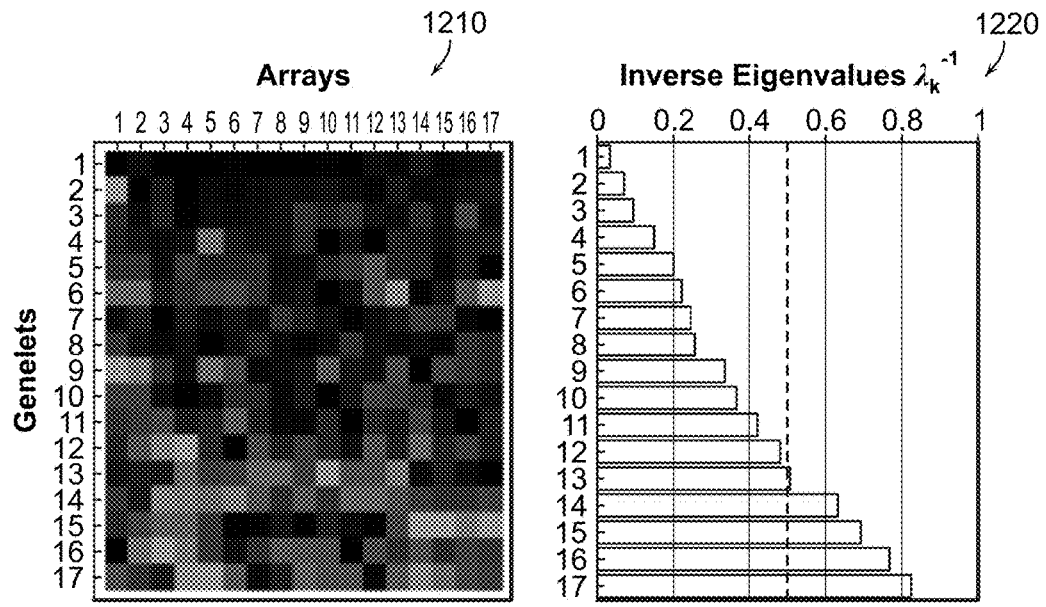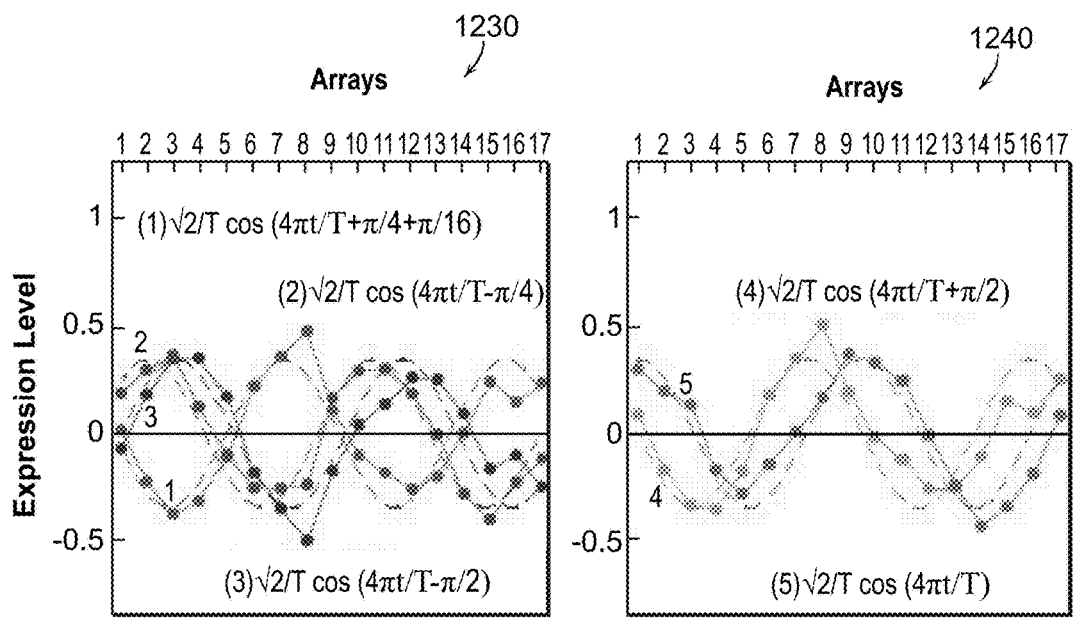
FIG. 6a  FIG. 6b  FIG. 6c  FIG. 6d

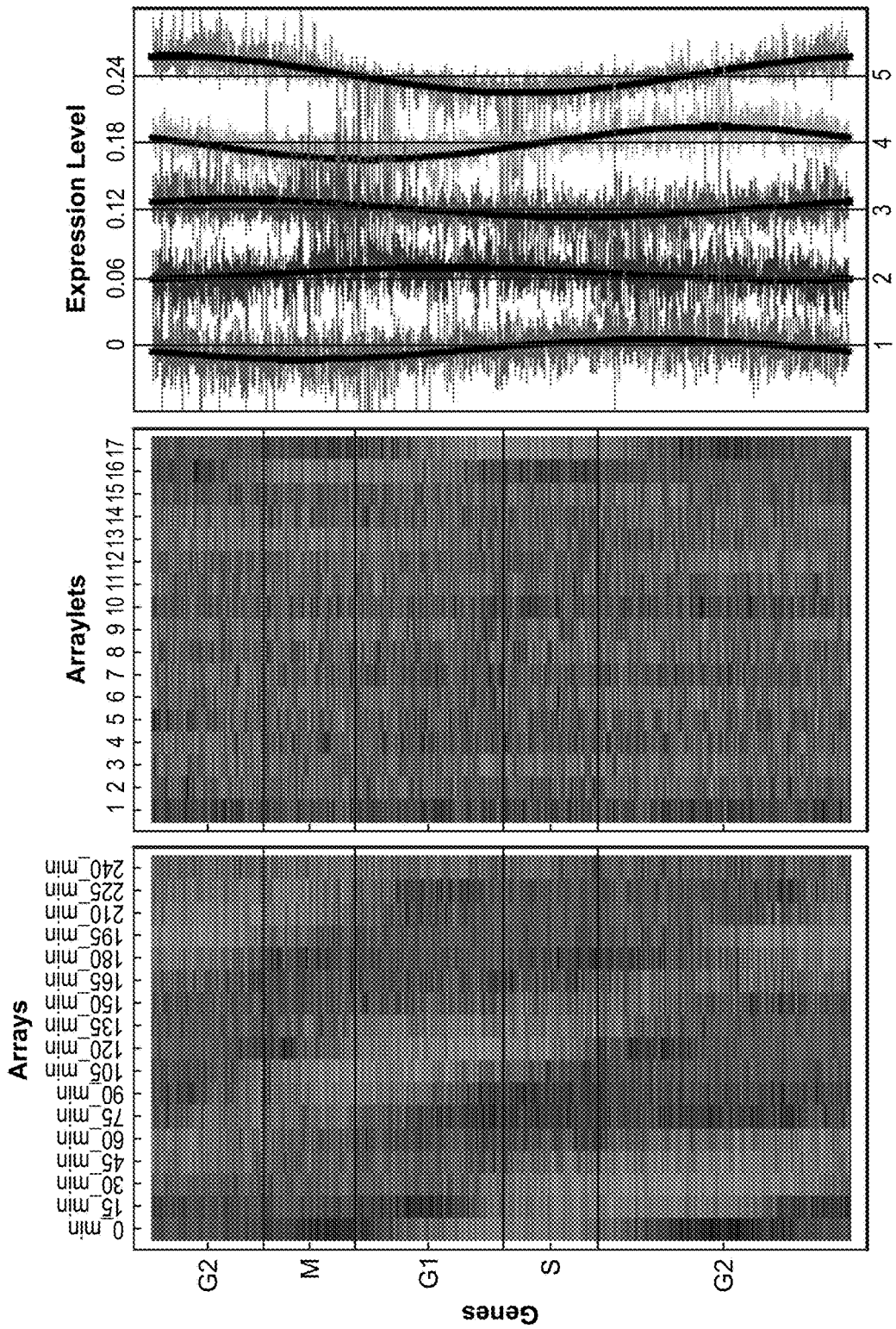

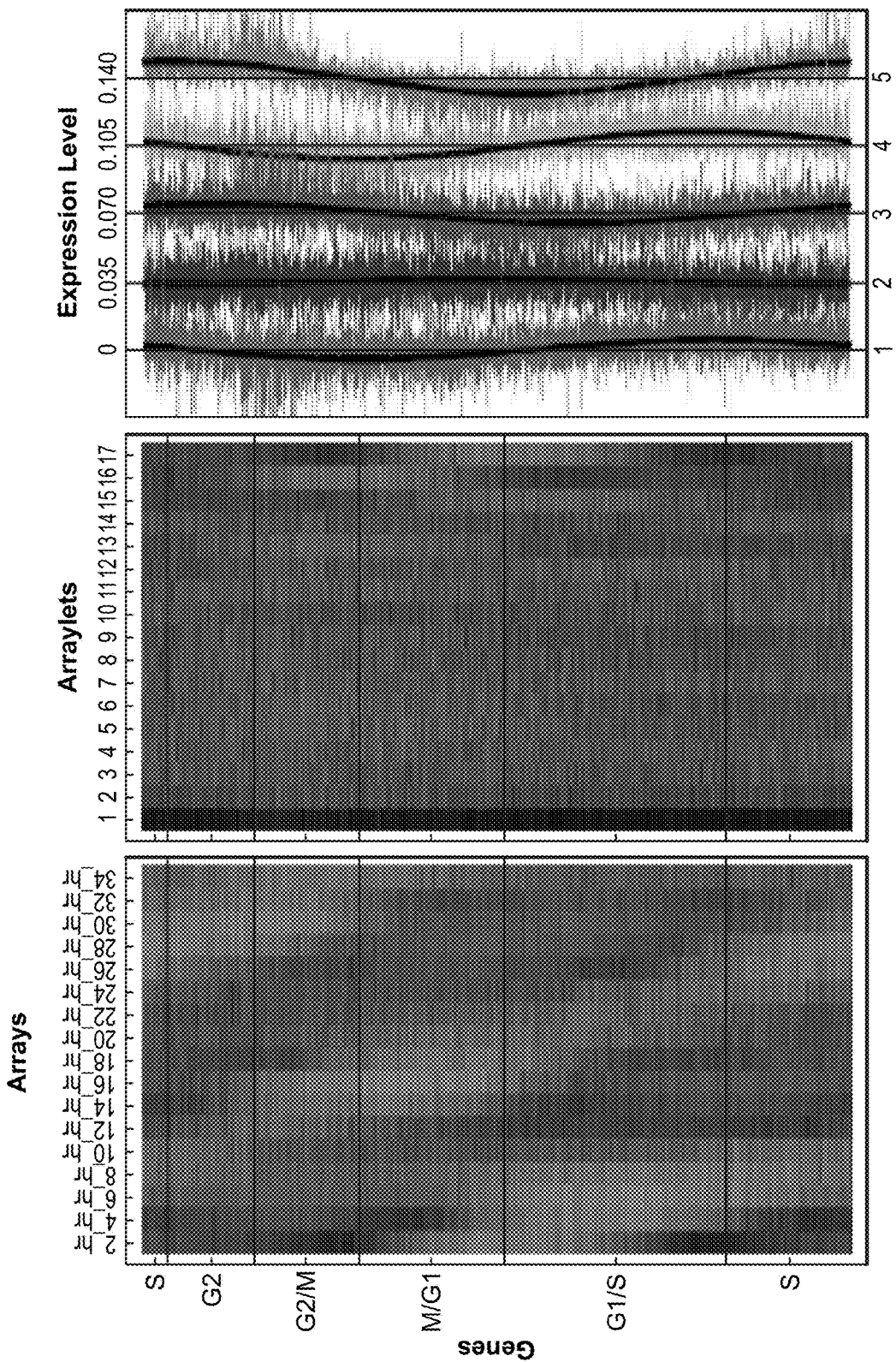

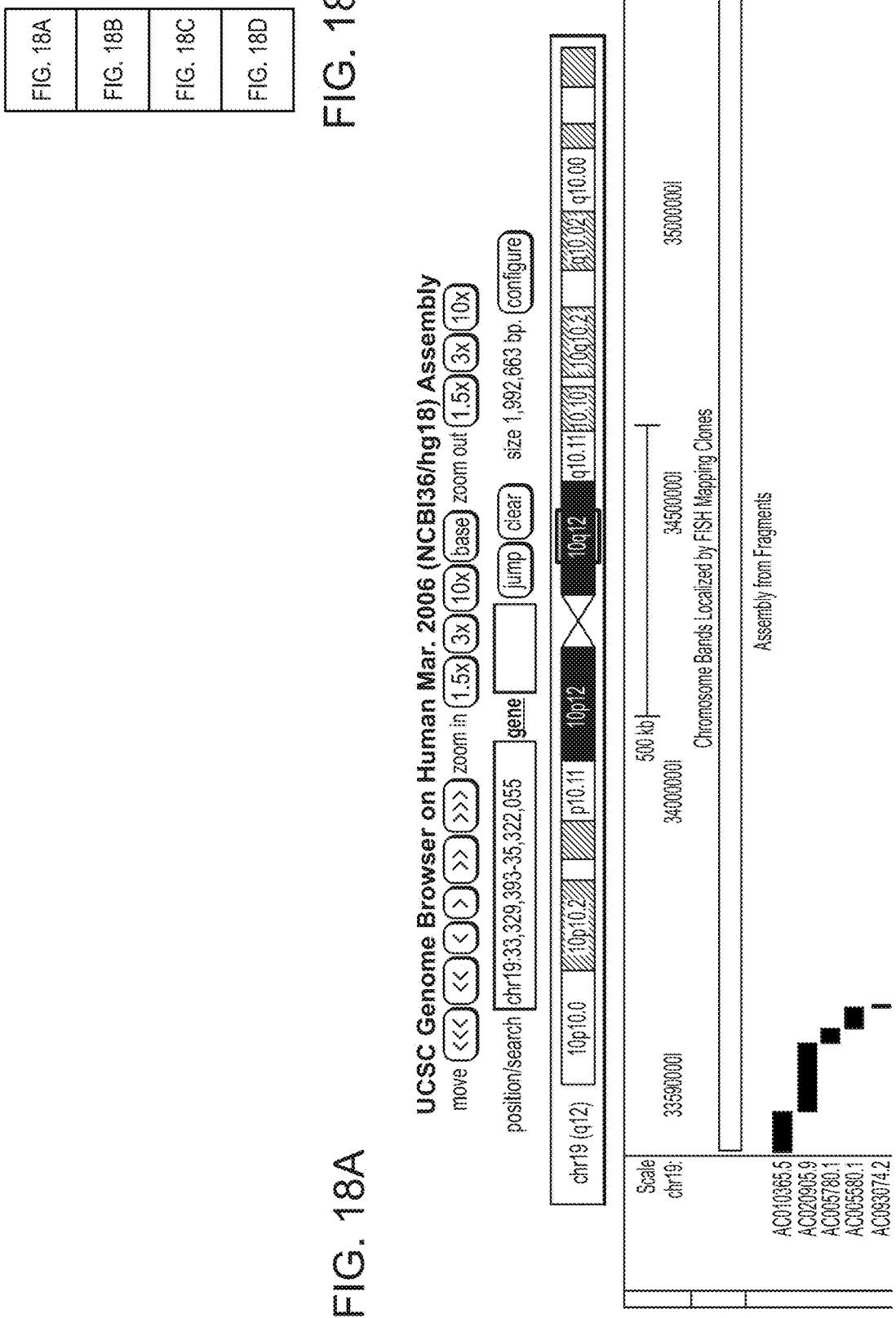

FIG. 18D

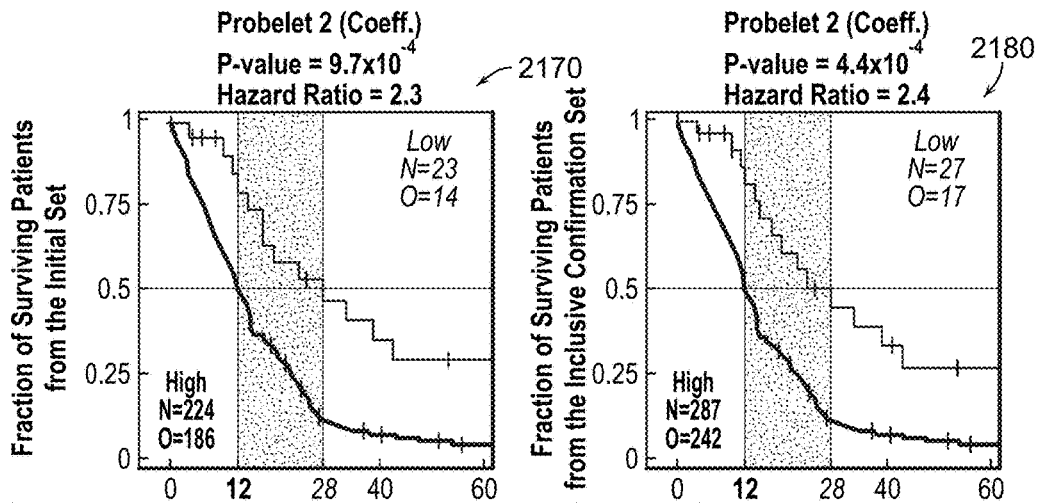
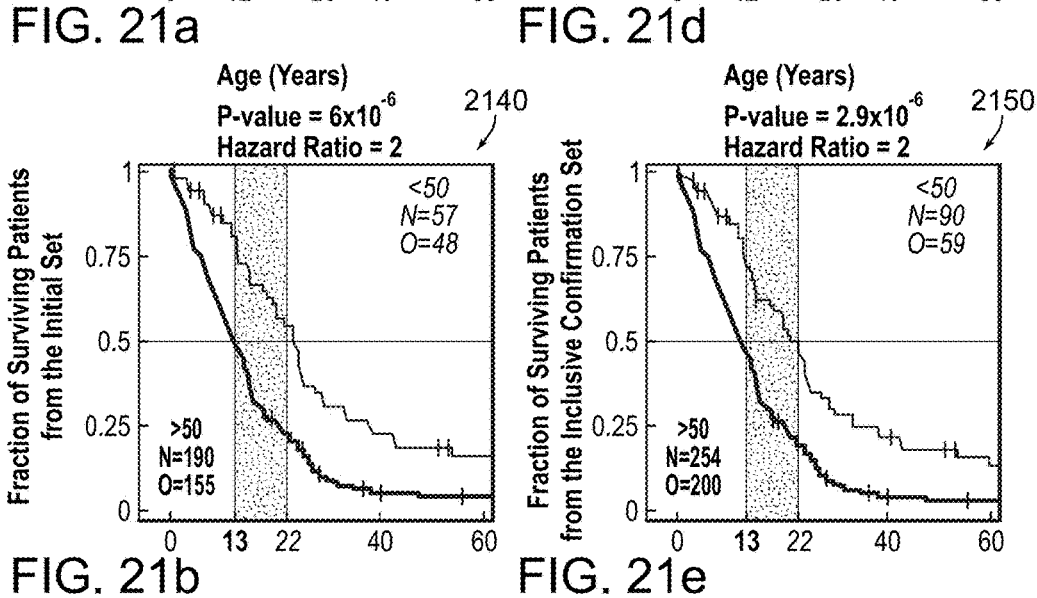
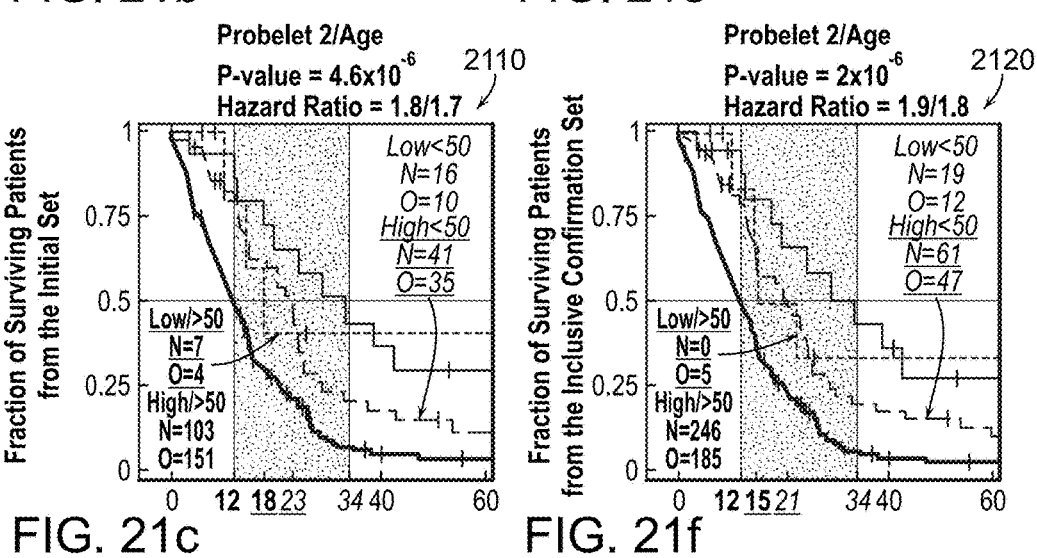
FIG. 21a  FIG. 21d
FIG. 21b  FIG. 21e
FIG. 21c  FIG. 21f

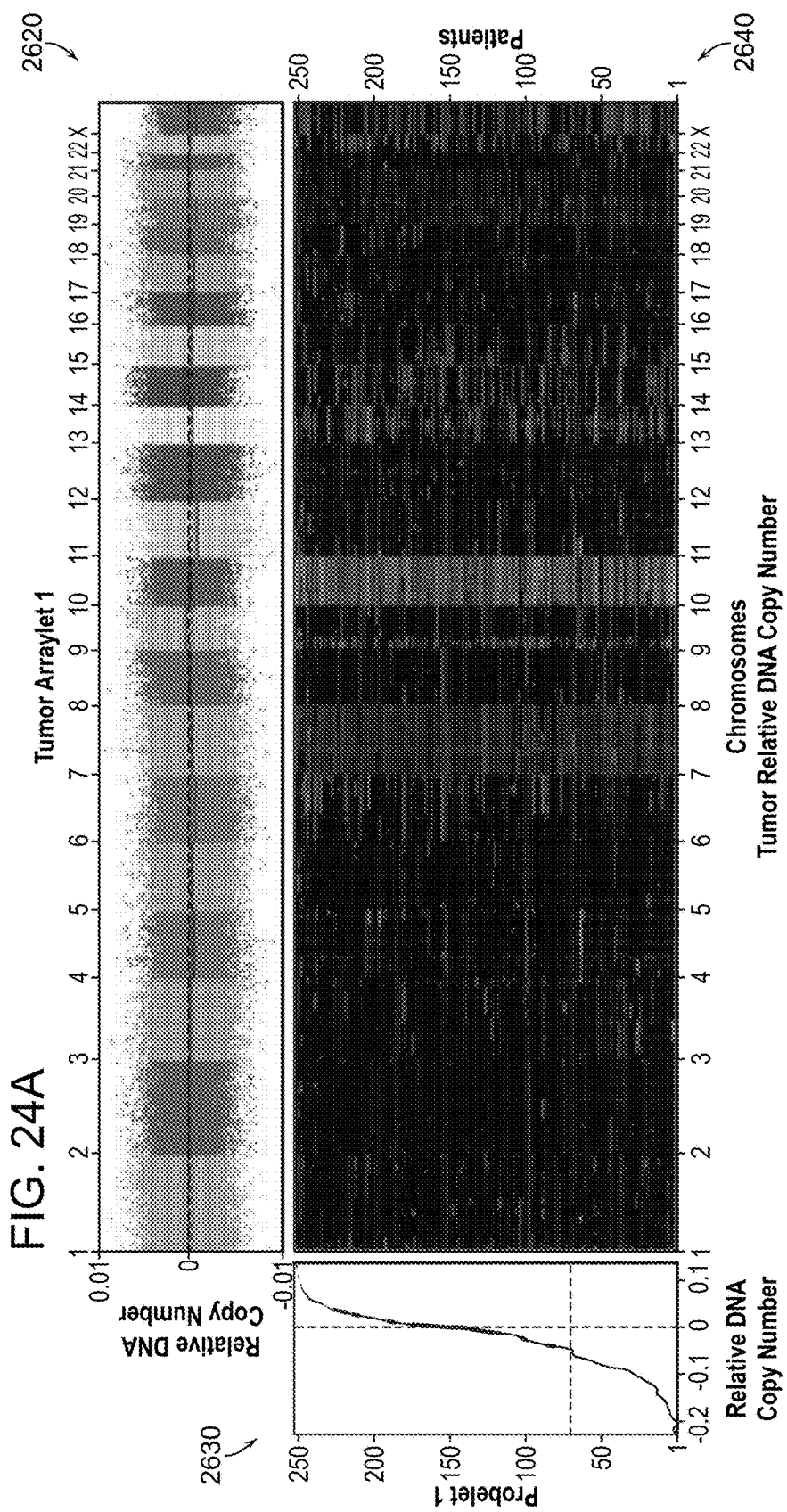

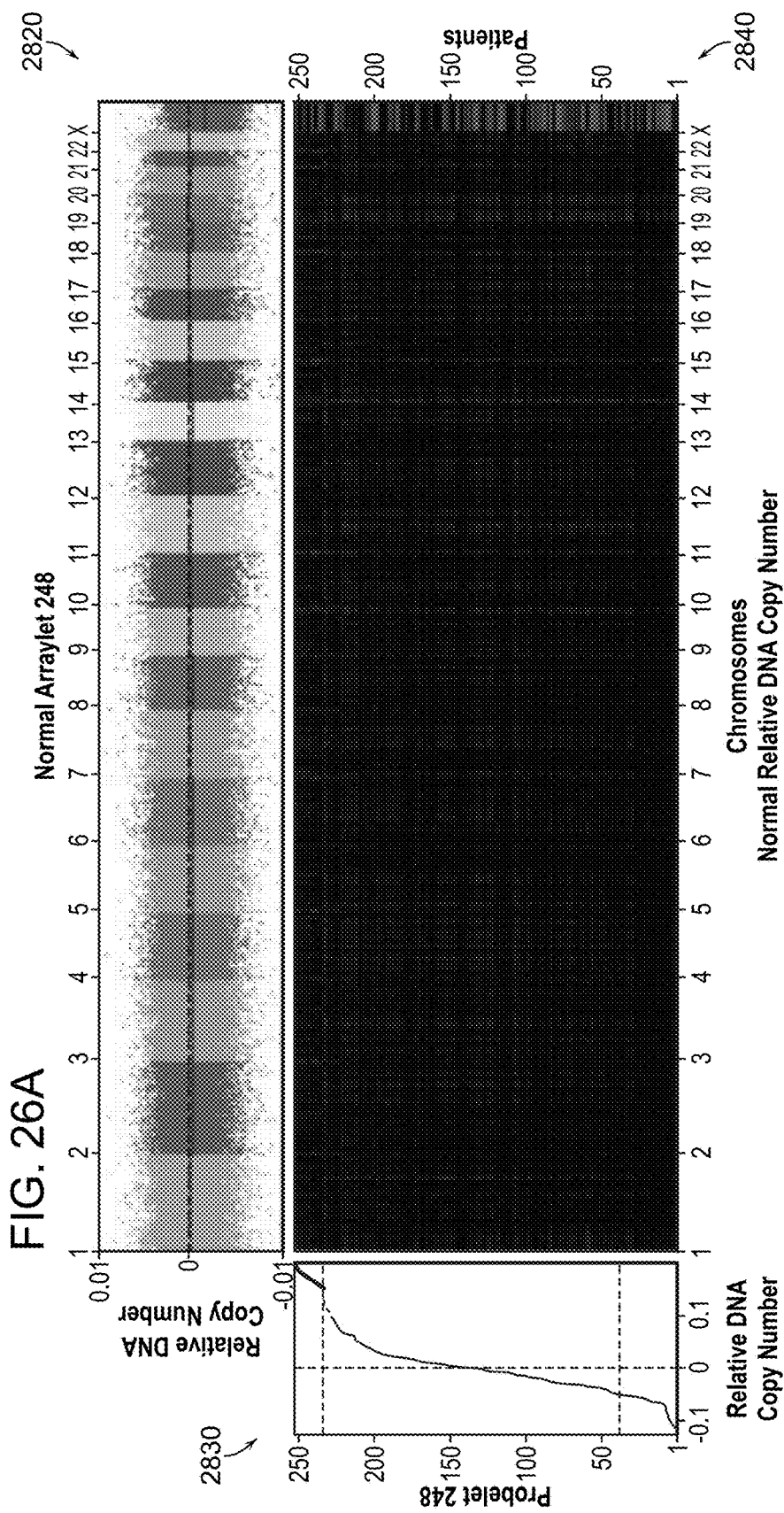

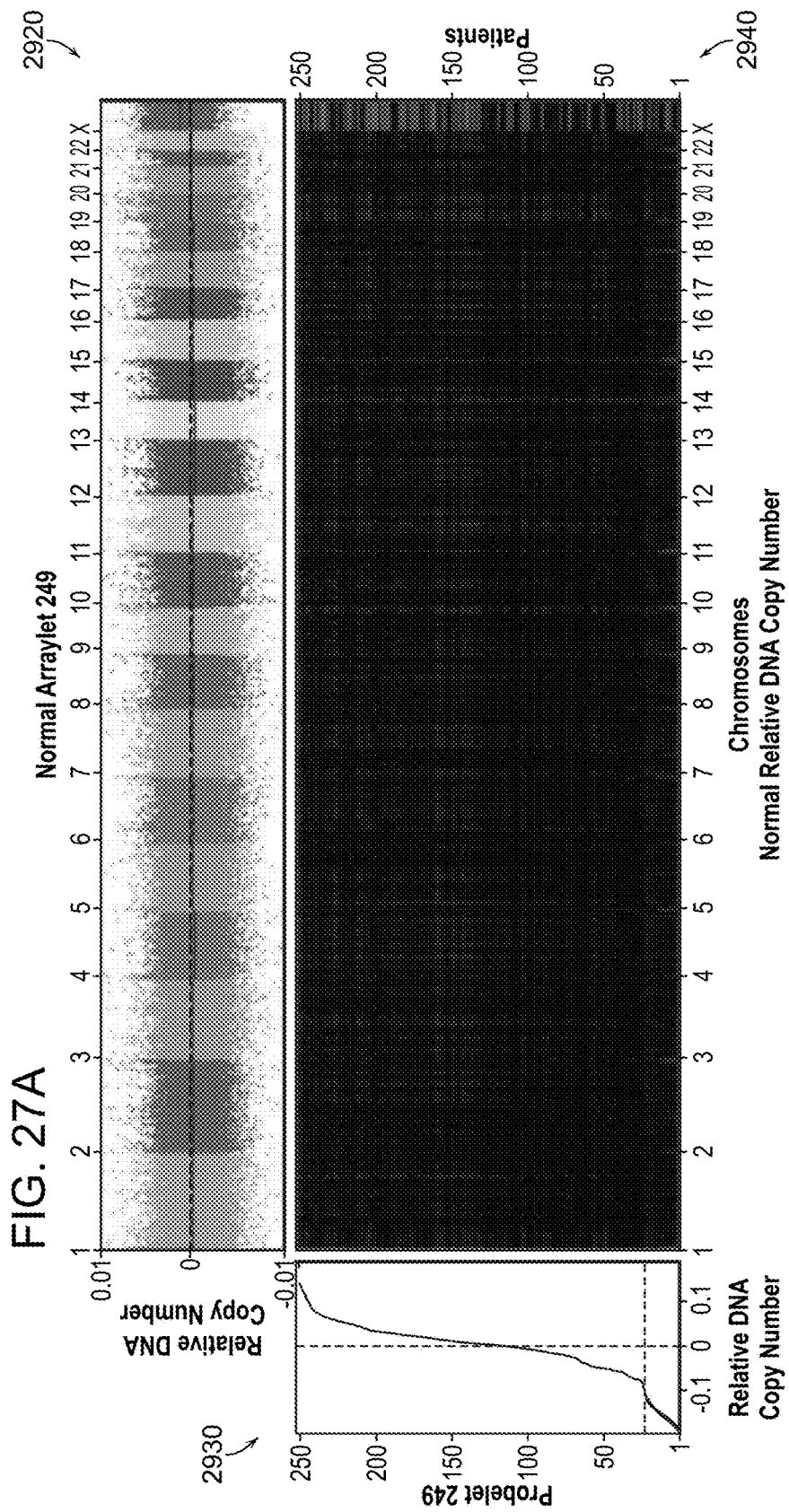

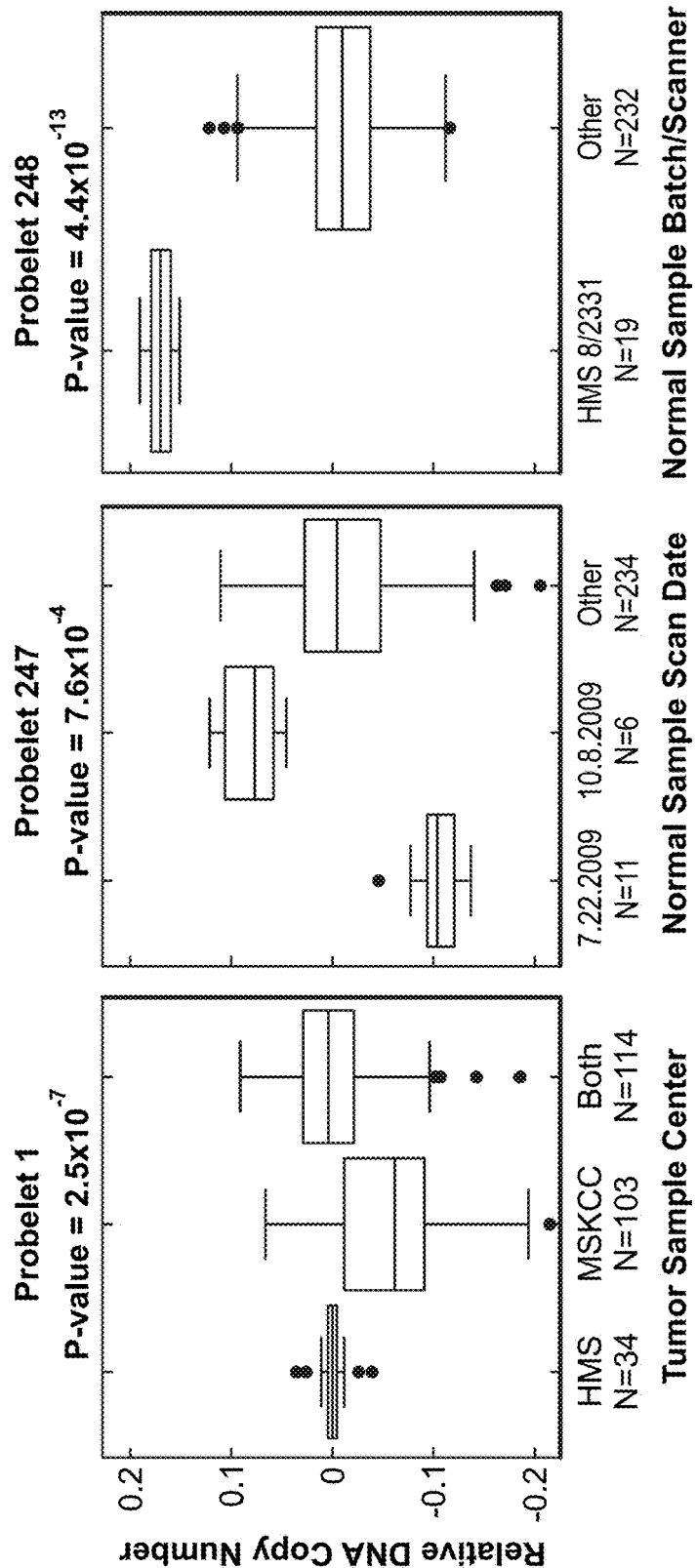

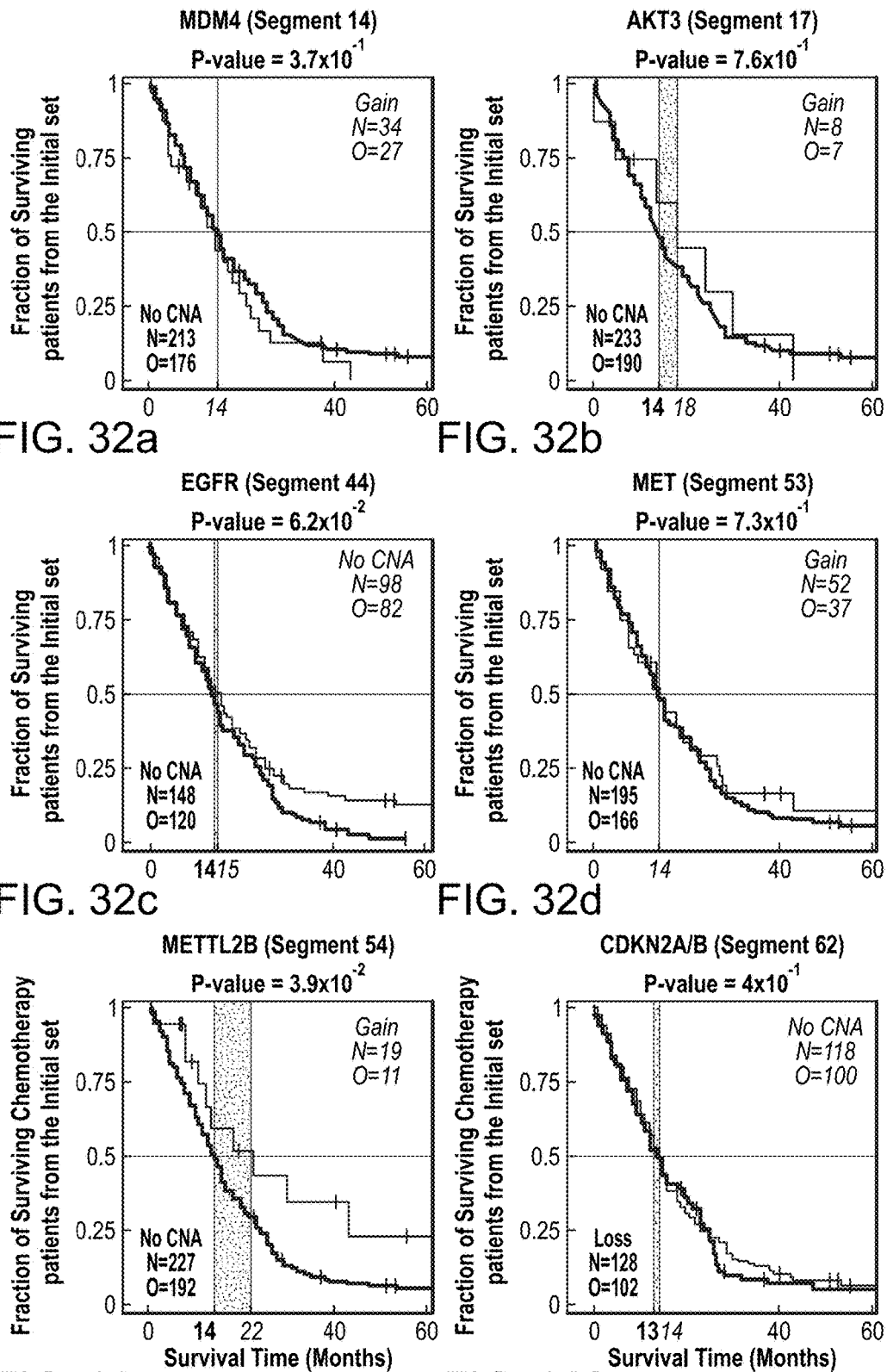

FIG. 34

| Cox Proportional Hazard Model | Predictor | Initial Set | | Inclusive Confirmation Set | | Independent Validation Set | |
|---|---|---|---|---|---|---|---|
| | | Hazard Ratio | P-value | Hazard Ratio | P-value | Hazard Ratio | P-value |
| Univariate | GSVD | 2.3 | $1.3 \times 10^{-3}$ | 2.4 | $6.5 \times 10^{-4}$ | 2.9 | $3.6 \times 10^{-4}$ |
| | Age | 2.0 | $7.9 \times 10^{-5}$ | 2.0 | $4.3 \times 10^{-6}$ | 2.7 | $1.7 \times 10^{-6}$ |
| Multivariate | GSVD | 1.8 | $2.2 \times 10^{-2}$ | 1.9 | $1.2 \times 10^{-2}$ | 2.0 | $2.2 \times 10^{-2}$ |
| | Age | 1.7 | $2.0 \times 10^{-3}$ | 1.8 | $1.0 \times 10^{-4}$ | 2.2 | $2.0 \times 10^{-4}$ |

FIG. 35

| Probelet | Phenotype | Relative DNA Copy Number | | | | Relative DNA Copy Number Gain | | | | Relative DNA Copy Number Loss | | | |
|---|---|---|---|---|---|---|---|---|---|---|---|---|---|
| | | Annotation | $n$ | $K$ | $k$ | Annotation | $n$ | $K$ | $k$ | P-value | $n$ | $K$ | $k$ | P-value |
| 1 | Tumor Sample Center | HMS | 183 | 34 | 34 | MSKCC | 68 | 103 | 55 | $3.9 \times 10^{-15}$ |
| 246 | Patient Gender | Female | 86 | 86 | 84 | $8.5 \times 10^{-6}$ | Male | 165 | 165 | 163 | $8.0 \times 10^{-62}$ |
| 247 | Normal Sample Scan Date | 10.8.2009 | 51 | 6 | 6 | $5.5 \times 10^{-5}$ | 7.22.2009 | 38 | 11 | 10 | $2.0 \times 10^{-8}$ |
| 248 | Normal Sample Batch/Scanner | HMS 8/2331 | 19 | 19 | 19 | $6.2 \times 10^{-29}$ | | | | | |
| 249 | Normal Sample Batch/Scanner | 4.18.2007 | 26 | 9 | 9 | $3.3 \times 10^{-10}$ | HMS 8/2331 | 22 | 19 | 19 | $9.6 \times 10^{-26}$ |
| 250 | Normal Sample Scan Date | | | | | | 7.22.2009 | 25 | 11 | 9 | $1.1 \times 10^{-8}$ |
| 251 | Normal Sample Center | HMS | 139 | 46 | 46 | $2.8 \times 10^{-14}$ | MSKCC | 112 | 101 | 89 | $2.1 \times 10^{-32}$ |

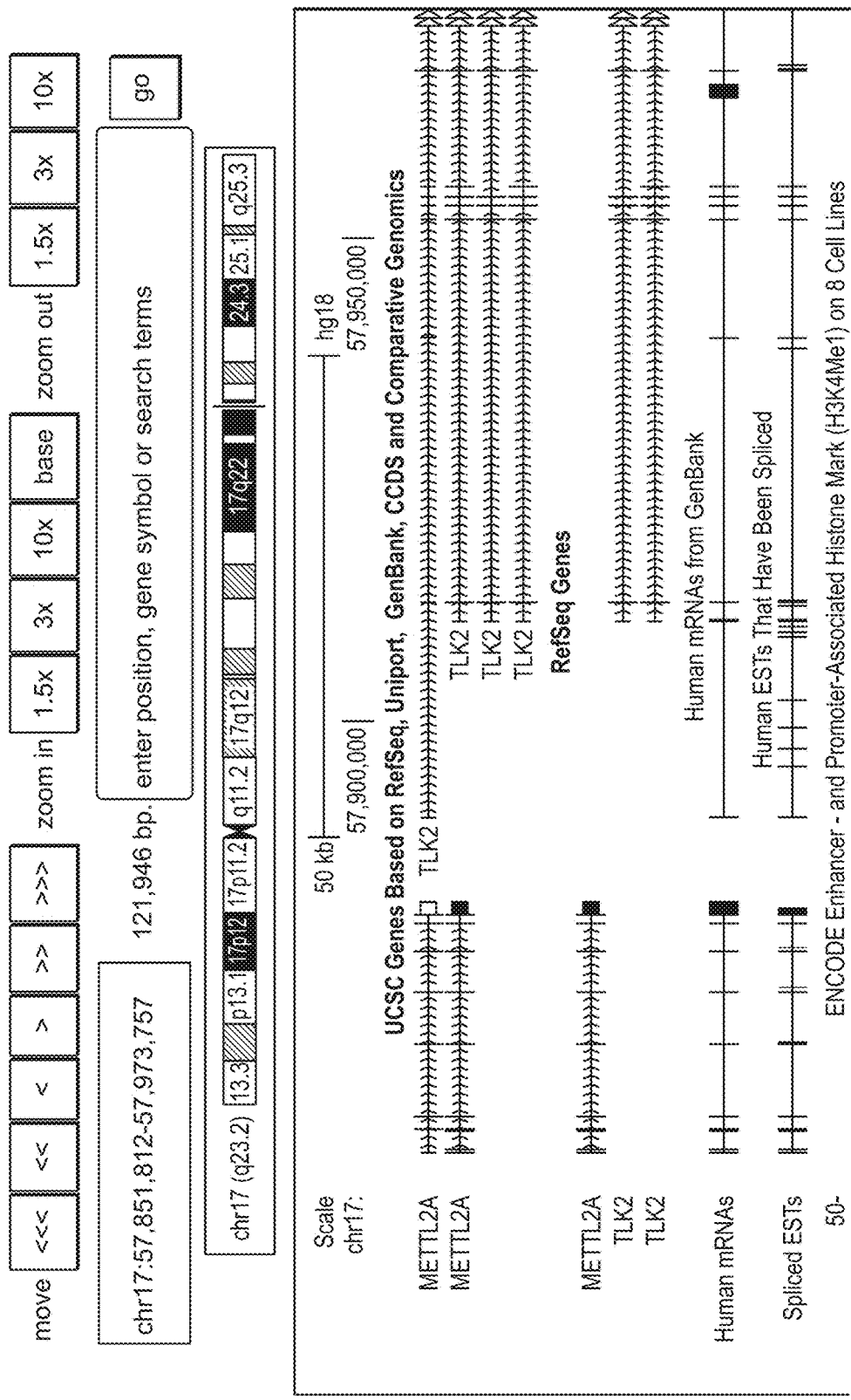
FIG. 37A UCSC Genome Browser on Human Mar. 2006 (NCBI36/hg18) Assembly

| Cox Proportional Hazard Model | Predictor | Initial Set | | Inclusive Confirmation Set | | Independent Validation Set | |
|---|---|---|---|---|---|---|---|
| | | Hazard Ratio | P-value | Hazard Ratio | P-value | Hazard Ratio | P-value |
| Univariate | GSVD | 2.4 | $1.2 \times 10^{-3}$ | 2.4 | $6.4 \times 10^{-4}$ | 2.8 | $1.3 \times 10^{-3}$ |
| | Chemotherapy | 2.6 | $1.5 \times 10^{-8}$ | 2.7 | $6.3 \times 10^{-11}$ | 2.2 | $7.3 \times 10^{-4}$ |
| Multivariate | GSVD | 3.0 | $5.2 \times 10^{-5}$ | 3.1 | $2.5 \times 10^{-5}$ | 3.3 | $2.3 \times 10^{-4}$ |
| | Chemotherapy | 3.1 | $7.9 \times 10^{-11}$ | 3.2 | $1.9 \times 10^{-13}$ | 2.7 | $3.0 \times 10^{-5}$ |

GENETIC ALTERATIONS IN GLIOMA

RELATED APPLICATIONS

This application is the U.S. National Stage of International Application No. PCT/US2012/062855, filed Oct. 31, 2012, published in English, and claims the benefit of U.S. Provisional Application No. 61/553,870, filed Oct. 31, 2011, and U.S. Provisional Application No. 61/553,840, filed Oct. 31, 2011, each of the foregoing applications is incorporated by reference in its entirety.

GOVERNMENT LICENSE RIGHTS

This invention was made with government support under grant number R01 HG004302 awarded by National Institutes of Health. The government has certain rights in this invention.

FIELD

The subject technology relates generally to computational biology and its use to identify genetic patterns related to cancer.

BACKGROUND

In many areas of science, especially in biotechnology, the number of high-dimensional datasets recording multiple aspects of a single phenomenon is increasing. This increase is accompanied by a fundamental need for mathematical frameworks that can compare multiple large-scale matrices with different row dimensions. In the field of biotechnology, these matrices may represent biological reality through large-scale molecular biological data such as, for example, mRNA expression measured by DNA microarray.

Recent efforts have focused on developing ways of modeling and analyzing large-scale molecular biological data through the use of the matrices and their generalizations in different types of genomic data. One of the goals of these efforts is to computationally predict mechanisms that govern the activity of DNA and RNA. For example, matrices have been used to predict global causal coordination between DNA replication origin activity and mRNA expression from mathematical modeling of DNA microarray data. The mathematical variables that is patterns uncovered in the data correlate with activities of cellular elements such as regulators or transcription factors. The operations, such as classification, rotation, or reconstruction in subspaces of these patterns, simulate experimental observation of the correlations and possibly even the causal coordination of these activities.

These types of analyses also have the potential to be extended to the study of pathological diseases to identify patterns that correlate and possibly coordinate with the diseases.

SUMMARY

Glioblastoma multiforme (GBM), the most common malignant brain tumor found in human adults, exhibits a range of copy-number alterations (CNA), some of which are believed to play a role in the cancer's pathogenesis. GBM copy number alteration data are available from The Cancer Genome Atlas (TCGA). Large-scale gene expression and DNA methylation profiling efforts have also identified GBM molecular subtypes, distinguished by small numbers of biomarkers.

Despite traditional bioinformatic efforts, GBM is characterized by poor prognosis with a median survival time of approximately 10-14 months. Furthermore, the age of the patient at diagnosis is still generally considered the best prognostic predictor. While it is generally believed that the tumor is sporadic, there are some known risk factors including, sex (male), age (over 50 years old), ethnicity (Caucasians, Asians), etc. Traditional treatments of GBM include, but are not limited to, chemotherapy, radiation, radiosurgery, corticosteroids, antiangiogenic therapy, surgery, etc.

Therefore, there is a need to model and analyze the large scale molecular biological data of GBM patients in order to identify factors (e.g., genes) and mechanisms that allow one to make predictions on the course of the disease. The subject technology identifies and utilizes such genes that are useful in the diagnosis and prognosis of GBM.

According to various embodiments of the subject technology, genetic segments and methods for performing diagnosis and prognosis of malignant glioblastoma have been provided. In some embodiments, methods of estimating an outcome for a patient having a high-grade glioma, comprise: obtaining a value of an indicator of a copy number of each of at least one nucleotide sequence, each sequence having at least 90 percent sequence identity to at least one of (i) a respective chromosome segment in cells of the glioma, and (ii) at least one gene on the segment; wherein the segment is selected from the group consisting of 17:57,851,812-17:57,973,757; 7:127,892,509-7:127,947,649; 12:33,854-12:264,310; and 19:33,329,393-19:35,322,055; and estimating, by a processor and based on the value, at least one of a predicted length of survival of the patient, a probability of survival of the patient, or a predicted response of the patient to a therapy for the glioma.

Alternatively, the nucleotide sequences may have at least about 85 percent sequence identity, at least about 95% sequence identity, at least about 96% sequence identity, at least about 97% sequence identity, at least about 98% sequence identity, at least about 99% sequence identity, or 100% sequence identity to at least one of (i) a respective chromosome segment in cells of the glioma, and (ii) at least one gene on the segment; wherein the segment is selected from the group consisting of 17:57,851,812-17:57,973,757; 7:127,892,509-7:127,947,649; 12:33,854-12:264,310; and 19:33,329,393-19:35,322,055.

Sequence similarity or identity can be identified using a suitable sequence alignment algorithm, such as ClustalW2 (ebi.ac.uk/Tools/clustalw2/index.html) or "BLAST 2 Sequences" using default parameters (Tatusova, T. et al, FEMS Microbiol. Lett, 174:187-188 (1999)).

In some embodiments, methods for estimating an outcome for a patient having a high-grade glioma, comprise: obtaining a value of an indicator of increased expression of at least one nucleotide sequence, each sequence having at least 90 percent sequence identity to at least one gene on a respective chromosome segment in cells of the glioma, wherein the segment is selected from the group consisting of 17:57,851,812-17:57,973,757; 7:127,892,509-7:127,947, 649; 12:33,854-12:264,310; and 19:33,329,393-19:35,322, 055; and estimating, by a processor and based on the value, at least one of a predicted length of survival of the patient, a probability of survival of the patient, or a predicted response of the patient to a therapy for the glioma.

Alternatively, the nucleotide sequences may have at least about 85 percent sequence identity, at least about 95% sequence identity, at least about 96% sequence identity, at least about 97% sequence identity, at least about 98% sequence identity, at least about 99% sequence identity, or 100% sequence identity to at least one gene on a respective chromosome segment in cells of the glioma, wherein the segment is selected from the group consisting of 17:57,851, 812-17:57,973,757; 7:127,892,509-7:127,947,649; 12:33, 854-12:264,310; and 19:33,329,393-19:35,322,055.

In some embodiments, the nucleotide sequence comprises DNA. In some embodiments, the nucleotide sequence comprises mRNA.

In some embodiments, the indicator comprises at least one of a mRNA level, a gene product quantity (such as the expression level of a protein encoded by the gene), a gene product activity level (such as the activity level of a protein encoded by the gene), or a copy number of: at least one of (i) the at least one gene or (ii) the one or more chromosome segments.

In some embodiments, the indicator of increased expression reflects an enhanced probability of survival of the patient relative to a probability of survival of patients without the increased expression.

In some embodiments, the indicator comprises the mRNA level and is measured by a technique selected from the group consisting of: northern blotting, gene expression profiling, serial analysis of gene expression, and any combination thereof. In some embodiments, the gene product level is measured by a technique selected from the group consisting of enzyme-linked immunosorbent assay, fluorescent microscopy, and any combination thereof.

In some embodiments, the therapy comprises at least one of chemotherapy or radiotherapy.

In some embodiments, the copy number increase relative to a copy number of the at least one nucleotide sequence in normal cells reflects an enhanced probability of survival of the patient relative to a probability of survival of patients without the increased copy number.

In some embodiments, the at least one nucleotide sequence has at least 90 percent sequence identity to at least one of Tlk2, Mettl2a, or Mettl2b.

In some embodiments, the estimating comprises comparing the copy number to a copy number of the at least one nucleotide sequence found in normal cells of the patient. In some embodiments, the estimating comprises comparing the copy number to a copy number of the at least one nucleotide sequence found in cells of at least one person who does not have a glioma. In some embodiments, the estimating is further based on at least one of age, sex, or ethnicity.

In some embodiments, the high-grade glioma comprises an astrocytoma. In some embodiments, the high-grade glioma comprises a glioblastoma multiforme.

In some embodiments, the copy number is determined by a technique selected from the group consisting of: fluorescent in-situ hybridization, complementary genomic hybridization, array complementary genomic hybridization, fluorescence microscopy, or any combination thereof.

In some embodiments, the at least one gene comprises at least one of: Tlk2, Mettl2a, Mettl2b, Jarid1a, Ak096077, Ccne1, Slc6a12, Slc6a13, Iqsec3, Pop4, Plekhf1, C19orf12, C19orf2, Bc068609, Bc122525, Ak055100, Uqcrf51, Ak094793, Rpp29, or Dkfzp762d096.

In some embodiments, non-transitory machine-readable mediums encoded with instructions executable by a processing system to perform a method of estimating an outcome for a patient having a high-grade glioma, are provided. The instructions comprise code for: receiving a value of an indicator of a copy number of each of at least one nucleotide sequence, each sequence having at least 90 percent sequence identity to at least one of (i) a respective chromosome segment in cells of the glioma, and (ii) at least one gene on the segment; wherein the segment is selected from the group consisting of 17:57,851,812-17:57,973,757; 7:127,892,509-7:127,947,649; 12:33,854-12:264,310; and 19:33,329,393-19:35,322,055; and estimating, by a processor and based on the value, at least one of a predicted length of survival of the patient, a probability of survival of the patient, or a predicted response of the patient to a therapy for the glioma.

Alternatively, the nucleotide sequences may have at least about 85 percent sequence identity, at least about 95% sequence identity, at least about 96% sequence identity, at least about 97% sequence identity, at least about 98% sequence identity, at least about 99% sequence identity, or 100% sequence identity to at least one of (i) a respective chromosome segment in cells of the glioma, and (ii) at least one gene on the segment; wherein the segment is selected from the group consisting of 17:57,851,812-17:57,973,757; 7:127,892,509-7:127,947,649; 12:33,854-12:264,310; and 19:33,329,393-19:35,322,055.

In some embodiments, non-transitory machine-readable mediums encoded with instructions executable by a processing system to perform a method of estimating an outcome for a patient having a high-grade glioma, are provided. The instructions comprise code for: receiving a value of an indicator of increased expression of at least one nucleotide sequence, each sequence having at least 90 percent sequence identity to at least one gene on a respective chromosome segment in cells of the glioma, wherein the segment is selected from the group consisting of 17:57,851,812-17:57, 973,757; 7:127,892,509-7:127,947,649; 12:33,854-12:264, 310; and 19:33,329,393-19:35,322,055; and estimating, by a processor and based on the value, at least one of a predicted length of survival of the patient, a probability of survival of the patient, or a predicted response of the patient to a therapy for the glioma.

Alternatively, the nucleotide sequences may have at least about 85 percent sequence identity, at least about 95% sequence identity, at least about 96% sequence identity, at least about 97% sequence identity, at least about 98% sequence identity, at least about 99% sequence identity, or 100% sequence identity to at least one gene on a respective chromosome segment in cells of the glioma, wherein the segment is selected from the group consisting of 17:57,851, 812-17:57,973,757; 7:127,892,509-7:127,947,649; 12:33, 854-12:264,310; and 19:33,329,393-19:35,322,055.

In some embodiments, systems for estimating an outcome for a patient having a high-grade glioma, comprise: a receiving module that receives a value of an indicator of a copy number of each of at least one nucleotide sequence, each sequence having at least 90 percent sequence identity to at least one of (i) a respective chromosome segment in cells of the glioma, and (ii) at least one gene on the segment; wherein the segment is selected from the group consisting of 17:57,851,812-17:57,973,757; 7:127,892,509-7:127,947, 649; 12:33,854-12:264,310; and 19:33,329,393-19:35,322, 055; and a processing module that estimates, based on the value, at least one of a predicted length of survival of the patient, a probability of survival of the patient, or a predicted response of the patient to a therapy for the glioma.

Alternatively, the nucleotide sequences may have at least about 85 percent sequence identity, at least about 95% sequence identity, at least about 96% sequence identity, at least about 97% sequence identity, at least about 98% sequence identity, at least about 99% sequence identity, or 100% sequence identity to at least one of (i) a respective chromosome segment in cells of the glioma, and (ii) at least one gene on the segment; wherein the segment is selected from the group consisting of 17:57,851,812-17:57,973,757; 7:127,892,509-7:127,947,649; 12:33,854-12:264,310; and 19:33,329,393-19:35,322,055.

In some embodiments, systems for estimating an outcome for a patient having a high-grade glioma, comprise: a receiving module that receives a value of an indicator of increased expression of at least one nucleotide sequence, each sequence having at least 90 percent sequence identity to at least one gene on a respective chromosome segment in cells of the glioma, wherein the segment is selected from the group consisting of 17:57,851,812-17:57,973,757; 7:127,892,509-7:127,947,649; 12:33,854-12:264,310; and 19:33,329,393-19:35,322,055; and a processing module that estimates, based on the value, at least one of a predicted length of survival of the patient, a probability of survival of the patient, or a predicted response of the patient to a therapy for the glioma.

Alternatively, the nucleotide sequences may have at least about 85 percent sequence identity, at least about 95% sequence identity, at least about 96% sequence identity, at least about 97% sequence identity, at least about 98% sequence identity, at least about 99% sequence identity, or 100% sequence identity to at least one gene on a respective chromosome segment in cells of the glioma, wherein the segment is selected from the group consisting of 17:57,851,812-17:57,973,757; 7:127,892,509-7:127,947,649; 12:33,854-12:264,310; and 19:33,329,393-19:35,322,055.

In some embodiments, methods for estimating an outcome for a patient having a high-grade glioma, comprise: obtaining a value of an indicator of a copy number of at least one of: (i) one or more chromosome segments in cells of the glioma and (ii) a gene on the one or more segments, wherein the one or more segments comprises at least one of: 17:57,851,812-17:57,973,757; 7:127,892,509-7:127,947,649; 12:33,854-12:264,310; and 19:33,329,393-19:35,322,055; and estimating, by a processor or based on the value, at least one of a predicted length of survival, a probability of survival, or a predicted response to therapy for the glioma.

Alternatively, the nucleotide sequences may have at least about 85 percent sequence identity, at least about 95% sequence identity, at least about 96% sequence identity, at least about 97% sequence identity, at least about 98% sequence identity, at least about 99% sequence identity, or 100% sequence identity to at least one of (i) a respective chromosome segment in cells of the glioma, and (ii) at least one gene on the segment; wherein the segment is selected from the group consisting of 17:57,851,812-17:57,973,757; 7:127,892,509-7:127,947,649; 12:33,854-12:264,310; and 19:33,329,393-19:35,322,055.

In some embodiments, methods for estimating an outcome for a patient having a high-grade glioma, comprise: obtaining a value of an indicator of increased expression of at least one gene on one or more chromosome segments in cells of the glioma, wherein the one or more segments comprises at least one of: 17:57,851,812-17:57,973,757; 7:127,892,509-7:127,947,649; 12:33,854-12:264,310; and 19:33,329,393-19:35,322,055; and estimating, by a processor and based on the value, at least one of a predicted length of survival, a probability of survival, or a predicted response to therapy for the glioma.

In some embodiments, the indicator comprises at least one of a mRNA level, a gene product quantity, a gene product activity level, or a copy number of: at least one of (i) the at least one gene or (ii) the one or more chromosome segments In some embodiments, methods for performing a prognosis of a patient having malignant glioblastoma comprise obtaining a tumor cell and a healthy cell from the patient; measuring a parameter that includes at least one of mRNA level, gene product or activity level, or copy number of a gene or other sequence on a chromosome segment in the tumor cell and the healthy cell, wherein the chromosome segment is selected from the group consisting of: chr17:57,851,812-chr17:57,973,757; chr7:127,892,509-chr7:127,947,649; chr12:33,854-chr12:264,310; chr19:33,329,393-chr19:35,322,055; and any combination thereof; estimating, based on the comparison of the parameter between the tumor cell and the healthy cell, a probability of survival of the patient at a later time.

In some embodiments, the malignant glioblastoma is malignant glioblastoma multiforme.

In some embodiments, a gain in at least one of the mRNA level, the gene product level, or the copy number of the gene in the tumor cell relative to the healthy cell increases the probability of survival of the patient.

In some embodiments, the gene product level of the gene is measured by a technique selected from the group consisting of: enzyme-linked immunosorbent assay, fluorescence microscopy, and any combination thereof.

In some embodiments, the age of the patient at diagnosis is considered in estimating the probability of survival.

In some embodiments, methods of diagnosing a subtype of malignant glioblastoma are provided. The method comprises obtaining a tumor cell and a healthy cell from a patient having malignant glioblastoma. Measuring at least one of mRNA level, gene product level, or copy number of a gene on a chromosome segment in the tumor cell and the healthy cell, wherein the chromosome segment is selected from the group consisting of: chr17:57,851,812-chr17:57,973,757; chr7:127,892,509-chr7:127,947,649; chr12:33,854-chr12:264,310; chr19:33,329,393-chr19:35,322,055; and any combination thereof. Identifying the subtype of malignant glioblastoma, based on the comparison of at least one of the mRNA level, the gene product level, or the copy number. In certain embodiments, the method may further comprise providing a treatment based on the subtype of malignant glioblastoma. In some embodiments, the treatment is selected from the group consisting of: chemotherapy, surgery, radiotherapy, and any combination thereof.

In some embodiments, the subtype is selected from the group consisting of: increased response to chemotherapy, lack of increased response to chemotherapy, increased life expectancy, lack of increased life expectancy, and any combination thereof.

In some embodiments, the gene is selected from the group consisting of Tlk2, Mettl2a, or Mettl2b, and any combination thereof. In some embodiments, a gain in at least one of the mRNA level, the gene product level (e.g., level of a protein encoded by the gene), or the copy number of Tlk2, Mettl2a, or both indicates that the subtype is the increased response to chemotherapy.

In some embodiments, a method for tracking the progress of malignant glioblastoma in a patient is provided. The method comprises obtaining a first tumor cell and a healthy cell from the patient at a first time point; measuring at least one of mRNA level, gene product level, or copy number of a gene on a chromosome segment in the tumor cell and the healthy cell, wherein the chromosome segment is selected from the group consisting of: chr17:57,851,812-chr17:57, 973,757; chr7:127,892,509-chr7:127,947,649; chr12:33, 854-chr12:264,310; chr19:33,329,393-chr19:35,322,055; and any combination thereof. Forming a first pattern that comprises the comparison of at least one of the mRNA level, the gene product level, or the copy number of the gene between the first tumor cell and the first healthy cell. Obtaining a second tumor cell from the patient at a second time point. Measuring at least one of mRNA level, gene product level, or copy number of a gene on a chromosome segment in the tumor cell and the healthy cell, wherein the chromosome segment is selected from the group consisting of: chr17:57,851,812-chr17:57,973,757; chr7:127,892,509-chr7:127,947,649; chr12:33,854-chr12:264,310; chr19:33,329,393-chr19:35,322,055; and any combination thereof. Forming a second pattern that comprises the comparison of at least one of the mRNA level, gene product level (e.g., protein encoded by the gene), or the copy number of the gene between the second tumor cell and the healthy cell. Determining the progress of the malignant glioblastoma by comparing the first pattern with the second pattern.

In some embodiments, the first pattern and the second pattern both comprise the comparison of the mRNA level of the gene. In some embodiments, the first pattern and the second pattern both comprise the comparison of the gene product (e.g., protein encoded by the gene) level of the gene. In some embodiments, the first pattern and the second pattern both comprise the comparison of the copy number of the gene.

In some embodiments, the second time point is about 1 month after the first time point. In some embodiments, the second time point is from about 3 months to about 6 months after the first time point.

In some embodiments, the method may further comprise administering a treatment based on the first pattern. In certain optional embodiments, the method may further comprise administering a treatment based on the second pattern.

The term "normal cell" (or "healthy cell") as used herein, refers to a cell that does not exhibit a disease phenotype. For example, in a diagnosis of glioma, a normal cell (or a non-cancerous cell) refers to a cell that is not a tumor cell (non-malignant, non-cancerous, or without DNA damage characteristic of a tumor or cancerous cell). The term a "tumor cell" (or "cancer cell") refers to a cell displaying one or more phenotype of a tumor, such as glioma. The terms "tumor" or "cancer" refer to the presence of cells possessing characteristics typical of cancer-causing cells, such as uncontrolled proliferation, immortality, metastatic potential, rapid growth or proliferation rate, and certain characteristic morphological features.

Normal cells can be cells from a healthy subject. Alternatively, normal cells can be non-malignant, non-cancerous cells from a subject having glioma.

The comparison of the mRNA level, the gene product level, or the copy number of a particular nucleotide sequence between a normal cell and a tumor cell can be determined in parallel experiments, in which one sample is based on a normal cell, and the other sample is based on a tumor cell. Alternatively, the mRNA level, the gene product level, or the copy number of a particular nucleotide sequence in a normal cell can be a pre-determined "control," such as a value from other experiments, a known value, or a value that is present in a database (e.g., a table, electronic database, spreadsheet, etc.).

Optionally, methods described herein further comprise outputting the medical estimate (e.g., outcome for a patient having a high-grade glioma; predicted length of survival of the patient, probability of survival of the patient, predicted response of the patient to a therapy for the glioma; diagnosing a subtype of malignant glioblastoma; the patient's probability of developing glioma; the presence or the absence of glioma; the actual or predicted onset, progression, severity, or treatment outcome of glioma, etc.). The estimate can be informed to either a physician, or the patient. Optionally, appropriate recommendations can be made (such as a treatment regimen, a preventative treatment regimen, an exercise regimen, a dietary regimen, a life style adjustment etc.) to reduce the risk of developing glioma, or design a treatment regiment that is likely to be effective in treating glioma.

In another aspect, the subject technology provide a method for reducing the proliferation or viability of a glioma cancer cell (such as a glioblastoma multiforme cell), comprising: contacting the cancer cell with an inhibitor that (i) down-regulates the expression level of a gene selected from the group consisting of: Tlk2, Mettl2a, Mettl2b, and a combination thereof; or (ii) down-regulates the activity of a protein selected from TLK2, METTL2A, METTL2B, and a combination thereof.

Suitable inhibitors include, for example, an RNA effector molecule that down-regulates expression of a gene selected from the group consisting of: Tlk2, Mettl2a, Mettl2b, and a combination thereof. Exemplary RNA effector molecules include an siRNA or shRNA that targets Tlk2, Mettl2a, Mettl2b, or a combination thereof.

Suitable inhibitors can also be an antibody, or an antigen-binding fragment thereof, that binds TLK2, METTL2A, METTL2B, or a combination thereof.

Optionally, the cancer cell may be further treated with a chemotherapeutic drug, such as an alkylating agent, an anti-metabolite, an anti-mitototic, a alkaloid, podophyllotoxin, a taxane, a topoisomerase inhibitor, a cytotoxic antibiotic, or a combination thereof.

In another aspect, the subject technology provide a method of treating glioma (such as glioblastoma multiforme), comprising: administering to a patient in need thereof an inhibitor that (i) down-regulates the expression level of a gene selected from the group consisting of: Tlk2, Mettl2a, Mettl2b, and a combination thereof; or (ii) down-regulates the activity of a protein selected from TLK2, METTL2A, METTL2B, and a combination thereof.

Suitable inhibitors include, for example, an RNA effector molecule that down-regulates expression of a gene selected from the group consisting of: Tlk2, Mettl2a, Mettl2b, and a combination thereof. Exemplary RNA effector molecules include an siRNA or shRNA that targets Tlk2, Mettl2a, Mettl2b, or a combination thereof.

Suitable inhibitors can also be an antibody, or an antigen-binding fragment thereof, that binds TLK2, METTL2A, METTL2B, or a combination thereof.

Optionally, the patient may be further treated with a chemotherapeutic drug (such as an alkylating agent, an anti-metabolite, an anti-mitototic, a alkaloid, podophyllotoxin, a taxane, a topoisomerase inhibitor, a cytotoxic antibiotic, or a combination thereof), radiation, or surgery.

In general, standard gene and protein nomenclature is followed herein. Unless the description indicates otherwise, gene symbols are generally italicized, with first letter in upper case all the rest in lower case; and a protein encoded by a gene generally uses the same symbol as the gene, but without italics and all in upper case.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

FIG. 6 is a diagram illustrating a right basis vector of FIG. 4 and mRNA expression oscillations in three organisms, according to some embodiments.

FIG. 11 is a diagram illustrating an example of S. pombe global mRNA expression reconstructed in the five-dimensional approximately common HO GSVD subspace, according to some embodiments.

FIG. 13 is a diagram illustrating a human global mRNA expression reconstructed in the five-dimensional approximately common HO GSVD subspace, according to some embodiments.

FIG. 24 is a diagram illustrating a first most tumor-exclusive probelet and a corresponding tumor arraylet uncovered by GSVD of the patient-matched GBM and normal blood aCGH profiles, according to some embodiments.

FIG. 26 is a diagram illustrating another normal-exclusive probelet and a corresponding normal arraylet uncovered by GSVD, according to some embodiments.

FIG. 27 is a diagram illustrating yet another normal-exclusive probelet and a corresponding normal arraylet uncovered by GSVD, according to some embodiments.

FIG. 32A-32L are diagrams illustrating survival analyses of patients classified by copy number changes in selected segments, according to some embodiments.

FIG. 34 is a table illustrating proportional hazard models of three sets of patients classified by GSVD, according to some embodiments.

FIG. 35 is a table illustrating enrichment of significant probelets in TCGA annotations, according to some embodiments.

FIG. 42 is a Table showing the Cox proportional hazard models of the three sets of patients classified by GSVD, chemotherapy or both, according to some embodiments. In each set of patients, the multivariate Cox proportional hazard ratios for GSVD and chemotherapy are similar and do not differ significantly from the corresponding univariate hazard ratios. This means that GSVD and chemotherapy are independent prognostic predictors. The P-values are calculated without adjusting for multiple comparisons.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

I. Overview of Glioma

A glioma is a type of tumor arising from glial cells and originating in the brain or spinal cord. Gliomas are classified by cell type, by grade, and by location. Gliomas are named according to the specific type of cell they share histological features with, but not necessarily originate from. The main types of gliomas are ependymomas, astrocytomas, oligodendrogliomas, and mixed tumors such as oligoastrocytomas.

Gliomas are further categorized according to their grade, as determined by pathologic evaluation of the tumor. Low-grade gliomas (WHO grade II) are well-differentiated (not anaplastic), portending a better prognosis. High-grade (WHO grade III-IV) gliomas are undifferentiated or anaplastic; these are malignant and carry a worse prognosis.

The most common grading system used is the World Health Organization (WHO) grading system for astrocytoma, under which tumors are graded from I (least advanced disease—best prognosis) to IV (most advanced disease—worst prognosis).

Glioblastoma multiforme, anaplastic astrocytoma, and higher grade oligodendrogliomas are known as high-grade gliomas. Anaplastic astrocytoma, malignant astrocytoma, and astrocytoma grade III are names referring to the same tumor. Glioblastoma, glioblastoma multiforme, and grade IV astrocytoma also refer to the same tumor.

II. Genomic Tensor Analysis for Medical Assessment and Prediction

The subject technology provides advances in the generalizations of tensor computations that provides the basis for mathematical models that can compare and integrate different types of large-scale molecular biological datasets, such as, but not limited to, mRNA expression levels, DNA microarray data, DNA copy number alterations, etc.

Figure 1:
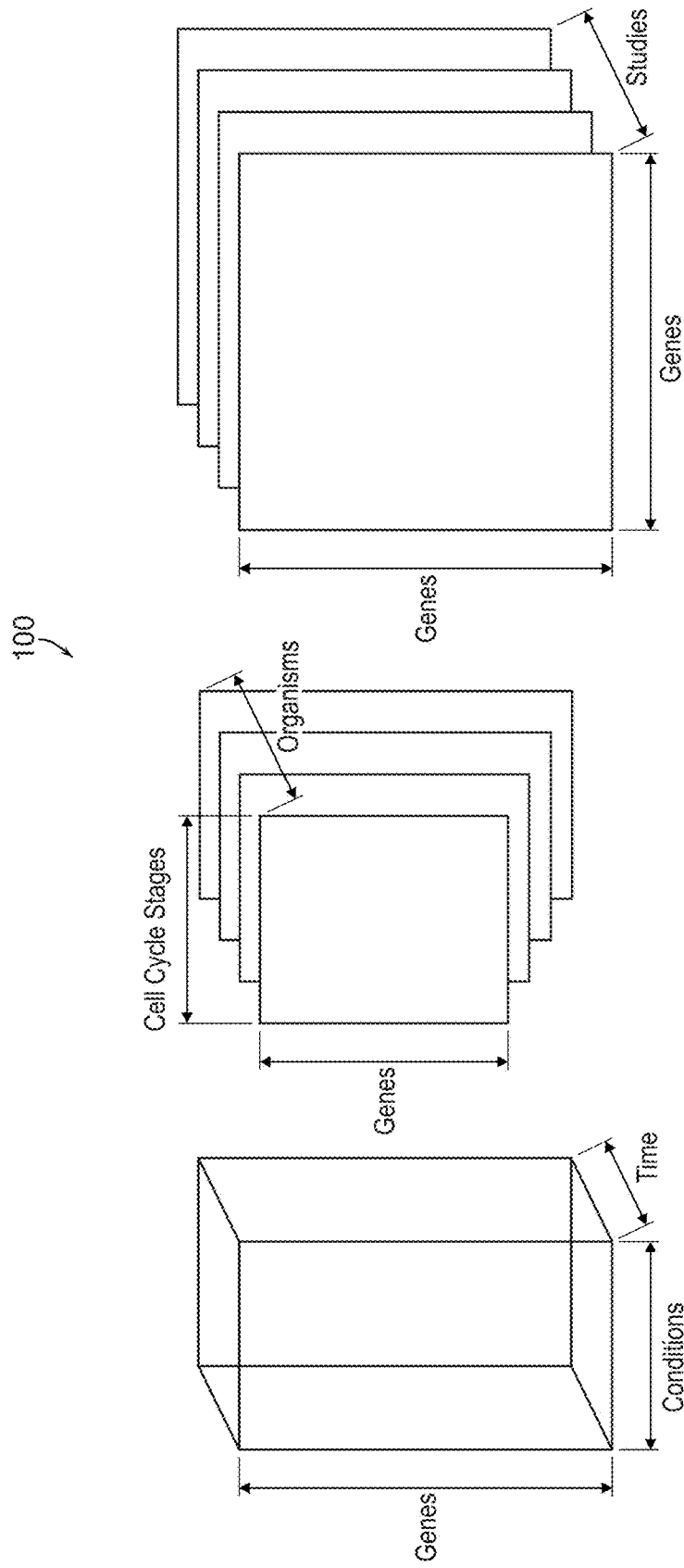
FIG. 1 is a high-level diagram illustrating examples of tensors including biological datasets, according to some embodiments.

FIG. 1 is a high-level diagram illustrating suitable examples of tensors 100, according to some embodiments of the subject technology. In general, a tensor representing a number of biological datasets may comprise an $N^{th}$-order tensor including a number of multi-dimensional (e.g., two or three dimensional) matrices. Datasets may relate to biological information as shown in FIG. 1. An $N^{th}$-order tensor may include a number of biological datasets. Some of the biological datasets may correspond to one or more biological samples. Some of the biological dataset may include a number of biological data arrays, some of which may be associated with one or more subjects.

Referring to the specific embodiments illustrated in FIG. 1, tensor (a) represents a third order tensor (i.e., a cuboid), in which each dimension (e.g., gene, condition, and time) represents a degree of freedom in the cuboid. If the cuboid is unfolded into a matrix, these degrees of freedom and along with it, most of the data included in the tensor may be lost. However, decomposing the cuboid using a tensor decomposition technique, such as a higher-order eigen-value decomposition (HOEVD) or a higher-order single value decomposition (HOSVD) may uncover patterns of variations (e.g., of mRNA expression) across genes, time points and conditions.

As shown in FIG. 1, tensor (b) is a biological dataset that may be associated with genes across one or more organisms. Each data array also includes cell cycle stages. In this case, the tensor decomposition may allow, for example, the integration of global mRNA expressions measured for one or more organisms, the removal of experimental artifacts, and the identification of significant combinations of patterns of expression variation across the genes, for various organisms and for different cell cycle stages.

Similarly, tensor (c) contains biological datasets associated with a network K of N-genes by N-genes. The network K represents the number of studies on the genes. The tensor decomposition (e.g., HOEVD) in this case may allow, for example, uncovering important relationships among the genes (e.g., pheromone-response-dependent relation or orthogonal cell-cycle-dependent relation). An example of a tensor comprising a three-dimensional array is discussed below in reference to FIG. 2.

Figure 2:
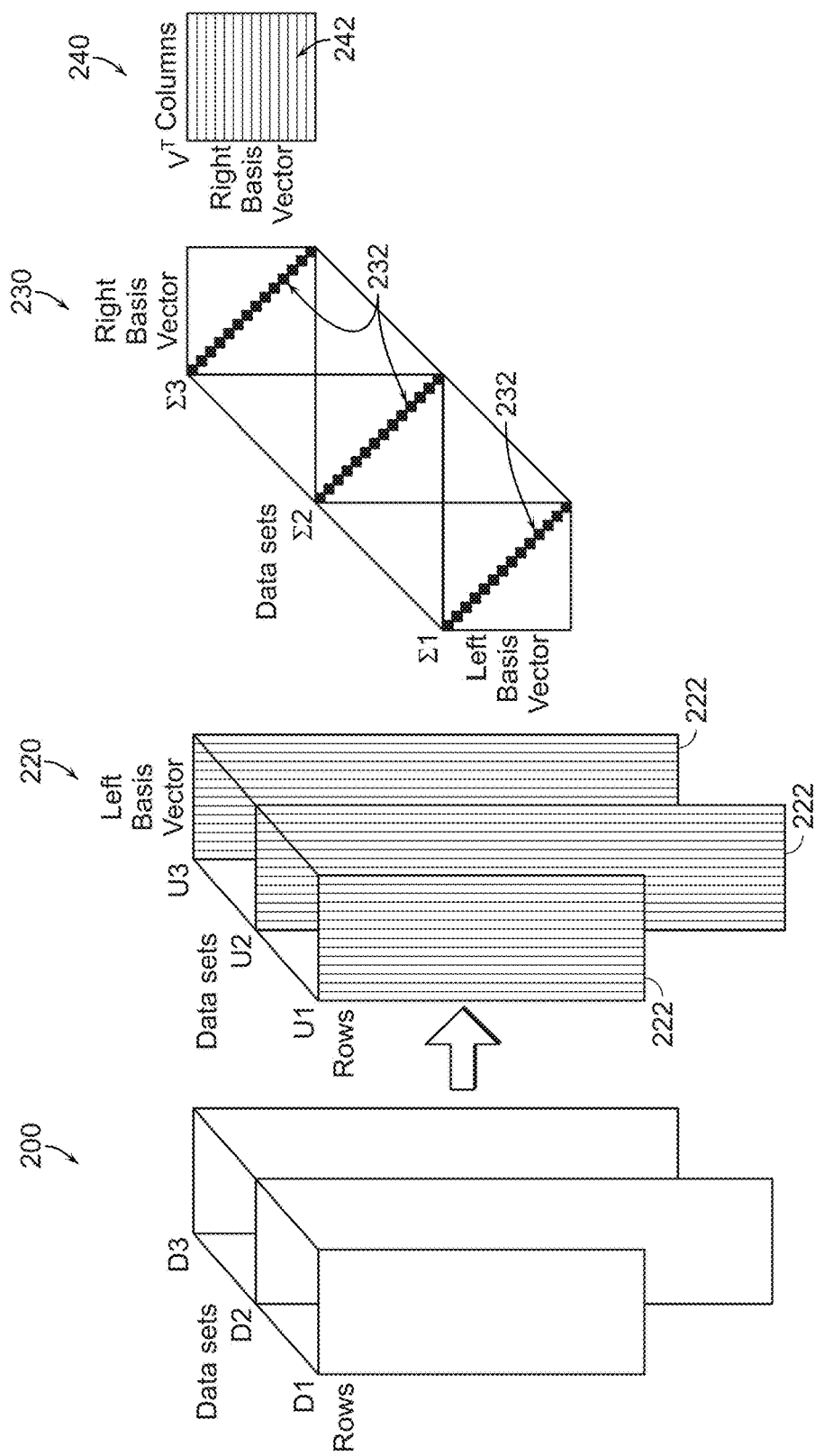
FIG. 2 is a high-level diagram illustrating a linear transformation of a three-dimensional array, according to some embodiments.

FIG. 2 is a high-level diagram illustrating a linear transformation of a number of two dimensional (2-D) arrays forming a three-dimensional (3-D) array 200, according to some embodiments. The 3-D array 200 may be stored in memory 300 (see FIG. 3). The 3-D array 200 may include an N number of biological datasets (e.g., D1, D2, and D3) that correspond to, for example, genetic sequences. In some cases, the 3-D array 200 may comprise an N number of 2-D data arrays (D1, D2, D3, . . . $D_N$) (for clarity only D1-D3 are shown in FIG. 2). In this case, N is equal to 3. However, this is not intended to be limiting as N may be any number (1 or greater). In some embodiments, N is greater than 2.

In some cases, each biological dataset may correspond to a tissue type and include an M number of biological data arrays. Each biological data array may be associated with a patient or, more generally, an organism. Each biological data array may include a plurality of data units (e.g., genes, chromosome segments, chromosomes). Each 2-D data array can store one set of the biological datasets and includes M columns. Each column can store one of the M biological data arrays corresponding to a subject such as a patient.

A linear transformation such as a tensor decomposition algorithm may be applied to the 3-D array 200 to generate a plurality of eigen 2-D arrays 220, 230, and 240. The eigen 2-D arrays 220, 230, and 240 can then be analyzed to determine one or more characteristics related to a disease (see Example 2).

Each data array generally comprises measurable data. In some embodiments, each data array may comprise biological data that represent a physical reality such as the specific stage of a cell cycle. In some embodiments the biological data may be measured by, for example, DNA microarray technology, sequencing technology, protein microarray, mass spectrometry in which protein abundance levels are measured on a large proteomic scale as well as traditional measurement technologies (e.g., immunohistochemical staining). Suitable examples of biological data include, but are not limited to, mRNA expression level, gene product level, DNA copy number, micro-RNA expression, presence of DNA methylation, binding of proteins to DNA or RNA, and the like. In some embodiments, the biological data may be derived from a patient-specific sample including a normal tissue, a disease-related tissue or a culture of a patient's cell (normal and/or disease-related).

In some embodiments, the biological datasets may comprise genes from one or more subjects along with time points and/or other conditions. A tensor decomposition of the $N^{th}$-order tensor may allow for the identification of abnormal patterns (e.g., abnormal copy number variations) in a subject. In some cases, these patterns may identify genes that may correlate or possibly coordinate with a particular disease. Once these genes are identified, they may be useful in the diagnosis, prognosis, and potentially treatment of the disease.

For example, a tensor decomposition may identify genes that enables classification of patients into subgroups based on patient-specific genomic data. In some cases, the tensor decomposition may allow for the identification of a particular disease subtype. In some cases, the subtype may be a patient's increased response to a therapeutic method such as chemotherapy, lack of increased response to chemotherapy, increased life expectancy, lack of increased life expectancy and the like. Thus, the tensor decomposition may be advantageous in the treatment of patient's disease by allowing subgroup- or subtype-specific therapies (e.g., chemotherapy, surgery, radiotherapy, etc.) to be designed. Moreover, these therapies may be tailored based on certain criteria, such as, the correlation between an outcome of a therapeutic method and a global genomic predictor.

In facilitating or enabling prognosis of a disease, the tensor decomposition may also predict a patient's survival. An $N^{th}$-order tensor may include a patient's routine examinations data, in which case decomposition of the tensor may allow for the designing of a personalized preventive regimen for the patient based on analyses of the patient's routine examinations data. In some embodiments, the biological datasets may be associated with imaging data including magnetic resonance imaging (MRI) data, electro cardiogram (ECG) data, electromyography (EMG) data or electroencephalogram (EEG) data. A biological datasets may also be associated with vital statistics, phenotypical data, as well as molecular biological data (e.g., DNA copy number, mRNA expression level, gene product level, etc.). In some cases, prognosis may be estimated based on an analysis of the biological data in conjunction with traditional risk factors such as, age, sex, race, etc.

Tensor decomposition may also identify genes useful for performing diagnosis, prognosis, treatment, and tracking of a particular disease. Once these genes are identified, the genes may be analyzed by any known techniques in the relevant art. For example, in order to perform a diagnosis, prognosis, treatment, or tracking of a disease, the DNA copy number may be measured by a technique such as, but not limited to, fluorescent in-situ hybridization, complementary genomic hybridization, array complementary genomic hybridization, and fluorescence microscopy. Other commonly used techniques to determine copy number variations include, e.g. oligonucleotide genotyping, sequencing, southern blotting, dynamic allele-specific hybridization (DASH), paralogue ratio test (PRT), multiple amplicon quantification (MAQ), quantitative polymerase chain reaction (QPCR), multiplex ligation dependent probe amplification (MLPA), multiplex amplification and probe hybridization (MAPH), quantitative multiplex PCR of short fluorescent fragment (QMPSF), dynamic allele-specific hybridization, fluorescence in situ hybridization (FISH), semiquantitative fluorescence in situ hybridization (SQ-FISH) and the like. For more detail description of some of the methods described herein, see, e.g. Sambrook, *Molecular Cloning—A Laboratory Manual*, Cold Spring Harbor Laboratory, Cold Spring Harbor, N.Y., (1989), Kallioniemi et al., *Proc. Natl. Acad Sci USA*, 89:5321-5325 (1992), and *PCR Protocols, A Guide to Methods and Applications*, Innis et al, Academic Press, Inc. N.Y., (1990).

The mRNA level may be measured by a technique such as, northern blotting, gene expression profiling, and serial analysis of gene expression. Other commonly used techniques include RT-PCR and microarray technology. In a typical microarray experiment, a microarray is hybridized with differentially labeled RNA or DNA populations derived from two different samples. Ratios of fluorescence intensity (red/green, R/G) represent the relative expression levels of the mRNA corresponding to each cDNA/gene represented on the microarray. Real-time polymerase chain reaction, also called quantitative real time PCR (QRT-PCR) or kinetic polymerase chain reaction, may be highly useful to determine the expression level of a mRNA because the technique can simultaneously quantify and amplify a specific part of a given polynucleotide.

The gene product level may be measured by a technique such as, enzyme-linked immunosorbent assay (ELISA) and fluorescence microscopy. When the gene product is a protein, traditional methodologies for protein quantification include 2-D gel electrophoresis, mass spectrometry and antibody binding. Commonly used antibody-based techniques include immunoblotting (western blotting), immunohistological assay, enzyme linked immunosorbent assay (ELISA), radioimmunoassay (RIA), or protein chips. Gel electrophoresis, immunoprecipitation and mass spectrometry may be carried out using standard techniques, for example, such as those described in Molecular Cloning A Laboratory Manual, 2 nd Ed., ed. by Sambrook, Fritsch and Maniatis (Cold Spring Harbor Laboratory Press: 1989), Harlow and Lane, Antibodies: A Laboratory Manual (1988 Cold Spring Harbor Laboratory), G. Suizdak, Mass Spectrometry for Biotechnology (Academic Press 1996), as well as other references cited herein.

In some embodiments, the tensor decomposition of the $N^{th}$-order tensor may allow for the removal of normal pattern copy number alterations and/or an experimental variation from a genomic sequence. Thus, a tensor decomposition of the $N^{th}$-order tensor may permit an improved prognostic prediction of the disease by revealing real disease-associated changes in chromosome copy numbers, focal copy number alterations (CNAs), non-focal CNAs and the like. A tensor decomposition of the $N^{th}$-order tensor may also allow integrating global mRNA expressions measured in multiple time courses, removal of experimental artifacts, and identification of significant combinations of patterns of expression variation across genes, time points and conditions.

In some embodiments, applying the tensor decomposition algorithm may comprise applying at least one of a higher-order singular value decomposition (HOSVD), a higher-order generalized singular value decomposition (HO GSVD), a higher-order eigen-value decomposition (HO-EVD), or parallel factor analysis (PARAFAC) to the $N^{th}$-order tensor. The PARAFAC method is known in the art and will not be described with respect to the present embodiments. In some embodiments, HOSVD may be utilized to decompose a 3-D array 200, as described in more detail herein.

Referring again to FIG. 2, eigen 2-D arrays generated by HOSVD may comprise a set of N left-basis 2-D arrays 220. Each of the left-basis arrays 220 (e.g., U1, U2, U3, . . . $U_N$) (for clarity, only U1-U3 are shown in FIG. 2) may correspond, for example, to a tissue type and can include an M number of columns, each of which stores a left-basis vector 222 associated with a patient. The eigen 2-D arrays 230 comprise a set of N diagonal arrays (Σ1, Σ2, Σ3, . . . ΣN) (for clarity only Σ1-Σ3 are shown in FIG. 2). Each diagonal array (e.g., Σ1, Σ2, Σ3, . . . or ΣN) may correspond to a tissue type and can include an N number of diagonal elements 232. The 2-D array 240 comprises a right-basis array, which can include a number of right-basis vectors 242.

In some embodiments, decomposition of the $N^{th}$-order tensor may be employed for disease related characterization such as identifying genes or chromosomal segments useful for diagnosing, tracking a clinical course, estimating a prognosis or treating the disease.

Figure 3:
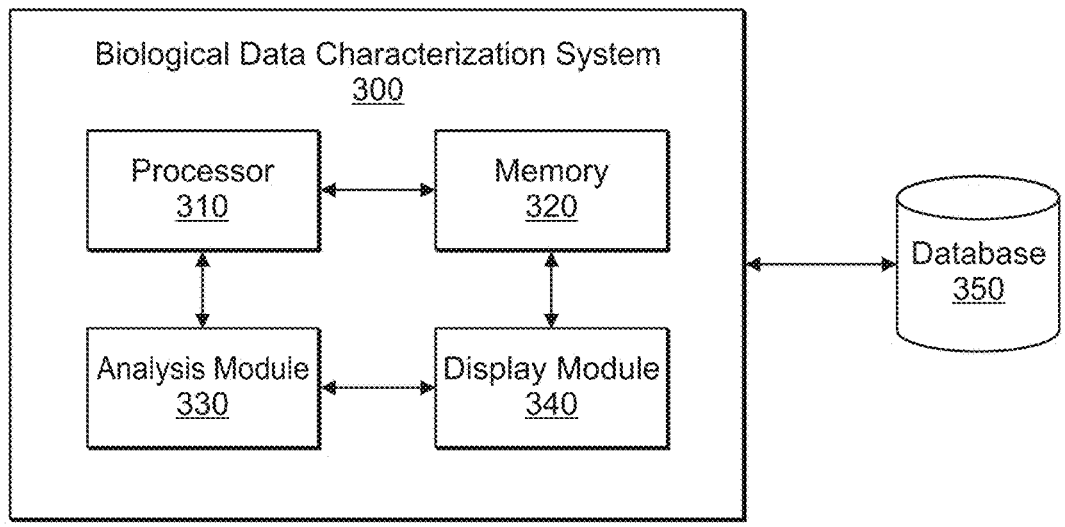
FIG. 3 is a block diagram illustrating a biological data characterization system coupled to a database, according to some embodiments.

FIG. 3 is a block diagram illustrating an exemplary biological data characterization system 300 coupled to a database 350, according to some embodiments. In certain aspects, the biological characterization system 300 may be implemented using hardware or a combination of software and hardware, either in a dedicated server, or integrated into another entity, or distributed across multiple entities.

In some embodiments, the biological data characterization system 300 may be a computer system. The system 300 includes a processor 310, memory 320, an analysis module 330 and a display module 340. Processor 310 may include one or more processors and may be coupled to memory 320. Memory 320 may retrieve information related to the $N^{th}$-order tensors 100 of FIG. 1 or the 3-D array 200 of FIG. 2 from a database 350 coupled to the system 300 and store tensors 100 or the 3-D array 200 along with 2-D eigen-arrays 220, 230, and 240 of FIG. 2. Database 350 may be coupled to system 300 via a network (e.g., Internet, wide area network (WAN), local area network (LAN), etc.). In some embodiments, system 300 may encompass database 350.

A computer system can include a bus or other communication mechanism for communicating information, and a processor (e.g., processor 310) coupled with bus for processing information. By way of example, the computer system may be implemented with one or more processors. Processor 310 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

A computer system can include, in addition to hardware, code that creates an execution environment for the computer program in question, e.g., code that constitutes processor firmware, a protocol stack, a database management system, an operating system, or a combination of one or more of them stored in an included memory (e.g., memory 320), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus for storing information and instructions to be executed by processor. Memory 320 may also include machine-readable medium, such as magnetic or optical disks. The processor 310 and the memory 320 can be supplemented by, or incorporated in, special purpose logic circuitry.

The term "machine-readable storage medium" or "computer readable medium" as used herein refers to any medium or media that participates in providing instructions to processor 310 for execution. Such a medium may take many forms, including, but not limited to, non-volatile media, volatile media, and transmission media. Non-volatile media include, for example, optical or magnetic disks, such as data storage device. Volatile media include dynamic memory, such as memory 320. Transmission media include coaxial cables, copper wire, and fiber optics, including the wires that comprise bus. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

The instructions may be stored in the memory 320 and implemented in one or more computer program products, i.e., one or more modules of computer program instructions encoded on a computer readable medium for execution by, or to control the operation of, the computer system 300, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 320 may also be used for storing temporary variable or other intermediate information during execution of instructions to be executed by processor 310.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Processor 310 can apply a tensor decomposition algorithm, such as HOSVD, HO GSVD, or HOEVD, to tensor 100 or 3-D array 200 in order to generate eigen 2-D arrays 220, 230 and 240. In some embodiments, processor 310 may apply the HOSVD or HO GSVD algorithms to data obtained from array comparative genomic hybridization (aCGH) of patient-matched normal and glioblastoma multiforme (GBM) blood samples (see Example 2). Application of HOSVD algorithm may remove one or more normal pattern copy number alterations (PCAs) or experimental variations from the aCGH data. A HOSVD algorithm can also reveal GBM-associated changes in at least one of chromosome copy numbers, focal CNAs, and unreported CNAs existing in the aCGH data. Analysis module 330 can perform disease related characterizations as discussed above. For example, analysis module 330 can facilitate various analyses of eigen 2-D arrays 230 of FIG. 2 by assigning each diagonal element 232 of FIG. 2 to an indicator of a significance of a respective element of a right-basis vector 222 of FIG. 2, as described herein in more detail. A display module 240 can display 2-D arrays 220, 230, 240 and any other graphical or tabulated data resulting from analyses performed by analysis module 330. Display module 330 may comprise software and/or firmware and may use one or more display units such as cathode ray tubes (CRTs) or flat panel displays.

Figure 4:
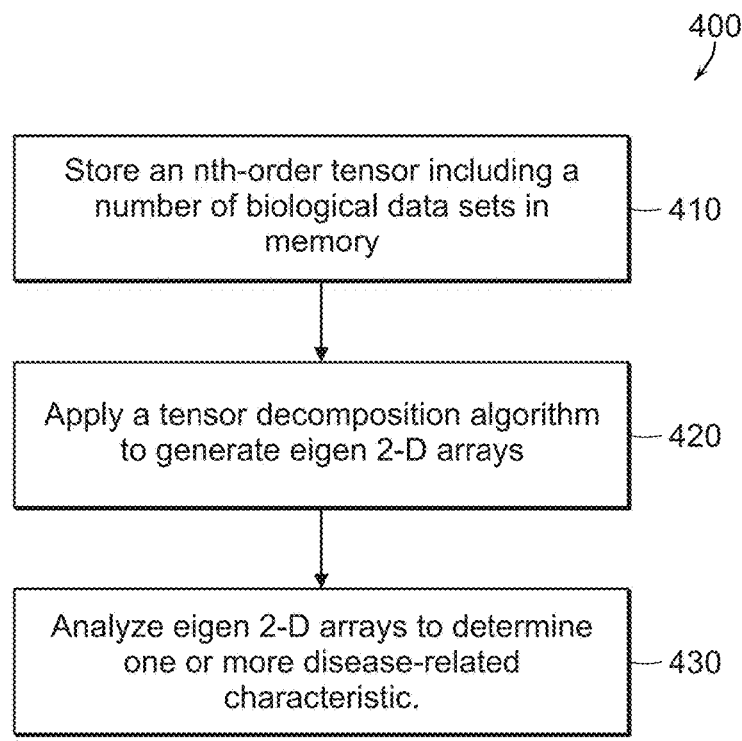
FIG. 4 is a flowchart of a method for disease related characterization of biological data, according to some embodiments.

FIG. 4 is a flowchart of a method 400 for genomic prognostic prediction, according to some embodiments. Method 400 includes storing the $N^{th}$-tensors 100 of FIG. 1 or 3-D array 200 of FIG. 2 in memory 320 of FIG. 3 (410). A tensor decomposition algorithm such as HOSVD, HO GSVD or HOEVD may be applied by processor 310 of FIG. 3 to the datasets stored in tensors 100 or 3-D array 200 to generate eigen 2-D arrays 220, 230, and 240 of FIG. 2 (420). A generated eigen 2-D arrays 220, 230, and 240 may be analyzed by analysis module 330 to determine one or more disease-related characteristics (430).

A HOSVD algorithm is mathematically described herein with respect to N>2 matrices (i.e., arrays $D_1$-$D_N$) of 3-D array 200. Each matrix can be a real $m_i \times n$ matrix. Each matrix is exactly factored as $D_i = U_i \Sigma_i V^T$, where V, identical in all factorizations, is obtained from the balanced eigensystem $SV = V\Lambda$ of the arithmetic mean S of all pairwise quotients $A_i A_j^{-1}$ of the matrices $A_i = D_i^T D_i$, where i is not equal to j, independent of the order of the matrices $D_i$. It can be proved that this decomposition extends to higher orders, all of the mathematical properties of the GSVD except for column-wise orthogonality of the matrices $U_i$ (e.g., 2-D arrays 120 of FIG. 1). It can be proved that matrix S is nondefective. In other words, S has n independent eigenvectors and that V is real and the eigenvalues of S (i.e., $\lambda_1$, $\lambda_2$, ... $\lambda_N$) satisfy $\lambda_k \geq 1$.

In the described HO GSVD comparison of two matrices, the kth diagonal element of $\Sigma_i = \text{diag}(\sigma_{i,k})$ (e.g., the $k_{th}$ element 132 of FIG. 1) is interpreted in the factorization of the $i_{th}$ matrix $D_i$ as indicating the significance of the $k_{th}$ right basis vector $v_k$ in $D_i$ in terms of the overall information that $v_k$ captures in $D_i$. The ratio $\sigma_{i,k}/\sigma_{j,k}$ indicates the significance of $v_k$ in $D_i$ relative to its significance in $D_j$. It can also be proved that an eigenvalue $\lambda_k = 1$ corresponds to a right basis vector $v_k$ of equal significance in all matrices $D_i$ and $D_j$ for all i and j when the corresponding left basis vector $u_{i,k}$ is orthonormal to all other left basis vectors in $U_i$ for all i. Detailed description of various analysis results corresponding to application of the HOSVD to a number of datasets obtained from patients and other subjects will be discussed below. For clarity, a more detailed treatment of the mathematical aspects of HOSVD is skipped here but provided in the attached Appendices A, B, and C. Disclosures in Appendix A have also been published as Lee et al., (2012) *GSVD Comparison of Patient-Matched Normal and Tumor aCGH Profiles Reveals Global Copy-Number Alterations Predicting Glioblastoma Multiforme Survival*, in PLoS ONE 7(1): e30098. doi:10.1371/journal.pone.0030098. Disclosures in Appendices B and C have been published as Ponnapalli et al., (2011) *A Higher-Order Generalized Singular Value Decomposition for Comparison of Global mRNA Expression from Multiple Organisms* in PLoS ONE 6(12): e28072. doi:10.1371/journal.pone.0028072.

A HOEVD tensor decomposition method can be used for decomposition of higher order tensors. Herein, as an example, the HOEVD tensor decomposition method is described in relation with a the third-order tensor of size K-networks×N-genes×N-genes as follows:

Higher-Order EVD (HOEVD). Let the third-order tensor $\{\hat{a}_k\}$ of size K-networks×N-genes×N-genes tabulate a series of K genome-scale networks computed from a series of K genome-scale signals $\{\hat{e}_k\}$, of size N-genes×$M_k$-arrays each, such that $\hat{a}_k = \hat{e}_k \hat{e}_k^T$ for all k=1, 2, . . . , K. We define and compote a HOEVD of the tensor of networks $\{\hat{a}_k\}$, $$\hat{a} \equiv \sum_{k=1}^{K} \hat{a}_k = \hat{u}\left(\sum_{k=1}^{K} \hat{\varepsilon}_k^2\right)\hat{u}^T = \hat{u}\hat{\varepsilon}^2\hat{u}^T, \quad [5]$$

using the SVD of the appended signals $\hat{e} \equiv (\hat{e}_1, \hat{e}_2, \ldots, \hat{e}_K) = \hat{u}\hat{\varepsilon}\hat{v}^T$, where the mth column of $\hat{u}$, $|\alpha_m\rangle \equiv \hat{u}|m\rangle$, lists the genome-scale expression of the mth eigenarray of $\hat{e}$. Whereas the matrix EVD is equivalent to the matrix SVD for a symmetric nonnegative matrix, this tensor HOEVD is different from the tensor higher-order SVD (14-16) for the series of symmetric nonnegative matrices $\{\hat{a}_k\}$, where the higher-order SVD is computed from the SVD of the appended networks $(\hat{a}_1, \hat{a}_2, \ldots, \hat{a}_K)$ rather than the appended signals. This HOEVD formulates the overall network computed from the appended signals $\hat{a} = \hat{e}\hat{e}^T$ as a linear superposition of a series of $M \equiv \Sigma_{k=1}^K M_k$ rank-1 symmetric "subnetworks" that are decorrelated of each other, $\hat{a} = \Sigma_{m=1}^{M}\varepsilon_m^2|\alpha_m\rangle\langle\alpha_m|$. Each subnetwork is also decoupled of all other subnetworks in the overall network $\hat{a}$, since $\hat{\varepsilon}$ is diagonal.

This HOEVD formulates each individual network in the tensor $\{\hat{a}_k\}$ as a linear superposition of this series of M rank-1 symmetric decorrelated subnetworks and the series of M(M−1)/2 rank-2 symmetric couplings among these subnetworks (FIG. 39), such that $$\hat{a}_k = \sum_{m=1}^{M}\varepsilon_{k,m}^2|\alpha_m\rangle\langle\alpha_m| + \sum_{m=1}^{M}\sum_{l=m+1}^{M}\varepsilon_{k,lm}^2(|\alpha_l\rangle\langle\alpha_m| + |\alpha_m\rangle\langle\alpha_l|), \quad [6]$$

for all k=1, 2, . . . , K. The subnetworks are not decoupled in any one of the networks $\{\hat{a}_k\}$, since, in general, $\{\hat{\varepsilon}_k^2\}$ are symmetric but not diagonal, such that $\varepsilon_{k,lm}^2 \equiv \langle l|\hat{\varepsilon}_k^2|m\rangle = \langle m|\hat{\varepsilon}_k^2|l\rangle \neq 0$. The significance of the mth subnetwork in the kth network is indicated by the mth fraction of eigenexpression of the kth network $p_{k,m} = \varepsilon_{k,m}^2/(\Sigma_{k=1}^K\Sigma_{m=1}^M\varepsilon_{k,m}^2) \geq 0$, i.e., the expression correlation captured by the mth subnetwork in the kth network relative to that captured by all subnetworks (and all couplings among them, where $\Sigma_{k=1}^K\varepsilon_{k,lm}^2 = 0$ for all l≠m) in all networks. Similarly, the amplitude of the fraction $p_{k,lm} = \varepsilon_{k,lm}^2/(\Sigma_{k=1}^K\Sigma m=1^M \varepsilon_{k,m}^2)$ indicates the significance of the coupling between the lth and mth subnetworks in the kth network. The sign of this fraction indicates the direction of the coupling, such that $p_{k,lm} > 0$ corresponds to a transition from the lth to the mth subnetwork and $p_{k,lm} < 0$ corresponds to the transition from the mth to the metric distribution of the annotations among the N-genes and the subsets of n⊆N genes with largest and smallest levels of expression in this eigenarray. He corresponding eigengene might be inferred to represent the corresponding biological process from its pattern of expression.

For visualization, we set the x correlations among the X pairs of genes largest in amplitude in each subnetwork and coupling equal to ±1, i.e., correlated or anticorrelated, respectively, according to their signs. Toe remaining correlations are set equal to 0, i.e., decorrelated. We compare the discretized subnetworks and couplings using Boolean functions (6).

Interpretation of the Subnetworks and Their Couplings.

We parallel- and antiparallel-associate each subnetwork or coupling with most likely expression correlations, or none thereof, according to the annotations of the two groups of x pairs of genes each, with largest and smallest levels of correlations in this subnetwork or coupling among all X=N (N−1)/2 pairs of genes, respectively. The P value of a given association by annotation is calculated by using combinatorics and assuming hypergeometric probability distribution of the Y pairs of annotations among the X pairs of genes, and of the subset of y⊆Y pairs of annotations among the subset of x⊆X pairs of genes, $P(x;y, Y, X) = \binom{X}{x}^{-1}\Sigma_{z=y}^{x}\binom{Y}{z}\binom{X-Y}{x-z}$, where $\binom{X}{x} = X!x!^{-1}(X-x)^{-1}$ is the binomial coefficient (17). The most likely association of a subnetwork with a pathway or of a coupling between two subnetworks with a transition between two pathways is that which corresponds to the smallest P value. Independently, we also parallel- and anti-parallel-associate each eigenarray with most likely cellular states, or none thereof, assuming hypergeo-metric distribution of the annotations among the N-genes and the subsets of n⊆N genes with largest and smallest levels of expression in this eigenarray. The corresponding eigengene might be inferred to represent the corresponding biological process from its pattern of expression. For visualization, we set the x correlations among the X pairs of genes largest in amplitude in each subnetwork and coupling equal to ±1, i.e., correlated or anticorrelated, respectively, according to their signs. The remaining correlations are set equal to 0, i.e., decorrelated. We compare the discretized subnetworks and couplings using Boolean functions (6).

Figure 39:
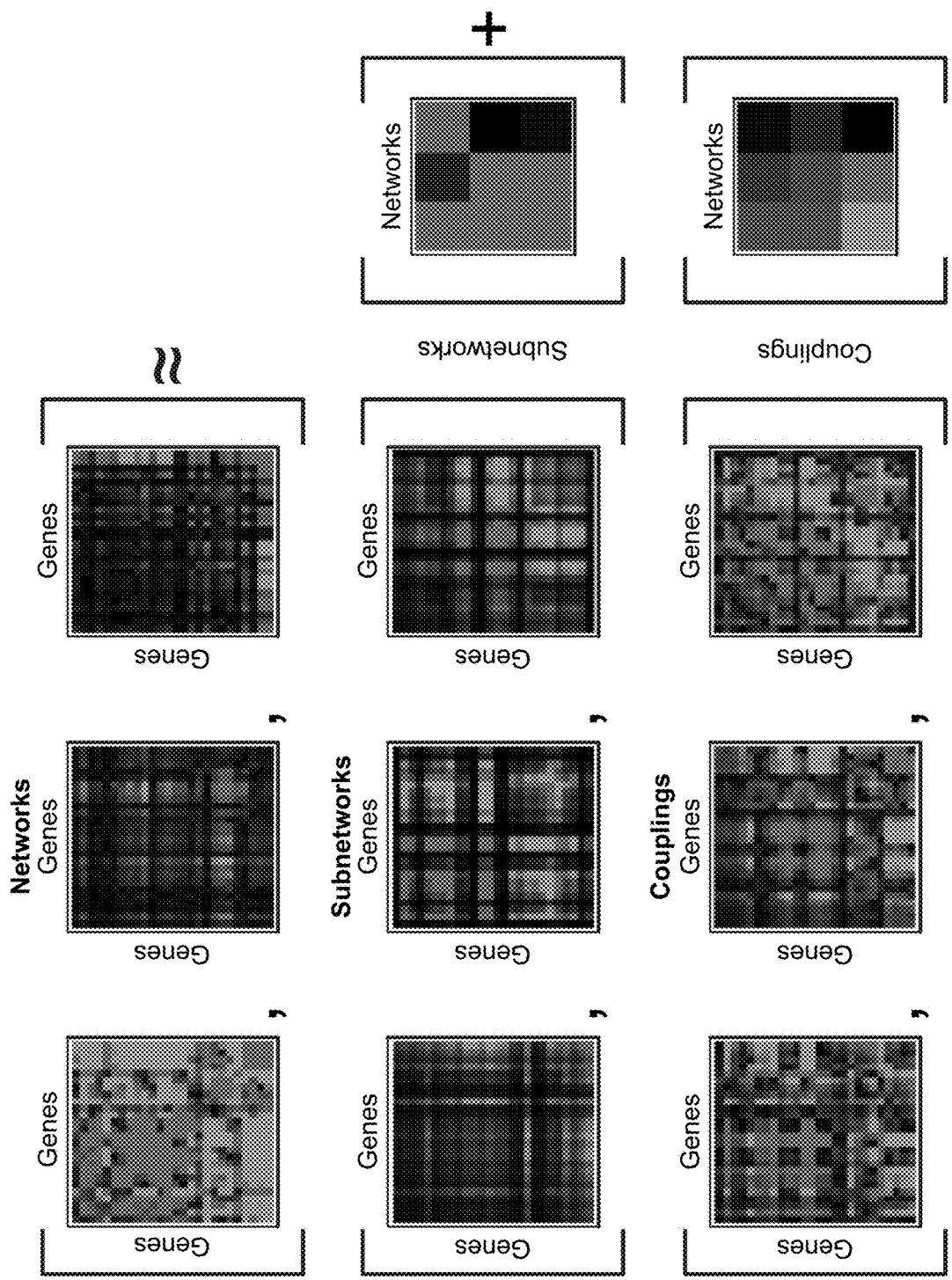
FIG. 39 is a diagram illustrating a higher-order EVD (HOEVD) of the third-order series of the three networks, according to some embodiments.

FIG. 39 is a higher-order EVD (HOEVD) of the third-order series of the three networks $\{\hat{a}_1, \hat{a}_2, \hat{a}_3\}$. The network $\hat{a}$ is the pseudoinverse projection of the network $\hat{a}_1$ onto a genome-scale proteins' DNA-binding basis signal of 2,476-genes×12-samples of development transcription factors (Mathematica Notebook 3 and Data Set 4), computed for the 1,827 genes at the intersection of $\hat{a}_1$ and the basis signal. The HOEVD is computed for the 868 genes at the intersection of $\hat{a}_1$, $\hat{a}_2$ and $\hat{a}_3$. Raster display of $a_k \approx \Sigma_{m=1}^{3}\varepsilon_{k,m}^2|\alpha_m\rangle\perp\langle\perp\alpha_m| + \Sigma_{m=1}^{3}\Sigma_{l=m+1}^{3}\varepsilon_{k,m}^2(|\alpha_l\rangle\perp\langle\perp\alpha_m| + |\alpha_m\rangle\perp\langle\perp\alpha_l|)$, for all k=1, 2, 3, visualizing each of the three networks as an approximate superposition of only the three most significant HOEVD subnetworks and the three couplings among them, in the subset of 26genes which constitute the 100 correlations in each subnetwork and coupling that are largest in amplitude among the 435 correlations of 30 traditionally classified cell cycle-regulated genes. This tensor HOEVD is different from the tensor higher-order SVD [14-161]for the series of symmetric nonnegative matrices $\{\hat{a}_1, \hat{a}_2, \hat{a}_3\}$. The subnetworks correlate with the genomic pathways that are manifest in the series of networks. The most significant subnetwork correlates with the response to the pheromone. This subnetwork does not contribute to the expression correlations of the cell cycle-projected network $\hat{a}_2$, where $\varepsilon_{2,1}^2 \approx 0$. The second and third subnetworks correlate with the two pathways of antipodal cell cycle expression oscillations, at the cell cycle stage $G_1$ vs. those at $G_2$, and at S vs. M, respectively. These subnetworks do not contribute to the expression correlations of the development-projected network $\hat{a}_3$, where $\varepsilon_{3,2}^2 \approx \varepsilon_{3,3}^2 \approx 0$. The couplings correlate with the transitions among these independent pathways that are manifest in the individual networks only. The coupling between the first and second subnetworks is associated with the transition between the two pathways of response to pheromone and cell cycle expression oscillations at $G_1$ vs. those $G_2$, i.e., the exit from pheromone-induced arrest and entry into cell cycle progression. The coupling between the first and third subnetworks is associated with the transition between the response to pheromone and cell cycle expression oscillations at S vs. those at M, i.e., cell cycle expression oscillations at $G_1/S$ vs. those at M. The coupling between the second and third subnetworks is associated with the transition between the orthogonal cell cycle expression oscillations at $G_1$ vs. those at $G_2$ and at S vs. M, i.e., cell cycle expression oscillations at the two antipodal cell cycle checkpoints of $G_1/S$ vs. $G_2/M$. All these couplings add to the expression correlation of the cell cycle-projected $â_2$, where $\varepsilon_{2,12}^2, \varepsilon_{2,13}^2, \varepsilon_{2,23}^2 > 0$; their contributions to the expression correlations of $â_1$ and the development-projected $â_3$ are negligible.

Figure 45A:
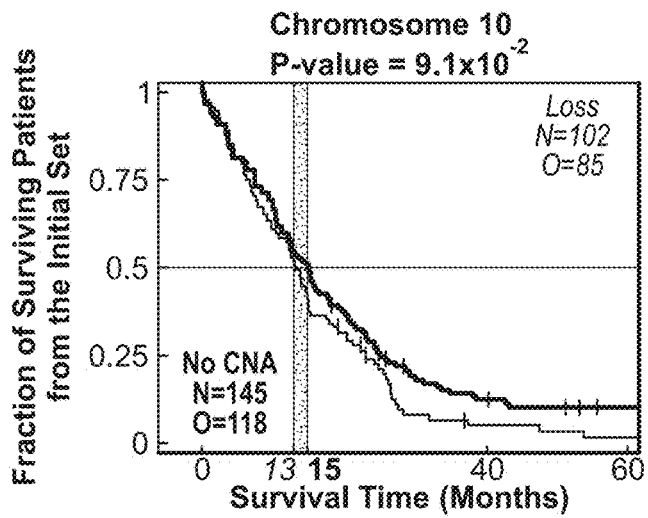
FIGS. 45A-45C are diagrams illustrating survival analyses of patients classified GBM-associated chromosome (10, 7, 9p) number changes, according to some embodiments.
Figure 45B:
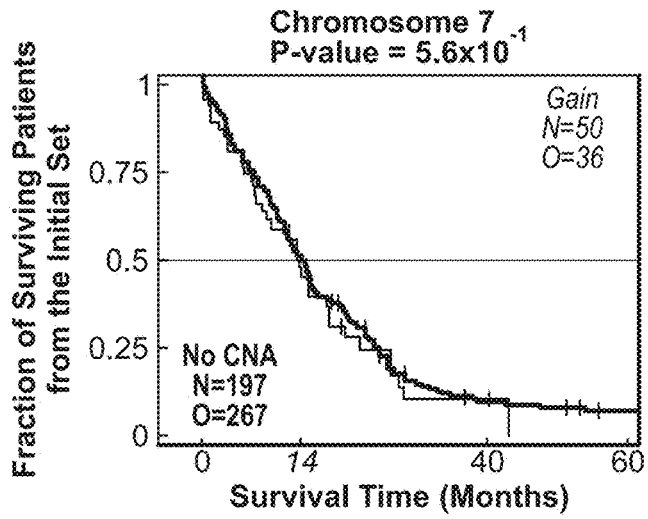
Figure 45C:
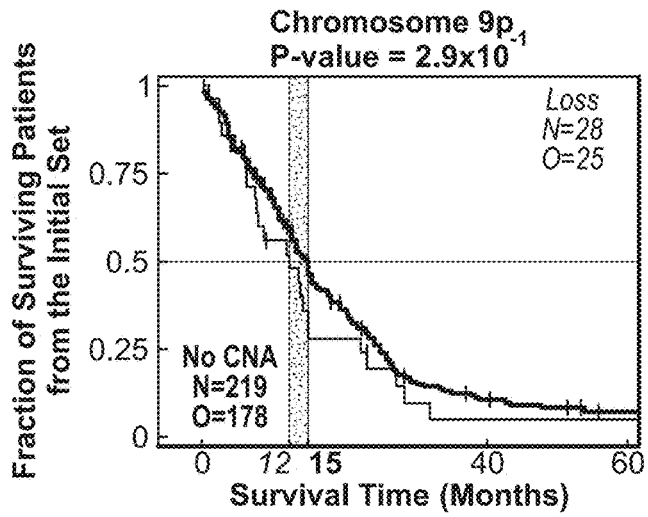
Figure 46:
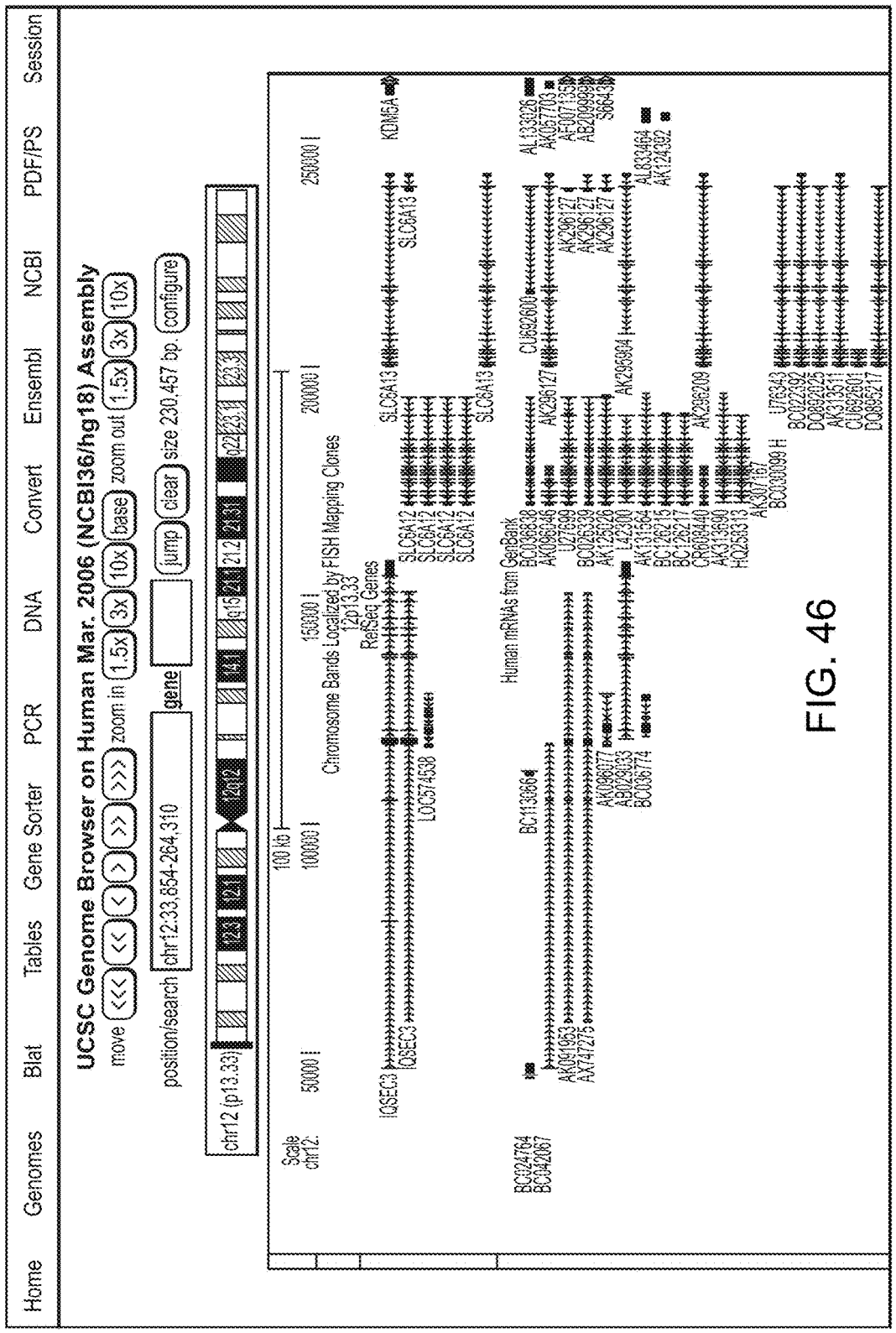
FIG. 46 is a diagram illustrating genes that are found in chromosomal segment 12:33,854-12:264,310 of the human genome, according to some embodiments. The diagram is a genetic map illustrating the coordinates of Mettl2b on segment chr7:127,892,509-chr7:127,947,649 on NCBI36/hg assembly of the human genome. Previous studies have shown that overexpression of Mettl2a/b has been linked to metastatic samples relative to primary prostate tumor samples; cAMP response element-binding (CREB) regulation in myeloid leukemia, and response to chemotherapy in breast cancer patients.

FIGS. 45A-45C show Kaplan-Meier survival analyses of an initial set of 251 patients classified by GBM-associated chromosome number changes. FIG. 45A shows KM survival analysis for 247 patients with TCGA annotations in the initial set of 251 patients, classified by number changes in chromosome 10. This figure shows almost overlapping KM curves with a KM median survival time difference of ~2 months, and a corresponding log-rank test P-value $\sim 10^{-1}$, meaning that chromosome 10 loss, frequently observed in GBM, is a poor predictor of GBM survival. FIG. 45B shows KM survival analysis for 247 patients classified by number changes in chromosome 7. This figure shows almost overlapping KM curves with a KM median survival time difference of <1 month and a corresponding log-rank test P-value$>5 \times 10^{-1}$, meaning that chromosome 7 gain is a poor predictor of GBM survival. FIG. 45C is a KM survival analysis for 247 patients classified by number changes in chromosome 9p. This figures shows a KM median survival time difference of ~3 months, and a log-rank test P-value$>10^{-1}$, meaning that chromosome 9p loss is a poor predictor of GBM survival.

Any of the methods and systems described herein may output a result (e.g., a genetic sequence, a data array, etc.) or at least a portion of a result. In some embodiments, the output may include, but are not limited to, a digital readout, a graphical display, a communication over a phone or computer network, a printer printout, etc.

III. Reducing the Proliferation or Viability of Cancer Cells

Also described herein are methods for reducing the proliferation or viability of a glioma cancer cell, and methods of treating glioma, by modulating the expression level of one or more genes located in the segments described herein, including 17:57,851,812-17:57,973,757; 7:127,892,509-7:127,947,649; 12:33,854-12:264,310; or 19:33,329,393-19:35,322,055, or modulating the activity of one or more proteins encoded by one or more of the segments described herein.

Also described herein are methods for reducing the proliferation or viability of a glioma cancer cell, and methods of treating glioma, by modulating the expression level of one or more of the following genes: Tlk2, Mettl2a, Mettl2b, Jarid1a, Ak096077, Ccne1, Slc6a12, Slc6a13, Iqsec3, Pop4, Plekhf1, C19orf12, C19orf2, Bc068609, Bc122525, Ak055100, Uqcrf51, Ak094793, Rpp29, or Dkfzp762d096, or modulating the activity of one or more proteins encoded by the following genes: Tlk2, Mettl2a, Mettl2b, Jarid1a, Ak096077, Ccne1, Slc6a12, Slc6a13, Iqsec3, Pop4, Plekhf1, C19orf12, C19orf2, Bc068609, Bc122525, Ak055100, Uqcrf51, Ak094793, Rpp29, or Dkfzp762d096.

For example, inhibitors can be used to reduce the expression of one or more genes described herein, or reduce the activity of one or more gene products (e.g., proteins encoded by the genes) described herein. Exemplary inhibitors include, e.g., RNA effector molecules that target a gene, antibodies that bind to a gene product, a dominant negative mutant of the gene product, etc. Inhibition can be achieved at the mRNA level, e.g., by reducing the mRNA level of a target gene using RNA interference. Inhibition can be also achieved at the protein level, e.g., by using an inhibitor or an antagonist that reduces the activity of a protein.

In one aspect, the disclosure provides a method for reducing the proliferation or viability of a glioma cancer cell comprising: contacting the cancer cell with an inhibitor that (i) down-regulates the expression level of a gene selected from the group consisting of: Tlk2, Mettl2a, Mettl2b, and a combination thereof; or (ii) down-regulates the activity of a protein selected from TLK2, METTL2A, METTL2B, and a combination thereof.

In another aspect, the disclosure provides a method of treating glioma, comprising: administering to a patient in need thereof an inhibitor that (i) down-regulates the expression level of a gene selected from the group consisting of: Tlk2, Mettl2a, Mettl2b, and a combination thereof; or (ii) down-regulates the activity of a protein selected from TLK2, METTL2A, METTL2B, and a combination thereof.

Exemplary inhibitors that reduce the expression of one or more genes described herein, or reduce the activity of one or more gene products described herein include, e.g., RNA effector molecules that target a gene, antibodies that bind to a gene product, a dominant negative mutant of the gene product, etc.

For the treatment of glioma, a therapeutically effective amount of an inhibitor is administered, which is an amount that, upon single or multiple dose administration to a subject (such as a human patient), prevents, cures, delays, reduces the severity of, and/or ameliorating at least one symptom of glioma, prolongs the survival of the subject beyond that expected in the absence of treatment, or increases the responsiveness or reduces the resistance of a subject to another therapeutic treatment (e.g., increasing the sensitivity or reducing the resistance to a chemotherapeutic drug).

The term "treatment" or "treating" refers to a therapeutic, preventative or prophylactic measures.

Also described herein are the use of the inhibitors described herein for reducing the proliferation or viability of a glioma cancer cell, or for treating glioma; and the use of the inhibitors described herein in the manufacture of a medicament for reducing the proliferation or viability of a glioma cancer cell, or for treating glioma.

1. RNA Effector Molecules

In certain embodiments, the inhibitor is an RNA effector molecule, such as an antisense RNA, or a double-stranded RNA that mediates RNA interference. RNA effector molecules that are suitable for the subject technology has been disclosed in detail in WO 2011/005786, and is described brief below.

RNA effector molecules are ribonucleotide agents that are capable of reducing or preventing the expression of a target gene within a host cell, or ribonucleotide agents capable of forming a molecule that can reduce the expression level of a target gene within a host cell. A portion of a RNA effector molecule, wherein the portion is at least 10, at least 12, at least 15, at least 17, at least 18, at least 19, or at least 20 nucleotide long, is substantially complementary to the target gene. The complementary region may be the coding region, the promoter region, the 3' untranslated region (3'-UTR), and/or the 5'-UTR of the target gene. Preferably, at least 16 contiguous nucleotides of the RNA effector molecule are complementary to the target sequence (e.g., at least 17, at least 18, at least 19, or more contiguous nucleotides of the RNA effector molecule are complementary to the target sequence). The RNA effector molecules interact with RNA transcripts of target genes and mediate their selective degradation or otherwise prevent their translation.

RNA effector molecules can comprise a single RNA strand or more than one RNA strand. Examples of RNA effector molecules include, e.g., double stranded RNA (dsRNA), microRNA (miRNA), antisense RNA, promoter-directed RNA (pdRNA), Piwi-interacting RNA (piRNA), expressed interfering RNA (eiRNA), short hairpin RNA (shRNA), antagomirs, decoy RNA, DNA, plasmids and aptamers. The RNA effector molecule can be single-stranded or double-stranded. A single-stranded RNA effector molecule can have double-stranded regions and a double-stranded RNA effector can have single-stranded regions. Preferably, the RNA effector molecules are double-stranded RNA, wherein the antisense strand comprises a sequence that is substantially complementary to the target gene.

Complementary sequences within a RNA effector molecule, e.g., within a dsRNA (a double-stranded ribonucleic acid) may be fully complementary or substantially complementary. Generally, for a duplex up to 30 base pairs, the dsRNA comprises no more than 5, 4, 3 or 2 mismatched base pairs upon hybridization, while retaining the ability to regulate the expression of its target gene.

In some embodiments, the RNA effector molecule comprises a single-stranded oligonucleotide that interacts with and directs the cleavage of RNA transcripts of a target gene. For example, single stranded RNA effector molecules comprise a 5' modification including one or more phosphate groups or analogs thereof to protect the effector molecule from nuclease degradation. The RNA effector molecule can be a single-stranded antisense nucleic acid having a nucleotide sequence that is complementary to a "sense" nucleic acid of a target gene, e.g., the coding strand of a double-stranded cDNA molecule or a RNA sequence, e.g., a pre-mRNA, mRNA, miRNA, or pre-miRNA. Accordingly, an antisense nucleic acid can form hydrogen bonds with a sense nucleic acid target.

Given a coding strand sequence (e.g., the sequence of a sense strand of a cDNA molecule), antisense nucleic acids can be designed according to the rules of Watson-Crick base pairing. The antisense nucleic acid can be complementary to the coding or noncoding region of a RNA, e.g., the region surrounding the translation start site of a pre-mRNA or mRNA, e.g., the 5' UTR. An antisense oligonucleotide can be, for example, about 10 to 25 nucleotides in length (e.g., 10, 11, 12, 13, 14, 15, 16, 17, 18, 19, 20, 21, 22, 23, or 24 nucleotides in length). In some embodiments, the antisense oligonucleotide comprises one or more modified nucleotides, e.g., phosphorothioate derivatives and/or acridine substituted nucleotides, designed to increase its biological stability of the molecule and/or the physical stability of the duplexes formed between the antisense and target nucleic acids. Antisense oligonucleotides can comprise ribonucleotides only, deoxyribonucleotides only (e.g., oligodeoxynucleotides), or both deoxyribonucleotides and ribonucleotides. For example, an antisense agent consisting only of ribonucleotides can hybridize to a complementary RNA and prevent access of the translation machinery to the target RNA transcript, thereby preventing protein synthesis. An antisense molecule including only deoxyribonucleotides, or deoxyribonucleotides and ribonucleotides, can hybridize to a complementary RNA and the RNA target can be subsequently cleaved by an enzyme, e.g., RNAse H, to prevent translation. The flanking RNA sequences can include 2'-O-methylated nucleotides, and phosphorothioate linkages, and the internal DNA sequence can include phosphorothioate internucleotide linkages. The internal DNA sequence is preferably at least five nucleotides in length when targeting by RNAseH activity is desired.

In certain embodiments, the RNA effector comprises a double-stranded ribonucleic acid (dsRNA), wherein said dsRNA (a) comprises a sense strand and an antisense strand that are substantially complementary to each other; and (b) wherein said antisense strand comprises a region of complementarity that is substantially complementary to one of the target genes, and wherein said region of complementarity is from 10 to 30 nucleotides in length.

In some embodiments, RNA effector molecule is a double-stranded oligonucleotide. Typically, the duplex region formed by the two strands is small, about 30 nucleotides or less in length. Such dsRNA is also referred to as siRNA. For example, the siRNA may be from 15 to 30 nucleotides in length, from 10 to 26 nucleotides in length, from 17 to 28 nucleotides in length, from 18 to 25 nucleotides in length, or from 19 to 24 nucleotides in length, etc.

The duplex region can be of any length that permits specific degradation of a desired target RNA through a RISC pathway, but will typically range from 9 to 36 base pairs in length, e.g., 15 to 30 base pairs in length. For example, the duplex region may be 15 to 30 base pairs, 15 to 26 base pairs, 15 to 23 base pairs, 15 to 22 base pairs, 15 to 21 base pairs, 15 to 20 base pairs, 15 to 19 base pairs, 15 to 18 base pairs, 15 to 17 base pairs, 18 to 30 base pairs, 18 to 26 base pairs, 18 to 23 base pairs, 18 to 22 base pairs, 18 to 21 base pairs, 18 to 20 base pairs, 19 to 30 base pairs, 19 to 26 base pairs, 19 to 23 base pairs, 19 to 22 base pairs, 19 to 21 base pairs, 19 to 20 base pairs, 20 to 30 base pairs, 20 to 26 base pairs, 20 to 25 base pairs, 20 to 24 base pairs, 20 to 23 base pairs, 20 to 22 base pairs, 20 to 21 base pairs, 21 to 30 base pairs, 21 to 26 base pairs, 21 to 25 base pairs, 21 to 24 base pairs, 21 to 23 base pairs, or 21 to 22 base pairs.

The two strands forming the duplex structure of a dsRNA can be from a single RNA molecule having at least one self-complementary region, or can be formed from two or more separate RNA molecules. Where the duplex region is formed from two strands of a single molecule, the molecule can have a duplex region separated by a single stranded chain of nucleotides (a "hairpin loop") between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are formed by separate RNA strands, the two strands can be optionally covalently linked. Where the two strands are connected covalently by means other than a hairpin loop, the connecting structure is referred to as a "linker."

A double-stranded oligonucleotide can include one or more single-stranded nucleotide overhangs, which are one or more unpaired nucleotide that protrudes from the terminus of a duplex structure of a double-stranded oligonucleotide, e.g., a dsRNA. A double-stranded oligonucleotide can comprise an overhang of at least one nucleotide; alternatively the overhang can comprise at least two nucleotides, at least three nucleotides, at least four nucleotides, at least five nucleotides or more. The overhang(s) can be on the sense strand, the antisense strand or any combination thereof. Furthermore, the nucleotide(s) of an overhang can be present on the 5' end, 3' end, or both ends of either an antisense or sense strand of a dsRNA.

In one embodiment, at least one end of a dsRNA has a single-stranded nucleotide overhang of 1 to 4, generally 1 or 2 nucleotides.

The overhang can comprise a deoxyribonucleoside or a nucleoside analog. Further, one or more of the internucleoside linkages in the overhang can be replaced with a phosphorothioate. In some embodiments, the overhang comprises one or more deoxyribonucleoside or the overhang comprises one or more dT, e.g., the sequence 5'-dTdT-3' or 5'-dTdTdT-3'. In some embodiments, overhang comprises the sequence 5'-dT*dT-3, wherein * is a phosphorothioate internucleoside linkage.

An RNA effector molecule as described herein can contain one or more mismatches to the target sequence. Preferably, a RNA effector molecule as described herein contains no more than three mismatches. If the antisense strand of the RNA effector molecule contains one or more mismatches to a target sequence, it is preferable that the mismatch(s) is (are) not located in the center of the region of complementarity, but are restricted to be within the last 5 nucleotides from either the 5' or 3' end of the region of complementarity. For example, for a 23-nucleotide RNA effector molecule agent RNA, the antisense strand generally does not contain any mismatch within the central 13 nucleotides.

In some embodiments, the RNA effector molecule is a promoter-directed RNA (pdRNA) which is substantially complementary to a noncoding region of an mRNA transcript of a target gene. In one embodiment, the pdRNA is substantially complementary to the promoter region of a target gene mRNA at a site located upstream from the transcription start site, e.g., more than 100, more than 200, or more than 1,000 bases upstream from the transcription start site. In another embodiment, the pdRNA is substantially complementary to the 3'-UTR of a target gene mRNA transcript. In one embodiment, the pdRNA comprises dsRNA of 18-28 bases optionally having 3' di- or tri-nucleotide overhangs on each strand. In another embodiment, the pdRNA comprises a gapmer consisting of a single stranded polynucleotide comprising a DNA sequence which is substantially complementary to the promoter or the 3'-UTR of a target gene mRNA transcript, and flanking the polynucleotide sequences (e.g., comprising the 5 terminal bases at each of the 5' and 3' ends of the gapmer) comprises one or more modified nucleotides, such as 2' MOE, 2'OMe, or Locked Nucleic Acid bases (LNA), which protect the gapmer from cellular nucleases.

pdRNA can be used to selectively increase, decrease, or otherwise modulate expression of a target gene. Without being limited to theory, it is believed that pdRNAs modulate expression of target genes by binding to endogenous antisense RNA transcripts which overlap with noncoding regions of a target gene mRNA transcript, and recruiting Argonaute proteins (in the case of dsRNA) or host cell nucleases (e.g., RNase H) (in the case of gapmers) to selectively degrade the endogenous antisense RNAs. In some embodiments, the endogenous antisense RNA negatively regulates expression of the target gene and the pdRNA effector molecule activates expression of the target gene. Thus, in some embodiments, pdRNAs can be used to selectively activate the expression of a target gene by inhibiting the negative regulation of target gene expression by endogenous antisense RNA. Methods for identifying antisense transcripts encoded by promoter sequences of target genes and for making and using promoter-directed RNAs are known, see, e.g., WO 2009/046397.

In some embodiments, the RNA effector molecule comprises an aptamer which binds to a non-nucleic acid ligand, such as a small organic molecule or protein, e.g., a transcription or translation factor, and subsequently modifies (e.g., inhibits) activity. An aptamer can fold into a specific structure that directs the recognition of a targeted binding site on the non-nucleic acid ligand. Aptamers can contain any of the modifications described herein.

In some embodiments, the RNA effector molecule comprises an antagomir. Antagomirs are single stranded, double stranded, partially double stranded or hairpin structures that target a micro RNA. An antagomir consists essentially of or comprises at least 10 or more contiguous nucleotides substantially complementary to an endogenous miRNA and more particularly a target sequence of an miRNA or pre-miRNA nucleotide sequence. Antagomirs preferably have a nucleotide sequence sufficiently complementary to a miRNA target sequence of about 12 to 25 nucleotides, such as about 15 to 23 nucleotides, to allow the antagomir to hybridize to the target sequence. More preferably, the target sequence differs by no more than 1, 2, or 3 nucleotides from the sequence of the antagomir. In some embodiments, the antagomir includes a non-nucleotide moiety, e.g., a cholesterol moiety, which can be attached, e.g., to the 3' or 5' end of the oligonucleotide agent.

In some embodiments, antagomirs are stabilized against nucleolytic degradation by the incorporation of a modification, e.g., a nucleotide modification. For example, in some embodiments, antagomirs contain a phosphorothioate comprising at least the first, second, and/or third internucleotide linkages at the 5' or 3' end of the nucleotide sequence. In further embodiments, antagomirs include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In some embodiments, antagomirs include at least one 2'-O-methyl-modified nucleotide.

In some embodiments, the RNA effector molecule is a promoter-directed RNA (pdRNA) which is substantially complementary to a noncoding region of an mRNA transcript of a target gene. The pdRNA can be substantially complementary to the promoter region of a target gene mRNA at a site located upstream from the transcription start site, e.g., more than 100, more than 200, or more than 1,000 bases upstream from the transcription start site. Also, the pdRNA can substantially complementary to the 3'-UTR of a target gene mRNA transcript. For example, the pdRNA comprises dsRNA of 18 to 28 bases optionally having 3' di- or tri-nucleotide overhangs on each strand. The dsRNA is substantially complementary to the promoter region or the 3'-UTR region of a target gene mRNA transcript. In another embodiment, the pdRNA comprises a gapmer consisting of a single stranded polynucleotide comprising a DNA sequence which is substantially complementary to the promoter or the 3'-UTR of a target gene mRNA transcript, and flanking the polynucleotide sequences (e.g., comprising the five terminal bases at each of the 5' and 3' ends of the gapmer) comprising one or more modified nucleotides, such as 2'MOE, 2'OMe, or Locked Nucleic Acid bases (LNA), which protect the gapmer from cellular nucleases.

Expressed interfering RNA (eiRNA) can be used to selectively increase, decrease, or otherwise modulate expression of a target gene. Typically, eiRNA, the dsRNA is expressed in the first transfected cell from an expression vector. In such a vector, the sense strand and the antisense strand of the dsRNA can be transcribed from the same nucleic acid sequence using e.g., two convergent promoters at either end of the nucleic acid sequence or separate promoters transcribing either a sense or antisense sequence. Alternatively, two plasmids can be cotransfected, with one of the plasmids designed to transcribe one strand of the dsRNA while the other is designed to transcribe the other strand. Methods for making and using eiRNA effector molecules are known in the art. See, e.g., WO 2006/033756; U.S. Patent Pubs. No. 2005/0239728 and No. 2006/0035344.

In some embodiments, the RNA effector molecule comprises a small single-stranded Piwi-interacting RNA (piRNA effector molecule) which is substantially complementary to a target gene, and which selectively binds to proteins of the Piwi or Aubergine subclasses of Argonaute proteins. A piRNA effector molecule can be about 10 to 50 nucleotides in length, about 25 to 39 nucleotides in length, or about 26 to 31 nucleotides in length. See, e.g., U.S. Patent Application Pub. No. 2009/0062228.

MicroRNAs are a highly conserved class of small RNA molecules that are transcribed from DNA in the genomes of plants and animals, but are not translated into protein. Pre-microRNAs are processed into miRNAs. Processed microRNAs are single stranded ~17 to 25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. MicroRNAs cause post-transcriptional silencing of specific target genes, e.g., by inhibiting translation or initiating degradation of the targeted mRNA. In some embodiments, the miRNA is completely complementary with the target nucleic acid. In other embodiments, the miRNA has a region of noncomplementarity with the target nucleic acid, resulting in a "bulge" at the region of noncomplementarity. In some embodiments, the region of noncomplementarity (the bulge) is flanked by regions of sufficient complementarity, e.g., complete complementarity, to allow duplex formation. For example, the regions of complementarity are at least 8 to 10 nucleotides long (e.g., 8, 9, or 10 nucleotides long).

miRNA can inhibit gene expression by, e.g., repressing translation, such as when the miRNA is not completely complementary to the target nucleic acid, or by causing target RNA degradation, when the miRNA binds its target with perfect or a high degree of complementarity. In further embodiments, the RNA effector molecule can include an oligonucleotide agent which targets an endogenous miRNA or pre-miRNA. For example, the RNA effector can target an endogenous miRNA which negatively regulates expression of a target gene, such that the RNA effector alleviates miRNA-based inhibition of the target gene.

The miRNA can comprise naturally occurring nucleobases, sugars, and covalent internucleotide (backbone) linkages, or comprise one or more non-naturally-occurring features that confer desirable properties, such as enhanced cellular uptake, enhanced affinity for the endogenous miRNA target, and/or increased stability in the presence of nucleases. In some embodiments, an miRNA designed to bind to a specific endogenous miRNA has substantial complementarity, e.g., at least 70%, 80%, 90%, or 100% complementary, with at least 10, 20, or or more bases of the target miRNA. Exemplary oligonucleotide agents that target miRNAs and pre-miRNAs are described, for example, in U.S. Patent Pubs. No. 20090317907, No. 20090298174, No. 20090291907, No. 20090291906, No. 20090286969, No. 20090236225, No. 20090221685, No. 20090203893, No. 20070049547, No. 20050261218, No. 20090275729, No. 20090043082, No. 20070287179, No. 20060212950, No. 20060166910, No. 20050227934, No. 20050222067, No. 20050221490, No. 20050221293, No. 20050182005, and No. 20050059005.

A miRNA or pre-miRNA can be 10 to 200 nucleotides in length, for example from 16 to 80 nucleotides in length. Mature miRNAs can have a length of 16 to 30 nucleotides, such as 21 to 25 nucleotides, particularly 21, 22, 23, 24, or 25 nucleotides in length. miRNA precursors can have a length of 70 to 100 nucleotides and can have a hairpin conformation. In some embodiments, miRNAs are generated in vivo from pre-miRNAs by the enzymes cDicer and Drosha. miRNAs or pre-miRNAs can be synthesized in vivo by a cell-based system or can be chemically synthesized. miRNAs can comprise modifications which impart one or more desired properties, such as superior stability, hybridization thermodynamics with a target nucleic acid, targeting to a particular tissue or cell-type, and/or cell permeability, e.g., by an endocytosis-dependent or -independent mechanism. Modifications can also increase sequence specificity, and consequently decrease off-site targeting.

Optionally, an RNA effector may biochemically modified to enhance stability or other beneficial characteristics.

Oligonucleotides can be modified to prevent rapid degradation of the oligonucleotides by endo- and exo-nucleases and avoid undesirable off-target effects. The nucleic acids featured in the invention can be synthesized and/or modified by methods well established in the art, such as those described in CURRENT PROTOCOLS IN NUCLEIC ACID CHEMISTRY (Beaucage et al., eds., John Wiley & Sons, Inc., NY). Modifications include, for example, (a) end modifications, e.g., 5' end modifications (phosphorylation, conjugation, inverted linkages, etc.), or 3' end modifications (conjugation, DNA nucleotides, inverted linkages, etc.); (b) base modifications, e.g., replacement with stabilizing bases, destabilizing bases, or bases that base pair with an expanded repertoire of partners, removal of bases (abasic nucleotides), or conjugated bases; (c) sugar modifications (e.g., at the 2' position or 4' position) or replacement of the sugar; as well as (d) internucleoside linkage modifications, including modification or replacement of the phosphodiester linkages. Specific examples of oligonucleotide compounds useful in this invention include, but are not limited to RNAs containing modified backbones or no natural internucleoside linkages. RNAs having modified backbones include, among others, those that do not have a phosphorus atom in the backbone. Specific examples of oligonucleotide compounds useful in this invention include, but are not limited to oligonucleotides containing modified or non-natural internucleoside linkages. Oligonucleotides having modified internucleoside linkages include, among others, those that do not have a phosphorus atom in the internucleoside linkage.

Modified internucleoside linkages include (e.g., RNA backbones) include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Additionally, both the sugar and the internucleoside linkage may be modified, i.e., the backbone, of the nucleotide units are replaced with novel groups. One such oligomeric compound, an RNA mimetic that has been shown to have excellent hybridization properties, is referred to as a peptide nucleic acid (PNA).

Modified oligonucleotides can also contain one or more substituted sugar moieties. The RNA effector molecules, e.g., dsRNAs, can include one of the following at the 2' position: H (deoxyribose); OH (ribose); F; O—, S—, or N-alkyl; O—, S—, or N-alkenyl; O—, S— or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Other modifications include 2'-methoxy (2'-OCH$_3$), 2'-aminopropoxy (2'-OCH$_2$CH$_2$CH$_2$NH$_2$) and 2'-fluoro (2'-F).

The oligonucleotides can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to oligonucleotide molecules has been shown to increase oligonucleotide molecule stability in serum, and to reduce off-target effects. Elmen et al., 33 Nucl. Acids Res. 439-47 (2005); Mook et al., 6 Mol. Cancer. Ther. 833-43 (2007); Grunweller et al., 31 Nucl. Acids Res. 3185-93 (2003); U.S. Pat. Nos. 6,268,490; 6,670,461; 6,794,499; 6,998,484; 7,053,207; 7,084,125; and 7,399,845.

2. Delivery Methods of RNA Effector Molecules

The delivery of RNA effector molecules to cells can be achieved in a number of different ways. Several suitable delivery methods are well known in the art. For example, the skilled person is directed to WO 2011/005786, which discloses exemplary delivery methods can be used in this invention at pages 187-219, the teachings of which are incorporated herein by reference.

A reagent that facilitates RNA effector molecule uptake may be used. For example, an emulsion, a cationic lipid, a non-cationic lipid, a charged lipid, a liposome, an anionic lipid, a penetration enhancer, a transfection reagent or a modification to the RNA effector molecule for attachment, e.g., a ligand, a targeting moiety, a peptide, a lipophillic group, etc.

For example, RNA effector molecules can be delivered using a drug delivery system such as a nanoparticle, a dendrimer, a polymer, a liposome, or a cationic delivery system. Positively charged cationic delivery systems facilitate binding of a RNA effector molecule (negatively charged) and also enhance interactions at the negatively charged cell membrane to permit efficient cellular uptake. Cationic lipids, dendrimers, or polymers can either be bound to RNA effector molecules, or induced to form a vesicle, liposome, or micelle that encases the RNA effector molecule. See, e.g., Kim et al., 129 J. Contr. Release 107-16 (2008). Methods for making and using cationic-RNA effector molecule complexes are well within the abilities of those skilled in the art. See e.g., Sorensen et al 327 J. Mol. Biol. 761-66 (2003); Verma et al., 9 Clin. Cancer Res. 1291-1300 (2003); Arnold et al., 25 J. Hypertens. 197-205 (2007).

The RNA effector molecules described herein can be encapsulated within liposomes or can form complexes thereto, in particular to cationic liposomes. Alternatively, the RNA effector molecules can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a C1-20 alkyl ester (e.g., isopropylmyristate IPM), monoglyceride, diglyceride, or acceptable salts thereof.

The lipid to RNA ratio (mass/mass ratio) (e.g., lipid to dsRNA ratio) can be in ranges of from about 1:1 to about 50:1, from about 1:1 to about 25:1, from about 3:1 to about 15:1, from about 4:1 to about 10:1, from about 5:1 to about 9:1, or about 6:1 to about 9:1, inclusive.

A cationic lipid of the formulation can comprise at least one protonatable group having a pKa of from 4 to 15. The cationic lipid can be, for example, N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA), 2,2-Dilinoleyl-4-dimethylaminoethyl-[1,3]-dioxolane, or a mixture thereof. The cationic lipid can comprise from about 20 mol % to about 70 mol %, inclusive, or about 40 mol % to about 60 mol %, inclusive, of the total lipid present in the particle. In one embodiment, cationic lipid can be further conjugated to a ligand.

A non-cationic lipid can be an anionic lipid or a neutral lipid, such as distearoyl-phosphatidylcholine (DSPC), dioleoylphosphatidylcholine (DOPC), dipalmitoyl-phosphatidylcholine (DPPC), dioleoylphosphatidylglycerol (DOPG), dipalmitoyl-phosphatidylglycerol (DPPG), dioleoyl-phosphatidylethanolamine (DOPE), palmitoyloleoyl-phosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE),16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, inclusive, of about 10 mol %, to about 58 mol %, inclusive, if cholesterol is included, of the total lipid present in the particle.

3. Antibodies

In certain embodiments, the inhibitor is an antibody that binds to a gene product described herein (e.g., a protein encoded by the gene), such as a neutralizing antibody that reduces the activity of the protein.

The term "antibody" refers to an immunoglobulin or fragment thereof, and encompasses any such polypeptide comprising an antigen-binding fragment of an antibody. The term includes but is not limited to polyclonal, monoclonal, monospecific, polyspecific, humanized, human, single-chain, chimeric, synthetic, recombinant, hybrid, mutated, grafted, and in vitro generated antibodies.

An antibody may also refer to antigen-binding fragments of an antibody. Examples of antigen-binding fragments include, but are not limited to, Fab fragments (consisting of the $V_L$, $V_H$, $C_L$ and $C_H1$ domains); Fd fragments (consisting of the $V_H$ and $C_H1$ domains); Fv fragments (referring to a dimer of one heavy and one light chain variable domain in tight, non-covalent association); dAb fragments (consisting of a $V_H$ domain); isolated CDR regions; (Fab')$_2$ fragments, bivalent fragments (comprising two Fab fragments linked by a disulphide bridge at the hinge region), scFv (referring to a fusion of the $V_L$ and $V_H$ domains, linked together with a short linker), and other antibody fragments that retain antigen-binding function. The part of the antigen that is specifically recognized and bound by the antibody is referred to as the "epitope."

An antigen-binding fragment of an antibody can be produced by conventional biochemical techniques, such as enzyme cleavage, or recombinant DNA techniques known in the art. These fragments may be produced by proteolytic cleavage of intact antibodies by methods well known in the art, or by inserting stop codons at the desired locations in the vectors using site-directed mutagenesis, such as after $C_H1$ to produce Fab fragments or after the hinge region to produce (Fab')$_2$ fragments. For example, Papain digestion of antibodies produces two identical antigen-binding fragments, called "Fab" fragments, each with a single antigen-binding site, and a residual "Fc" fragment. Pepsin treatment of an antibody yields an F(ab')2 fragment that has two antigen-combining sites and is still capable of cross-linking antigen. Single chain antibodies may be produced by joining $V_L$ and $V_H$ coding regions with a DNA that encodes a peptide linker connecting the $V_L$ and $V_H$ protein fragments An antigen-binding fragment/domain may comprise an antibody light chain variable region ($V_L$) and an antibody heavy chain variable region ($V_H$); however, it does not have to comprise both. Fd fragments, for example, have two $V_H$ regions and often retain some antigen-binding function of the intact antigen-binding domain. Examples of antigen-binding fragments of an antibody include (1) a Fab fragment, a monovalent fragment having the $V_L$, $V_H$, $C_L$ and $C_H1$ domains; (2) a F(ab')$_2$ fragment, a bivalent fragment having two Fab fragments linked by a disulfide bridge at the hinge region; (3) a Fd fragment having the two $V_H$ and $C_H1$ domains; (4) a Fv fragment having the $V_L$ and $V_H$ domains of a single arm of an antibody, (5) a dAb fragment (Ward et al., 1989) *Nature* 341:544-546), that has a $V_H$ domain; (6) an isolated complementarity determining region (CDR), and (7) a single chain Fv (scFv). Although the two domains of the Fv fragment, $V_L$ and $V_H$, are coded for by separate genes, they can be joined, using recombinant DNA methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). These antibody fragments are obtained using conventional techniques known to those with skill in the art, and the fragments are evaluated for function in the same manner as are intact antibodies.

Antibodies described herein, or an antigen-binding fragment thereof, can be prepared, for example, by recombinant DNA technologies and/or hybridoma technology. For example, a host cell may be transfected with one or more recombinant expression vectors carrying DNA fragments encoding the immunoglobulin light and heavy chains of the antibody, or an antigen-binding fragment of the antibody, such that the light and heavy chains are expressed in the host cell and, preferably, secreted into the medium in which the host cell is cultured, from which medium the antibody can be recovered. Antibodies derived from murine or other non-human species can be humanized, e.g., by CDR drafting.

Standard recombinant DNA methodologies may be used to obtain antibody heavy and light chain genes or a nucleic acid encoding the heavy or light chains, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al.

4. Combination Therapy

The inhibitors described herein may be used in combination with another therapeutic agent. Further, the methods of treatment described herein may be carried out in combination with another treatment regimen, such as chemotherapy, radiotherapy, surgery, etc.

Suitable chemotherapeutic drugs include, e.g., alkylating agents, anti-metabolites, anti-mitotics, alkaloids (e.g., plant alkaloids and terpenoids, or vinca alkaloids), podophyllotoxin, taxanes, topoisomerase inhibitors, cytotoxic antibiotics, or a combination thereof. Examples of these chemotherapeutic drugs include CDDP, methotrexate, vincristine, adriamycin, bleomycin, carmustine, hydroxyurea, hydrazine, nitrosoureas, triazenes such as dacarabzine and temozolomide, nitrogen mustards such as chlorambucil, cyclophosphamide, isofamide, mechlorethamine, melphalan, uracil mustard; aziridine such as thiotepa; methanesulphonate esters such as busulfan; platinum complexes such as cisplatin, carboplatin; bioreductive alkylators, such as mitomycin and altretemine. Chemotherapeutic drugs also include proteasome inhibitors such as salinosporamides, bortezomib, PS-519, and omuralide.

The inhibitors described herein can also be administered in combination with radiotherapy or surgery. For example, an inhibitor can be administered prior to, during or after surgery or radiotherapy. Administration during surgery can be as a bathing solution for the operation site.

Additionally, the RNA effector molecules described herein may be used in combination with additional RNA effector molecules that target additional genes (such as a growth factor, or an oncogene) to enhance efficacy. For example, certain oncogenes are known to increase the malignancy of a tumor cell. Some oncogenes, usually involved in early stages of cancer development, increase the chance that a normal cell develops into a tumor cell. Accordingly, one or more oncogenes may be targeted in addition to Tlk2, Mettl2a, or Mettl2b. Commonly seen oncogenes include growth factors or mitogens (such as Platelet-derived growth factor), receptor tyrosine kinases (such as HER2/neu, also known as ErbB-2), cytoplasmic tyrosine kinases (such as the Src-family, Syk-ZAP-70 family and BTK family of tyrosine kinases), regulatory GTPases (such as Ras), cytoplasmic serine/threonine kinases (such as cyclin dependent kinases) and their regulatory subunits, and transcription factors (such as myc).

5. Administration

Inhibitors described herein may be formulated into pharmaceutical compositions. The pharmaceutical compositions usually one or more pharmaceutical carrier(s) and/or excipient(s). A thorough discussion of such components is available in Gennaro (2000) Remington: The Science and Practice of Pharmacy (20th edition). Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Formulation of the pharmaceutical composition will vary according to the route of administration selected.

The amounts of an inhibitor in a given dosage will vary according to the size of the individual to whom the therapy is being administered as well as the characteristics of the disorder being treated. In exemplary treatments, it may be necessary to administer about 1 mg/day, about 5 mg/day, about 10 mg/day, about 20 mg/day, about 50 mg/day, about 75 mg/day, about 100 mg/day, about 150 mg/day, about 200 mg/day, about 250 mg/day, about 400 mg/day, about 500 mg/day, about 800 mg/day, about 1000 mg/day, about 1600 mg/day or about 2000 mg/day. The doses may also be administered based on weight of the patient, at a dose of 0.01 to 50 mg/kg. The glycoprotein may be administered in a dose range of 0.015 to 30 mg/kg, such as in a dose of about 0.015, about 0.05, about 0.15, about 0.5, about 1.5, about 5, about 15 or about 30 mg/kg.

The compositions described herein may be administered to a subject orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well.

Standard dose-response studies, first in animal models and then in clinical testing, can reveal optimal dosages for particular diseases and patient populations.

To facilitate a better understanding of the subject technology, the following examples of preferred embodiments are given. In no way should the following examples be read to limit, or to define, the scope of the subject technology.

EXAMPLE 1

In this Example, a high-order generalized singular value decomposition (HO GSVD) was used to compare a genome-scale cell-cycle mRNA expression from S. pombe, S. cerevisiae, and human.

Referring to FIG. 4, the HO GSVD algorithm was used to decompose a 3-D array 410 into left basis arrays 420, diagonal arrays 430 and right basis array 440. Each data set stored in one of the 2-D arrays D1-D3 may represent a biological data set related to a tissue type (e.g., tumor, normal, etc.) and may be retrieved from database 350 of FIG. 2. The structure of the patient-matched but probe-independent tumor and normal data sets D1-D3 of the initial set of patients (e.g., N=251 patients in Example 2), each data set including, for example, M-arrays (e.g., M1=212,696-tumor probes or M2=211,227-normal in Example 2) may be an order of magnitude higher than that of a single matrix. The patients, the tumor and normal probes as well as the tissue types, each represent a degree of freedom.

Figure 5:
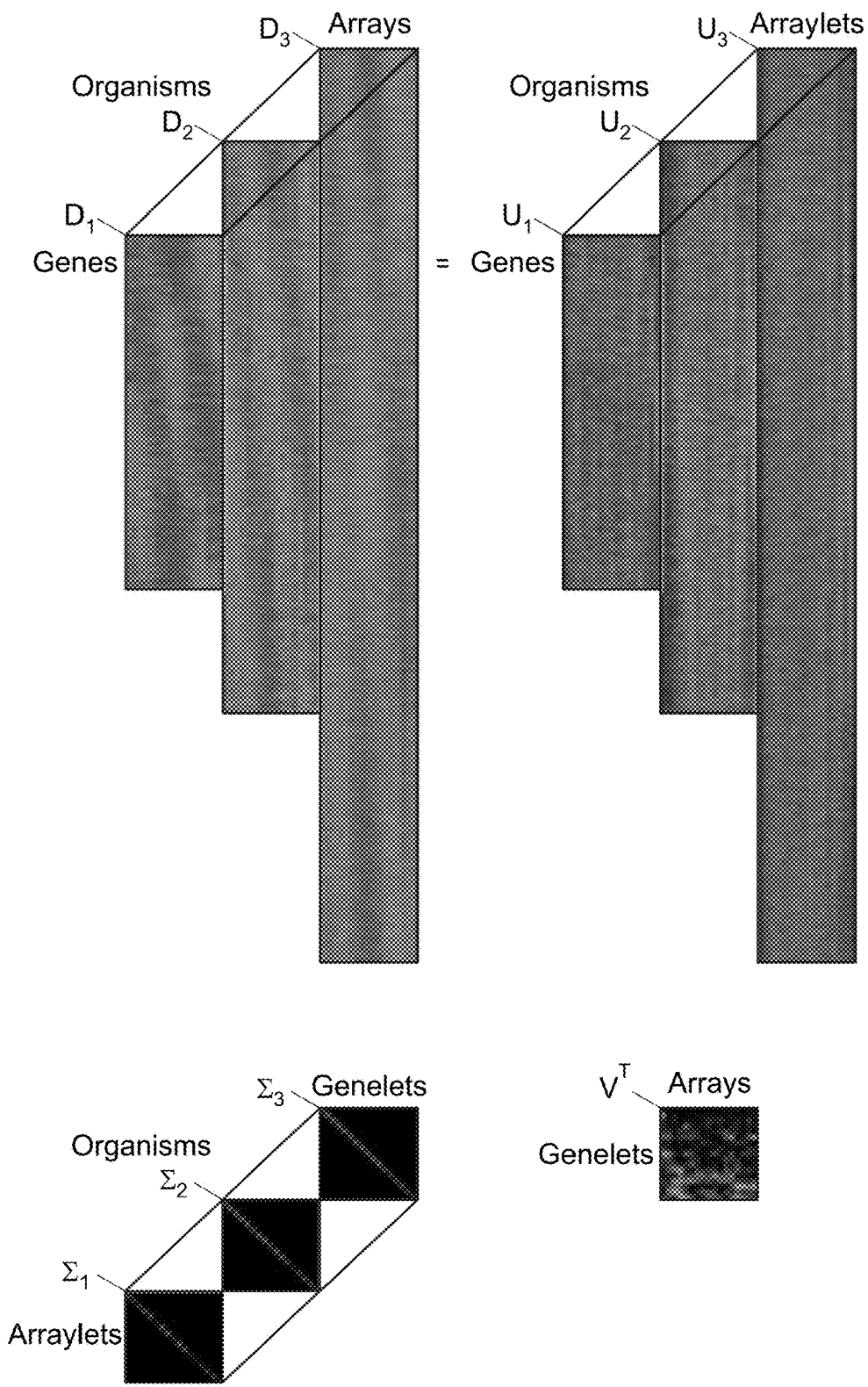
FIG. 5 is a diagram illustrating a high-order generalized singular value decomposition (HO GSVD) of biological data, according to some embodiments.
Figure 7A:
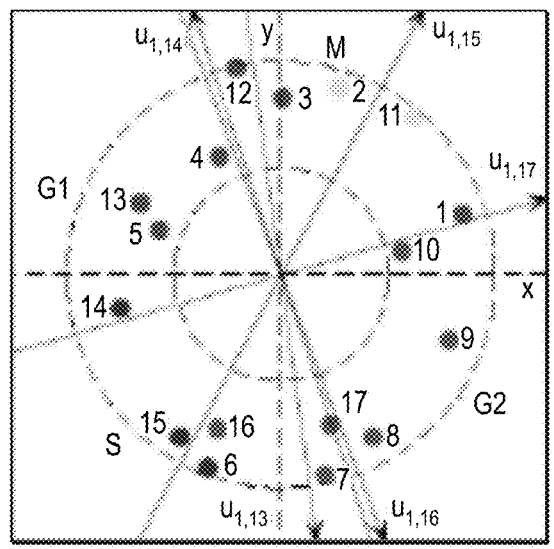
FIG. 7 is a diagram illustrating an HO GSVD reconstruction and classification of a number of mRNA expressions, according to some embodiments.
Figure 7B:
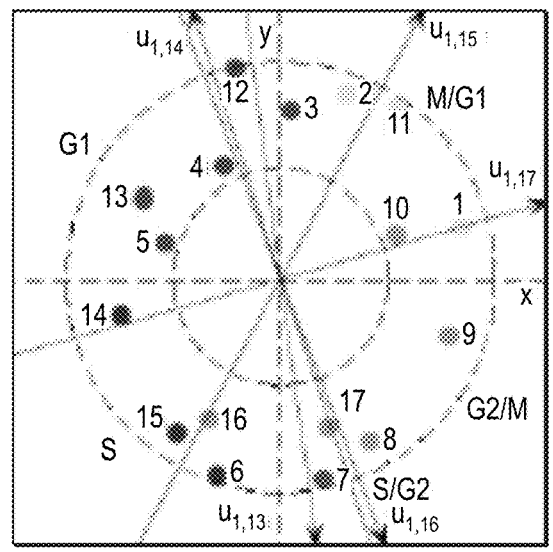
Figure 7C:
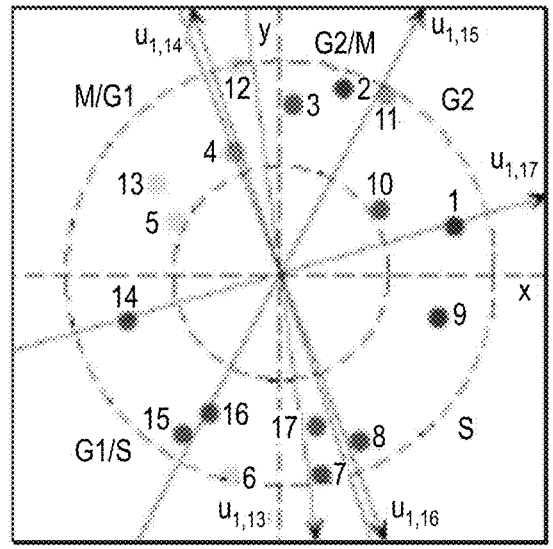
Figure 7D:
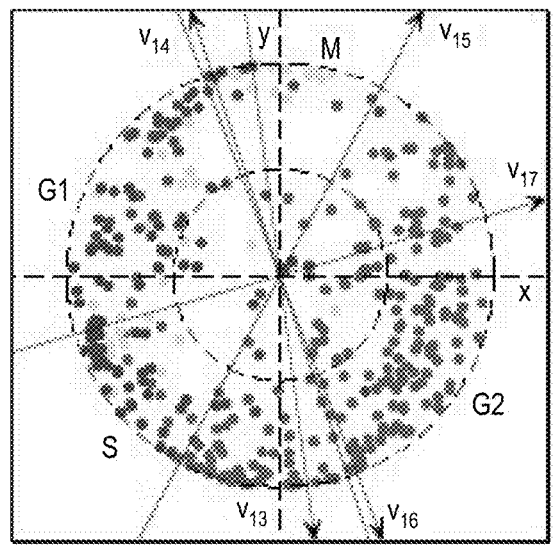
Figure 7E:
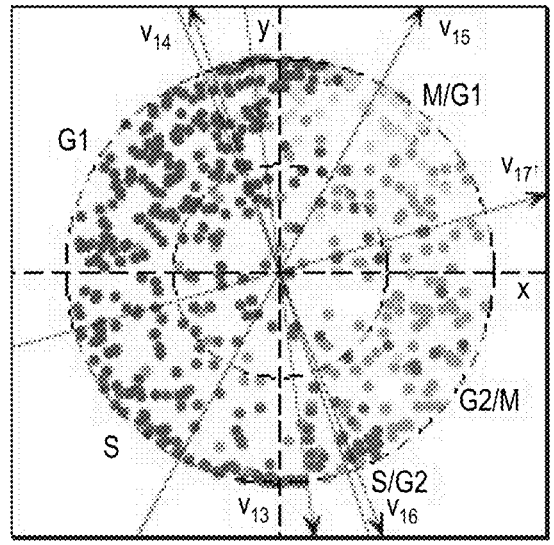
Figure 7F:
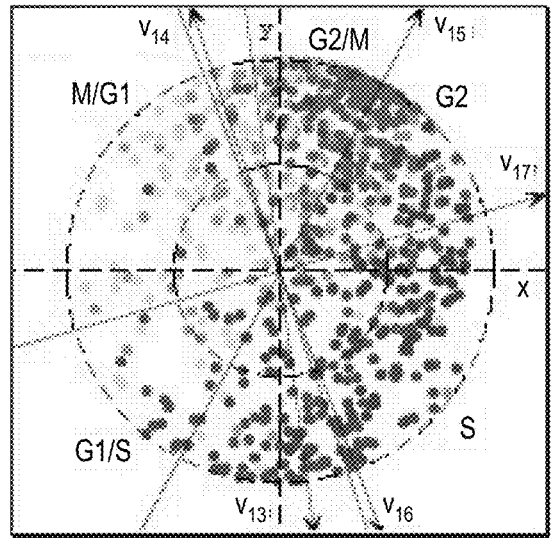
Figure 7G:
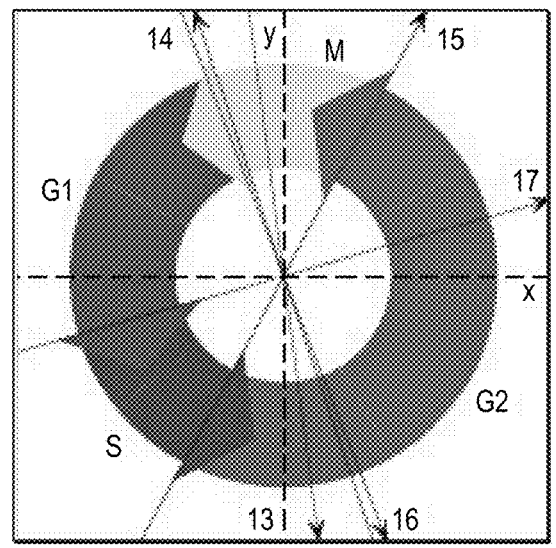
Figure 7H:
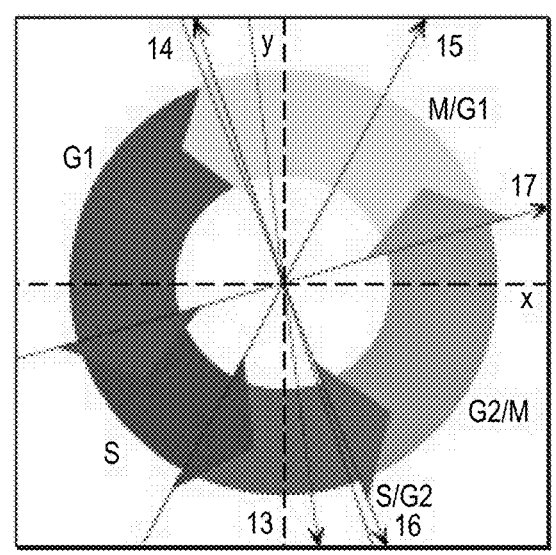
Figure 7I:
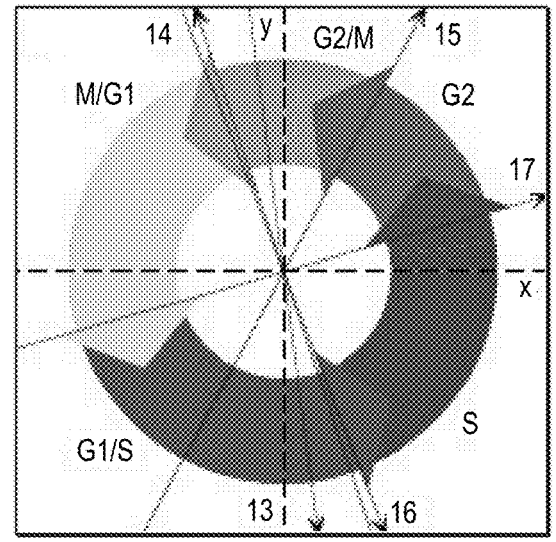
Figure 8A:
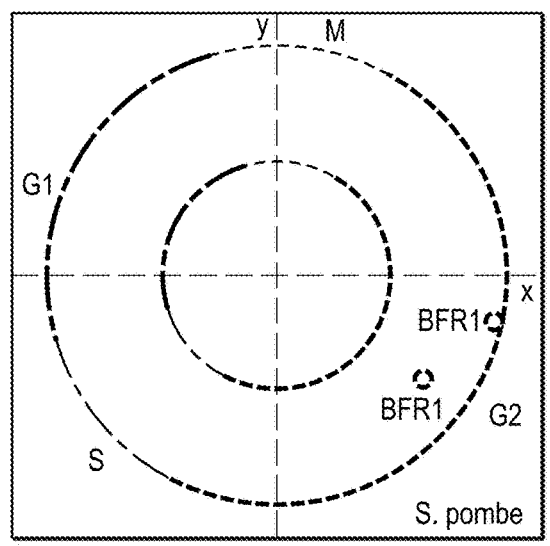
FIG. 8 is a diagram illustrating simultaneous HO GSVD sequence-independent classification of a number of genes, according to some embodiments.
Figure 8B:
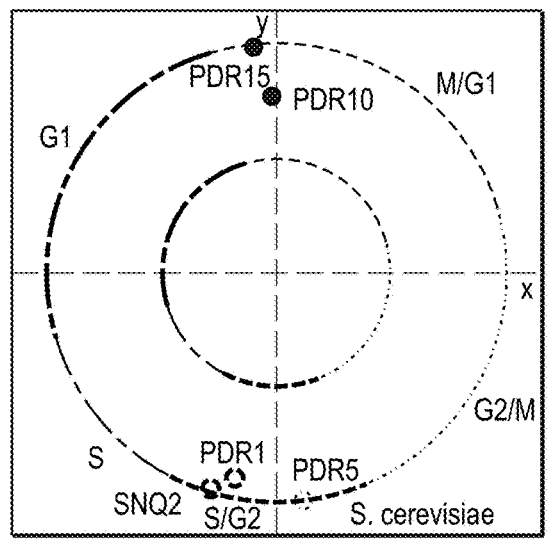
Figure 8C:
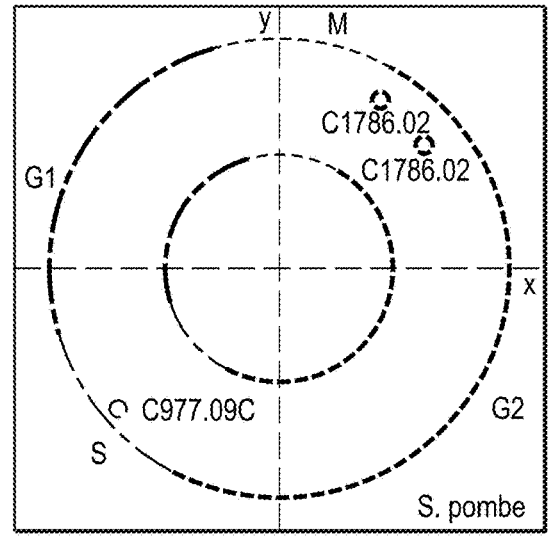
Figure 8D:
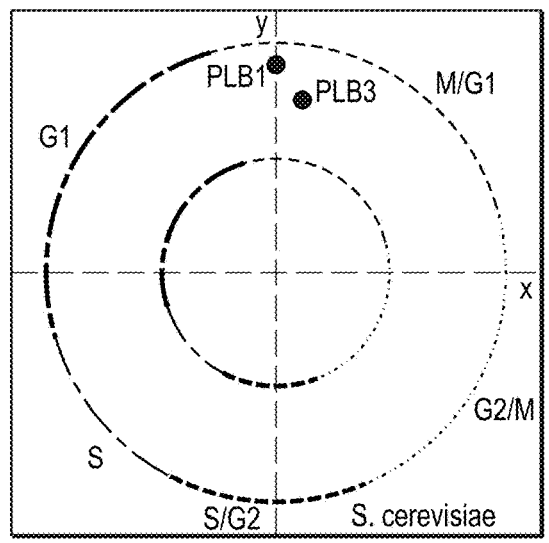
Figure 8E:
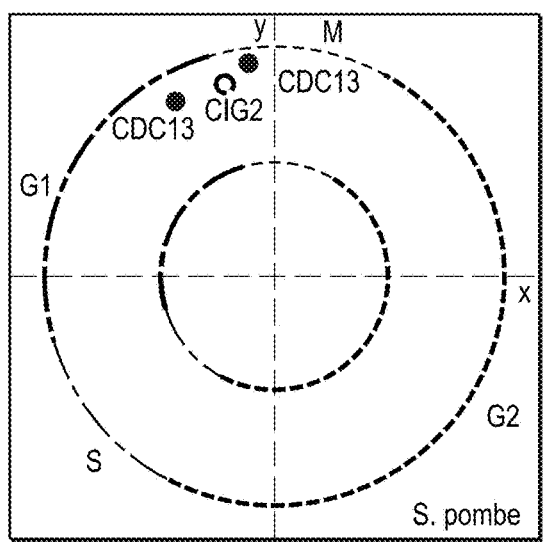
Figure 8F:
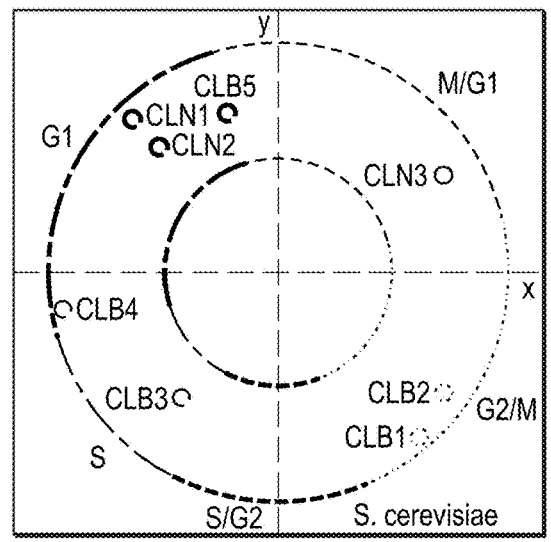
Figure 8G:
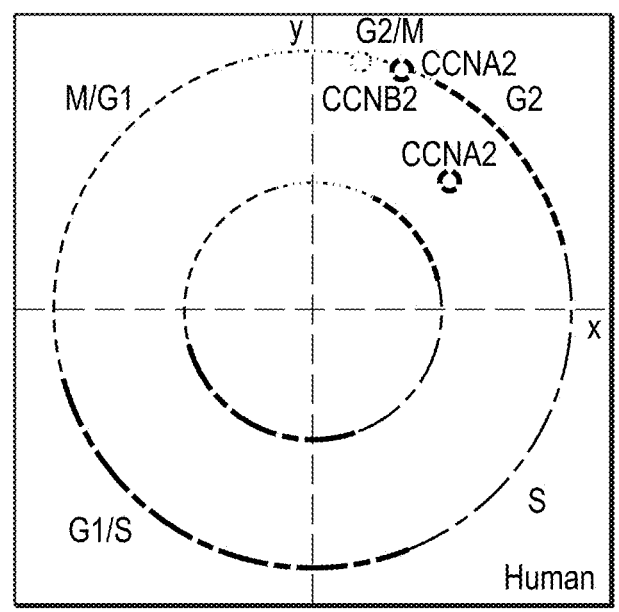

FIG. 5 is a diagram illustrating a HO GSVD of biological data, according to some embodiments. In this raster display, the S. pombe, S. cerevisiae and human global mRNA expression datasets are tabulated as organism-specific genes×17-arrays matrices $D_1$, $D_2$ and $D_3$. Overexpression, no change in expression, and underexpression have been centered at gene- and array-invariant expression. The underlying assumption is that there exists a one-to-one mapping among the 17 columns of the three matrices but not necessarily among their rows. These matrices are transformed to the reduced diagonalized matrices $\Sigma_1$, $\Sigma_2$ and $\Sigma_3$, each of 17-"arraylets," i.e., left basis vectors×17-"genelets," i.e., right basis vectors, by using the organism-specific genes×17-arraylets transformation matrices $U_1$, $U_2$ and $U_3$ and the shared 17-genelets×17-arrays transformation matrix $V^T$. For this particular V, this decomposition extends to higher orders all of the mathematical properties of the GSVD except for orthogonality of the arraylets, i.e., left basis vectors that form the matrices $U_1$, $U_2$ and $U_3$. Thus, the genelets, i.e., right basis vectors $v_k$ are defined to be of equal significance in all the datasets when the corresponding arraylets $u_{1,k}$, $u_{2,k}$ and $u_{3,k}$ are orthonormal to all other arraylets in $U_1$, $U_2$ and $U_3$, and when the corresponding higher-order generalized singular values are equal: $\sigma_{1,k}=\sigma_{2,k}=\sigma_{3,k}$. Like the GSVD for two organisms, the HO GSVD provides a sequence-independent comparative mathematical framework for datasets from more than two organisms, where the mathematical variables and operations represent biological reality: genelets of common significance in the multiple datasets, and the corresponding arraylets, represent cell-cycle checkpoints or transitions from one phase to the next, common to S. pombe, S. cerevisiae and human. Simultaneous reconstruction and classification of the three datasets in the common subspace that these patterns span outlines the biological similarity in the regulation of their cell-cycle programs. Notably, genes of significantly different cell-cycle peak times but highly conserved sequences are correctly classified.

FIG. 6 is a diagram illustrating a right basis array 1210 and patterns of expression variation across time, according to some embodiments. The right basis array 1210 and bar chart 1220 and graphs 1230 and 1240 relate to application of HO GSVD algorithm for decomposition of global mRNA expression for multiple organisms, (a) Right basis array 1210 displays the expression of 17 genelets across 17 time points, with overexpression, no change in expression and underexpression around the array-invariant, i.e., time-invariant expression, (b) The bar chart 1220 depicts the corresponding inverse eigenvalues $\lambda_k^{-1}$ showing that the 13th through the 17th genelets may be approximately equally significant in the three data sets with $\lambda_k$ having a value approximately between 1 and 2, where the five corresponding arraylets in each data set are ε=0.33-orthonormal to all other arraylets (see FIG. 22). (c) The line-joined graph 1230 of the 13th (1), 14th (3) and 15th (2) genelets in the two-dimensional subspace that approximates the five-dimensional HO GSVD subspace, normalized to zero average and unit variance, (d) The line-joined graphs 1240 show the projected 16th (4) and 17th (5) genelets in the two-dimensional subspace. The five genelets describe expression oscillations of two periods in the three time courses.

FIG. 7 is a diagram illustrating an HO GSVD reconstruction and classification of a number of mRNA expressions, according to some embodiments. Specifically, charts (a) to (i) shown in FIG. 7, relate to the simultaneous HO GSVD reconstruction and classification of S. pombe, S. cerevisiae and human global mRNA expression in the approximately common HO GSVD subspace. In charts (a-c) S. pombe, S. cerevisiae and human array expression are projected from the five-dimensional common HO GSVD subspace onto the two-dimensional subspace that approximates the common subspace. The arrays are color-coded according to their previous cell-cycle classification. The arrows describe the projections of the k=13, . . . , 17 arraylets of each data set. The dashed unit and half-unit circles outline 100% and 50% of added-up (rather than canceled-out) contributions of these five arraylets to the overall projected expression. In charts (d-f), expression of 380, 641 and 787 cell cycle-regulated genes of S. pombe, S. cerevisiae and human, respectively, are color-coded according to previous classifications. Charts (g-i) show the HO GSVD pictures of the S. pombe, S. cerevisiae and human cell-cycle programs. The arrows describe the projections of the k=13, . . . , 17 shared genelets and organism-specific arraylets that span the common HO GSVD subspace and represent cell-cycle checkpoints or transitions from one phase to the next.

FIG. 8 is a diagram illustrating simultaneous HO GSVD sequence-independent classification of a number of genes, according to some embodiments. The genes under consideration in FIG. 8 are genes of significantly different cell-cycle peak times but highly conserved sequences. Chart (a) shows the S. pombe gene BFR1 and chart (b) shows its closest S. cerevisiae homologs. In chart (c), the S. pombe and in chart (d), S. cerevisiae closest homologs of the S. cerevisiae gene PLB1 are shown. Chart (e) shows the S. pombe cyclin-encoding gene CIG2 and its closest S. pombe. Shown in chart (f) and (g) are the S. cerevisiae and human homologs, respectively.

Figures 9A, 9B, 9C:
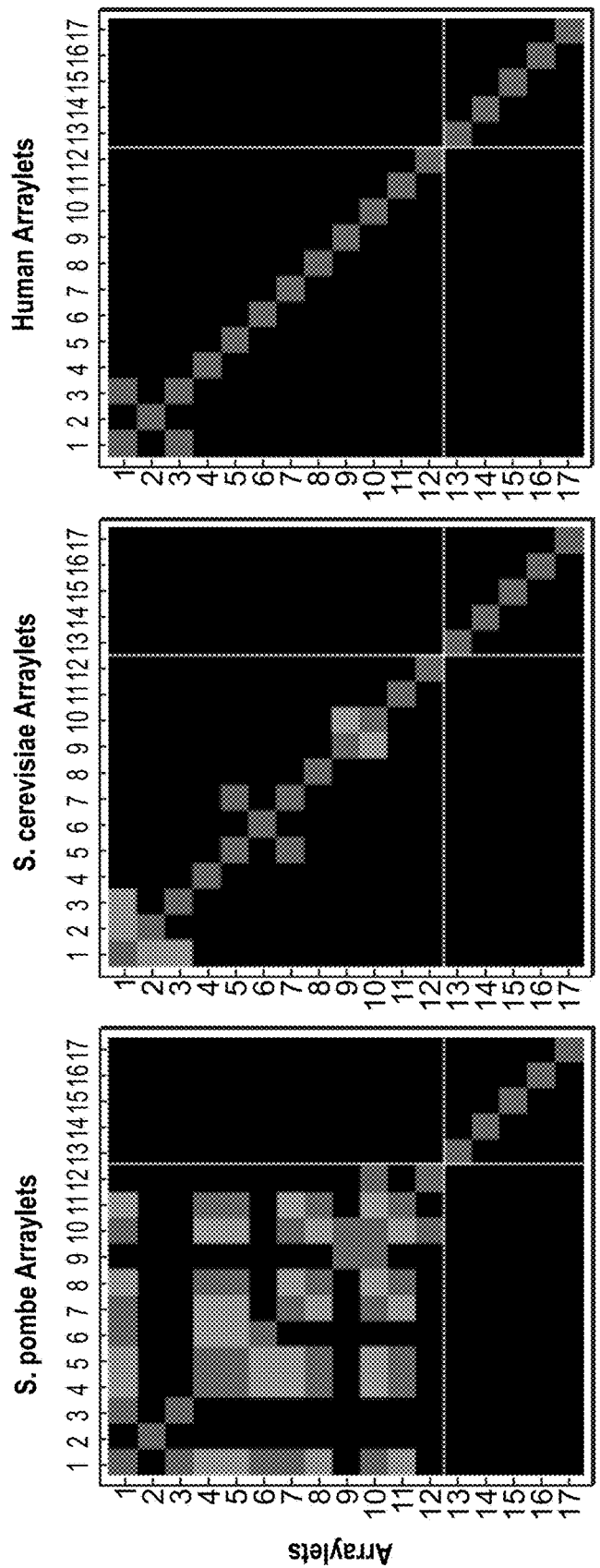
FIG. 9 is a diagram illustrating simultaneous correlations among the n=17 array lets in one organism, according to some embodiments.

FIG. 9 is a diagram illustrating simultaneous correlations among n=17 arraylets in one organism, according to some embodiments. Raster displays of $U_i^T U_i$, with correlations≥ε=0.33, ≤−ε, and ∈(−ε, ε), show that for k=13, . . . , 17 the arraylets $u_{i,k}$ with k=13, . . . , 17, that correspond to 1≤$\lambda_k$≤2, are ∈=0.33-orthonormal to all other arraylets in each data set. The corresponding five genelets, $v_k$ are approximately equally significant in the three data sets with $\sigma_{1,k}$:$\sigma_{2,k}$:$\sigma_{3,k}$~1:1:1 in the S. pombe, S. cerevisiae and human datasets, respectively (FIG. 6). Following Theorem 3, therefore, these genelets span the, these arraylets and genelets may span the approximately "common HO GSVD subspace" for the three data sets.

Figure 10:
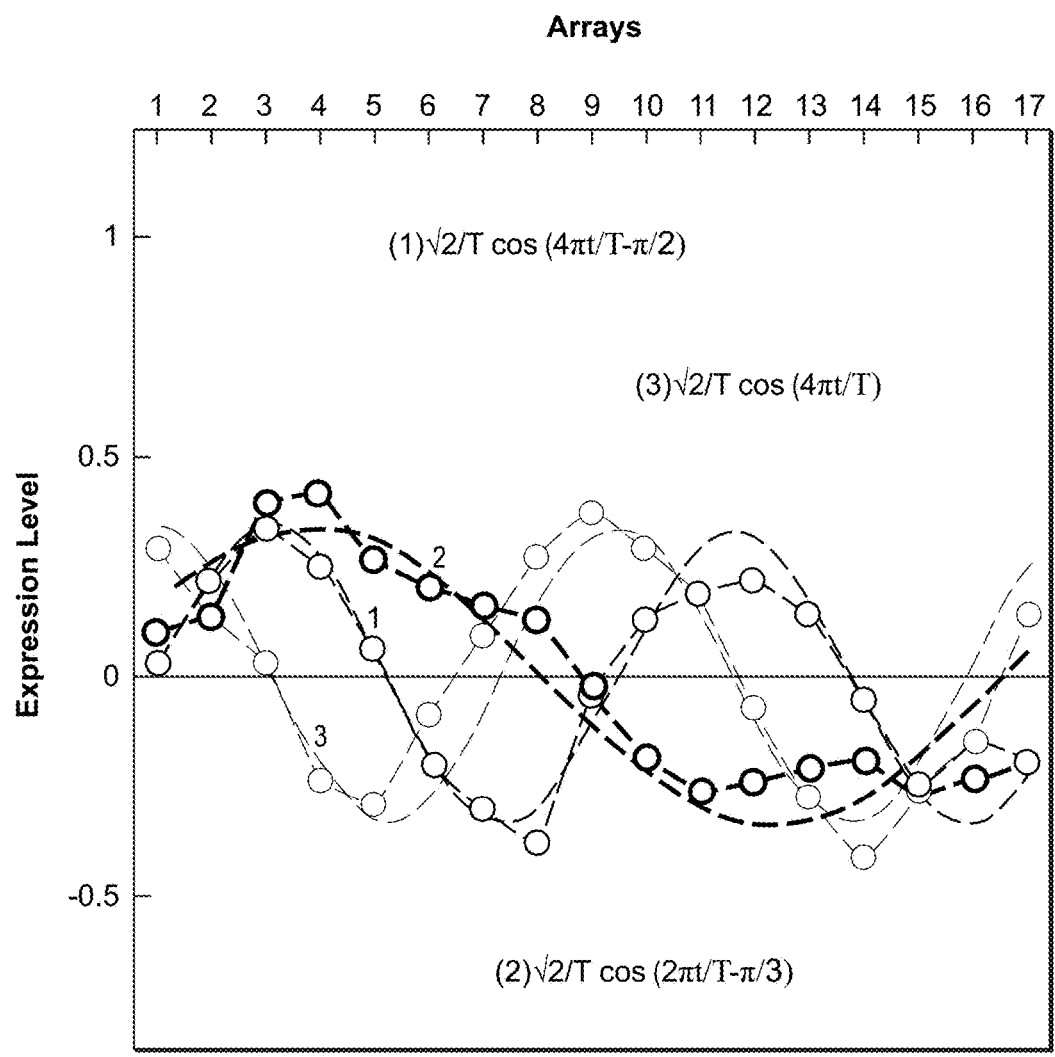
FIG. 10 is a diagram illustrating three dimensional least squares approximation of the five-dimensional approximately common HO GSVD subspace, according to some embodiments.

FIG. 10 is a diagram illustrating three dimensional least squares approximation of the five-dimensional approximately common HO GSVD subspace, according to some embodiments. Line-joined graphs of the first (1), second (2) and third (3) most significant orthonormal vectors in the least squares approximation of the genelets $v_k$ with k=13, . . . , 17 are shown. These orthonormal vectors span the common HO GSVD subspace. This five-dimensional subspace may be approximated with the two orthonormal vectors x and y, which fit normalized cosine functions of two periods, and 0- and −π/2-initial phases, i.e., normalized zero-phase cosine and sine functions of two periods, respectively.

FIG. 11 is a diagram illustrating an example of an mRNA expression (S. pombe global mRNA expression) reconstructed in the five-dimensional approximately common HO GSVD subspace, according to some embodiments. The example mRNA expression may include S. pombe global mRNA expression reconstructed in the five-dimensional common HO GSVD subspace with genes sorted according to their phases in the two-dimensional subspace that approximates it. Chart (a) is an expression of the sorted 3167 genes in the 17 arrays, centered at their gene- and array-invariant levels, showing a traveling wave of expression. Chart (b) shows an expression of the sorted genes in the 17 arraylets, centered at their arraylet-invariant levels. Arraylets k=13, . . . , 17 display the sorting. Chart (c) depicts line-joined graphs of the 13th (1), 14th (2), 15th (3), 16th (4) and 17th (5) arraylets t one-period cosines with initial phases similar to those of the corresponding genelets (similar to probelets in FIG. 5).

FIG. 12 is a diagram illustrating another example of an mRNA expression (S. cerevisiae global mRNA expression) reconstructed in the five-dimensional approximately common HO GSVD subspace, according to some embodiments. The example mRNA expression includes S. cerevisiae global mRNA expression reconstructed in the five-dimensional common HO GSVD subspace with genes sorted according to their phases in the two-dimensional subspace that approximates it. Chart (a) is an expression of the sorted 4772 genes in the 17 arrays, centered at their gene- and array-invariant levels, showing a traveling wave of expression. Chart (b) shows an expression of the sorted genes in the 17 arraylets, centered at their arraylet-invariant levels, where arraylets k=13, . . . , 17 display the sorting. Chart (c) depicts line-joined graphs of the 13th (1), 14th (2), 15th (3), 16th (4) and 17th (5) arraylets fit one-period cosines with initial phases similar to those of the corresponding genelets.

FIG. 13 is a diagram illustrating a human global mRNA expression reconstructed in the five-dimensional approximately common HO GSVD subspace, according to some embodiments. The genes are sorted according to their phases in the two-dimensional subspace that approximates them. Chart (a) is an expression of the sorted 13,068 genes in the 17 arrays, centered at their gene- and array-invariant levels, showing a traveling wave of expression. Chart (b) shows an expression of the sorted genes in the 17 arraylets, centered at their arraylet-invariant levels, where arraylets k=13, . . . , 17 display the sorting. Chart (c) shows line-joined graphs of the 13th (1), 14th (2), 15th (3), 16th (4) and 17th (5) arraylets fit one-period cosines with initial phases that may be similar to those of the corresponding genelets.

EXAMPLE 2

According to embodiments described above, a generalized singular value decomposition (GSVD) has been used to identify a global pattern of tumor-exclusive co-occurring CNAs that is correlated and possibly coordinated with GBM survival. This pattern is revealed by GSVD comparison of array comparative genomic hydridization (aCGH) data from patient-matched GBM and normal blood samples from The Cancer Genome Atlas (TCGA).

To identify CNAs that may be related to GBM, TCGA patient-matched GBM and normal blood aCGH profiles were compared. Agilent Human aCGH 244A-measured 365 tumor and 360 normal profiles were selected, corresponding to the same N=251 patients. Each profile lists $\log_2$ of the TCGA level 1 background-subtracted intensity in the sample relative to the PROMEGA® DNA reference, with signal to background >2.5 for both the sample and reference in more than 90% of the 223,603 autosomal probes on the microarray. The profiles were organized in one tumor and one normal dataset, of $M_1$=212,696 and $M_2$=211,227 autosomal and X chromosome probes, each probe with valid data in at least 99% of either the tumor or normal arrays, respectively. Each profile was centered at its autosomal median copy number. The <0.2% missing data entries in the tumor and normal datasets were estimated by using SVD. Within each set, the medians of profiles of samples from the same patient were taken.

Comparison of the tumor and normal datasets using GSVD generated several significant probelets. The two most significant probelets that arose were analyzed by correlating or anticorrelating each probelet with relative copy-number gain or loss across a group of patients according to the TCGA annotations of the group of n patients with largest or smallest relative copy numbers in this probelet among all N patients, respectively. Additional experimental details are provided in the attached Appendix A.

Figure 36:
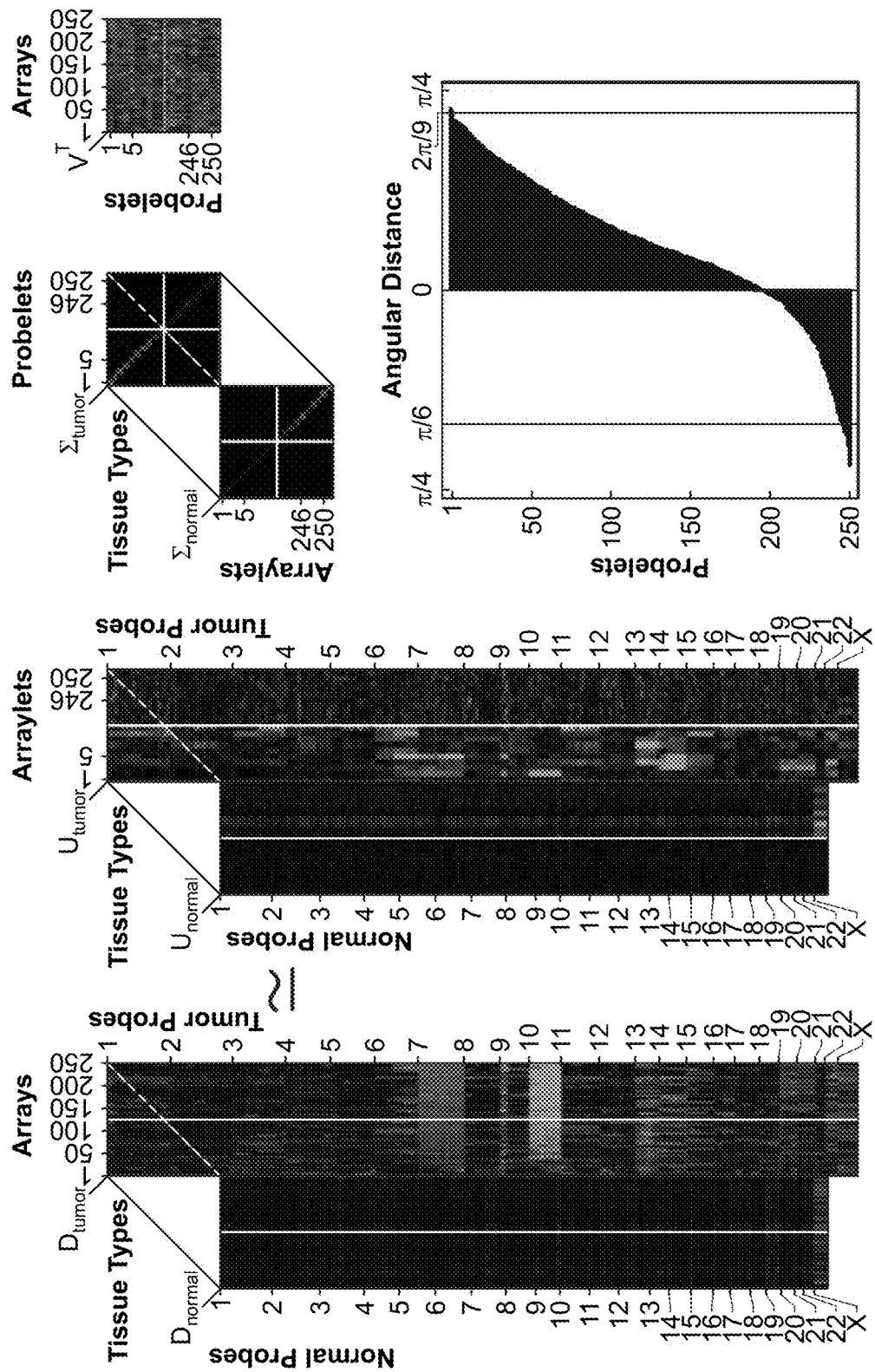
FIG. 36 are diagrams illustrating GSVD of TCGA patient matched tumor and normal aCGH profiles, according to some embodiments.

FIG. 36 is a diagram illustrating HO GSVD of biological data related to patient and normal samples, according to some embodiments. It shows the generalized singular value decomposition (GSVD) of the TCGA patient-matched tumor and normal aCGH profiles. The structure of the patient-matched but probe-independent tumor and normal datasets $D_1$ and $D_2$, of the initial set of N=251 patients, i.e., N-arrays×$M_1$=212,696-tumor probes and $M_2$=211,227-normal probes, is of an order higher than that of a single matrix. The patients, the tumor and normal probes as well as the tissue types, each represent a degree of freedom. Unfolded into a single matrix, some of the degrees of freedom are lost and much of the information in the datasets might also be lost.

The GSVD simultaneously separated the paired data sets into paired weighted sums of N outer products of two patterns each: one pattern of copy-number variation across the patients, i.e., a "probelet" $v_n^T$ (e.g., a row of right basis array), which is identical for both the tumor and normal data sets, combined with either the corresponding tumor-specific pattern of copy-number variation across the tumor probes, i.e., the "tumor arraylet" $u_{1,n}$, (e.g., vectors of array $U_1$ of left basis arrays) or the corresponding normal-specific pattern across the normal probes, i.e., the "normal arraylet" $u_{2,n}$ (e.g., vectors of array $U_2$ of left basis arrays). This can be depicted in a raster display, with relative copy-number gain, no change, and loss, explicitly showing the first though the 10th and the 242nd through the 251st probelets and corresponding tumor and normal arraylets, which may capture approximately 52% and 71% of the information in the tumor and normal data set, respectively.

The significance of the probelet $v_n^T$ (e.g., rows of right basis array) in the tumor data set (e.g., $D_1$ of the 3-D array) relative to its significance in the normal data set (e.g., $D_2$ of the 3-D array) is defined in terms of an "angular distance" that is proportional to the ratio of these weights, as shown in the following expression:

$$-\pi/4 \leq \theta_n = \arctan(\sigma_{1,n}/\sigma_{2,n}) - \pi/4 \leq \pi/4.$$

This significance is depicted in a bar chart display, showing that the first and second probelets are almost exclusive to the tumor data set with angular distances >2π/9, the 247th to 251st probelets are approximately exclusive to the normal data set with angular distances <−π/6, and the 246th probelet is relatively common to the normal and tumor data sets with an angular distance >−π/6. It may be found and confirmed that the second most tumor-exclusive probelet, the most significant probelet in the tumor data set, significantly correlates with GBM prognosis. The corresponding tumor arraylet describes a global pattern of tumor-exclusive co-occurring CNAs, including most known GBM-associated changes in chromosome numbers and focal CNAs, as well as several previously unreported CNAs, including the biochemically putative drug target-encoding Tlk2. It can also be found and validated that a negligible weight of the global pattern in a patient's GBM aCGH profile is indicative of a significantly longer GBM survival time. It was shown that the GSVD provides a mathematical framework for comparative modeling of DNA microarray data from two organisms. Recent experimental results verify a computationally predicted genomewide mode of regulation, and demonstrate that GSVD modeling of DNA microarray data can be used to correctly predict previously unknown cellular mechanisms. The GSVD comparative modeling of aCGH data from patient-matched tumor and normal samples draws a mathematical analogy between the prediction of cellular modes of regulation and the prognosis of cancers.

The GSVD identified pattern includes most known GBM-associated changes in chromosome numbers and focal CNAs (e.g., Mdm4, Akt3, Egfr, Met, etc.), as well as several previously unreported CNAs. Chromosome 10 loss, chromosome 7 gain and even loss of 9p, which are dominant in the global pattern, have been known to be associated with poorer GBM prognosis. However, the Kaplan-Meier (KM) curves (FIG. 14) for the groups of patients with either one of these chromosome number changes almost overlap the curves for the patients with no changes.

FIG. 14 shows Kaplan-Meier survival analyses of an initial set of 251 patients classified by GBM-associated chromosome number changes. Plot 2320 shows KM survival analysis for 247 patients with TCGA annotations in the initial set of 251 patients, classified by number changes in chromosome 10. This figure shows almost overlapping KM curves with a KM median survival time difference of ~2 months, and a corresponding log-rank test P-value ~$10^{-1}$, suggesting that chromosome 10 loss, frequently observed in GBM, is a poor predictor of GBM survival. Plot 2340 shows KM survival analysis for 247 patients classified by number changes in chromosome 7. This figure shows almost overlapping KM curves with a KM median survival time difference of <1 month and a corresponding log-rank test P-value>5×$10^{-1}$, suggesting that chromosome 7 gain is a poor predictor of GBM survival. Plot 2360 is a KM survival analysis for 247 patients classified by number changes in chromosome 9p. This figures shows a KM median survival time difference of ~3 months, and a log-rank test P-value>$10^{-1}$, suggesting that chromosome 9p loss is a poor predictor of GBM survival.

Previously unreported CNAs identified by GSVD techniques include Tlk2 (SEQ ID NOs: 1-4), Mettl2a (SEQ ID NOs: 5-6), Mettl2b (SEQ ID NOs: 7-8), Jarid1a (SEQ ID NOs: 9-10), Ak096077 (SEQ ID NO: 11), Slc6a12 (SEQ ID NOs: 12-18), Slc6a13 (SEQ ID NOs: 19-21), Iqsec3 (SEQ ID NOs: 22-24), Ccne1 (SEQ ID NOs: 25-27), Pop4 (SEQ ID NO: 28), Plekhf1 (SEQ ID NOs: 29-31), C19orf12 (SEQ ID NOs: 32-33), C19orf2 (SEQ ID NOs: 34-37), Bc068609 (SEQ ID NO: 38), Bc122525 (SEQ ID NO: 39), Ak055100 (SEQ ID NO: 40), Uqcrf51 (SEQ ID NOs: 41), Ak094793 (SEQ ID NO: 42), Rpp29 (SEQ ID NO: 43), and Dkfzp762d096 (SEQ ID NOs: 44-45). For example, the segment encompassing Tlk2/Mettl2a (17q23.2) was amplified in ~22% of the patients; segment encompassing Mettl2b (7q32.1) was amplified in ~8% of the patients; Jarid1a (12p13.33), Ak096077, Slc6a12, Slc6a13, and Iqsec3 was amplified in ~4% of the patients; and segment encompassing Ccne1 (19q12), Pop4, Plekhf1, C19orf12, C19orf2, Bc068609, Bc122525, Ak055100, Uqcrf51, Ak094793, Rpp29, and Dkfzp762d096 was amplified in ~4% of the patients. Moreover, these identified genes primarily reside in 4 genetic segments: chr17:57,851,812-chr17:57,973,757 (SEQ ID NO: 46) encompassing Tlk2 and Mettl2a (FIG. 15); chr7:127,892,509-chr7:127,947,649 (SEQ ID NO: 47) encompassing Mettl2b (FIG. 16); chr12:33,854-chr12:264,310 (SEQ ID NO: 48) encompassing Jarid1a, Ak096077, Slc6a12, Slc6a13, and Iqsec3 (FIG. 17); and chr19:33,329,393-chr19:35,322,055 (SEQ ID NO: 49) encompassing Ccne1, Pop4, Plekhf1, C19orf12, C19orf2, Bc068609, Bc122525, Ak055100, Uqcrf51, Ak094793, Rpp29, and Dkfzp762d096 (FIG. 18). These genetic segments were obtained from the NCBI36/hg18 assembly of the human genome (Human March 2006) University of California at Santa Cruz (UCSC) Genome Browser (genome.ucsc.edu/cgi-bin/hgTracks?org=human). The SEQ IDs of the specified genes include the 5' UTR, 3'UTR, coding region, and intron. In some embodiments, the present invention may be practiced using a portion of the gene sequences (e.g., coding region; 5'UTR, coding region, 3'UTR; coding region and intron; etc.). In some cases, multiple sequences (corresponding e.g., to SNP's, isoforms, etc.) for a specified gene has been provided.

Human Mettl2a gene is assigned with Gene ID No: 339175 in GenBank. The gene encodes methyltransferase like 2A (METTL2A), a member of the methyltransferase superfamily (EC 2.1.1.-). Human Mettl2b gene is assigned with Gene ID No: 55798 in GenBank. The gene encodes methyltransferase like 2B (METTL2B), also a member of the methyltransferase superfamily. See, Zhang et al., (2001), Identification of a novel family of putative methyltransferases that interact with human and *Drosophila presenilins*, Gene 280 (1-2): 135-44.

Methylase, also known as methyltransferase (MTase), is a type of transferase enzyme that transfers a methyl group from a donor to an acceptor. Methylation often occurs on nucleic bases in DNA or amino acids in protein structures. Methylransferases use a reactive methyl group bound to sulfur in S-adenosyl methionine (SAM) as the methyl donor.

Human Tlk2 gene is assigned with Gene ID No: 11011 in GenBank. The gene encodes Serine/threonine-protein kinase tousled-like 2 (TLK2, E.C. 2.7.11.1), a serine/threonine kinase that is implicated in chromatin remodeling, DNA replication, and mitosis. See, e.g., Hashimoto et al., *PKU-beta/TLK1 regulates myosin II activities, and is required for accurate equaled chromosome segregation*; Mutat. Res. 2008; 657:63-7; Li et al., *Tousled-like kinase in a microbial eukaryote regulates spindle assembly and S-phase progression by interacting with Aurora kinase and chromatin assembly factors*, J. Cell. Sci. 2007; 120:3883-94; Sillje et al., *Identification of human Asf1 chromatin assembly factors as substrates of Tousled-like kinases*, Curr. Biol. 2001; 11:1068-73.

The Tousled-like kinases (TLKs) function in processes of chromatin assembly, including replication, transcription, repair, and chromosome segregation. TLKs interact specifically (and phosphorylate) with the chromatin assembly factor ASF1, a histone H3-H4 chaperone, histone H3 itself at Ser10, and also RAD9, a key protein involved in DNA repair and cell cycle signaling following DNA damage. These interactions are believed to be responsible for the action of TLKs in double-stranded break repair and radioprotection and also in the propagation of the DNA damage response. Benedetti (The Tousled-Like Kinases as Guardians of Genome Integrity, ISRN Molecular Biology, volume 2012 (2012), Article ID 627596, doi: 10.5402/2012/627596) proposes that TLKs play key roles in maintenance of genome integrity in many organisms of both kingdoms. TLKs are known to play a role in DNA repair (IR and UV), and are relevant to genome integrity and cancer development.

Figure 15:
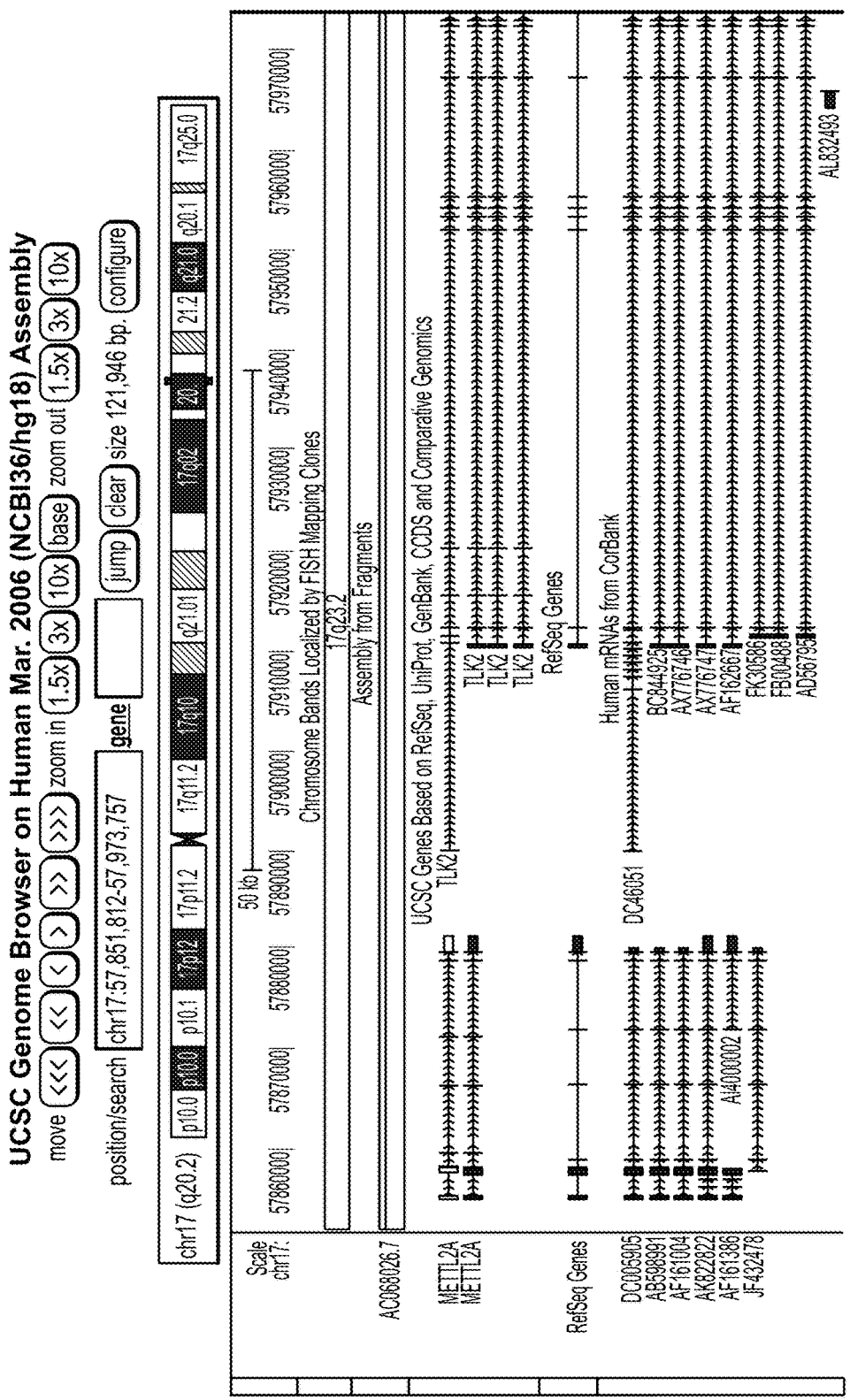
FIG. 15 is a diagram illustrating genes and their gene accession numbers that are found in chromosomal segment chr17:57,851,812-chr17:57,973,757 on NCBI36/hg18 assembly of the human genome (Human March 2006 UCSC Genome Bioinformatics Site genome.ucsc.edu), according to some embodiments.

FIG. 15 shows a diagram of a genetic map illustrating the coordinates of Tlk2 and Mettl2a on segment chr17:57,851,812-chr17:57,973,757onNCBI36/hg18 assembly of the human genome (Human March 2006 UCSC Genome Bioinformatics Site; genome.ucsc.edu), according to some embodiments. Copy-number amplification of TLK2 has been correlated with overexpression in several other cancers. Previous studies have shown that the human gene TLK2, with homologs in the plant *Arabidopsis thaliana* but not in the yeast *Saccharomyces cerevisiae*, encodes for a multicellular organisms-specific serine/threonine protein kinase, a biochemically putative drug target, whose activity directly depends on ongoing DNA replication.

Figure 16:
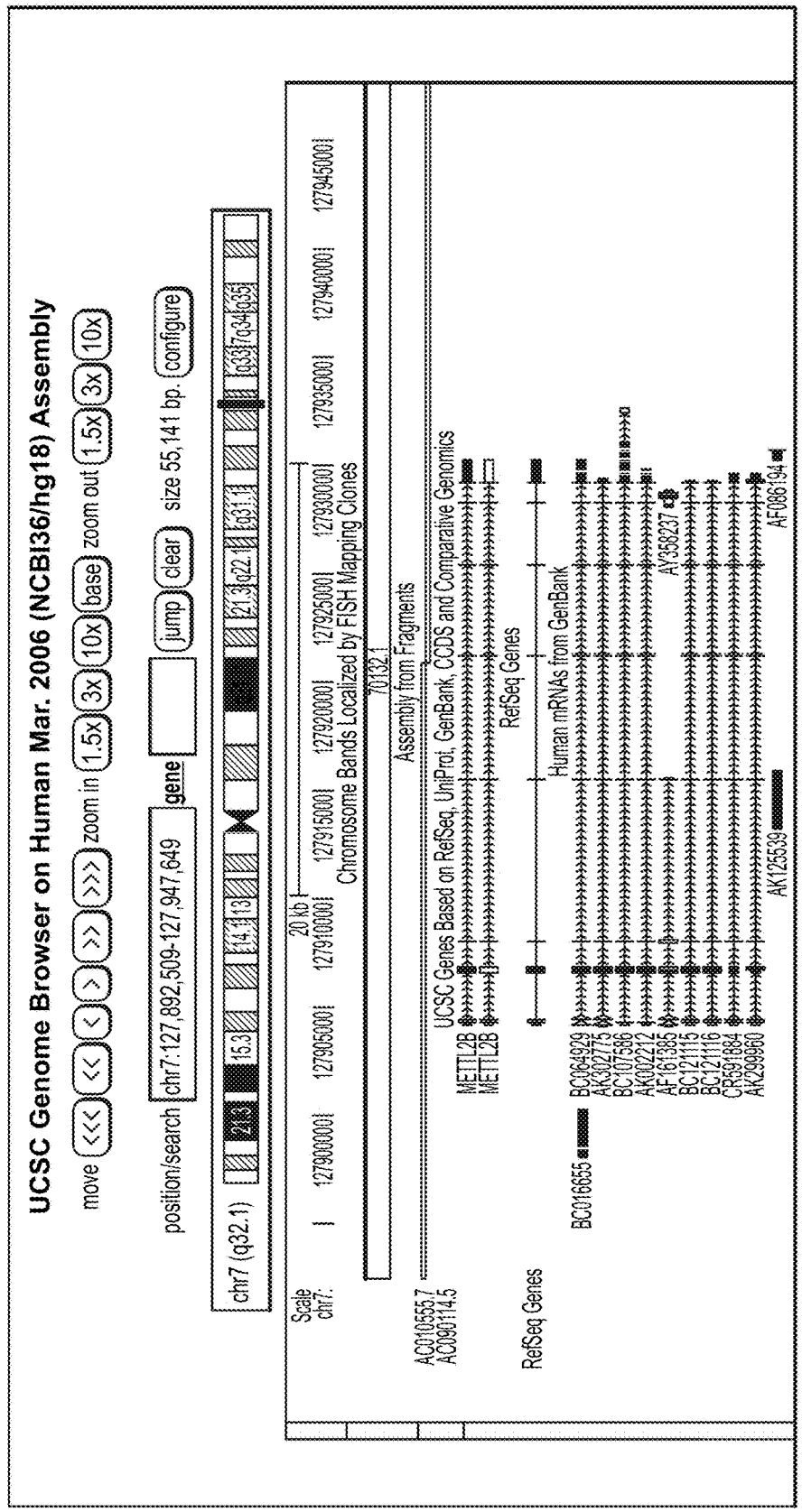
FIG. 16 is a diagram illustrating gene and its gene accession number that is found in chromosomal segment chr7:127,892,509-chr7:127,947,649 on NCBI36/hg18 assembly of the human genome (Human March 2006 UCSC Genome Bioinformatics Site; genome.ucsc.edu), according to some embodiments.

FIG. 16 shows a diagram of a genetic map illustrating the coordinates of Mettl2b on segment chr7:127,892,509-chr7:127,947,649 on NCBI36/hg assembly of the human genome (Fiuman March 2006 UCSC Genome Bioinformatics Site; genome.ucsc.edu), according to some embodiments. Previous studies have shown that overexpression of METTL2A/B has been linked to metastatic samples relative to primary prostate tumor samples; cAMP response element-binding (CREB) regulation in myeloid leukemia, and response to chemotherapy in breast cancer patients.

Figure 17A:
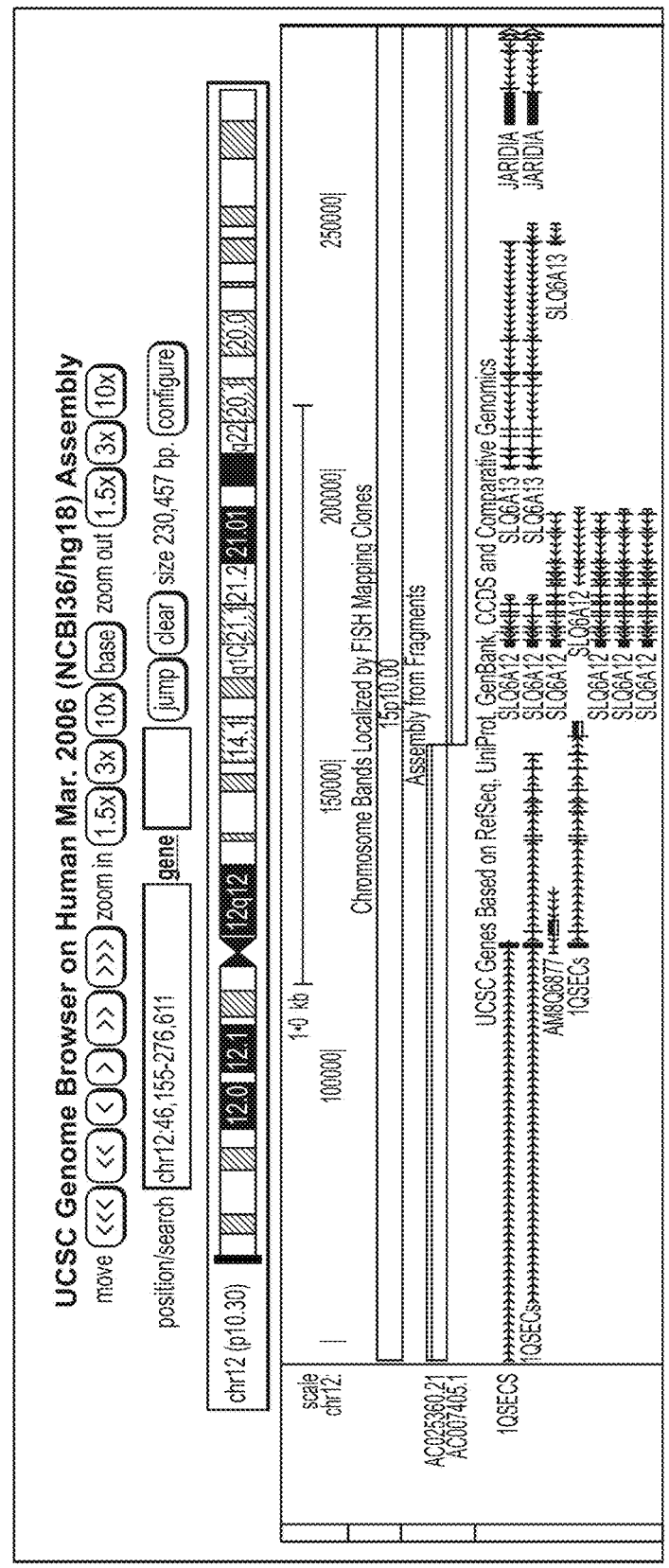
FIG. 17 is a diagram illustrating genes and their gene accession numbers that are found in chromosomal segment chr12:33,854-chr12:264,310 on NCBI36/hg18 assembly of the human genome (Human March 2006 UCSC Genome Bioinformatics Site; genome.ucsc.edu), according to some embodiments.
Figure 17B:
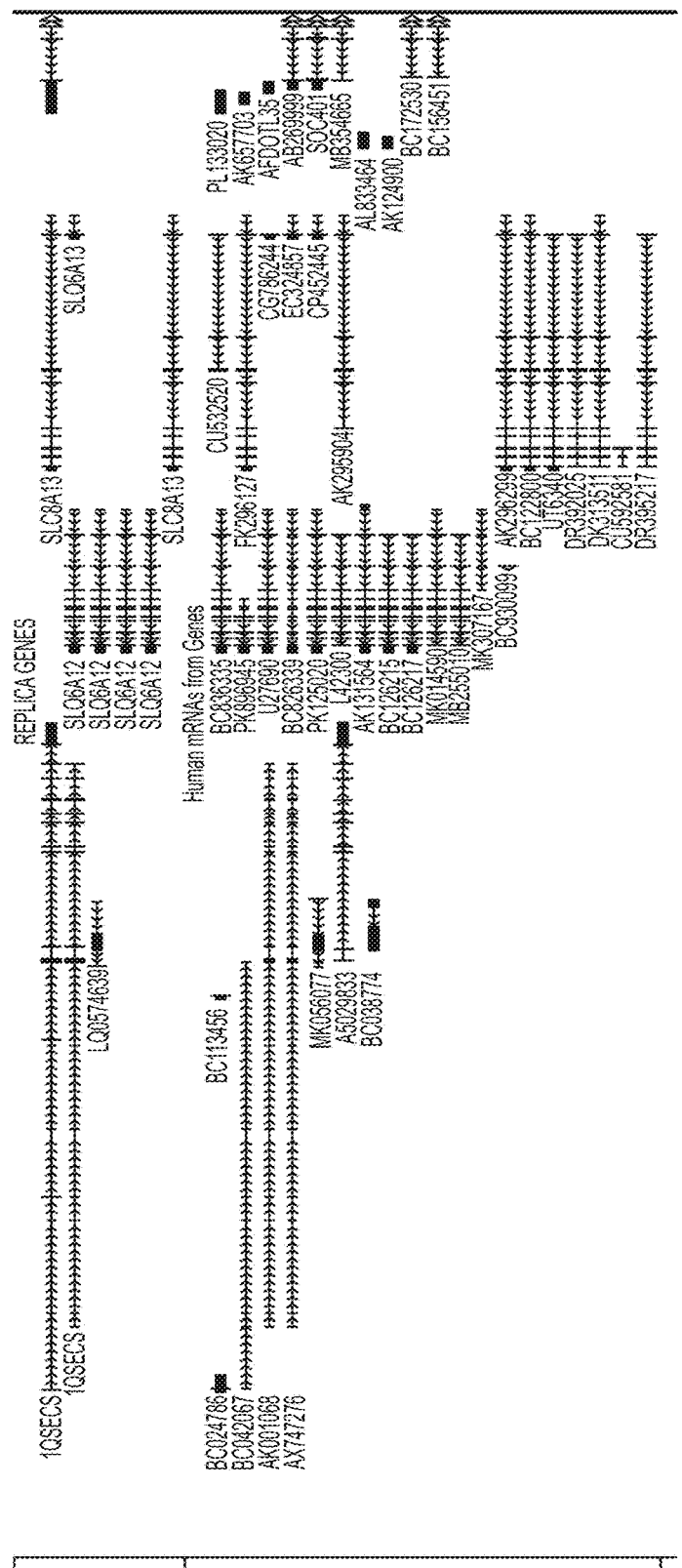
Figure 18B:
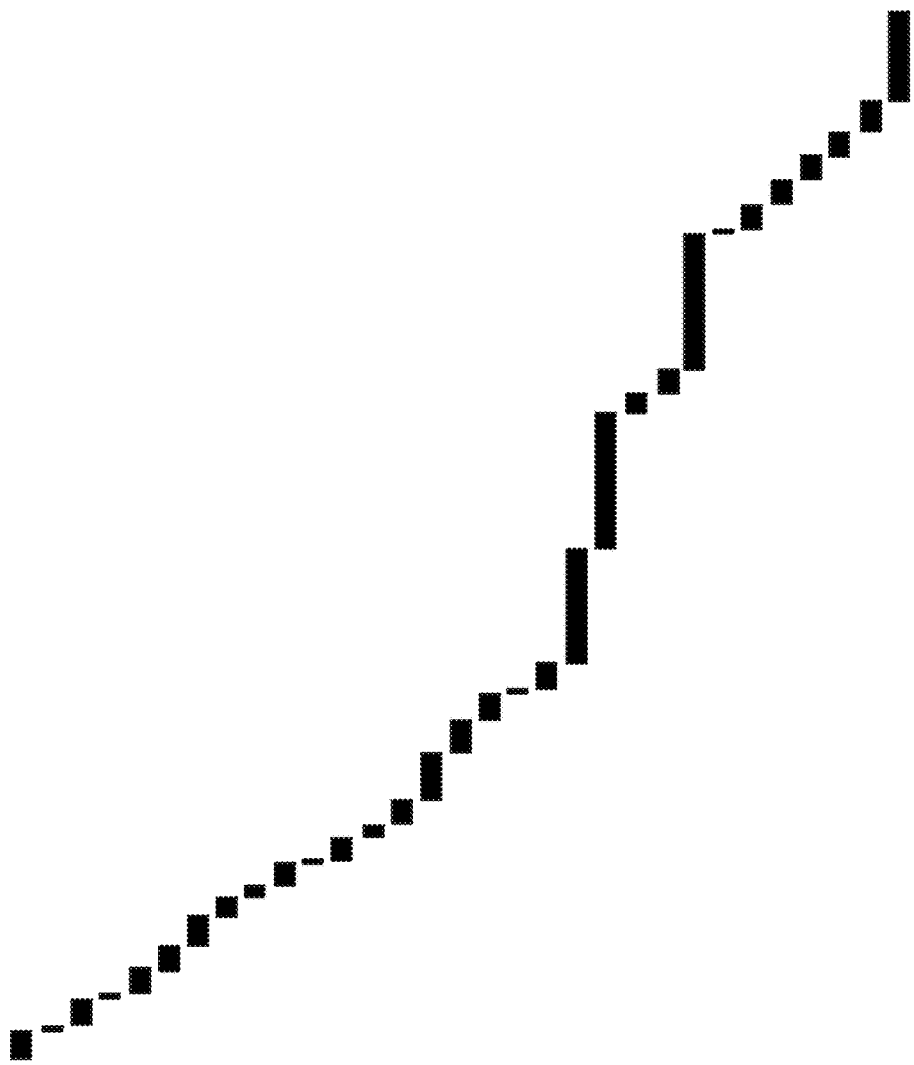
FIG. 18 is a diagram illustrating genes and their gene accession numbers that are found in chromosomal segment chr19:33,329,393-chr19:35-322,055 on NCBI36/hg18 assembly of the human genome (Human March 2006 UCSC Genome Bioinformatics Site genome.ucsc.edu), according to some embodiments.
Figure 18C:
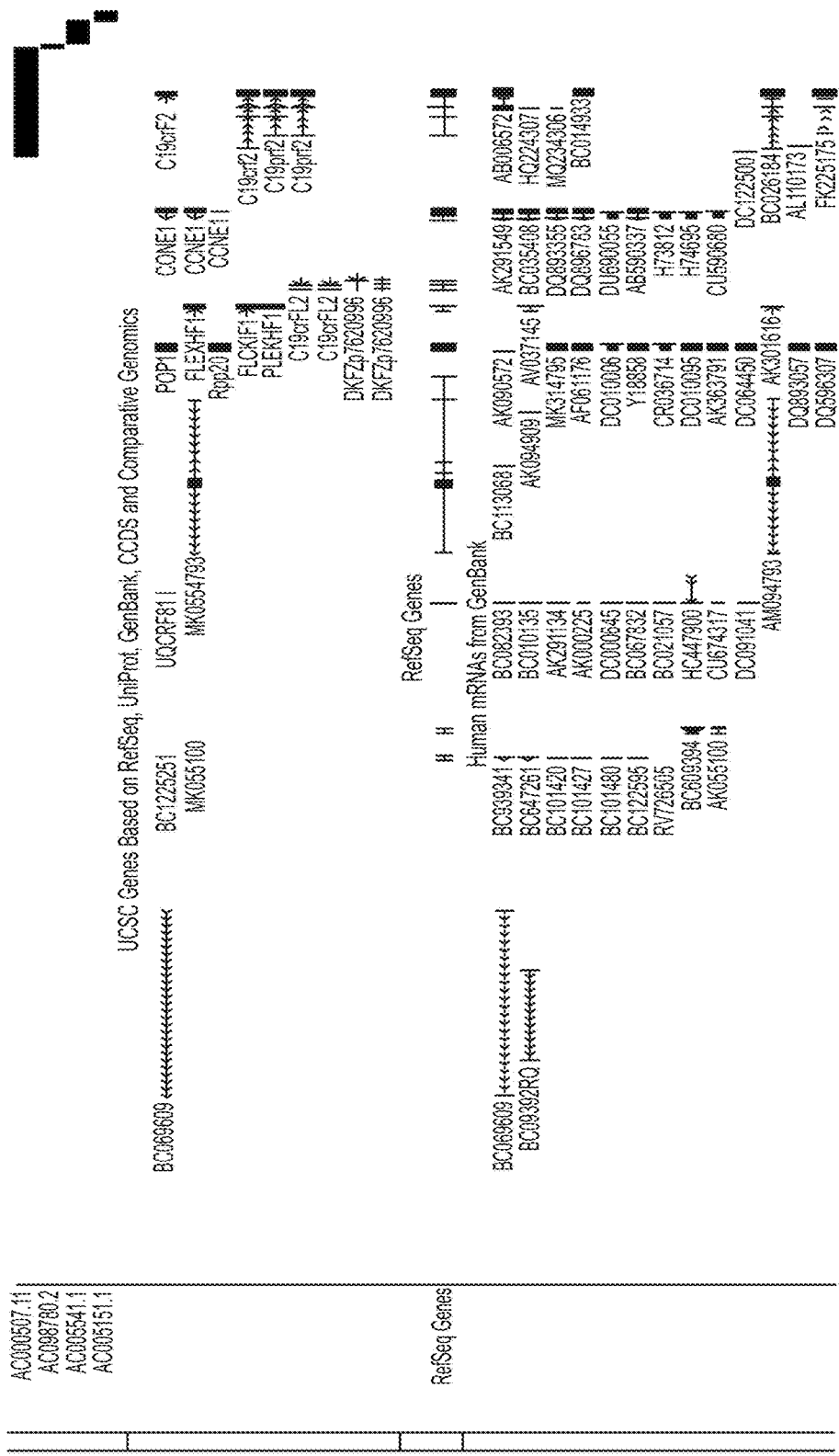

FIG. 17 shows a diagram of a genetic map illustrating the coordinates of Jarid1a, Ak096077, Slc6a12, Slc6a, and Iqsec3 on segment chr12:33,854-chr12:264,310 on NCBI36/hg assembly of the human genome (Fiuman March 2006 UCSC Genome Bioinformatics Site; genome.ucsc.edu), according to some embodiments. Previous studies have shown that the protein encoded by Jarid1a, a retinoblastoma tumor suppressor (Rb)-binding protein, has a role in cancer drug tolerance. SLC6A12 and SLC6A13 are also known biochemically putative carriers of drugs that may pass through the blood-brain barrier. IQSEC3 is a guanine nucleotide exchange factor (GEF) for ADP-ribosylation factor (ARF) that regulates transport along the secretion pathway.

FIG. 18 shows a diagram of a genetic map illustrating the coordinates of Ccne1, Pop4, Plekhf1, C19orf12, C19orf2, Bc068609, Bc122525, Ak055100, Uqcrf51, Ak094793, Rpp29, and Dkfzp762d096 on segment chr19:33, 329,393-chr19:35,322,055 on NCBI36/hg assembly of the human genome (Fiuman March 2006 UCSC Genome Bioinformatics Site; genome.ucsc.edu), according to some embodiments. Previous studies have shown that CCNE1 regulates entry into the DNA synthesis phase of the cell division cycle. Moreover, copy number amplification of Ccne1 has been linked with several cancers but not GBM. Recent studies suggest that there is a link between amplicon-dependent expression of Ccne1 together with the flanking genes Pop4, Plekhf1, C19orf12, and C19orf2 on the segment and primary treatment of ovarian cancer may be due to rapid repopulation of the tumor after chemotherapy.

The amplified DNA segments in GBM described herein also overlap with amplified DNA segments in human neural progenitor cells during development. See, Fischer et al. (Genome-Wide Gene Amplification during Differentiation of Neural Progenitor Cells In Vitro, PLoS ONE 7(5): e37422. doi: 10.1371/journal.pone.0037422, 2012). Accordingly, segments described herein are highly relevant as therapeutic targets for GBM.

Figure 19A:
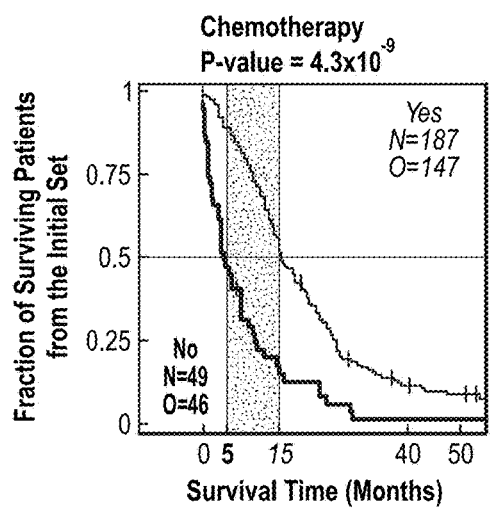
FIGS. 19A-19B are diagrams illustrating survival analyses of patients classified by chemotherapy treatment (FIG. 19A) and chemotherapy and GSVD pattern (FIG. 19B).
Figure 19B:
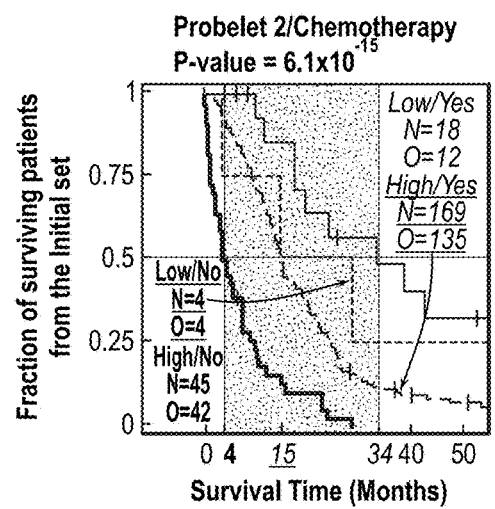

FIGS. 19A-19B are plots showing survival analyses of 236 patients with TCGA chemotherapy annotations in the initial set of 251 patients, classified by chemotherapy alone or GSVD and chemotherapy both. FIG. 19A shows almost overlapping KM curves with a KM median survival time difference of ~10 months and a corresponding log-rank test P-value ~4.3×10$^{-9}$. The graph illustrates the KM and Cox survival analyses of the 236 patients with TCGA chemotherapy annotations in the initial set of 251 patients, classified by chemotherapy, show that lack of chemotherapy, with a KM median survival time difference of about 10 months and a univariate hazard ratio of 2.6 (FIG. 42), confers more than twice the hazard of chemotherapy. FIG. 19B shows 236 patients classified by treatment to both GSVD and chemotherapy, showing similar multivariate Cox hazard ratios, of 3 and 3.1, respectively. This indicates that GSVD and chemotherapy are independent prognostic predictors. Providing GSVD framework increased the KM median survival time difference by at least ~11 months and in some cases, 30 months and 36 months with a corresponding log-rank test P-value ~6.1×10$^{-15}$. With a KM median survival time difference of ~30 months, GSVD and chemotherapy combined make a better predictor than chemotherapy alone.

FIG. 20 is a diagram illustrating significant probelets and corresponding tumor and normal arraylets uncovered by GSVD of the patient-matched GBM and normal blood aCGH profiles, according to some embodiments, (a) A chart 2010 is a plot of the second tumor arraylet and describes a global pattern of tumor-exclusive co-occurring CNAs across the tumor probes. The probes are ordered, and their copy numbers are colored, according to each probe's chromosomal location. Segments (black lines) identified by circular binary segmentation (CBS) include most known GBM-associated focal CNAs, e.g., Epidermal growth factor receptor (EGFR) amplification. CNAs previously unrecognized in GBM may include an amplification of a segment containing the biochemically putative drug target-encoding.

Chart 2015 shows a plot of a probelet that may be identified as the second most tumor-exclusive probelet, which may also be identified as the most significant probelet in the tumor data set, describes the corresponding variation across the patients. The patients are ordered and classified according to each patient's relative copy number in this probelet. There are 227 patients with high (>0.02) and 23 patients with low, approximately zero, numbers in the second probelet. One patient remains unclassified with a large negative (<-0.02) number. This classification may significantly correlate with GBM survival times.

Chart 2020 is a raster display of the tumor data set, with relative gain, no change, and loss of DNA copy numbers, which may show the correspondence between the GBM profiles and the second probelet and tumor arraylet. Chromosome 7 gain and losses of chromosomes 9p and 10, which may be dominant in the second tumor arraylet (see 2220 in FIG. 22), may be negligible in the patients with low copy numbers in the second probelet, but may be distinct in the remaining patients (see 2240 in FIG. 22). This may illustrate that the copy numbers listed in the second probelet correspond to the weights of the second tumor arraylet in the GBM profiles of the patients.

Chart 2030 is a plot of the 246th normal arraylet, which describes an X chromosome-exclusive amplification across the normal probes. A chart 2035 shows a plot of the 246th probelet, which may be approximately common to both the normal and tumor data sets, and second most significant in the normal data set (see 2240 in FIG. 22), may describe the corresponding copy-number amplification in the female relative to the male patients. Classification of the patients by the 246th probelet may agree with the copy-number gender assignments (see table in FIG. 34), also for three patients with missing TCGA gender annotations and three additional patients with conflicting TCGA annotations and copy-number gender assignments.

Chart 2040 is a raster display of the normal data set, which may show the correspondence between the normal blood profiles and the 246th probelet and normal arraylet. X chromosome amplification, which may be dominant in the 246th normal arraylet (Chart 2040), may be distinct in the female but nonexisting in the male patients (Chart 2035). Note also that although the tumor samples exhibit female-specific X chromosome amplification (Chart 2020), the second tumor arraylet (Chart 2010) exhibits an unsegmented X chromosome copy-number distribution that is approximately centered at zero with a relatively small width.

Figure 21G:
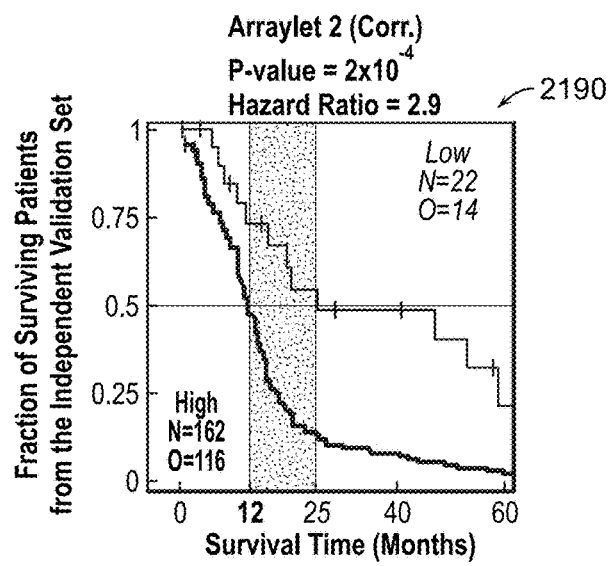
FIG. 21 is a diagram illustrating survival analyses of three sets of patients classified by GSVD, age at diagnosis or both, according to some embodiments.
Figure 21H:
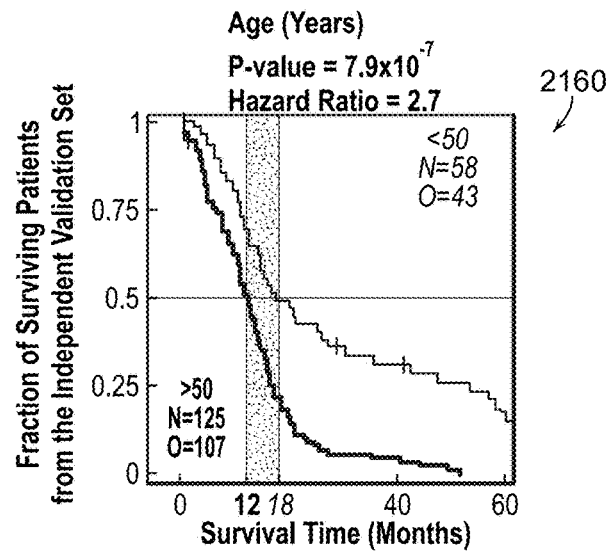
Figure 21I:
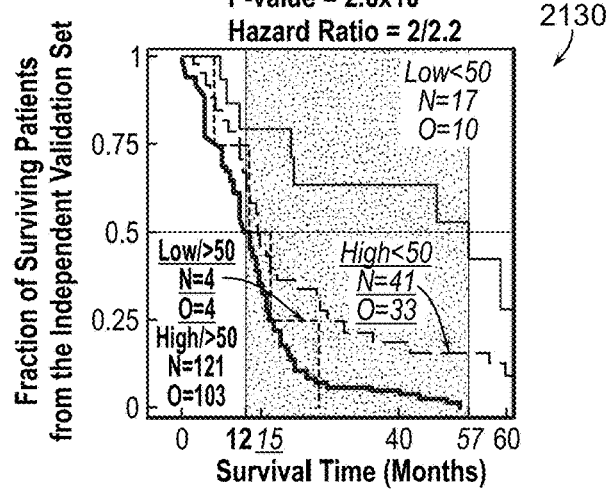

FIG. 21 is a diagram illustrating survival analyses of three sets of patients classified by GSVD, age at diagnosis or both, according to some embodiments. A graph 2110 shows Kaplan-Meier curves for the 247 patients with TCGA annotations in the initial set of 251 patients, classified by copy numbers in the second probelet, which was computed by GSVD for 251 patients, which may indicate a KM median survival time difference of nearly 16 months, with the corresponding log-rank test P-value<10$^{-3}$. The univariate Cox proportional hazard ratio is 2.3, with a P-value<10$^{-2}$ (see table in FIG. 34), which suggests that high relative copy numbers in the second probelet confer more than twice the hazard of low numbers.

More particularly, GSVD has classified the GBM patients into two groups of significantly different prognosis. This classification is according to the copy number listed in the second significant probelet, which correspond to the weights of the second tumor arraylet in the GBM aCGH profiles of the patients. A group of 227 patients, 224 of which with TCGA annotations, displayed high (>0.02) relative copy numbers in the second probelet, and a KM median survival time ~13 months (2110). A group of 23 patients displayed low, approximately zero, relatively copy numbers in the second probelet, and a KM survival time of ~29 months, which is more than twice longer than that of the previous group.

Referring again to FIG. 21, graph 2120 shows KM and Cox survival analyses for the 247 patients classified by age, i.e., >50 or <50 years old at diagnosis, which may indicate that the prognostic contribution of age, with a KM median survival time difference of nearly 11 months and a univariate hazard ratio of 2, is comparable to that of GSVD.

Graph 2130 shows survival analyses for the 247 patients classified by both GSVD and age, which may indicate similar multivariate Cox hazard ratios, of 1.8 and 1.7, that do not differ significantly from the corresponding univariate hazard ratios, of 2.3 and 2, respectively. This suggests that GSVD and age are independent prognostic predictors. With a KM median survival time difference of approximately 22 months, GSVD and age combined make a better predictor than age alone.

Graph 2140 shows survival analyses for the 334 patients with TCGA annotations and a GSVD classification in the inclusive confirmation set of 344 patients, classified by copy numbers in the second probelet, which was computed by GSVD for the 344 patients, which indicates a KM median survival time difference of nearly 16 months and a univariate hazard ratio of 2.4, and confirmed the survival analyses of the initial set of 251 patients.

A graph 2150 shows survival analyses for the 334 patients classified by age confirmed that the prognostic contribution of age, with a KM median survival time difference of approximately 10 months and a univariate hazard ratio of 2, is comparable to that of GSVD. A graph 2160 shows survival analyses for the 334 patients classified by both GSVD and age, which may indicate similar multivariate Cox hazard ratios, of 1.9 and 1.8, that may not differ significantly from the corresponding univariate hazard ratios, and a KM median survival time difference of nearly 22 months, with the corresponding log-rank test P-value<$10^{-5}$. This result suggests that the prognostic contribution of GSVD is independent of age, and that combined with age, GSVD makes a better predictor than age alone.

Graph 2170 shows survival analyses for the 183 patients with a GSVD classification in the independent validation set of 184 patients, classified by correlations of each patient's GBM profile with the second tumor arraylet, which can be computed by GSVD for the 251 patients, which may indicate a KM median survival time difference of nearly 12 months and a univariate hazard ratio of 2.9, and may validate the survival analyses of the initial set of 251 patients. A graph 2180 shows survival analyses for the 183 patients classified by age, which suggests that the prognostic contribution of age is comparable to that of GSVD.

Graph 2190 shows survival analyses for the 183 patients classified by both GSVD and age, which may indicate similar multivariate Cox hazard ratios, of 2 and 2.2, and a KM median survival time difference of nearly 41 months, with the corresponding log-rank test P-value<$10^{-5}$. This result suggests that the prognostic contribution of GSVD is independent of age, and that combined with age, GSVD is a better predictor than age alone, also for patients with measured GBM aCGH profiles in the absence of matched normal blood profiles.

Figure 22A:
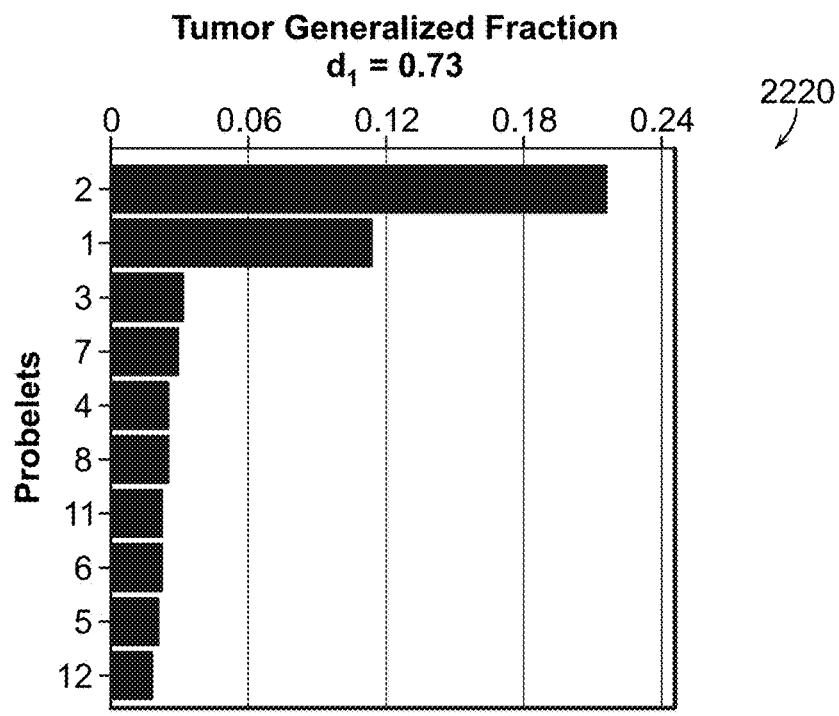
FIG. 22 is a diagram illustrating survival analyses of an initial set of a number of patients classified by GBM-associated chromosome number changes, according to some embodiments.
Figure 22B:
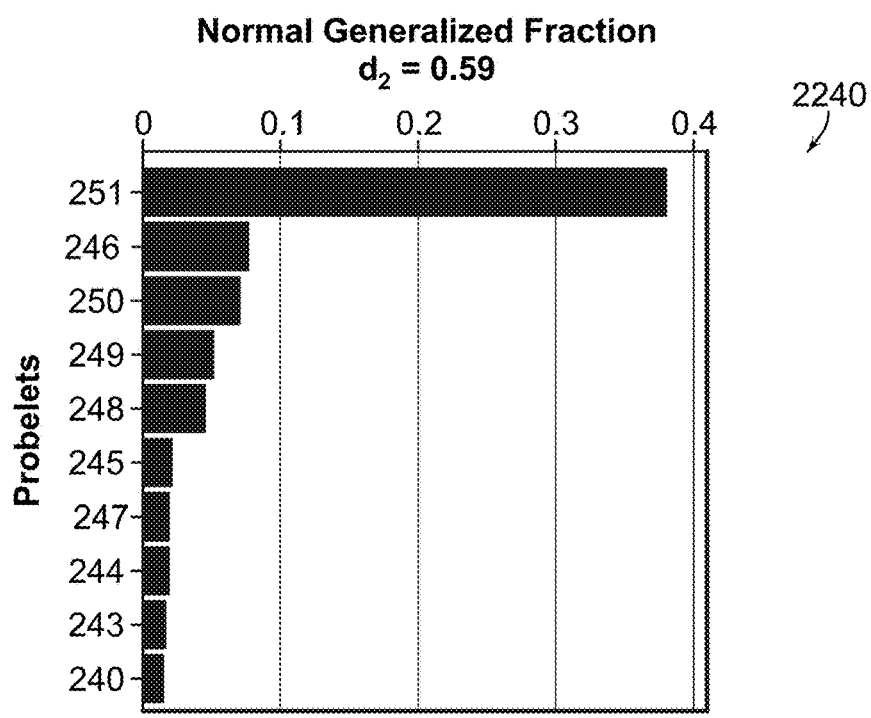

FIG. 22 is a diagram illustrating the most significant probelets in tumor and normal data sets, age at diagnosis or both, according to some embodiments. Bar charts 2220 and 2240 show the ten significant probelets in the tumor data set and the generalized fraction that each probelet captures in this data set. The generalized fraction are given as $P_{1,n}$ and $P_{2,n}$ below in terms of the normalized values for $\sigma^2_{1,n}$ and $\sigma^2_{2,n}$:

$$p_{1,n} = \sigma^2_{1,n} \bigg/ \sum_{n=1}^{N} \sigma^2_{1,n},$$

$$p_{2,n} = \sigma^2_{2,n} \bigg/ \sum_{n=1}^{N} \sigma^2_{2,n}.$$

The results shown in bar charts 2220 and 2240 suggests that the two most tumor-exclusive probelets, i.e., the first probelet (see FIG. 24) and the second probelet (see FIG. 20, 2010-2020), with angular distances >$2\pi/9$, may also be the two most significant probelets in the tumor data set, with ~11% and 22% of the information in this data set, respectively. The "generalized normalized Shannon entropy" of the tumor dataset is $d_1$=0.73. Bar chart 2240 shows ten significant probelets in the normal data set and the generalized fraction that each probelet captures in this data set, which suggests that the five most normal-exclusive probelets, the 247th to 251st probelets (see FIGS. 25-29), with angular distances approximately <≈−$\pi/6$, may be among the seven most significant probelets in the normal data set, capturing together ~56% of the information in this data set. The 246th probelet (see FIG. 20, 2030-2040), which is relatively common to the normal and tumor data sets with an angular distance >−$\pi/6$, may be the second most significant probelet in the normal data set with ~8% of the information. The generalized entropy of the normal dataset, $d_2$=0.59, is smaller than that of the tumor dataset. This means that the normal dataset is more redundant and less complex than the tumor dataset.

Figure 23:
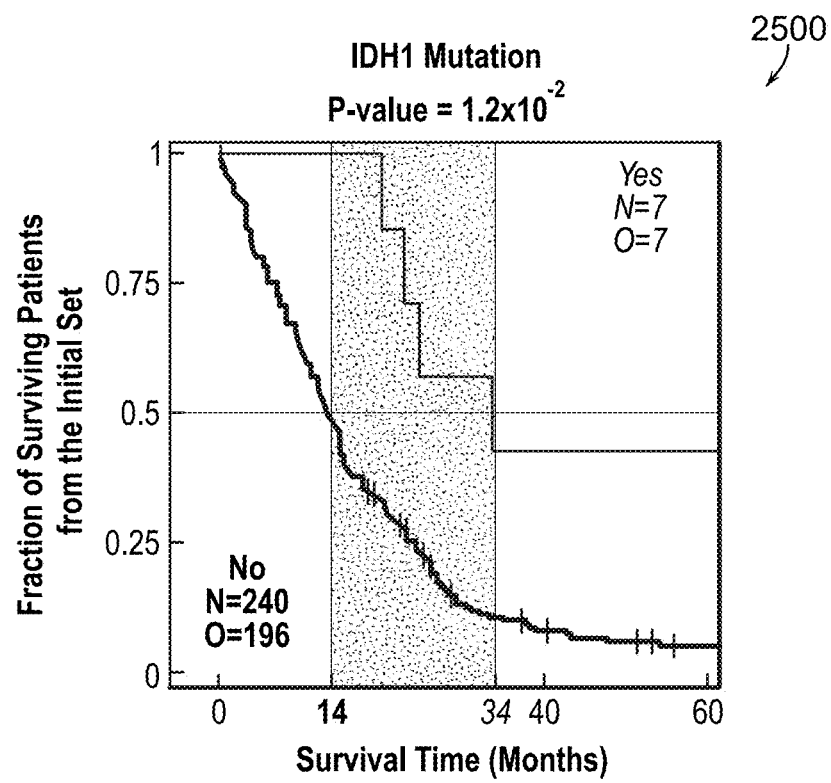
FIG. 23 is a diagram illustrating a survival analysis of an initial set of a number of patients classified by a mutation in one of the genes, according to some embodiments.

FIG. 23 is a diagram illustrating a survival analysis of an initial set of a number of patients, according to some embodiments. Graph 2500 shows a result of a KM survival analysis of an initial set of 251 patients classified by a mutation in the gene Idh1.

FIG. 24 is a diagram illustrating a significant probelet and corresponding tumor arraylet, according to some embodiments. This probelet may be the first most tumor-exclusive probelet, which is shown with corresponding tumor arraylet uncovered by GSVD of the patient-matched GBM and normal blood aCGH profiles. A plot 2620 of the first tumor array let describes unsegmented chromosomes (black lines), each with copy-number distributions which were approximately centered at zero with relatively large, chromosome-invariant widths. The probes are ordered, and their copy numbers are colored, according to each probe's chromosomal location.

Graph 2630 of the first most tumor-exclusive probelet, which is also the second most significant probelet in the tumor data set (see 2220 in FIG. 22), describes the corresponding variation across the patients. The patients were ordered according to each patient's relative copy number in this probelet. These copy numbers may significantly correlate with the genomic center where the GBM samples were hybridized at, HMS, MSKCC, or multiple locations, with the P-values<$10^{-5}$ (see Table in FIG. 35 and FIG. 30). A raster display 2640 of the tumor data set, with relative gain, no change, and loss of DNA copy numbers, may indicate the correspondence between the GBM profiles and the first probelet and tumor array let.

Figures 25A, 25B, 25C:
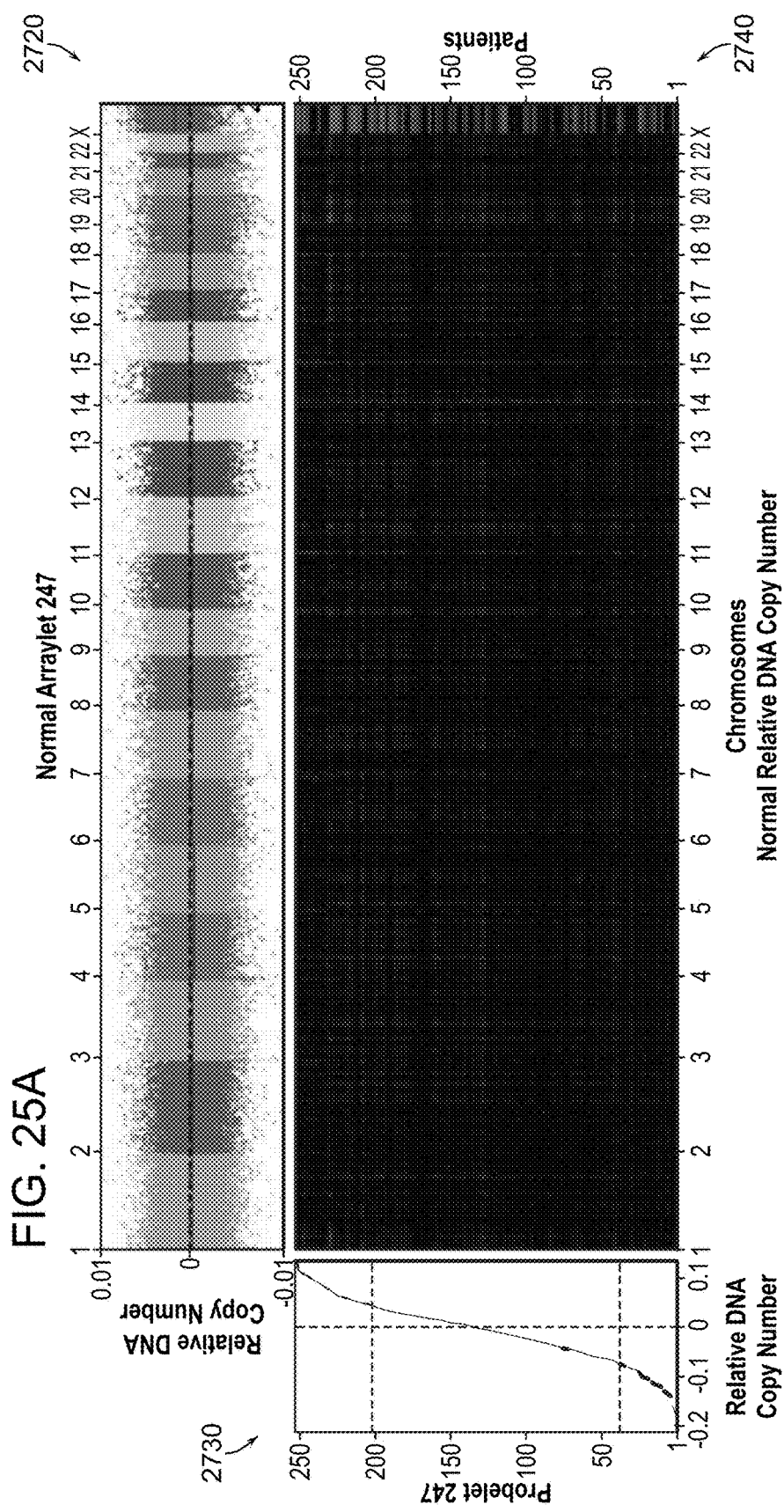
FIG. 25 is a diagram illustrating a normal-exclusive probelet and a corresponding normal arraylet uncovered by GSVD, according to some embodiments.

FIG. 25 is a diagram illustrating a normal-exclusive probelet and corresponding normal arraylet uncovered by GSVD, according to some embodiments. The normal-exclusive probelet is 247th, normal-exclusive probelet and corresponding normal arraylet is uncovered by GSVD. (a) A plot 2720 of the 247th normal arraylet describes copy-number distributions which were approximately centered at zero with relatively large, chromosome-invariant widths. The normal probes are ordered, and their copy numbers are colored, according to each probe's chromosomal location, (b) A plot 2730 of the 247th probelet may describe the corresponding variation across the patients. Copy numbers in this probelet may correlate with the date of hybridization of the normal blood samples, 7.22.2009, 10.8.2009, or other, with the P-values<$10^{-3}$ (see the Table in FIG. 35 and FIG. 30). (c) A raster display 2740 of the normal data set shows the correspondence between the normal blood profiles and the 247th probelet and normal arraylet.

FIG. 26 is a diagram illustrating a normal-exclusive probelet and corresponding normal arraylet uncovered by GSVD, according to some embodiments. The normal-exclusive probelet is 248th, normal-exclusive probelet and the corresponding normal arraylet was uncovered by GSVD. (a) A Plot 2820 of the 248th normal arraylet describes copy-number distributions which are approximately centered at zero with relatively large, chromosome-invariant widths, (b) A Plot 2830 of the 248th probelet describes the corresponding variation across the patients. Copy numbers in this probelet may significantly correlate with the tissue batch/hybridization scanner of the normal blood samples, HMS 8/2331 and other, with the P-values<$10^{-12}$ (see the Table in FIG. 35 and FIG. 30). (c) A raster display 2840 of the normal data set suggests the correspondence between the normal blood profiles and the 248th probelet and normal arraylet.

FIG. 27 is a diagram illustrating another normal-exclusive probelet and corresponding normal arraylet uncovered by GSVD, according to some embodiments. The normal-exclusive probelet is 249th, normal-exclusive probelet and the corresponding normal arraylet was uncovered by GSVD. (a) A Plot 2920 of the 249th normal arraylet describes copy-number distributions which were approximately centered at zero with relatively large, chromosome-invariant widths, (b) A Plot 2930 of the 249th probelet describes the corresponding variation across the patients. Copy numbers in this probelet may significantly correlate with the tissue batch/hybridization scanner of the normal blood samples, HMS 8/2331 and other, with the P-values<$10^{-12}$ (see the Table in FIG. 35 and FIG. 30). (c) A raster display 2940 of the normal data set suggests the correspondence between the normal blood profiles and the 249th probelet and normal arraylet.

Figures 28A, 28B, 28C:
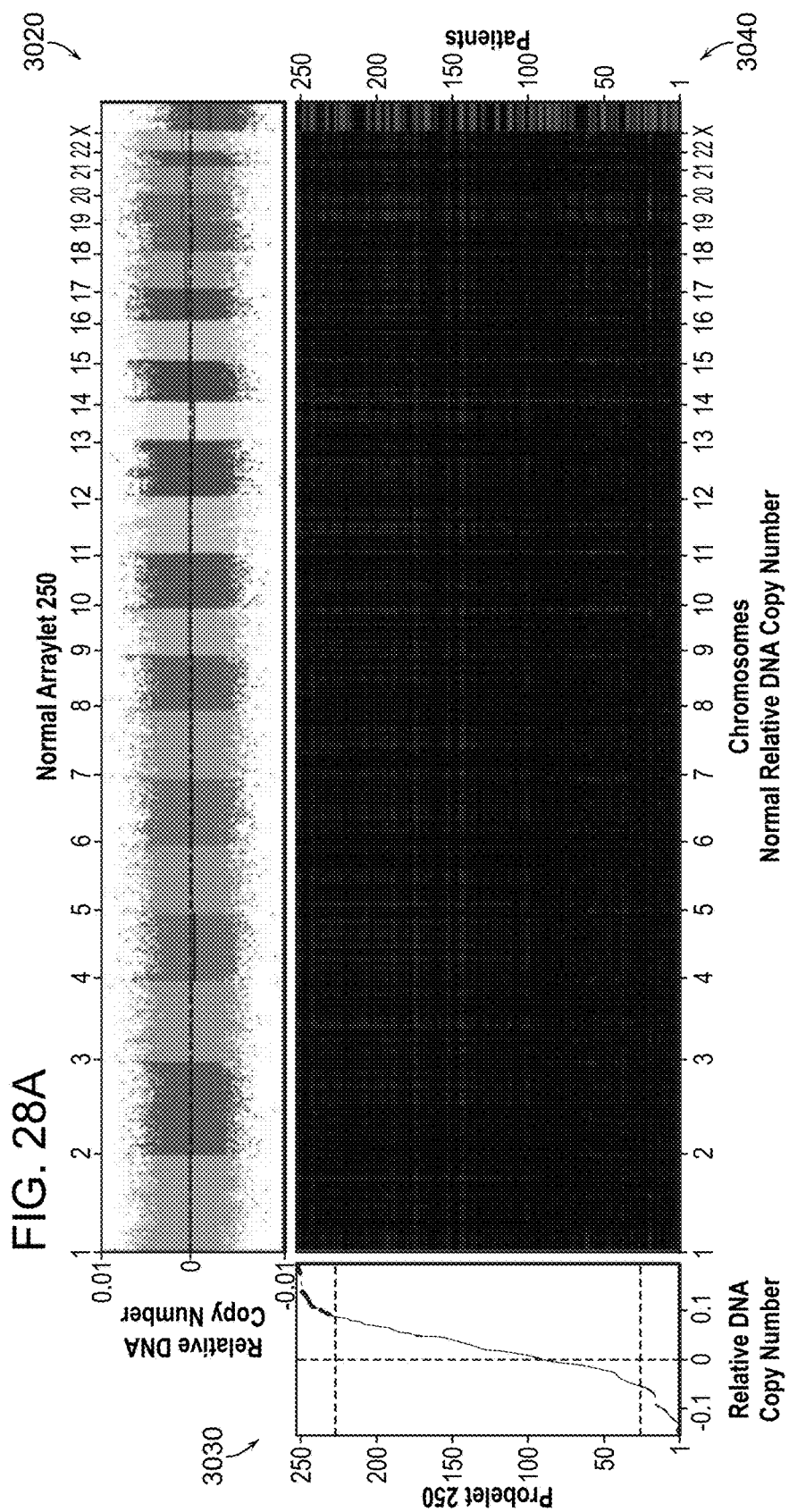
FIG. 28 is a diagram illustrating yet another normal-exclusive probelet and corresponding normal arraylet uncovered by GSVD, according to some embodiments.

FIG. 28 is a diagram illustrating yet another normal-exclusive probelet and corresponding normal arraylet uncovered by GSVD, according to some embodiments. The normal-exclusive probelet is 250th, normal-exclusive probelet and the corresponding normal arraylet is uncovered by GSVD. (a) A Plot 3020 of the 250th normal arraylet describes copy-number distributions which are approximately centered at zero with relatively large, chromosome-invariant widths, (b) A Plot 3030 of the 248th probelet may describe the corresponding variation across the patients. Copy numbers in this probelet may correlate with the date of hybridization of the normal blood samples, Apr. 18, 2007, Jul. 22, 2009, or other, with the P-values<$10^{-3}$ (see the Table in FIG. 35 and FIG. 30). (c) A raster display 3040 of the normal data set may show the correspondence between the normal blood profiles and the 250th probelet and normal arraylet.

Figures 29A, 29B, 29C:
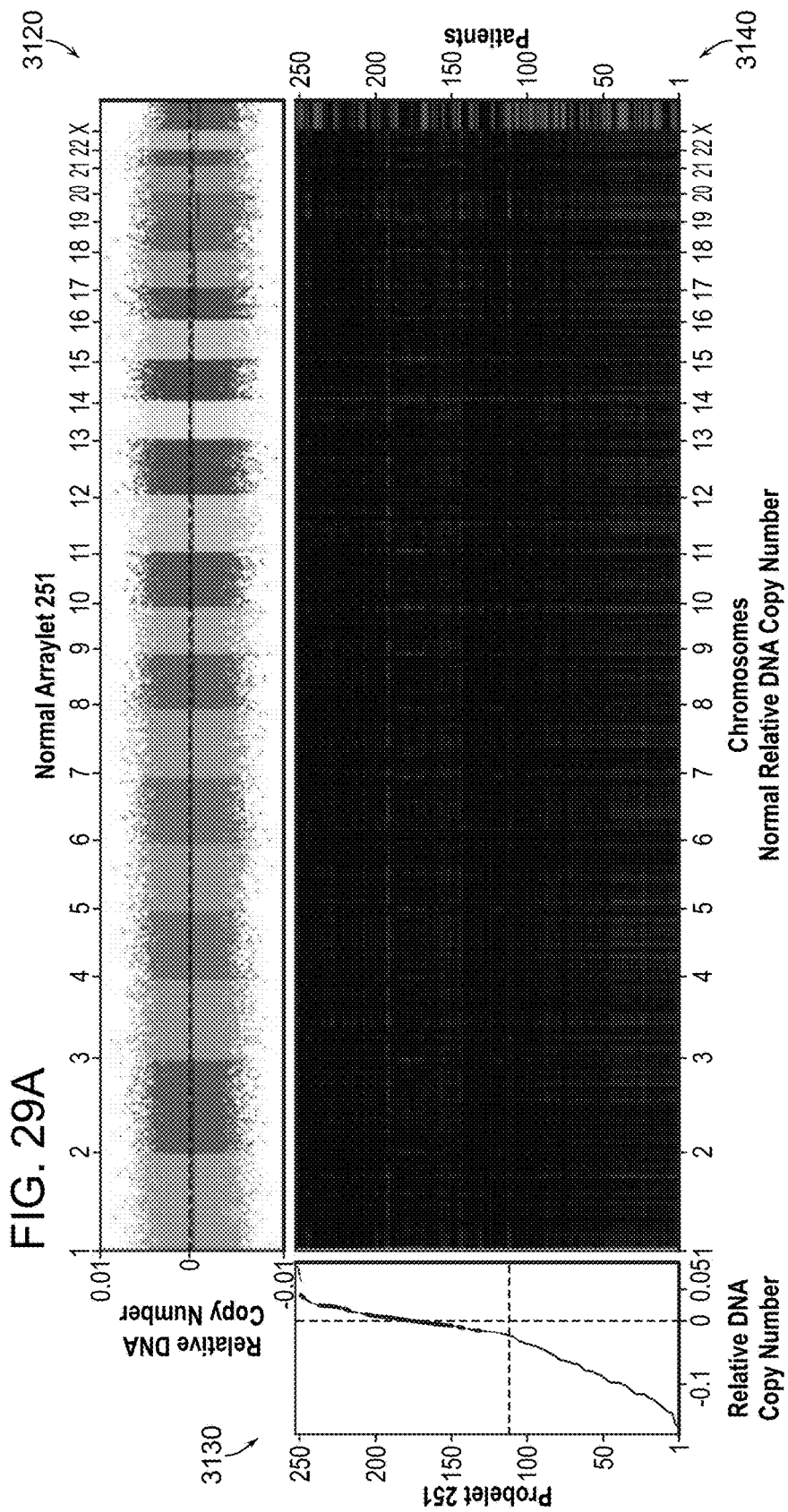
FIG. 29 is a diagram illustrating a first most normal-exclusive probelet and corresponding normal arraylet uncovered by GSVD, according to some embodiments.

FIG. 29 is a diagram illustrating a first most normal-exclusive probelet and corresponding normal arraylet uncovered by GSVD, according to some embodiments. The normal-exclusive probelet is 251st, normal-exclusive probelet and the corresponding normal arraylet was uncovered by GSVD. (a) A Plot 3120 of the 251st normal arraylet describes unsegmented chromosomes (black lines), each with copy-number distributions which are approximately centered at zero with relatively large, chromosome-invariant widths, (b) A Plot 3130 of the first most normal-exclusive probelet, which may also be the most significant probelet in the normal data set (see FIG. 22, 2240), describes the corresponding variation across the patients. Copy numbers in this probelet may significantly correlate with the genomic center where the normal blood samples were hybridized at, HMS, MSKCC or multiple locations, with the P-values<$10^{-13}$ (see the Table in FIG. 35 and FIG. 30). (c) A raster display 3140 of the normal data set suggests the correspondence between the normal blood profiles and the 251 st probelet and normal arraylet.

Figures 30D, 30E, 30F:
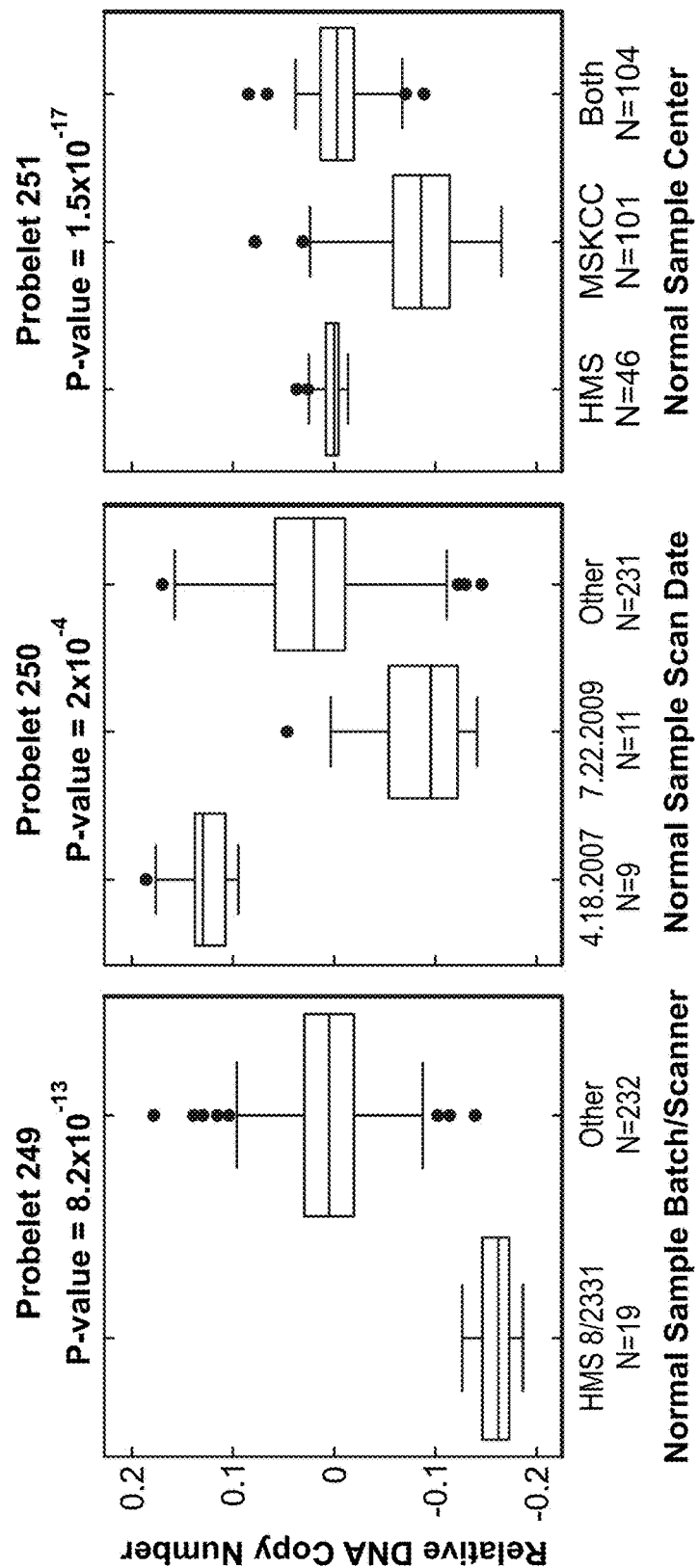
FIG. 30 is a diagram illustrating differences in copy numbers among the TCGA annotations associated with the significant probelets, according to some embodiments.

FIG. 30 is a diagram illustrating differences in copy numbers among the TCGA annotations associated with the significant probelets, according to some embodiments. Boxplot visualization of the distribution of copy numbers are shown of the (a) first, possibly the most tumor-exclusive probelet among the associated genomic centers where the GBM samples were hybridized at (see the Table in FIG. 35); (b) 247th, normal-exclusive probelet among the dates of hybridization of the normal blood samples; (c) 248th, normal-exclusive probelet between the associated tissue batches/hybridization scanners of the normal samples; (d) 249th, normal-exclusive probelet between the associated tissue batches/hybridization scanners of the normal samples; (e) 250th, normal-exclusive probelet among the dates of hybridization of the normal blood samples; (f) 251st, possibly the most normal-exclusive probelet among the associated genomic centers where the normal blood samples were hybridized at. The Mann-Whitney-Wilcoxon P-values correspond to the two annotations that may be associated with largest or smallest relative copy numbers in each probelet.

Figures 31A, 31B, 31C:
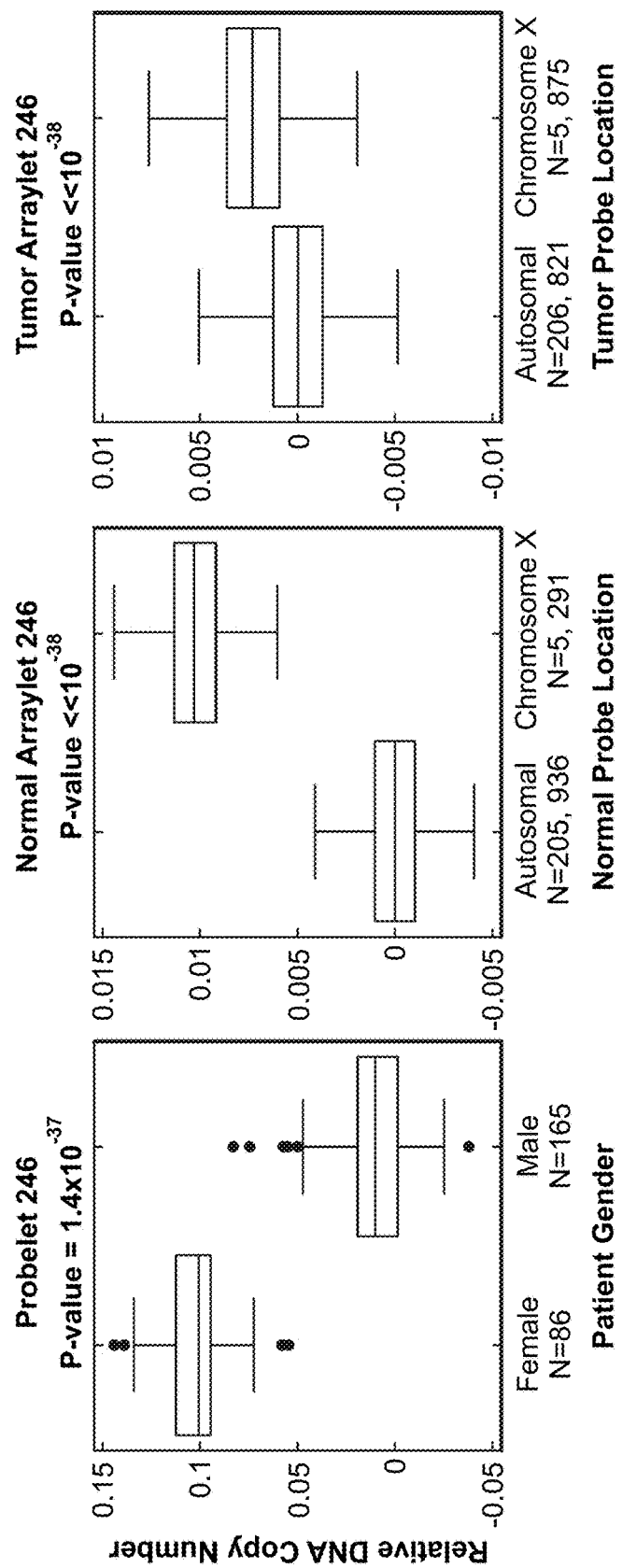
FIG. 31 is a diagram illustrating copy-number distributions of one of the probelet and the corresponding normal arraylet and tumor arraylet, according to some embodiments.

FIG. 31 is a diagram illustrating copy-number distributions of one of the probelet and the corresponding normal arraylet and tumor arraylet, according to some embodiments. Copy-number distributions relates to the 246th probelet and the corresponding 246th normal arraylet and 246th tumor arraylet. Boxplot visualization and Mann-Whitney-Wilcoxon P-values of the distribution of copy numbers are shown of the (a) 246th probelet, which may be approximately common to both the normal and tumor data sets, and may be the second most significant in the normal data set (see FIG. 22, 2240), between the gender annotations; (b) 246th normal arraylet between the autosomal and X chromosome normal probes; (c) 246th tumor arraylet between the autosomal and X chromosome tumor probes.

Several of the genes identified by the GSVD were further analyzed for their usefulness in the prognosis and diagnosis and GBM. These results are shown in FIGS. 32A-32L and 33A-33L.

FIG. 32A-32L are graphs illustrating a Kaplan-Meier survival analysis of an initial set of a number of patients classified by copy number changes in selected segments, according to some embodiments. The graphs show KM survival analyses of the initial set of 251 patients classified by copy number changes in selected segments containing GBM-associated genes or genes previously unrecognized in GBM. In the KM survival analyses for the groups of patients with either a CNA or no CNA in either one of the 130 segments identified by the global pattern, i.e., the second tumor-exclusive arraylet (Dataset S3), log-rank test P-values<$5 \times 10^{-2}$ are calculated for only 12 of the classifications. Of these, only six may correspond to a KM median survival time difference that is ≈>5 months, approximately a third of the ~16 months difference observed for the GSVD classification. One of these segments may contain the genes Tlk2 and Mettl2a, previously unrecognized in GBM. The KM median survival time can be calculated for the 56 patients with Tlk2 amplification, which is ~5 months longer than that for the remaining patients. This may suggest that drug-targeting the kinase and/or the methyltransferase-like protein that Tlk2 and Mettl2a encode, respectively, may affect not only the pathogenesis but also the prognosis of GBM.

Figure 32G:
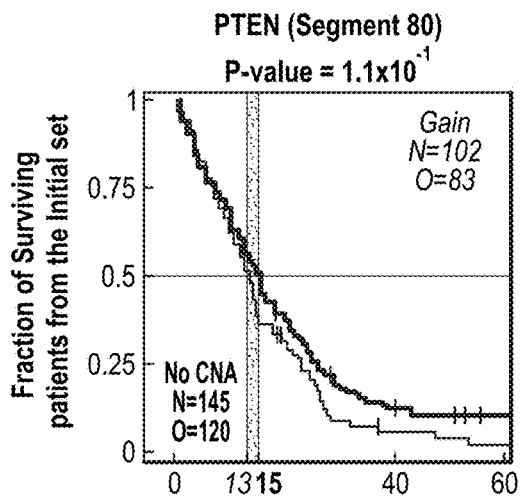
Figure 32H:
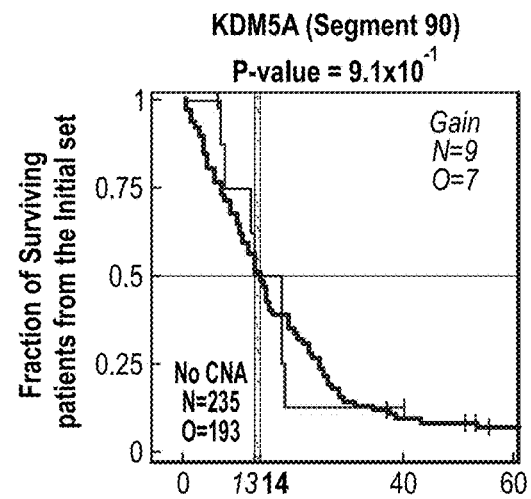
Figure 32I:
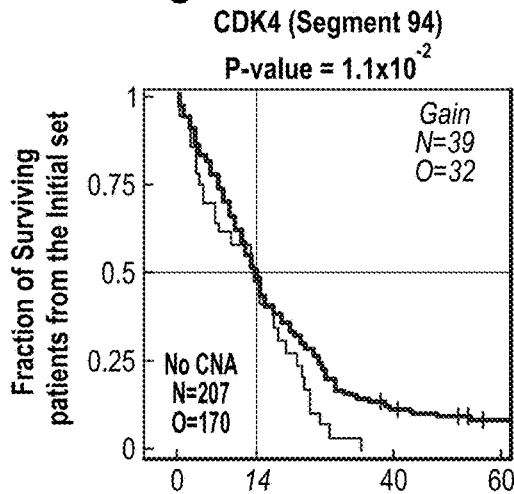
Figure 32J:
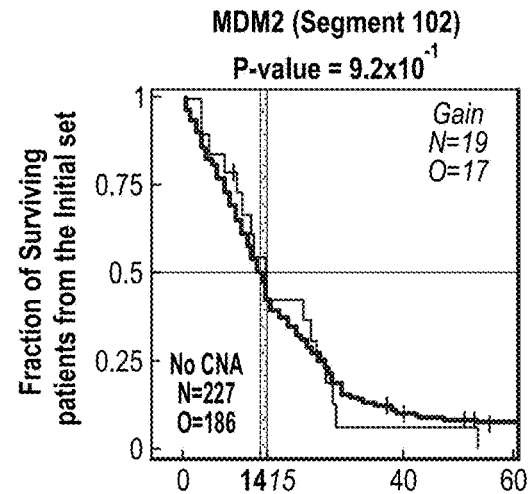
Figure 32K:
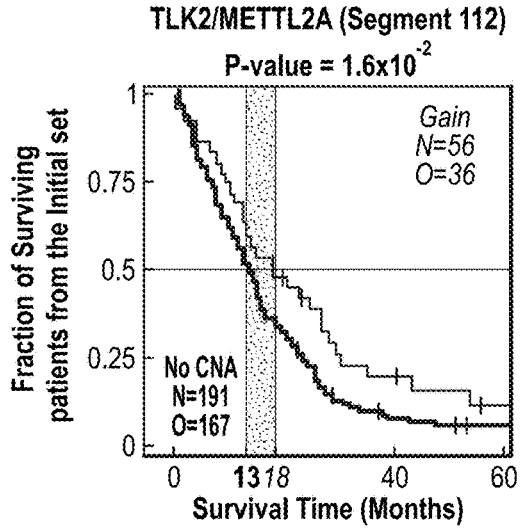
Figure 32L:
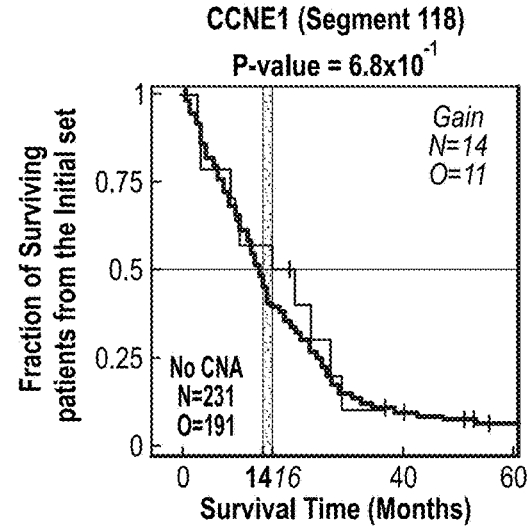

FIG. 32A is a KM analysis of 247 patients from the initial set of 251 patients, classified by copy number gain of a segment encompassing Mdm4. This figure shows almost overlapping KM curves and a corresponding log-rank test P-value ~$3.7 \times 10^{-1}$ FIG. 32B is a KM analysis of 241 patients from the initial set of 251 patients, classified by copy number gain of a segment encompassing Akt3. This figure shows almost overlapping KM curves with a KM median survival time difference of ~4 months and a corresponding log-rank test P-value ~$7.6 \times 10^{-1}$. FIG. 32C is a KM analysis of 246 patients from the initial set of 251 patients, classified by copy number gain of a segment encompassing Egfr. This figure shows almost overlapping KM curves with a KM median survival time difference of ~1 months and a corresponding log-rank test P-value ~6.2×10$^{-1}$. FIG. 32D is a KM analysis of 247 patients from the initial set of 251 patients, classified by copy number gain of a segment encompassing Met. This figure shows almost overlapping KM curves and a corresponding log-rank test P-value ~7.3×10$^{-1}$. FIG. 32E is a KM analysis of 246 patients from the initial set of 251 patients, classified by copy number gain of a segment (SEQ ID NO: 47) encompassing Mettl2b. This figure shows almost overlapping KM curves with a KM median survival time difference of ~8 months and a corresponding log-rank test P-value ~3.9×10$^{-2}$. FIG. 32F is a KM analysis of 246 patients from the initial set of 251 patients, classified by copy number loss of a segment encompassing Cdkn2a/b. This figure shows almost overlapping KM curves with a KM median survival time difference of ~1 month and a corresponding log-rank test P-value ~4×10$^{-1}$. FIG. 32G is a KM analysis of 247 patients from the initial set of 251 patients, classified by copy number loss of a segment encompassing Pten. This figure shows almost overlapping KM curves with a KM median survival time difference of ~2 months and a corresponding log-rank test P-value ~1.1×10$^{-1}$. FIG. 32H is a KM analysis of 244 patients from the initial set of 251 patients, classified by copy number gain of a segment (SEQ ID NO: 48) encompassing Jarid1a. This figure shows almost overlapping KM curves with a KM median survival time difference of ~1 months and a corresponding log-rank test P-value ~9.1×10$^{-1}$. FIG. 32I is a KM analysis of 246 patients from the initial set of 251 patients, classified by copy number gain of a segment encompassing Cdk4. This figure shows almost overlapping KM curves and a corresponding log-rank test P-value ~5.1×10$^{-2}$. FIG. 32J is a KM analysis of 246 patients from the initial set of 251 patients, classified by copy number gain of a segment encompassing Mdm2. This figure shows almost overlapping KM curves with a KM median survival time difference of ~1 months and a corresponding log-rank test P-value ~9.2×10$^{-1}$. FIG. 32K is a KM analysis of 247 patients from the initial set of 251 patients, classified by copy number gain of a segment (SEQ ID NO: 46) encompassing Tlk2/Mettl2a. This figure shows almost overlapping KM curves with a KM median survival time difference of ~5 months and a corresponding log-rank test P-value ~1.6×10$^{-2}$. FIG. 32L is a KM analysis of 245 patients from the initial set of 251 patients, classified by copy number gain of a segment (SEQ ID NO: 49) encompassing Ccne1. This figure shows almost overlapping KM curves with a KM median survival time difference of ~2 months and a corresponding log-rank test P-value ~6.8×10$^{-1}$.

More particularly, FIG. 32K shows that the KM median survival time for the 56 patients with TLK2/METTL2A amplification is ~5 months longer than that for the remaining 191 patients. This suggests that drug targeting the kinase encoded by Tlk2 and/or the methyltransferase-like protein encoded by Mettl2a encodes affect not only the pathogenesis but also the prognosis of GBM. FIG. 32E shows that the KM median survival time for 19 patients with Mettl2b amplification ~8 months longer than that for the remaining 227 patients. This also suggests that drug targeting the gene Mettl2b or the methyltransferase-like protein that it encodes may affect not only the pathogenesis but also the prognosis of GBM.

Figure 33A:
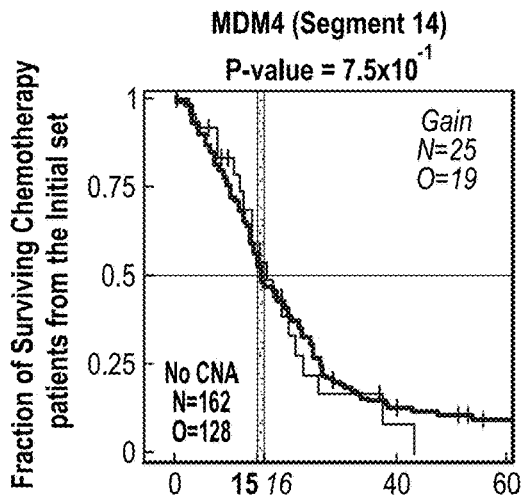
FIG. 33A-33L are diagrams illustrating survival analyses of patients undergoing chemotherapy classified by copy number changes in selected segments, according to some embodiments.
Figure 33B:
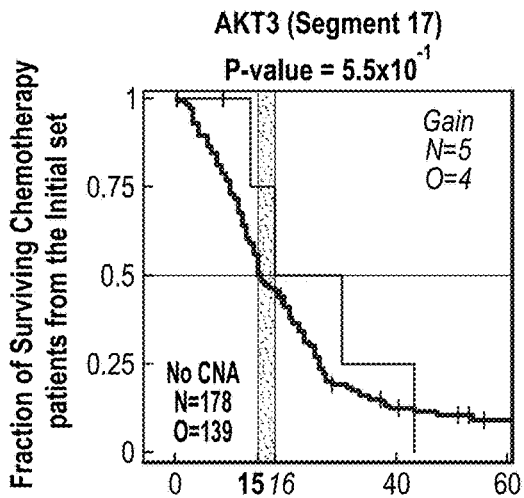
Figure 33C:
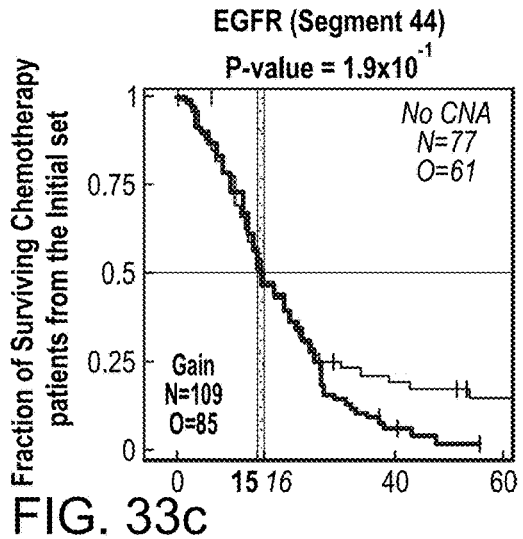
Figure 33D:
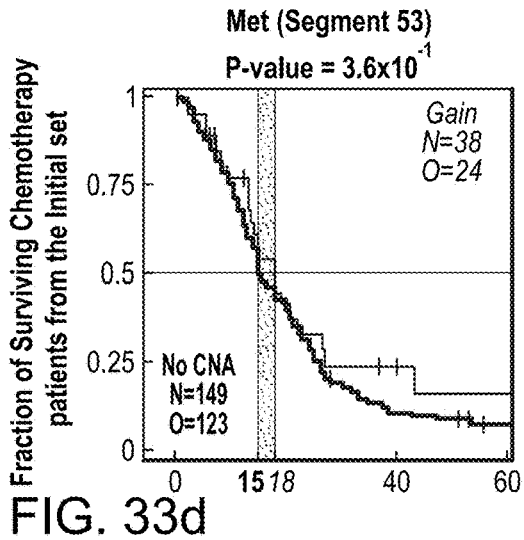
Figure 33E:
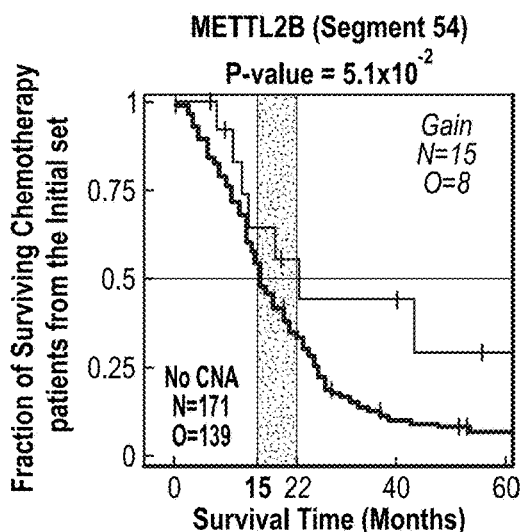
Figure 33F:
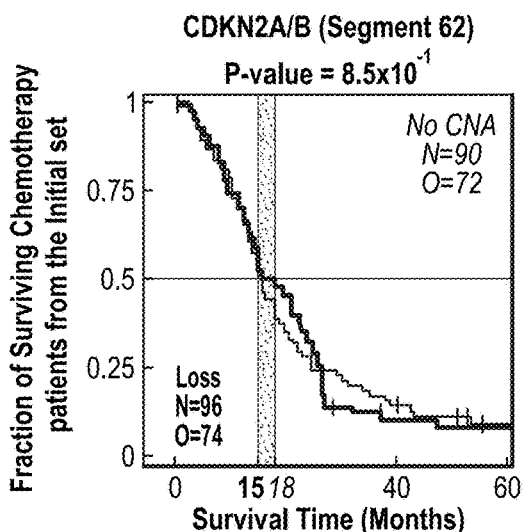
Figure 33G:
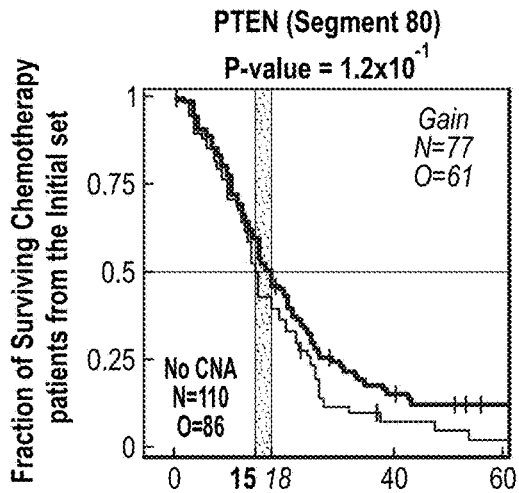
Figure 33H:
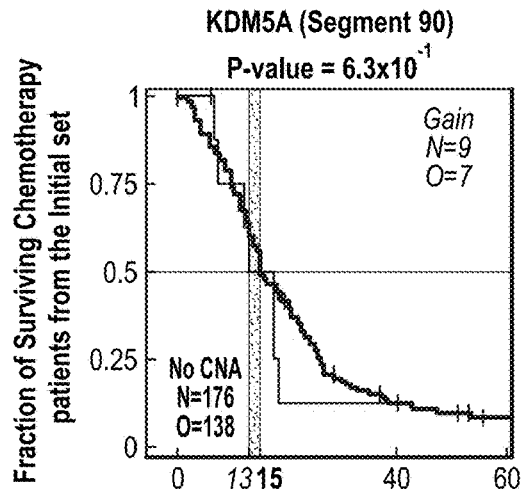
Figure 33I:
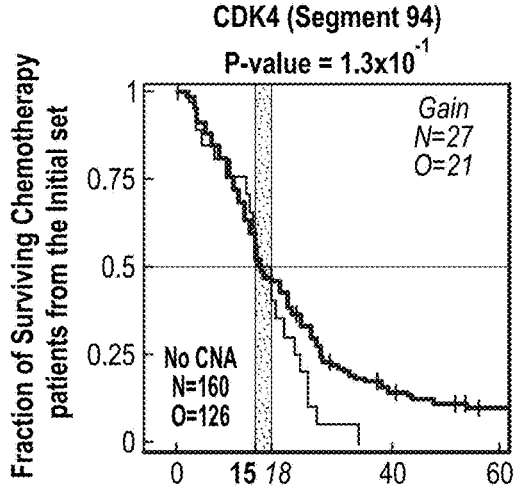
Figure 33J:
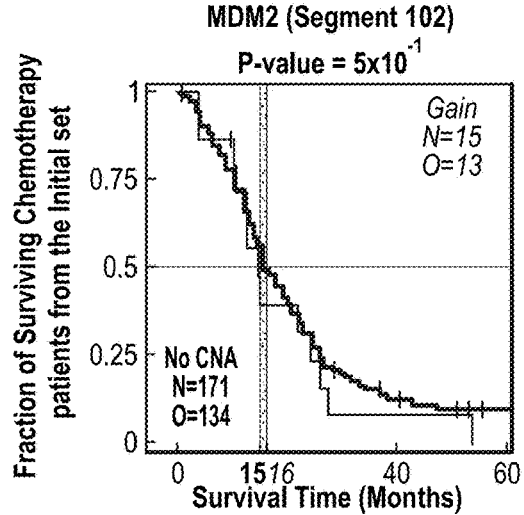
Figure 33K:
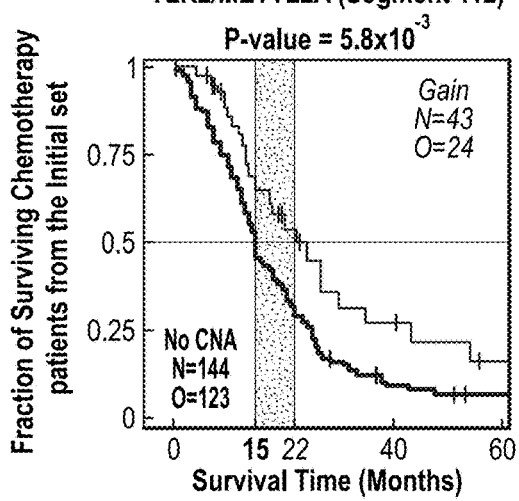
Figure 33L:
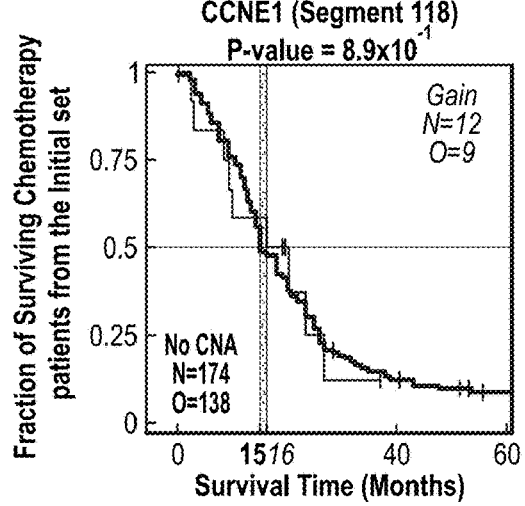

FIG. 33A-33L shows Kaplan-Meier survival analyses of patients under chemotherapy from initial set of 251 patients classified by copy number alterations. FIG. 33A is a KM analysis of 187 patients from the initial set of 251 patients, classified by copy number gain of a segment encompassing Mdm4. This figure shows almost overlapping KM curves with a KM median survival time difference of ~1 months and a corresponding log-rank test P-value ~7.5×10$^{-1}$. FIG. 33B is a KM analysis of 183 patients from the initial set of 251 patients, classified by copy number gain of a segment encompassing Akt3. This figure shows almost overlapping KM curves with a KM median survival time difference of ~3 months and a corresponding log-rank test P-value ~5.5×10$^{-1}$ FIG. 33C is a KM analysis of 186 patients from the initial set of 251 patients, classified by copy number gain of a segment encompassing Egfr. This figure shows almost overlapping KM curves with a KM median survival time difference of ~1 months and a corresponding log-rank test P-value ~1.9×10$^{-1}$. FIG. 33D is a KM analysis of 187 patients from the initial set of 251 patients, classified by copy number gain of a segment encompassing Met. This figure shows almost overlapping KM curves with a KM median survival time difference of ~3 months and a corresponding log-rank test P-value ~3.6×10$^{-1}$. FIG. 33E is a KM analysis of 186 patients from the initial set of 251 patients, classified by copy number gain of a segment (SEQ ID NO: 47) encompassing Mettl2b. This figure shows almost overlapping KM curves with a KM median survival time difference of ~7 months and a corresponding log-rank test P-value ~5.1×10$^{-2}$. FIG. 33F is a KM analysis of 186 patients from the initial set of 251 patients, classified by copy number loss of a segment encompassing Cdkn2a/b. This figure shows almost overlapping KM curves with a KM median survival time difference of ~3 month and a corresponding log-rank test P-value ~8.5×10$^{-1}$. FIG. 33G is a KM analysis of 187 patients from the initial set of 251 patients, classified by copy number loss of a segment encompassing Pten. This figure shows almost overlapping KM curves with a KM median survival time difference of ~3 months and a corresponding log-rank test P-value ~1.2×10$^{-1}$. FIG. 33H is a KM analysis of 185 patients from the initial set of 251 patients, classified by copy number gain of a segment (SEQ ID NO: 48) encompassing Jarid1a. This figure shows almost overlapping KM curves with a KM median survival time difference of ~2 months and a corresponding log-rank test P-value ~6.3×10$^{-1}$. FIG. 33I is a KM analysis of 187 patients from the initial set of 251 patients, classified by copy number gain of a segment encompassing Cdk4. This figure shows almost overlapping KM curves with a KM median survival time difference of ~3 months and a corresponding log-rank test P-value ~1.3×10$^{-1}$. FIG. 33J is a KM analysis of 186 patients from the initial set of 251 patients, classified by copy number gain of a segment encompassing Mdm2. This figure shows almost overlapping KM curves with a KM median survival time difference of ~1 months and a corresponding log-rank test P-value ~5×10$^{-1}$. FIG. 33K is a KM analysis of 187 patients from the initial set of 251 patients, classified by copy number gain of a segment (SEQ ID NO: 46) encompassing Tlk2/Mettl2a. This figure shows almost overlapping KM curves with a KM median survival time difference of ~7 months and a corresponding log-rank test P-value ~5.8×10$^{-3}$. FIG. 33L is a KM analysis of 186 patients from the initial set of 251 patients, classified by copy number gain of a segment (SEQ ID NO: 49) encompassing Ccne1. This figure shows almost overlapping KM curves with a KM median survival time difference of ~1 months and a corresponding log-rank test P-value ~8.9×10$^{-1}$.

More particularly, FIG. 33K shows that the KM survival time for the 43 chemotherapy patients with Tlk2/Mettl2a amplification is ~7 months longer than that for the remaining 144 chemotherapy patients. This suggests that drug targeting the kinase encoded by Tlk2 and/or the methyltransferase-like protein encoded by Mettl2a may affect a patient's response to chemotherapy. Thus, an amplification of the Tlk2/Mettl2a genes may lead to an increased response to chemotherapy, which can prolong the median life expectancy. FIG. 33E shows that the KM median survival time for the 15 chemotherapy patients with Mettl2b amplification is ~7 months longer than that for the remaining 171 chemotherapy patients. Mettl2b has high sequence similarity to Mettl2a. This suggests that drug targeting Mettl2b may also affect a patient's response to chemotherapy.

FIG. 34 is a table illustrating proportional hazard models of three sets of patients classified by GSVD, according to some embodiments. The Cox proportional hazard models of the three sets of patients are classified by GSVD, age at diagnosis or both. In each set of patients, the multivariate Cox proportional hazard ratios for GSVD and age may be similar and may not differ significantly from the corresponding univariate hazard ratios. This may indicate that GSVD and age are independent prognostic predictors.

FIG. 35 is a table illustrating enrichment of significant probelets in TCGA annotations, according to some embodiments. Probabilistic significance of the enrichment of the n patients, that may correspond to the largest or smallest relative copy numbers in each significant probelet, in the respective TCGA annotations are shown. The P-value of each enrichment can be calculated assuming hypergeometric probability distribution of the K annotations among N=251 patients of the initial set, and of the subset of k⊆K annotations among the subset of n patients, as described by:

$$P(k; n, N, K) = \binom{N}{n}^{-1} \sum_{i=k}^{n} \binom{K}{i}\binom{N-K}{n-i}.$$

EXAMPLE 3

This example shows that down-regulating the expression of Mettl2a gene, and also Tlk2 gene by RNAi reduces the viability of glioma cell lines.

Previous computational analyses identified the amplification of a particular DNA segment that is correlated with the brain cancer glioblastoma multiforme (GBM) patients' prognosis. This segment includes the Mettl2a gene, and also a portion of the Tlk2 gene (which encodes the TLK2 kinase,). This segment is referred herein as the "Mettl2a/Tlk2 segment."

Figure 37B:
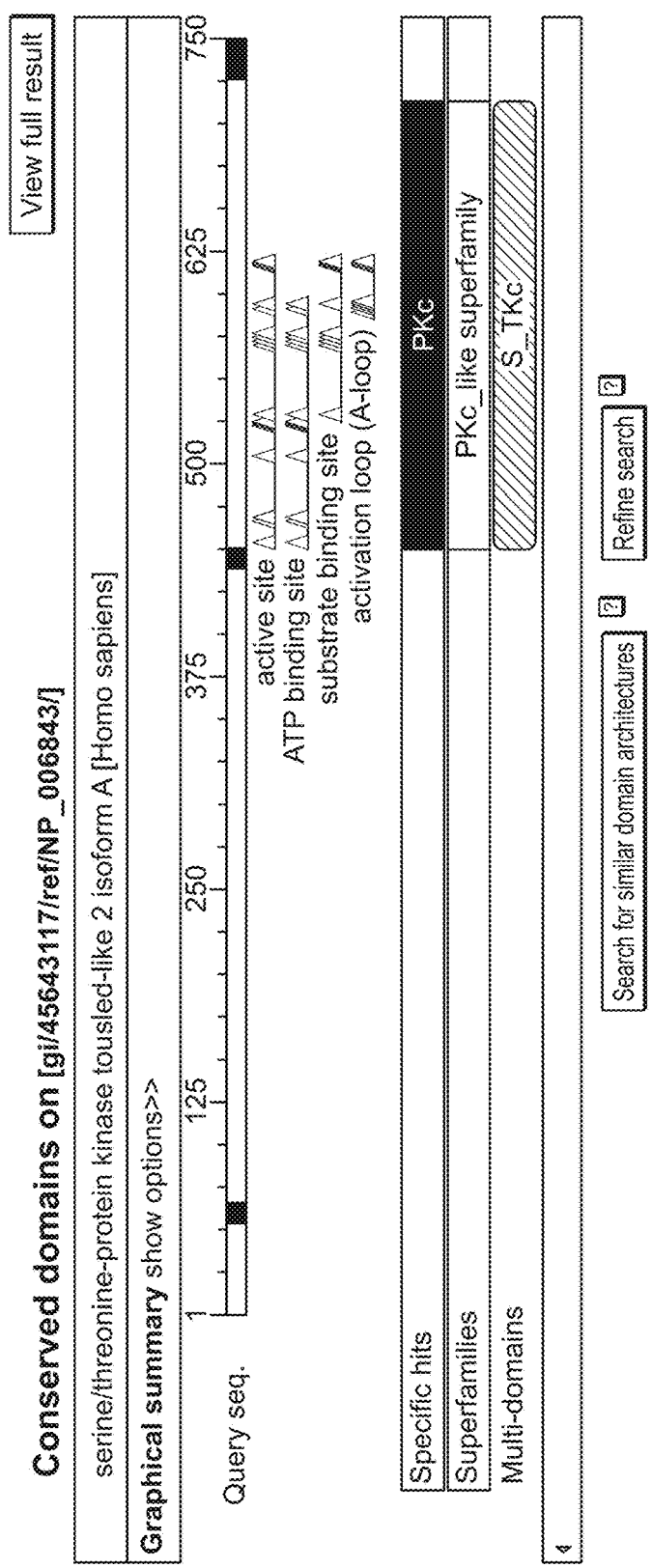
FIG. 37 is a diagram illustrating genes and their gene accession numbers that are found in chromosomal segment chr17:57,851,812-chr17:57,973,757 on NCBI36/hg18 assembly of the human genome (UCSC Genome Bioinformatics Site; genome.ucsc.edu), according to some embodiments.

Further analysis shows that the portion of the Tlk2 gene that is included in this segment starts at the 5' end of the Tlk2 gene, and ends just before the beginning of its kinase domain coding region, and after a "stop gained" genomic variation. See, FIG. 37A. The breakpoint in the Tlk2 gene results in a variant protein that does not have the kinase domain and a domain called "chromosome segregation protein SMC, common bacterial type." See, FIG. 37B. Further analysis shows that the breakpoint is at amino acid positions 176-177 of the TLK2 isoform A (NCBI Accession No. NP_006843; FIG. 37B).

Segmentation of the 450 TCGA aCGH GBM profiles showed that the Mettl2a/Tlk2 segment is present in a subset of ~2-3% of the GBM patients. The segmentation study is in agreement with previous statistics analyses, which identified all of these patients as having a gain in the Mettl2a/Tlk2 segment. The segmentation study also found that none of the patients have any other breakpoint in Tlk2 gene, beside the position that corresponds to 176-177 of the encoded protein.

In human, the Mettl2a gene and Tlk2 gene are located in the same strand, adjacent to each other, with Mettl2a at the upstream and Tlk2 at the downstream (FIG. 37A). This genomic configuration of Mettl2a and Tlk2 is conserved in the mouse and the zebrafish. Human Mettl8 and Tlk1 share the same configuration (which is also conserved in mouse and zebrafish).

The methyltransferase encoded by the Mettl2a gene has not been fully characterized. Petrossian et al. (Uncovering the Human Methyltransferasome, Molecular & Cellular Proteomics, 10, 10.1074/mcp.M110.000976) created a model, or profile, of each methyltransferase superfamily. These profiles were used to scan the human proteome database and detect novel methyltransferases. Clark et al. reports the characterization of DNA methyltransferase specificities using single-molecule, real-time DNA sequencing, Nucl. Acids Res. (2012) 40 (4): e29. doi: 10.1093/nar/gkr1146). Based on these studies, the methyltransferase encoded by the Mettl2a gene is likely a tRNA methyltransferase.

According to the NCBI UniGene page, homologues of human METTL2A include *S. cerevisiae* tRNA methyltransferase ABP140. In fact, human METTL2A, as well as the other members of its small family of human proteins, including METTL2B, METTL6, and METTL8, are all predicted orthologues of C-terminal methyltransferase Abp140. In *Saccharomyces cerevisiae,* 3-methylcytidine ($m^3C$) is found at position 32 of the tRNAs for Thr and Ser. The actin-binding protein ABP140 is the protein responsible for $m^3C$ formation in both tRNA$^{Thr1}$ and tRNA$^{Ser1}$. ABP140 consists of an N-terminal actin-binding sequence, and a C-terminal S-adenosylmethionine (Ado-Met) binding domain that catalyzes the addition of a methyl group at the 3-position of cytidine-32. See, Noma et al., Actin-binding protein ABP140 is a methyltransferase for 3-methylcytidine at position 32 of tRNAs in *Saccharomyces cerevisiae*, RNA, 2011; 17(6): 1111-1119. Sequence alignment of human METTL2Ap and yeast ABP140 (NCBI BLAST) showed that both N-terminal and C-terminal portions of METTL2A share sequence similarities with ABP140. The sequence similarity with ABP140 is not limited to the S-adenosylmethionine binding domain. As such, METTL2A may also bind to actin and involved in cell division.

Portion of the Tlk2 gene is in the same segment as Mettl2a gene, which suggests some interaction between the METTL2A protein and TLK2 protein (in particular, in a region other than the kinase domain). According to the NCBI gene page, METTL2A has been shown to bind MAPK6, a serine/threonine-protein kinase (Vinayagam et al., A directed protein interaction network for investigating intracellular signal transduction, Sci Signal. 2011 Sep. 6; 4(189):rs8). Further, TLK2's activity has been shown to be dependent upon ongoing DNA replication (Sillje et al., (1999), Mammalian homologues of the plant Tousled gene code for cell-cycle-regulated kinases with maximal activities linked to ongoing DNA replication, EMBO J. 18 (20): 5691-702). It is possible that both METTL2A and TLK2 are involved in cell division.

The NCI-60 MCF7 breast cancer cell line has a relative high mRNA Z-score. Z-score is useful for determining whether a gene is up- or down-regulated relative to the normal samples or all other tumor samples. Based on studies using this cell lines, the expression pattern of Tlk2 is believed to correlate with breast cancer risk. For example, Corpet et al. (Asf1b, the necessary Asf1 isoform for proliferation, is predictive of outcome in breast cancer, EMBO J. 2011; 30(3):480-93) reports that mammalian cells possess two isoforms of the histone H3-H4 chaperone anti-silencing function 1 (Asf1), Asf1a and Asf1b. Overexpression of Asf1b mRNA, but not ASF1a, correlated with poor clinical outcome in breast cancer. Since TLK2 was initially discovered in a screening assay for ASF1 binding proteins, the expression of TLK2 is likely associated with breast cancer risk as well. See also, Peng et al., *Transcriptional coactivator HCF-1 couples the histone chaperone Asf1b to HSV-1 DNA replication components*, Proc Natl Acad Sci USA. 2010, 107(6):2461-6.

NCBI BLASTP shows that the N-terminal region of TLK2 shares sequence similarities with ASF1b, but not ASF1a. This might suggest that the N-terminal region of TLK2 binds to ASF1b but not ASF1a. One possible explanation is that the N-terminal region of TLK2 inactivates ASF1b, because TLK2 binds to ASF1b but does not phosphorylate it.

Overexpression of Mettl2a gene was also linked with breast cancer patients' response to chemotherapy. For example, Millour, et al. (*Gene Expression Profiles Discriminate between Pathological Complete Response and Resistance to Neoadjuvant FEC100 in Breast Cancer*, Cancer Genomics & Proteomics 3: 89-96 (2006)) used cDNA nylon microarray screening to identify predictive markers for FEC100 (fluorouracil, epirubicin and cyclophosphamide treatment for breast cancer). A 14-gene classifier, including Mettl2, was generated and showed a strong classifying power. The NCI breast cancer cell line MCF7 also has a relative high mRNA Z-score of Mettl2a expression.

Accordingly, in vitro cell assays were carried out to determine whether down-regulating the expression of Mettl2a and Tlk2 gene can reduce the proliferation or viability of glioma cancer cells.

Figure 38A:
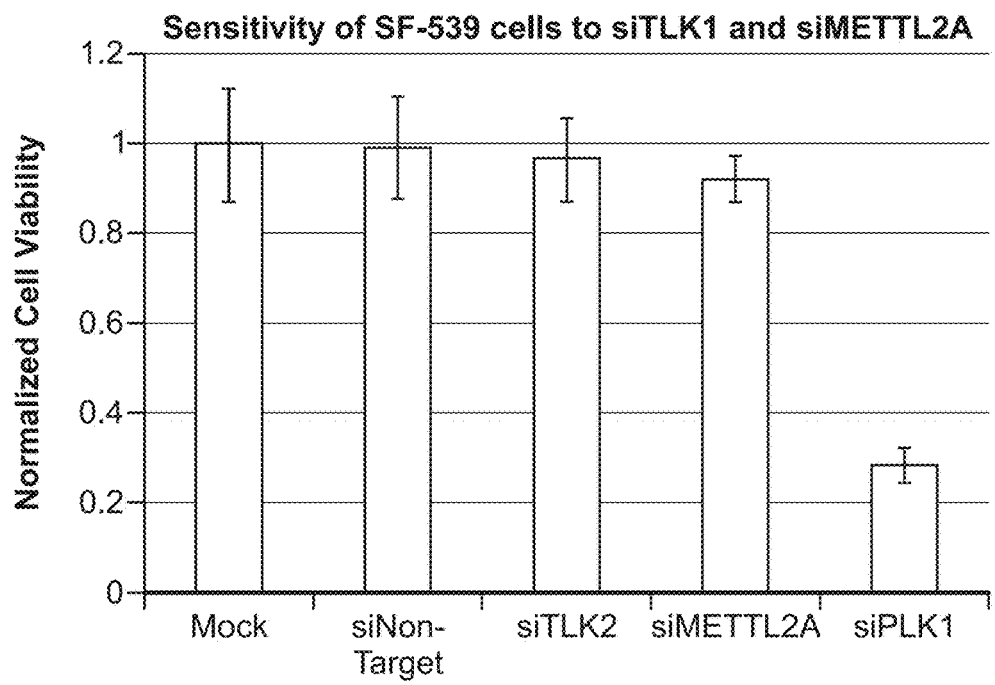
FIG. 38 shows that inhibition of the expression of Tlk2 and Mettl2a genes reduced the viability of SF-539 cells (A) and SF-295 cells (B). Samples were in triplicates, and the charts show the average of the triplicates+/−standard deviation. siRNA-mediated silencing in SF-295 cells was repeated once (also with triplicate samples). siRNA targeting Plk1 served as positive control for transfection efficiency and induction of cell death.
Figure 38B:
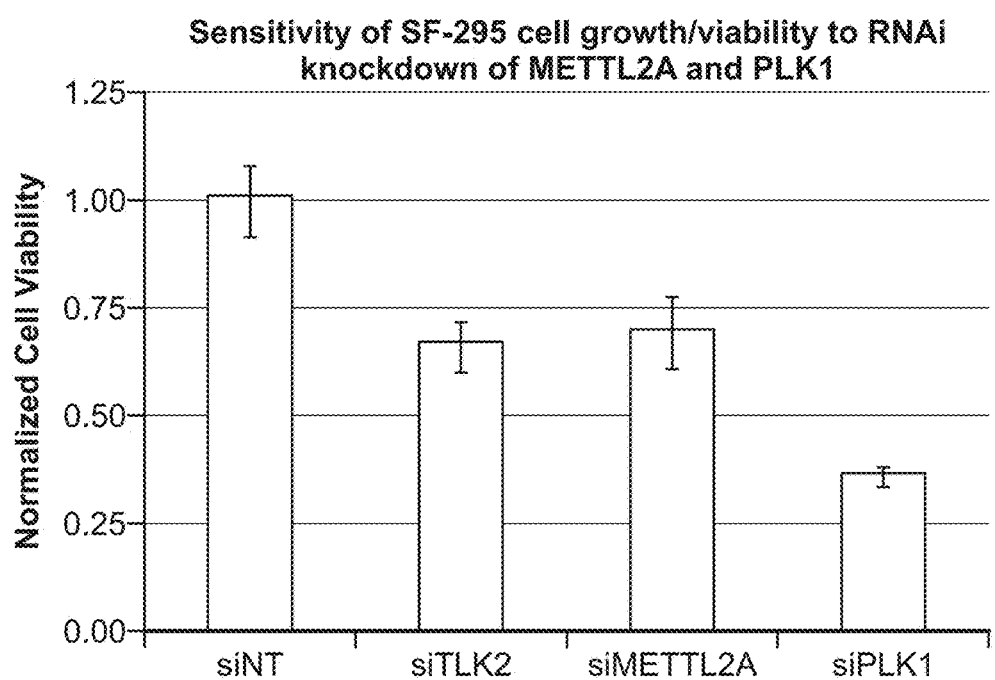

Two cell lines were used: SF-539 (FIG. 38A), derived from gliosarcoma primary tumor, and SF-295 (FIG. 38B), derived glioblastoma multiforme. See, Rutka et al., Establishment and characterization of a cell line from a human gliosarcoma, Cancer Res. 1986, 46(11):5893-902; Rutka, et al., Establishment and characterization of five cell lines derived from human malignant gliomas, Acta Neuropathologica; volume 75, (1987), 92-103, DOI: 10.1007/BF00686798. Four siRNA molecules were used: non-target siRNA, siRNA targeting Mettl2a, siRNA targeting Tlk2, siRNA targeting Plk1. Plk1 encodes Serine/threonine-protein kinase PLK1, also known as polo-like kinase 1 (PLK-1) or serine/threonine-protein kinase 13 (STPK13). Plk1 is a proto-oncogene whose overexpression is often observed in tumor cells. Knocking down PLK1 causes cell growth arrest and apoptotic induction. About 80,000 or 140,000 total cells in final volume of 10 mls growth media were plated, and the transfection of RNA was performed about 12-24 hours later. siRNA molecules were transfected using Lipofectamine, reaching a concentration of about equivalent to 40 nM siRNA per well.

As shown in FIG. 38, down-regulating the expression of Mettl2a gene by RNAi reduced the viability of the GBM cell line SF-295. The results were consistent in three different experiments, twice in cultures that went through approximately five (5) passages and once in a freshly thawed culture, each with triplicate samples. Down-regulating the expression of Tlk2 gene by RNAi also reduced the viability of the GBM cell line SF-295, in cultures that went through five passages. GBM cell line SF-295 is believed to show highest mRNA expression of Mettl2a among all NCI-60 GBM cell lines.

The results show that the reducing the expression level of Mettl2a and Tlk2 reduced the viability of GBM cell line SF-295, but not the gliosarcoma cell line SF-539.

It will be also appreciated by persons skilled in the art that numerous variations and/or modifications may be made to the specific embodiments disclosed herein, without departing from the scope or spirit of the disclosure as broadly described. The present embodiments are, therefore, to be considered in all respects illustrative and not restrictive of the subject technology.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "about", as used here, refers to +/−5% of a value.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

All publications and patents, and NCBI gene ID sequences cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the embodiments described herein.

Appendix A

GSVD Comparison of Patient-Matched Normal and Tumor aCGH Profiles Reveals Global Copy-Number Alterations Predicting Glioblastoma Multiforme Survival Cheng H. Lee[1,#], Benjamin O. Alpert[1,2,#], Preethi Sankaranarayanan[1,2], and Orly Alter[1,2,3,*]

1 Scientific Computing and Imaging (SCI) Institute,
2 Department of Bioengineering and
3 Department of Human Genetics, University of Utah, Salt Lake City, UT 84112, United States of America
* E-mail: orly@sci.utah.edu
These authors contributed equally to this work.

Abstract

Despite recent large-scale profiling efforts, the best prognostic predictor of glioblastoma multiforme (GBM) remains the patient's age at diagnosis. We describe a global pattern of tumor-exclusive co-occurring copy-number alterations (CNAs) that is correlated, possibly coordinated with GBM patients' survival and response to chemotherapy. The pattern is revealed by GSVD comparison of patient-matched but probe-independent GBM and normal aCGH datasets from The Cancer Genome Atlas (TCGA). We find that, first, the GSVD, formulated as a framework for comparatively modeling two composite datasets, removes from the pattern copy-number variations (CNVs) that occur in the normal human genome (e.g., female-specific X chromosome amplification) and experimental variations (e.g., in tissue batch, genomic center, hybridization date and scanner), without a-priori knowledge of these variations. Second, the pattern includes most known GBM-associated changes in chromosome numbers and focal CNAs, as well as several previously unreported CNAs in >3% of the patients. These include the biochemically putative drug target, cell cycle-regulated serine/threonine kinase-encoding *TLK2*, the cyclin E1-encoding *CCNE1*, and the Rb-binding histone demethylase-encoding *KDM5A*. Third, the pattern provides a better prognostic predictor than the chromosome numbers or any one focal CNA that it identifies, suggesting that the GBM survival phenotype is an outcome of its global genotype. The pattern is independent of age, and combined with age, makes a better predictor than age alone. GSVD comparison of matched profiles of a larger set of TCGA patients, inclusive of the initial set, confirms the global pattern. GSVD classification of the GBM profiles of an independent set of patients validates the prognostic contribution of the pattern.

Introduction

Glioblastoma multiforme (GBM), the most common brain tumor in adults, is characterized by poor prognosis [1]. GBM tumors exhibit a range of copy-number alterations (CNAs), many of which play roles in the cancer's pathogenesis [2–4]. Recent large-scale gene expression [5–7] and DNA methylation [8] profiling efforts identified GBM molecular subtypes, distinguished by small numbers of biomarkers. However, despite these efforts, GBM's best prognostic predictor remains the patient's age at diagnosis [9, 10].

To identify CNAs that might predict GBM patients' survival, we comparatively model patient-matched GBM and normal array CGH (aCGH) profiles from The Cancer Genome Atlas (TCGA) by using the generalized singular value decomposition (GSVD) [11]. Previously, we formulated the GSVD as a framework for comparatively modeling two composite datasets [12] (see also [13]), and illustrated its application in sequence-independent comparison of DNA microarray data from two organisms, where, as we showed, the mathematical variables and operations of the GSVD represent experimental or biological reality. The variables, subspaces of significant patterns that are uncovered in the simultaneous decomposition of the two datasets and are mathematically significant in either both (i.e., common to both) datasets or only one (i.e., exclusive to one) of the datasets, correlate with cellular programs that are either conserved in both or unique to only one of the organisms, respectively. The operation of reconstruction in the subspaces that are mathematically common to both datasets outlines the biological similarity in the regulation of the cellular programs that are conserved across the species. Reconstruction in the common and exclusive subspaces of either dataset outlines the differential regulation of the conserved relative to the unique programs in the corresponding organism.

We now find that also in probe-independent comparison of aCGH data from patient-matched tumor and normal samples, the mathematical variables of the GSVD, i.e., shared tumor and normal patterns of copy-number variation across the patients and the corresponding tumor- and normal-specific patterns of copy-number variation across the tumor and normal probes, represent experimental or biological reality. Patterns that are mathematically significant in both datasets represent copy-number variations (CNVs) in the normal human genome that are conserved in the tumor genome (e.g., female-specific X chromosome amplification). Patterns that are mathematically significant in the normal but not the tumor dataset represent experimental variations that exclusively affect the normal dataset. Similarly, some patterns that are mathematically significant in the tumor but not the normal dataset represent experimental variations that exclusively affect the tumor dataset.

One pattern, that is mathematically significant in the tumor but not the normal dataset, represents tumor-exclusive co-occurring CNAs, including most known GBM-associated changes in chromosome numbers and focal CNAs, as well as several previously unreported CNAs in >3% of the patients [14]. This pattern is correlated, possibly coordinated with GBM patients' survival and response to therapy. We find that the pattern provides a prognostic predictor that is better than the chromosome numbers or any one focal CNA that it identifies, suggesting that the GBM survival phenotype is an outcome of its global genotype. The pattern is independent of age, and combined with age, makes a better predictor than age alone.

We confirm our results with GSVD comparison of matched profiles of a larger set of TCGA patients, inclusive of the initial set. We validate the prognostic contribution of the pattern with GSVD classification of the GBM profiles of a set of patients that is independent of both the initial set and the inclusive confirmation set [15].

Methods

To compare TCGA patient-matched GBM and normal (mostly blood) aCGH profiles (Dataset S1 and Mathematica Notebooks S1 and S2), Agilent Human aCGH 244A-measured 365 tumor and 360 normal profiles were selected, corresponding to the same $N=251$ patients. Each profile lists $\log_2$ of the TCGA level 1 background-subtracted intensity in the sample relative to the Promega DNA reference, with signal to background >2.5 for both the sample and reference in more than 90% of the 223,603 autosomal probes on the microarray. The profiles are organized in one tumor and one normal dataset, of $M_1=212,696$ and $M_2=211,227$ autosomal and X chromosome probes, each probe with valid data in at least 99% of either the tumor or normal arrays, respectively. Each profile is centered at its autosomal median copy number. The <0.2% missing data entries in the tumor and normal datasets are estimated by using singular value decomposition (SVD) as described [12, 16]. Within each set, the medians of profiles of samples from the same patient are taken.

The structure of the patient-matched but probe-independent tumor and normal datasets $D_1$ and $D_2$, of $N$ patients, i.e., $N$-arrays × $M_1$-tumor and $M_2$-normal probes, is of an order higher than that of a single matrix. The patients, the tumor and normal probes as well as the tissue types, each represent a degree of freedom. Unfolded into a single matrix, some of the degrees of freedom are lost and much of the information in the datasets might also be lost.

To compare the tumor and normal datasets, therefore, we use the GSVD, formulated to simultaneously separate the paired datasets into paired weighted sums of $N$ outer products of two patterns each: One pattern of copy-number variation across the patients, i.e., a "probelet" $v_n^T$, which is identical for both the tumor and normal datasets, combined with either the corresponding tumor-specific pattern of copy-number variation across the tumor probes, i.e., the "tumor arraylet" $u_{1,n}$, or the corresponding normal-specific pattern across the normal probes, i.e., the "normal arraylet" $u_{2,n}$ (Figure 36), $$D_1 = U_1 \Sigma_1 V^T = \sum_{n=1}^{N} \sigma_{1,n} u_{1,n} \otimes v_n^T,$$
$$D_2 = U_2 \Sigma_2 V^T = \sum_{n=1}^{N} \sigma_{2,n} u_{2,n} \otimes v_n^T. \quad (1)$$

The probelets are, in general, non-orthonormal, but are normalized, such that $v_n^T v_n = 1$. The tumor and normal arraylets are orthonormal, such that $U_1^T U_1 = U_2^T U_2 = I$.

The significance of the probelet $v_n^T$ in either the tumor or normal dataset, in terms of the overall information that it captures in this dataset, is proportional to either of the weights $\sigma_{1,n}$ or $\sigma_{2,n}$, respectively (Figure 22), $$p_{1,n} = \sigma_{1,n}^2 / \sum_{n=1}^{N} \sigma_{1,n}^2,$$
$$p_{2,n} = \sigma_{2,n}^2 / \sum_{n=1}^{N} \sigma_{2,n}^2. \quad (2)$$

The "generalized normalized Shannon entropy" of each dataset, $$0 \leq d_1 = (\log N)^{-1} \sum_{n=1}^{N} p_{1,n} \log p_{1,n} \leq 1,$$
$$0 \leq d_2 = (\log N)^{-1} \sum_{n=1}^{N} p_{2,n} \log p_{2,n} \leq 1, \quad (3)$$

measures the complexity of the data from the distribution of the overall information among the different probelets and corresponding arraylets. An entropy of zero corresponds to an ordered and redundant dataset in which all the information is captured by a single probelet and its corresponding arraylet. An entropy of one corresponds to a disordered and random dataset in which all probelets and arraylets are of equal significance. The significance of the probelet $v_n^T$ in the tumor dataset relative to its significance in the normal dataset is defined in terms of an "angular distance" $\theta_n$ that is proportional to the ratio of these weights, $$-\pi/4 \leq \theta_n = \arctan(\sigma_{1,n}/\sigma_{2,n}) - \pi/4 \leq \pi/4. \quad (4)$$

An angular distance of $\pm \pi/4$ indicates a probelet that is exclusive to either the tumor or normal dataset, respectively, whereas an angular distance of zero indicates a probelet that is common to both the tumor and normal datasets. The probelets are arranged in decreasing order of their angular distances, i.e., their significance in the tumor dataset relative to the normal dataset.

We find that the two most tumor-exclusive mathematical patterns of copy-number variation across the patients, i.e., the first probelet (Figure 26) and the second probelet (Figure 20 a-c), with angular distances $> 2\pi/9$, are also the two most significant probelets in the tumor dataset, with ~11% and 22% of the information in this dataset, respectively. Similarly, the five most normal-exclusive probelets, the 247th to 251st probelets (Figures 27-31), with angular distances $\lesssim -\pi/6$, are among the seven most significant probelets in the normal dataset, capturing together ~56% of the information in this dataset.

The 246th probelet (Figure 20 d-f), which is the second most significant probelet in the normal dataset with ~8% of the information, is relatively common to the normal and tumor datasets with an angular distance $> -\pi/6$.

To biologically or experimentally interpret these significant probelets, we correlate or anticorrelate each probelet with relative copy-number gain or loss across a group of patients according to the TCGA annotations of the group of $n$ patients with largest or smallest relative copy numbers in this probelet among all $N$ patients, respectively. The $P$-value of a given association is calculated assuming hypergeometric probability distribution of the $K$ annotations among the $N$ patients, and of the subset of $k \subseteq K$ annotations among the subset of $n$ patients, as described [17], $P(k; n, N, K) = \binom{N}{n}^{-1} \sum_{i=k}^{n} \binom{K}{i}\binom{N-K}{n-i}$ (Table 1). We visualize the copy-number distribution between the annotations that are associated with largest or smallest relative copy numbers in each probelet by using boxplots, and by calculating the corresponding Mann-Whitney-Wilcoxon $P$-value (Figures 32-33). To interpret the corresponding tumor and normal arraylets, we map the tumor and normal probes onto the National Center for Biotechnology Information (NCBI) human genome sequence build 36, by using the Agilent Technologies probe annotations posted at the University of California at Santa Cruz (UCSC) human genome browser [18,19]. We segment each arraylet and assign each segment a $P$-value by using the circular binary segmentation (CBS) algorithm as described (Dataset S2) [20,21]. We find that the significant probelets and corresponding tumor and normal arraylets, as well as their interpretations, are robust to variations in the preprocessing of the data, e.g., in the data selection cutoffs.

Results

We find that, first, the GSVD identifies significant experimental variations that exclusively affect either the tumor or the normal dataset, as well as CNVs that occur in the normal human genome and are common to both datasets, without a-priori knowledge of these variations. The mathematically most tumor-exclusive probelet, i.e., the first probelet (Figure 26), correlates with tumor-exclusive experimental variation in the genomic center where the GBM samples were hybridized at, with the $P$-values $< 10^{-5}$ (Figures 35 and 32). Similarly, the five most normal-exclusive probelets, i.e., the 247th to 251st probelets (Figures 27-31), correlate with experimental variations among the normal samples in genomic center, DNA microarray hybridization or scan date as well as the tissue batch and hybridization scanner, with $P$-values $< 10^{-3}$. Consistently, the corresponding arraylets, i.e., the first tumor arraylet and the 247th to 251st normal arraylets, describe copy-number distributions which are approximately centered at zero with relatively large, chromosome-invariant widths.

Figures 20A, 20B, 20C:
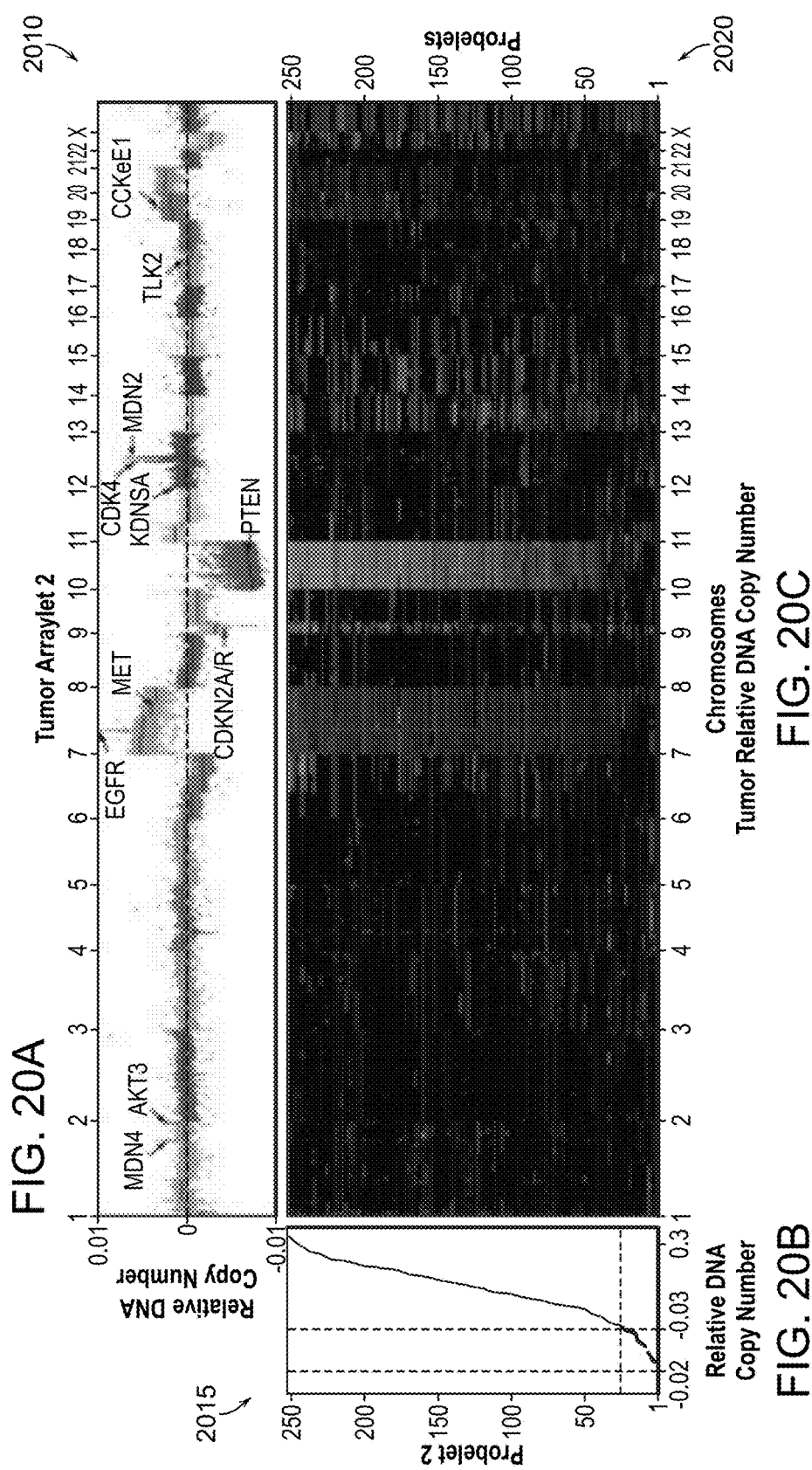
FIG. 20 is a diagram illustrating significant probelets and corresponding tumor and normal arraylets uncovered by GSVD of the patient-matched GBM and normal blood aCGH profiles, according to some embodiments.
Figures 20D, 20E, 20F:
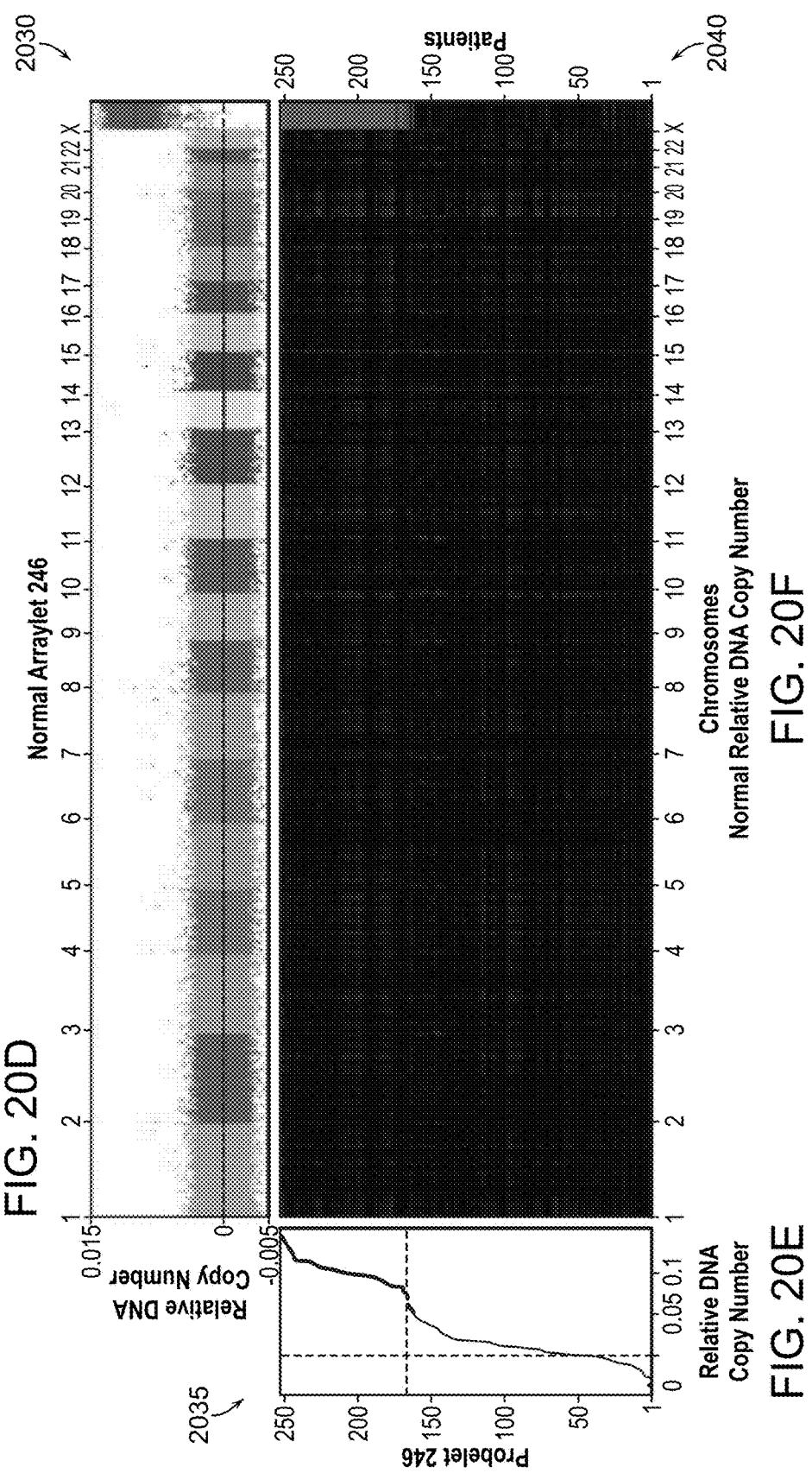

The 246th probelet (Figure 20e), which is mathematically approximately common to both the normal and tumor datasets, describes copy-number amplification in the female relative to the male patients that is biologically common to both the normal and tumor datasets. Consistently, both the 246th normal arraylet (Figure 20d) and 246th tumor arraylet describe an X chromosome-exclusive amplification. The $P$-values are $< 10^{-38}$ (Table 1 and Figure 33). To assign the patients gender, we calculate for each patient the standard deviation of the mean X chromosome number from the autosomal genomic mean in the patient's normal profile (Figure 20f). Patients with X chromosome amplification greater than twice the standard deviation are assigned the female gender. For three of the patients, this copy-number gender assignment conflicts with the TCGA gender annotation. For three additional patients, the TCGA gender annotation is missing. In all these cases, the classification of the patients by the 246th probelet agrees with the copy-number assignment.

Second, we find that the GSVD identifies a global pattern of tumor-exclusive co-occurring CNAs that includes most known GBM-associated changes in chromosome numbers and focal CNAs. This global pattern is described by the second tumor arraylet (Figure 20a and Dataset S3). The second most tumor-exclusive probelet (Figure 20b), which describes the corresponding copy-number variation across the patients, is the most significant probelet in the tumor dataset. Dominant in the global pattern, and frequently observed in GBM samples [2], is a co-occurrence of a gain of chromosome 7 and losses of chromosome 10 and the short arm of chromosome 9 (9p). To assign a chromosome gain or loss, we calculate for each tumor profile the standard deviation of the mean chromosome number from the autosomal genomic mean, excluding the outlying chromosomes 7, 9p and 10. The gain of chromosome 7 and the losses of chromosomes 10 and 9p are greater than twice the standard deviation in the global pattern as well as the tumor profiles of ~20%, 41% and 12% of the patients, respectively.

Focal CNAs that are known to play roles in the origination and development of GBM and are described by the global pattern include amplifications of segments containing the genes *MDM4* (1q32.1), *AKT3* (1q44), *EGFR* (7p11.2), *MET* (7q31.2), *CDK4* (12q14.1) and *MDM2* (12q15), and deletions of segments containing the genes *CDKN2A/B* (9p21.3) and *PTEN* (10q23.31), that occur in >3% of the patients. To assign a CNA in a segment, we calculate for each tumor profile the mean segment copy number. Profiles with segment amplification or deletion greater than twice the standard deviation from the autosomal genomic mean, excluding the outlying chromosomes 7, 9p and 10, or greater than one standard deviation from the chromosomal mean, when this deviation is consistent with the deviation from the genomic mean, are assigned a segment gain or loss, respectively. The frequencies of amplification or deletion we observe for these segments are similar to the reported frequencies of the corresponding focal CNAs [4].

Novel CNAs, previously unrecognized in GBM, are also revealed by the global pattern [14]. These include an amplification of a segment that contains *TLK2* (17q23.2) in ~22% of the patients, with the corresponding CBS $P$-value$< 10^{-140}$. Copy-number amplification of *TLK2* has been correlated with overexpression in several other cancers [22,23]. The human gene *TLK2*, with homologs in the plant *Arabidopsis thaliana* but not in the yeast *Saccharomyces cerevisiae*, encodes for a multicellular organisms-specific serine/threonine protein kinase, a biochemically putative drug target [24], which activity is directly dependent on ongoing DNA replication [25]. On the same segment with *TLK2*, we also find the gene *METTL2A*. Another amplified segment (CBS $P$-value$< 10^{-13}$) contains the homologous gene *METTL2B* (7q32.1). Overexpression of *METTL2A/B* was linked with prostate cancer metastasis [26], cAMP response element-binding (CREB) regulation in myeloid leukemia [27], and breast cancer patients' response to chemotherapy [28].

An amplification of a segment (CBS $P$-value$< 10^{-145}$) encompassing the cyclin E1-encoding *CCNE1* (19q12) is revealed in ~4% of the patients. Cyclin E1 regulates entry into the DNA synthesis phase of the cell division cycle. Copy number increases of *CCNE1* have been linked with multiple cancers [29,30], but not GBM. Amplicon-dependent expression of *CCNE1*, together with the genes *POP4*, *PLEKHF1*, *C19orf12* and *C19orf2* that flank *CCNE1* on this segment, was linked with primary treatment failure in ovarian cancer, possibly due to rapid repopulation of the tumor after chemotherapy [31].

Another rare amplification in ~4% of the patients, of a segment (CBS $P$-value$< 10^{-28}$) that overlaps with the 5' end of *KDM5A* (12p13.33), is also revealed. The protein encoded by *KDM5A*, a retinoblastoma tumor suppressor (Rb)-binding lysine-specific histone demethylase [32], has been recently implicated in cancer drug tolerance [33]. The same amplified segment includes the solute carrier (SLC) sodium-neurotransmitter symporters *SLC6A12/13*, biochemically putative carriers of drugs that might overcome the blood-brain barrier [34]. On the same segment we also find *IQSEC3*, a mature neuron-specific guanine nucleotide exchange factor (GEF) for the ADP-ribosylation factor (ARF) *ARF1*, a key regulator of intracellular membrane traffic [35].

Note that although the tumor samples exhibit female-specific X chromosome amplification (Figure 20c), the second tumor arraylet exhibits an unsegmented X chromosome copy-number distribution, that is approximately centered at zero with a relatively small width. This illustrates the mathematical separation of the global pattern of tumor-exclusive co-occurring CNAs, that is described by the second tumor arraylet, from all other biological and experimental variations that compose either the tumor or the normal dataset, such as the gender variation that is common to both datasets, and is described by the 246th probelet and the corresponding 246th tumor and 246th normal arraylets.

Third, we find that the GSVD classifies the patients into two groups of significantly different prognoses.

Figure 40:
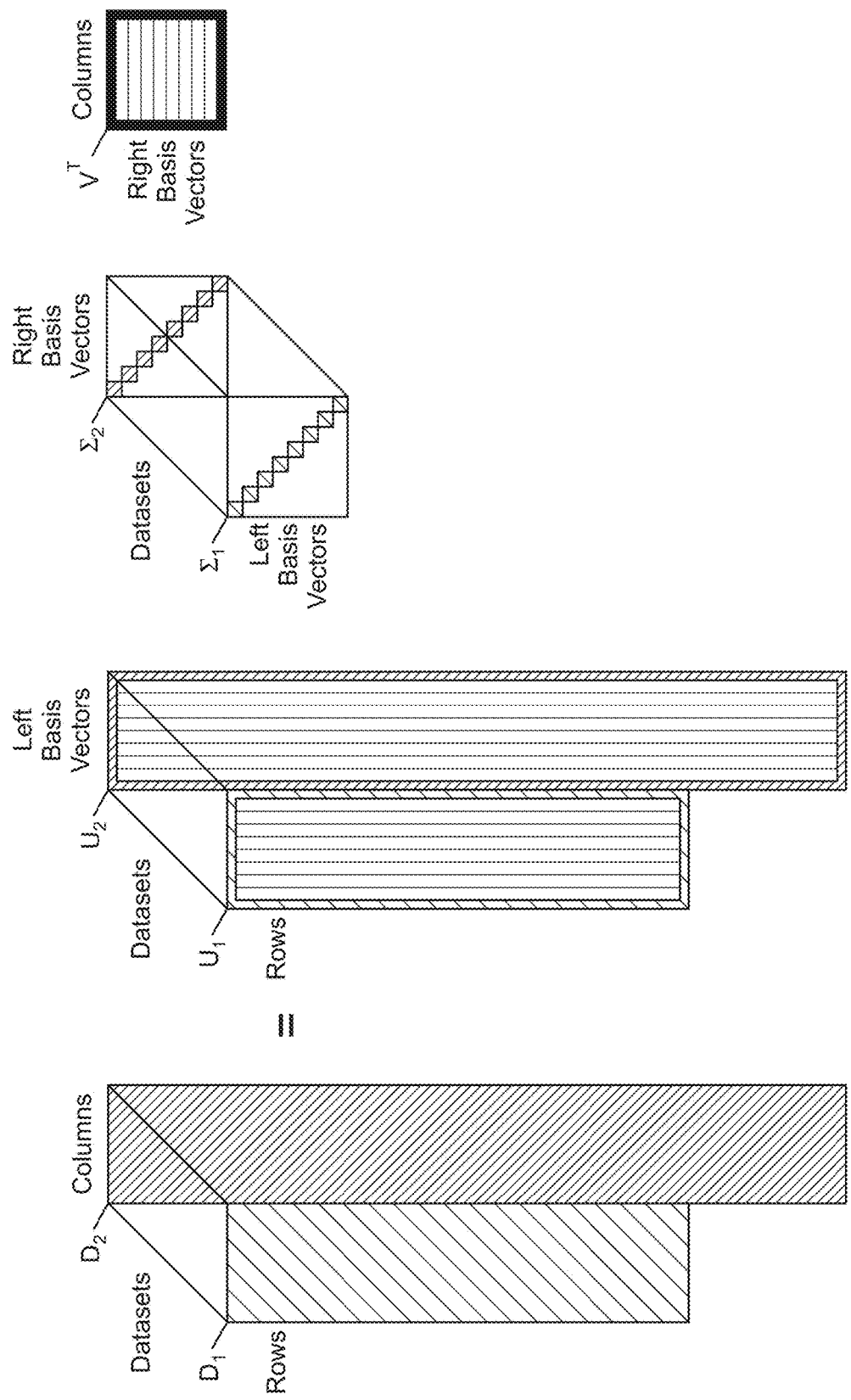
FIG. 40 is a diagram illustrating that the GSVD of two matrices $D_1$ and $D_2$ is reformulated as a linear transformation of the two matrices from the two rows×columns spaces to two reduced and diagonalized left basis vectors×right basis vectors spaces, according to some embodiments. The right basis vectors are shared by both datasets. Each right basis vector corresponds to two left basis vectors.

The classification is according to the copy numbers listed in the second probelet, which correspond to the weights of the second tumor arraylet in the GBM aCGH profiles of the patients. A group of 227 patients, 224 of which with TCGA annotations, displays high (>0.02) relative copy numbers in the second probelet, and a Kaplan-Meier (KM) [36] median survival time of ~13 months (Figure 21a). A group of 23 patients, i.e., ~10% of the patients, displays low, approximately zero, relative copy numbers in the second probelet, and a KM median survival time of ~29 months, which is more than twice longer than that of the previous group. The corresponding log-rank test $P$-value is $< 10^{-3}$. The univariate Cox [37] proportional hazard ratio is 2.3, with a $P$-value $< 10^{-2}$ (Table S1 in Appendix S1), meaning that high relative copy numbers in the second probelet confer more than twice the hazard of low numbers. Note that the cutoff of ±0.02 was selected to enable classification of as many of the patients as possible. Only one of the 251 patients has a negative copy number in the second probelet <-0.02, and remains unclassified. This patient is also missing the TCGA annotations. Survival analysis of only the chemotherapy patients classified by GSVD gives similar results (Figures 40 and 41a). The $P$-values are calculated without adjusting for multiple comparisons [38]. We observe, therefore, that a negligible weight of the global pattern in a patient's GBM aCGH profile is indicative of a significantly longer survival time, as well as an improved response to treatment among chemotherapy patients.

A mutation in the gene *IDH1* was recently linked with improved GBM prognosis [1,6] and associated with a CpG island methylator phenotype [8]. We find, however, only seven patients (six chmeotherapy patients), i.e., <3%, with *IDH1* mutation. This is less than a third of the 23 patients in the long-term survival group defined by the global pattern. The corresponding survival analyses are, therefore, statistically insignificant (Figures 25 and 42).

Chromosome 10 loss, chromosome 7 gain and even loss of 9p, which are dominant in the global pattern, have been suggested as indicators of poorer GBM prognoses for over two decades [2,3]. However, the KM survival curves for the groups of patients with either one of these chromosome number changes almost overlap the curves for the patients with no changes (Figure 23). The log-rank test $P$-values for all three classifications are $\gtrsim 10^{-1}$, with the median survival time differences $\lesssim 3$ months. Similarly, in the KM survival analyses of the groups of patients with either a CNA or no CNA in either one of the 130 segments identified by the global pattern (Figure 24), log-rank test $P$-values $< 5 \times 10^{-2}$ are calculated for only 12 of the classifications. Of these, only six correspond to a KM median survival time difference that is $\gtrsim 5$ months, approximately a third of the ~16 months difference observed for the GSVD classification.

Figure 43A:
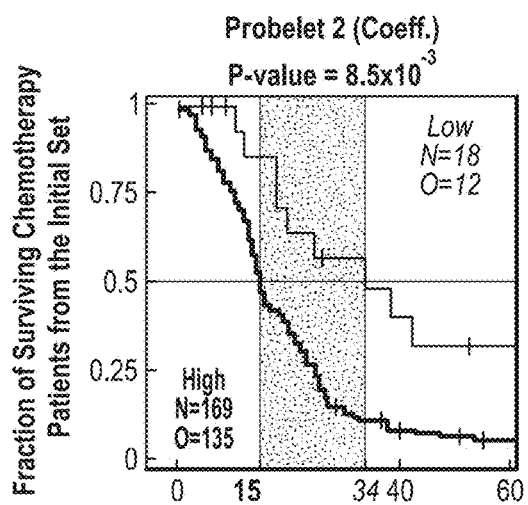
FIG. 43 is a diagram illustrating the Kaplan-Meier (KM) survival analyses of only the chemotherapy patients from the three sets classified by GSVD, according to some embodiments.
Figure 43B:
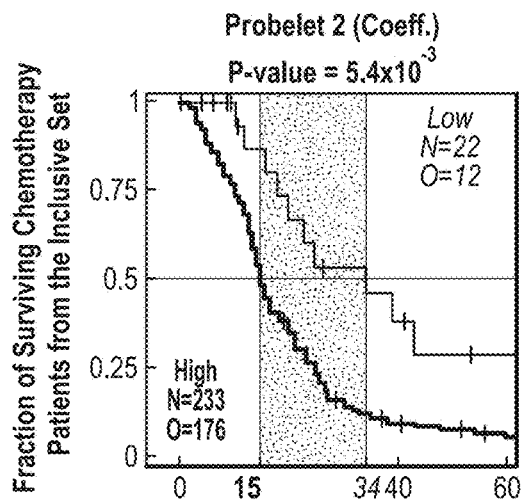
Figure 43C:
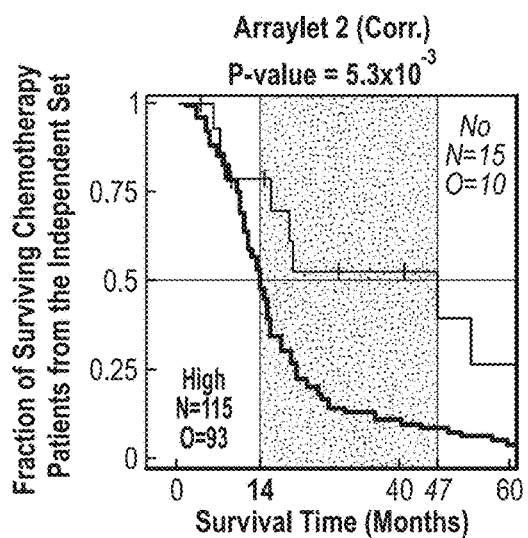
Figure 44:
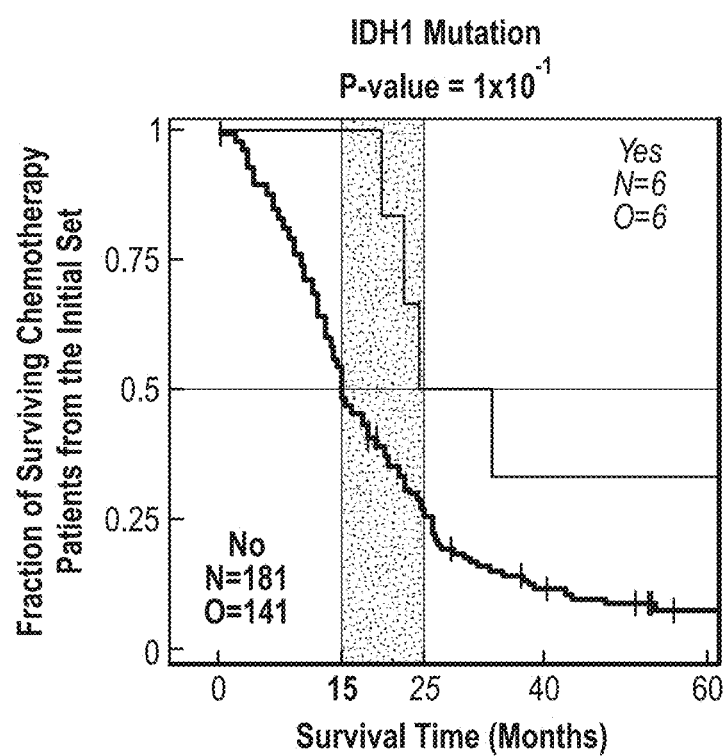
FIG. 44 is a diagram illustrating the KM survival analysis of only the chemotherapy patients in the initial set, classified by a mutation in IDH1, according to some embodiments.

One of these segments contains the genes *TLK2* and *METTL2A* and another segment contains the homologous gene *METTL2B*, previously unrecognized in GBM. The KM median survival times we calculate for the 56 patients with *TLK2/METTL2A* amplification and, separately, for the 19 patients with *METTL2B* amplifications are ~5 and 8 months longer than that for the remaining patients in each case. Similarly, the KM median survival times we calculate for the 43 chemotherapy patients with *TLK2/METTL2A* amplification and, separately, for the 15 chemotherapy patients with *METTL2B* amplification, are both ~7 months longer than that for the remaining chemotherapy patients in each case (Figure 43). This suggests that drug-targeting the kinase that *TLK2* encodes and/or the methyltransferase-like proteins that *METTL2A/B* encode may affect not only the pathogenesis but also the prognosis of GBM as well as the patient's response to chemotherapy.

Taken together, we find that the global pattern provides a better prognostic predictor than the chromosome numbers or any one focal CNA that it identifies. This suggests that the GBM survival phenotype is an outcome of its global genotype.

Despite the recent genome-scale molecular profiling efforts, age at diagnosis remains the best prognostic predictor for GBM in clinical use. The KM median survival time difference between the patients >50 or <50 years old at diagnosis is ~11 months, approximately two thirds of the ~16 months difference observed for the global pattern, with the log-rank test $P$-value $< 10^{-4}$ (Figure 21b). The univariate Cox proportional hazard ratio we calculate for age is 2, i.e., similar to that for the global pattern. Taken together, the prognostic contribution of the global pattern is comparable to that of age. Similarly we find that the prognostic contribution of the global pattern is comparable to that of chemotherapy (Figure 10a).

To examine whether the weight of the global pattern in a patient's GBM aCGH profile is correlated with the patient's age at diagnosis, we classify the patients into four groups, with prognosis of longer-term survival according to both, only one or neither of the classifications (Figure 21c). The KM curves for these four groups are significantly different, with the log-rank test $P$-value $< 10^{-4}$. Within each age group, the subgroup of patients with low relative copy numbers in the second probelet consistently exhibits longer survival than the remaining patients. The median survival time of the 16 patients <50 years old at diagnosis with low copy numbers in the second probelet is ~34 months, almost three times longer than the ~12 months median survival time of the patients >50 years old at diagnosis with high numbers in the second probelet. The multivariate Cox proportional hazard ratios for the global pattern and age are 1.8 and 1.7, respectively, with both corresponding $P$-values $< 3 \times 10^{-2}$. These ratios are similar, meaning that both a high weight of the global pattern in a patient's GBM aCGH profile and an age >50 years old at diagnosis confer similar relative hazard. These ratios also do not differ significantly from the univariate ratios of 2.3 and 2 for the global pattern and age, respectively. Taken together, the prognostic contribution of the global pattern is not only comparable to that of age, but is also independent of age. Combined with age, the global pattern makes a better predictor than age alone. Similarly, we find that the global pattern is independent of chemotherapy (Figure 10b).

To confirm the global pattern, we use GSVD to compare matched profiles of a larger, more recent, set of 344 TCGA patients, that is inclusive of the initial set of 251 patients [15]. Agilent Human aCGH 244A-measured 458 tumor and 459 normal profiles were selected, corresponding to the inclusive confirmation set of $N=344$ patients (Dataset S4). The profiles, centered at their autosomal median copy numbers, are organized in one tumor and one normal dataset, of $M_1=200,139$ and $M_2=198,342$ probes, respectively. Within each set, the medians of profiles of samples from the same patient are taken after estimating missing data by using SVD. We find that the significant probelets and corresponding tumor and normal arraylets, as well as their interpretations, are robust to the increase from 251 patients in the initial set to 344 patients in the inclusive confirmation set, and the accompanying decreases in tumor and normal probes, respectively.

The second tumor arraylet computed by GSVD for the 344 patients of the inclusive confirmation set correlates with that of the initial set, with the correlation ~0.99. To classify the patients according to the copy numbers listed in the corresponding second probelet of the inclusive confirmation set, the classification cutoff ±0.02 of the initial set of 251 patients is scaled by the norm of the copy numbers listed for these patients, resulting in the cutoff ±0.017. Only four of the 251 patients in the initial set, i.e., ~1.5%, with copy numbers that are near the classification cutoffs of both sets, change classification. Of the 344 patients, we find that 315 patients, 309 with TCGA annotations, display high (>0.017) and 27, i.e., ~8%, display low, approximately zero, relative copy numbers in the second probelet. Only two patients, one missing TCGA annotations, remain unclassified with large negative (<-0.017) copy numbers in the second probelet. Survival analyses of the inclusive confirmation set of 344 patients give qualitatively the same results as these of the initial set of 251 patients. These analyses confirm that a negligible weight of the global pattern, which is described by the second tumor arraylet, i.e., a low copy number in the second probelet, is indicative of a significantly longer survival time (Figure 21d). Survival analysis of only the chemotherapy patients in the inclusive confirmation set classified by GSVD gives similar results (Figure 41b). These analyses confirm that the prognostic contribution of the global pattern is comparable to that of age (Figure 21e) and is independent of age (Figure 21f). Similarly, we confirm that the global pattern is independent of chemotherapy (Figures 10 c and d in Appendix S1).

To validate the prognostic contribution of the global pattern, we classify GBM profiles of an independent set of 184 TCGA patients, that is mutually exclusive of the initial set of 251 patients. Agilent Human aCGH 244A-measured 280 tumor profiles were selected, corresponding to the independent validation set of 184 patients with available TCGA status annotations (Dataset S5). Each profile lists relative copy numbers in more than 97.5% of the 206,820 autosomal probes among the $M_1=212,696$ probes that define the second tumor arraylet computed by GSVD for the 251 patients of the initial set. Medians of profiles of samples from the same patient are taken. To classify the 184 patients according to the correlations of their GBM profiles with the second tumor arraylet of the initial set, the classification cutoff of the initial set of 251 patients is scaled by the norm of the correlations calculated for these patients, resulting in the cutoff ±0.15. For the profiles of 162 patients we calculate high (>0.15) and for 21, i.e., ~11%, low, approximately zero, correlation with the second tumor arraylet. One patient remains unclassified with a large negative (<-0.15) correlation.

Figure 41:
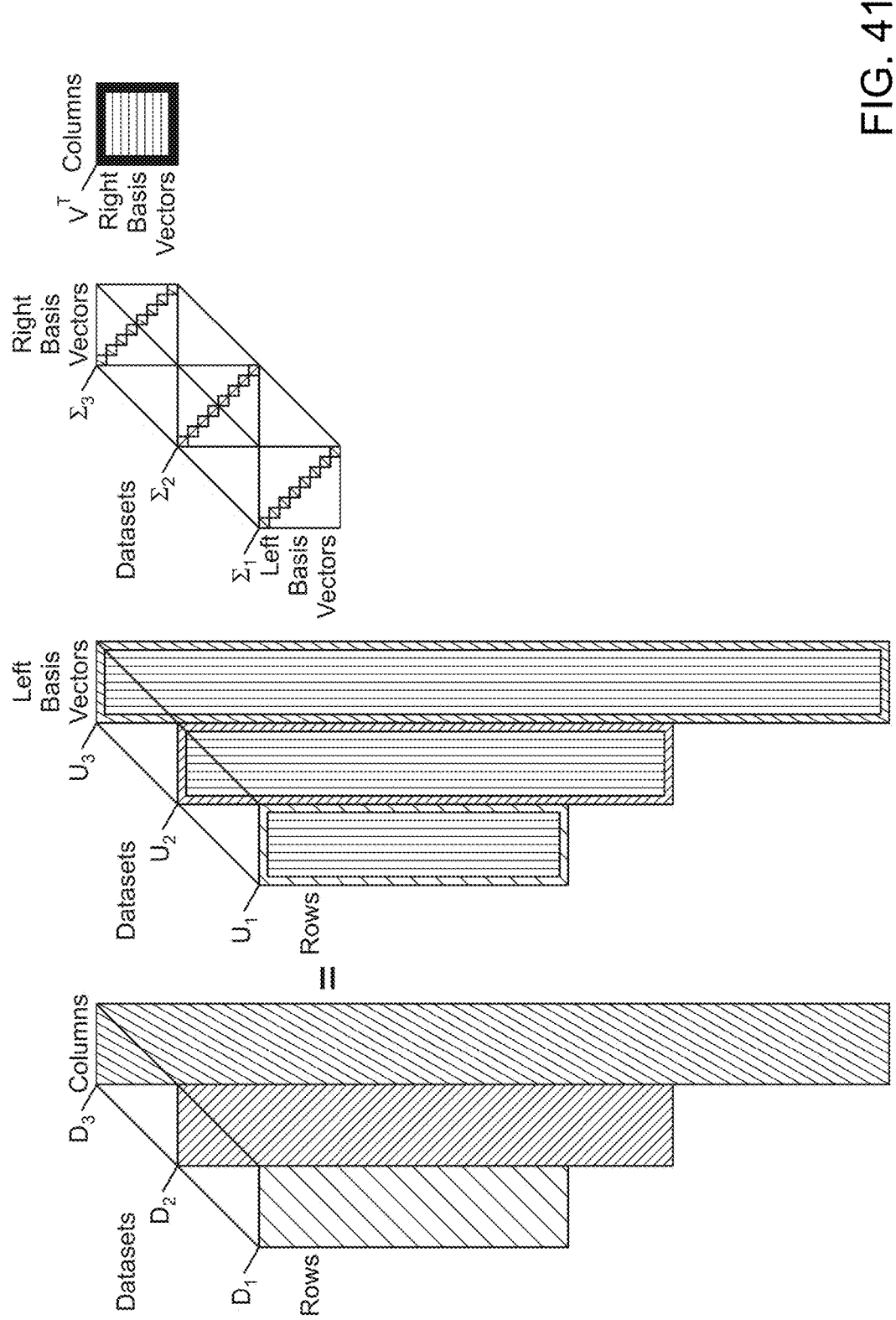
FIG. 41 is a diagram illustrating that the higher-order GSVD (HO GSVD) of three matrices $D_1$, $D_2$, and $D_3$ is a linear transformation of the three matrices from the three rows×columns spaces to three reduced and diagonalized left basis vectors×right basis vectors spaces, according to some embodiments. The right basis vectors are shared by all three datasets. Each right basis vector corresponds to three left basis vectors.

We find that survival analyses of the independent validation set of 184 patients give qualitatively the same results as these of the initial set of 251 patients and the inclusive confirmation set of 344 patients (Figures 21 $g$–$i$ and Figures 41$c$, and 10 $e$ and $f$ in Appendix S1). These analyses validate the prognostic contribution of the global pattern, which is computed by GSVD of patient-matched tumor and normal aCGH profiles, also for patients with measured GBM aCGH profiles in the absence of matched normal profiles.

Discussion

Previously, we showed that the GSVD provides a mathematical framework for sequence-independent comparative modeling of DNA microarray data from two organisms, where the mathematical variables and operations represent experimental or biological reality [12, 39]. The variables, subspaces of significant patterns that are common to both or exclusive to either one of the datasets, correlate with cellular programs that are conserved in both or unique to either one of the organisms, respectively. The operation of reconstruction in the subspaces common to both datasets outlines the biological similarity in the regulation of the cellular programs that are conserved across the species. Reconstruction in the common and exclusive subspaces of either dataset outlines the differential regulation of the conserved relative to the unique programs in the corresponding organism. Recent experimental results [40] verify a computationally predicted genome-wide mode of regulation [41, 42], and demonstrate that GSVD modeling of DNA microarray data can be used to correctly predict previously unknown cellular mechanisms.

Recently, we mathematically defined a higher-order GSVD (HO GSVD) for more than two large-scale matrices with different row dimensions and the same column dimension [13]. We proved that this novel HO GSVD extends to higher orders almost all of the mathematical properties of the GSVD. We showed, comparing global mRNA expression from the three disparate organisms *S. pombe*, *S. cerevisiae* and human, that the HO GSVD provides a sequence-independent comparative framework for more than two genomic datasets, where the variables and operations represent experimental or biological reality. The approximately common HO GSVD subspace represents biological similarity among the organisms. Simultaneous reconstruction in the common subspace removes the experimental artifacts, which are dissimilar, from the datasets.

We now show that also in probe-independent comparison of aCGH data from patient-matched tumor and normal samples, the mathematical variables of the GSVD, i.e., shared probelets and the corresponding tumor- and normal-specific arraylets, represent experimental or biological reality. Probelets that are mathematically significant in both datasets, correspond to normal arraylets representing copy-number variations (CNVs) in the normal human genome that are conserved in the tumor genome (e.g., female-specific X chromosome amplification) and are represented by the corresponding tumor arraylets. Probelets that are mathematically significant in the normal but not the tumor dataset represent experimental variations that exclusively affect the normal dataset. Similarly, some probelets that are mathematically significant in the tumor but not the normal dataset represent experimental variations that exclusively affect the tumor dataset.

We find that the mathematically second most tumor-exclusive probelet, which is also the mathematically most significant probelet in the tumor dataset, is statistically correlated, possibly biologically coordinated with GBM patients' survival and response to chemotherapy. The corresponding tumor arraylet describes a global pattern of tumor-exclusive co-occurring CNAs, including most known GBM-associated changes in chromosome numbers and focal CNAs, as well as several previously unreported CNAs, including the biochemically putative drug target-encoding *TLK2* [14]. We find that a negligible weight of the second tumor arraylet in a patient's GBM aCGH profile, mathematically defined by either the corresponding copy number in the second probelet, or by the correlation of the GBM profile with the second arraylet, is indicative of a significantly longer GBM survival time. This GSVD comparative modeling of aCGH data from patient-matched tumor and normal samples, therefore, draws a mathematical analogy between the prediction of cellular modes of regulation and the prognosis of cancers.

We confirm our results with GSVD comparison of matched profiles of a larger set of TCGA patients, inclusive of the initial set. We validate the prognostic contribution of the pattern with GSVD classification of the GBM profiles of a set of patients that is independent of both the initial set and the inclusive confirmation set [15].

Additional possible applications of the GSVD (and also the HO GSVD) in personalized medicine include comparisons of multiple patient-matched datasets, each corresponding to either (*i*) a set of large-scale molecular biological profiles (such as DNA copy numbers) acquired by a high-throughput technology (such as DNA microarrays) from the same tissue type (such as tumor or normal); or (*ii*) a set of biomedical images or signals; or (*iii*) a set of anatomical or clinical pathology test results or phenotypical observations (such as age). GSVD comparisons can uncover the relations and possibly even causal coordinations between these different recorded aspects of the same medical phenomenon. GSVD comparisons can be used to determine a single patient's medical status in relation to all the other patients in the set, and inform the patient's diagnosis, prognosis and treatment.

Acknowledgements

We thank CR Johnson, MA Saunders and CF Van Loan for insightful discussions of matrix and tensor computations, and H Colman, RL Jensen and JD Schiffman for helpful discussions of GBM cancer genomics. We also thank AM Gross for technical assistance.

References

1. Purow B, Schiff D (2009) Advances in the genetics of glioblastoma: are we reaching critical mass? Nat Rev Neurol 5: 419-426.

2. Wiltshire RN, Rasheed BK, Friedman HS, Friedman AH, Bigner SH (2000) Comparative genetic patterns of glioblastoma multiforme: potential diagnostic tool for tumor classification. Neuro Oncol 2: 164-173.

3. Nigro JM, Misra A, Zhang L, Smirnov I, Colman H, et al (2005) Integrated array-comparative genomic hybridization and expression array profiles identify clinically relevant molecular subtypes of glioblastoma. Cancer Res 65: 1678-1686.

4. Cancer Genome Atlas Research Network (2008) Comprehensive genomic characterization defines human glioblastoma genes and core pathways. Nature 455: 1061-1068.

5. Mischel PS, Shai R, Shi T, Horvath S, Lu KV, et al (2003) Identification of molecular subtypes of glioblastoma by gene expression profiling. Oncogene 22: 2361-2673.

6. Verhaak RG, Hoadley KA, Purdom E, Wang V, Qi Y, et al (2010) Integrated genomic analysis identifies clinically relevant subtypes of glioblastoma characterized by abnormalities in PDGFRA, IDH1, EGFR, and NF1. Cancer Cell 17: 98-110.

7. Colman H, Zhang L, Sulman EP, McDonald JM, Shooshtari NL, et al (2010) A multigene predictor of outcome in glioblastoma. Neuro Oncol 12: 49-57.

8. Noushmehr H, Weisenberger DJ, Diefes K, Phillips HS, Pujara K, et al (2010) Identification of a CpG island methylator phenotype that defines a distinct subgroup of glioma. Cancer Cell 17: 510-522.

9. Curran WJ Jr, Scott CB, Horton J, Nelson JS, Weinstein AS, et al (1993) Recursive partitioning analysis of prognostic factors in three Radiation Therapy Oncology Group malignant glioma trials. J Natl Cancer Inst 85: 704-710.

10. Gorlia T, van den Bent MJ, Hegi ME, Mirimanoff RO, Weller M, et al (2008) Nomograms for predicting survival of patients with newly diagnosed glioblastoma: prognostic factor analysis of EORTC and NCIC trial 26981-22981/CE.3. Lancet Oncol 9: 29-38.

11. Golub GH, Van Loan CF (1996) Matrix Computations. Baltimore: Johns Hopkins University Press, third edition, 694 p.

12. Alter O, Brown PO, Botstein D (2003) Generalized singular value decomposition for comparative analysis of genome-scale expression data sets of two different organisms. Proc Natl Acad Sci USA 100: 3351-3356.

13. Ponnapalli SP, Saunders MA, Van Loan CF, Alter O (2011) A higher-order generalized singular value decomposition for comparison of global mRNA expression from multiple organisms. PLoS ONE 6: e28072.

14. Lee CH, Alter O (2010) Known and novel copy number alterations in GBM and their patterns of co-occurrence are revealed by GSVD comparison of array CGH data from patient-matched normal and tumor TCGA samples. In: 60th Annual American Society of Human Genetics (ASHG) Meeting (November 2-6, 2010, Washington, DC).

15. Alpert BO, Sankaranarayanan P, Lee CH, Alter O (2011) Glioblastoma multiforme prognosis by using a patient's array CGH tumor profile and a generalized SVD-computed global pattern of copy-number alterations. In: 2nd DNA and Genome World Day (April 25-29, 2011, Dalian, China).

16. Nielsen TO, West RB, Linn SC, Alter O, Knowling MA, et al (2002) Molecular characterisation of soft tissue tumours: a gene expression study. Lancet 359: 1301-1307.

17. Tavazoie S, Hughes JD, Campbell MJ, Cho RJ, Church GM (1999) Systematic determination of genetic network architecture. Nat Genet 22: 281-285.

18. Kent WJ, Sugnet CW, Furey TS, Roskin KM, Pringle TH, et al (2002) The human genome browser at UCSC. Genome Res 12: 996-1006.

19. Fujita PA, Rhead B, Zweig AS, Hinrichs AS, Karolchik D, et al (2011) The UCSC Genome Browser database: update 2011. Nucleic Acids Res 39: D876-D882.

20. Olshen AB, Venkatraman ES, Lucito R, Wigler M (2004) Circular binary segmentation for the analysis of array-based DNA copy number data. Biostatistics 5: 557-572.

21. Venkatraman ES, Olshen AB (2007) A faster circular binary segmentation algorithm for the analysis of array CGH data. Bioinformatics 23: 657-663.

22. Heidenblad M, Lindgren D, Veltman JA, Jonson T, Mahlamäki EH, et al (2005) Microarray analyses reveal strong influence of DNA copy number alterations on the transcriptional patterns in pancreatic cancer: implications for the interpretation of genomic amplifications. Oncogene 24: 1794-1801.

23. Wang Q, Diskin S, Rappaport E, Attiyeh E, Mosse Y, et al (2006) Integrative genomics identifies distinct molecular classes of neuroblastoma and shows that multiple genes are targeted by regional alterations in DNA copy number. Cancer Res 66: 6050-6062.

24. Hopkins AL, Groom CR (2002) The druggable genome. Nat Rev Drug Discov 1: 727-730.

25. Silljé HH, Takahashi K, Tanaka K, Van Houwe G, Nigg EA (1999) Mammalian homologues of the plant Tousled gene code for cell-cycle-regulated kinases with maximal activities linked to ongoing DNA replication. EMBO J 18: 5691-5702.

26. Chandran UR, Ma C, Dhir R, Bisceglia M, Lyons-Weiler M, et al (2007) Gene expression profiles of prostate cancer reveal involvement of multiple molecular pathways in the metastatic process. BMC Cancer 7: 64.

27. Pellegrini M, Cheng JC, Voutila J, Judelson D, Taylor J, et al (2008) Expression profile of CREB knockdown in myeloid leukemia cells. BMC Cancer 8: 264.

28. Millour M, Charbonnel C, Magrangeas F, Minvielle S, Campion L, et al (2006) Gene expression profiles discriminate between pathological complete response and resistance to neoadjuvant FEC100 in breast cancer. Cancer Genomics Proteomics 3: 89-95.

29. Snijders AM, Nowee ME, Fridlyand J, Piek JM, Dorsman JC, et al (2003) Genome-wide-array-based comparative genomic hybridization reveals genetic homogeneity and frequent copy number increases encompassing CCNE1 in fallopian tube carcinoma. Oncogene 22: 4281-4286.

30. Campbell PJ, Yachida S, Mudie LJ, Stephens PJ, Pleasance ED, et al (2010) The patterns and dynamics of genomic instability in metastatic pancreatic cancer. Nature 467: 1109-1113.

31. Etemadmoghadam D, George J, Cowin PA, Cullinane C, Kansara M, et al (2010) Amplicon-dependent CCNE1 expression is critical for clonogenic survival after cisplatin treatment and is correlated with 20q11 gain in ovarian cancer. PLoS ONE 5: e15498.

32. Defeo-Jones D, Huang PS, Jones RE, Haskell KM, Vuocolo GA, et al (1991) Cloning of cDNAs for cellular proteins that bind to the retinoblastoma gene product. Nature 352: 251-254.

33. Sharma SV, Lee DY, Li B, Quinlan MP, Takahashi F, et al (2010) A chromatin-mediated reversible drug-tolerant state in cancer cell subpopulations. Cell 141: 69-80.

34. Pardridge WM (2005) The blood-brain barrier: bottleneck in brain drug development. NeuroRx 2: 3-14.

35. Hattori Y, Ohta S, Hamada K, Yamada-Okabe H, Kanemura Y, et al (2007) Identification of a neuron-specific human gene, KIAA1110, that is a guanine nucleotide exchange factor for ARF1. Biochem Biophys Res Commun 364: 737-742.

36. Kaplan EL, Meier P (1958) Nonparametric estimation from incomplete observations. J Amer Statist Assn 53: 457-481.

37. Cox DR (1972) Regression models and life-tables. J Roy Statist Soc B 34: 187-220.

38. Rothman KJ (1990) No adjustments are needed for multiple comparisons. Epidemiology 1: 43-46.

39. Alter O (2006) Discovery of principles of nature from mathematical modeling of DNA microarray data. Proc Natl Acad Sci USA 103: 16063-16064.

40. Omberg L, Meyerson JR, Kobayashi K, Drury LS, Diffley JF, et al (2009) Global effects of DNA replication and DNA replication origin activity on eukaryotic gene expression. Mol Syst Biol 5: 312.

41. Alter O, Golub GH (2004) Integrative analysis of genome-scale data by using pseudoinverse projection predicts novel correlation between DNA replication and RNA transcription. Proc Natl Acad Sci USA 101: 16577-16582.

42. Omberg L, Golub GH, Alter O (2007) A tensor higher-order singular value decomposition for integrative analysis of DNA microarray data from different studies. Proc Natl Acad Sci USA 104: 18371-18376.

Supporting Information

Mathematica Notebook S1. Generalized singular value decomposition (GSVD) of the TCGA patient-matched tumor and normal aCGH profiles. A Mathematica 8.0.1 code file, executable by Mathematica 8.0.1 and readable by Mathematica Player, freely available at http://www.wolfram.com/products/player/.
(NB)

Mathematica Notebook S2. Generalized singular value decomposition (GSVD) of the TCGA patient-matched tumor and normal aCGH profiles. A PDF format file, readable by Adobe Acrobat Reader.
(PDF)

Dataset S1. Initial set of 251 patients. A tab-delimited text format file, readable by both Mathematica and Microsoft Excel, reproducing The Cancer Genome Atlas (TCGA) [4] annotations of the initial set of 251 patients and the corresponding normal and tumor samples. The tumor and normal profiles of the initial set of 251 patients, in tab-delimited text format files, tabulating $\log_2$ relative copy number variation across 212,696 and 211,227 tumor and normal probes, respectively, are available at http://www.alterlab.org/GBM_prognosis/.
(TXT)

Dataset S2. Segments of the significant tumor and normal arraylets, computed by GSVD for the initial set of 251 patients. A tab-delimited text format file, readable by both Mathematica and Microsoft Excel, tabulating segments identified by circular binary segmentation (CBS) [20,21].
(TXT)

Dataset S3. Segments of the second tumor arraylet, computed by GSVD for the initial set of 251 patients. A tab-delimited text format file, readable by both Mathematica and Microsoft Excel, tabulating, for each of the 130 CBS segments of the second tumor arraylet, the segment's coordinates, the CBS $P$-value, and the log-rank test $P$-value corresponding to the Kaplan-Meier (KM) survival analysis of the initial set of 251 patients classified by either a gain or a loss of this segment.
(TXT)

Dataset S4. Inclusive confirmation set of 344 patients. A tab-delimited text format file, readable by both Mathematica and Microsoft Excel, reproducing the TCGA annotations of the inclusive confirmation set of 344 patients. The tumor and normal profiles of the inclusive confirmation set of 344 patients, in tab-delimited text format files, tabulating $\log_2$ relative copy number variation across 200,139 and 198,342 tumor and normal probes, respectively, are available at http://www.alterlab.org/GBM_prognosis/.
(TXT)

Dataset S5. Independent validation set of 184 patients. A tab-delimited text format file, readable by both Mathematica and Microsoft Excel, reproducing the TCGA annotations of the independent validation set of 184 patients. Tumor profiles of the independent validation set of 184 patients, in a tab-delimited text format file, tabulating $\log_2$ relative copy number variation across 212,696 autosomal and X chromosome probes, is available at http://www.alterlab.org/GBM_prognosis/.
(TXT)

Appendix

B

A higher-order generalized singular value decomposition for comparison of global mRNA expression from multiple organisms Sri Priya Ponnapalli[1], Michael A. Saunders[2], Charles F. Van Loan[3], and Orly Alter[4,*]

1 Department of Electrical and Computer Engineering, University of Texas at Austin, TX 78712, USA
2 Department of Management Science and Engineering, Stanford University, Stanford, CA 94305, USA
3 Department of Computer Science, Cornell University, Ithaca, NY 14853, USA
4 Scientific Computing and Imaging (SCI) Institute and Departments of Bioengineering and Human Genetics, University of Utah, Salt Lake City, UT 84112, USA
* E-mail: orly@sci.utah.edu

Abstract

The number of high-dimensional datasets recording multiple aspects of a single phenomenon is increasing in many areas of science, accompanied by a need for mathematical frameworks that can compare multiple large-scale matrices with different row dimensions. The only such framework to date, the generalized singular value decomposition (GSVD), is limited to two matrices. We mathematically define a higher-order GSVD (HO GSVD) for $N \geq 2$ matrices $D_i \in \mathbb{R}^{m_i \times n}$, each with full column rank. Each matrix is exactly factored as $D_i = U_i \Sigma_i V^T$, where $V$, identical in all factorizations, is obtained from the eigensystem $SV = V\Lambda$ of the arithmetic mean $S$ of all pairwise quotients $A_i A_j^{-1}$ of the matrices $A_i = D_i^T D_i$, $i \neq j$. We prove that this decomposition extends to higher orders almost all of the mathematical properties of the GSVD. The matrix $S$ is nondefective with $V$ and $\Lambda$ real. Its eigenvalues satisfy $\lambda_k \geq 1$. Equality holds if and only if the corresponding eigenvector $v_k$ is a right basis vector of equal significance in all matrices $D_i$ and $D_j$, that is $\sigma_{i,k}/\sigma_{j,k} = 1$ for all $i$ and $j$, and the corresponding left basis vector $u_{i,k}$ is orthogonal to all other vectors in $U_i$ for all $i$. The eigenvalues $\lambda_k = 1$, therefore, define the "common HO GSVD subspace." We illustrate the HO GSVD with a comparison of genome-scale cell-cycle mRNA expression from *S. pombe*, *S. cerevisiae* and human. Unlike existing algorithms, a mapping among the genes of these disparate organisms is not required. We find that the approximately common HO GSVD subspace represents the cell-cycle mRNA expression oscillations, which are similar among the datasets. Simultaneous reconstruction in the common subspace, therefore, removes the experimental artifacts, which are dissimilar, from the datasets. In the simultaneous sequence-independent classification of the genes of the three organisms in this common subspace, genes of highly conserved sequences but significantly different cell-cycle peak times are correctly classified.

Introduction

In many areas of science, especially in biotechnology, the number of high-dimensional datasets recording multiple aspects of a single phenomenon is increasing. This is accompanied by a fundamental need for mathematical frameworks that can compare multiple large-scale matrices with different row dimensions. For example, comparative analyses of global mRNA expression from multiple model organisms promise to enhance fundamental understanding of the universality and specialization of molecular biological mechanisms, and may prove useful in medical diagnosis, treatment and drug design [1]. Existing algorithms limit analyses to subsets of homologous genes among the different organisms, effectively introducing into the analysis the assumption that sequence and functional similarities are equivalent (e.g., [2]). However, it is well known that this assumption does not always hold, for example, in cases of nonorthologous gene displacement, when nonorthologous proteins in different organisms fulfill the same function [3]. For sequence-independent comparisons, mathematical frameworks are required that can distinguish and separate the similar from the dissimilar among multiple large-scale datasets tabulated as matrices with different row dimensions, corresponding to the different sets of genes of the different organisms. The only such framework to date, the generalized singular value decomposition (GSVD) [4–7], is limited to two matrices.

It was shown that the GSVD provides a mathematical framework for sequence-independent comparative modeling of DNA microarray data from two organisms, where the mathematical variables and operations represent biological reality [7,8]. The variables, significant subspaces that are common to both or exclusive to either one of the datasets, correlate with cellular programs that are conserved in both or unique to either one of the organisms, respectively. The operation of reconstruction in the subspaces common to both datasets outlines the biological similarity in the regulation of the cellular programs that are conserved across the species. Reconstruction in the common and exclusive subspaces of either dataset outlines the differential regulation of the conserved relative to the unique programs in the corresponding organism. Recent experimental results [9] verify a computationally predicted genome-wide mode of regulation that correlates DNA replication origin activity with mRNA expression [10,11], demonstrating that GSVD modeling of DNA microarray data can be used to correctly predict previously unknown cellular mechanisms.

We now define a higher-order GSVD (HO GSVD) for the comparison of $N \geq 2$ datasets. The datasets are tabulated as $N$ real matrices $D_i \in \mathbb{R}^{m_i \times n}$, each with full column rank, with different row dimensions and the same column dimension, where there exists a one-to-one mapping among the columns of the matrices. Like the GSVD, the HO GSVD is an exact decomposition, i.e., each matrix is exactly factored as $D_i = U_i \Sigma_i V^T$, where the columns of $U_i$ and $V$ have unit length and are the left and right basis vectors respectively, and each $\Sigma_i$ is diagonal and positive definite. Like the GSVD, the matrix $V$ is identical in all factorizations. In our HO GSVD, the matrix $V$ is obtained from the eigensystem $SV = V\Lambda$ of the arithmetic mean $S$ of all pairwise quotients $A_i A_j^{-1}$ of the matrices $A_i = D_i^T D_i$, or equivalently of all $S_{ij} = \frac{1}{2}(A_i A_j^{-1} + A_j A_i^{-1})$, $i \neq j$.

To clarify our choice of $S$, we note that in the GSVD, defined by Van Loan [5], the matrix $V$ can be formed from the eigenvectors of the unbalanced quotient $A_1 A_2^{-1}$ (Section 1 in Supplementary Appendix C). We observe that this $V$ can also be formed from the eigenvectors of the balanced arithmetic mean $S_{12} = \frac{1}{2}(A_1 A_2^{-1} + A_2 A_1^{-1})$. We prove that in the case of $N = 2$, our definition of $V$ by using the eigensystem of $S \equiv S_{12} = \frac{1}{2}(A_1 A_2^{-1} + A_2 A_1^{-1})$ leads algebraically to the GSVD (Supplementary Theorems S1–S5 in Appendix C), and therefore, as Paige and Saunders showed [6], can be computed in a stable way. We also note that in the GSVD, the matrix $V$ does not depend upon the ordering of the matrices $D_1$ and $D_2$. Therefore, we define our HO GSVD for $N \geq 2$ matrices by using the balanced arithmetic mean $S$ of all pairwise arithmetic means $S_{ij}$, each of which defines the GSVD of the corresponding pair of matrices $D_i$ and $D_j$, noting that $S$ does not depend upon the ordering of the matrices $D_i$ and $D_j$.

We prove that $S$ is nondefective (it has $n$ independent eigenvectors), and that its eigensystem is real (Theorem 1). We prove that the eigenvalues of $S$ satisfy $\lambda_k \geq 1$ (Theorem 2). As in our GSVD comparison of two matrices [7], we interpret the $k$th diagonal of $\Sigma_i = \text{diag}(\sigma_{i,k})$ in the factorization of the $i$th matrix $D_i$ as indicating the significance of the $k$th right basis vector $v_k$ in $D_i$ in terms of the overall information that $v_k$ captures in $D_i$. The ratio $\sigma_{i,k}/\sigma_{j,k}$ indicates the significance of $v_k$ in $D_i$ relative to its significance in $D_j$. We prove that an eigenvalue of $S$ satisfies $\lambda_k = 1$ if and only if the corresponding eigenvector $v_k$ is a right basis vector of equal significance in all $D_i$ and $D_j$, that is, $\sigma_{i,k}/\sigma_{j,k} = 1$ for all $i$ and $j$, and the corresponding left basis vector $u_{i,k}$ is orthonormal to all other vectors in $U_i$ for all $i$. We therefore mathematically define, in analogy with the GSVD, the "common HO GSVD subspace" of the $N \geq 2$ matrices to be the subspace spanned by the right basis vectors $v_k$ that correspond to the $\lambda_k = 1$ eigenvalues of $S$ (Theorem 3). We also show that each of the right basis vectors $\{v_k\}$ that span the common HO GSVD subspace is a generalized singular vector of all pairwise GSVD factorizations of the matrices $D_i$ and $D_j$ with equal corresponding generalized singular values for all $i$ and $j$ (Corollary 1).

Recent research showed that several higher-order generalizations are possible for a given matrix decomposition, each preserving some but not all of the properties of the matrix decomposition [12-14] (see also Supplementary Theorem S6 and Conjecture S1 in Appendix C). Our new HO GSVD extends to higher orders all of the mathematical properties of the GSVD except for complete column-wise orthogonality of the left basis vectors that form the matrix $U_i$ for all $i$, i.e., in each factorization.

We illustrate the HO GSVD with a comparison of cell-cycle mRNA expression from *S. pombe* [15,16], *S. cerevisiae* [17] and human [18]. Unlike existing algorithms, a mapping among the genes of these disparate organisms is not required (Supplementary Section 2 in Appendix C). We find that the common HO GSVD subspace represents the cell-cycle mRNA expression oscillations, which are similar among the datasets. Simultaneous reconstruction in this common subspace, therefore, removes the experimental artifacts, which are dissimilar, from the datasets. Simultaneous sequence-independent classification of the genes of the three organisms in the common subspace is in agreement with previous classifications into cell-cycle phases [19]. Notably, genes of highly conserved sequences across the three organisms [20,21] but significantly different cell-cycle peak times, such as genes from the ABC transporter superfamily [22-28], phospholipase B-encoding genes [29,30] and even the B cyclin-encoding genes [31,32], are correctly classified.

Methods

HO GSVD Construction

Suppose we have a set of $N$ real matrices $D_i \in \mathbb{R}^{m_i \times n}$ each with full column rank. We define a HO GSVD of these $N$ matrices as $$\begin{aligned} D_1 &= U_1 \Sigma_1 V^T, \\ D_2 &= U_2 \Sigma_2 V^T, \\ &\vdots \\ D_N &= U_N \Sigma_N V^T, \end{aligned} \quad (1)$$

where each $U_i \in \mathbb{R}^{m_i \times n}$ is composed of normalized left basis vectors, each $\Sigma_i = \mathrm{diag}(\sigma_{i,k}) \in \mathbb{R}^{n \times n}$ is diagonal with $\sigma_{i,k} > 0$, and $V$, identical in all matrix factorizations, is composed of normalized right basis vectors. As in the GSVD comparison of global mRNA expression from two organisms [7], in the HO GSVD comparison of global mRNA expression from $N \geq 2$ organisms, the shared right basis vectors $v_k$ of Equation (1) are the "genelets" and the $N$ sets of left basis vectors $u_{i,k}$ are the $N$ sets of "arraylets" (Figure 11 and Supplementary Section 2 in Appendix C). We obtain $V$ from the eigensystem of $S$, the arithmetic mean of all pairwise quotients $A_i A_j^{-1}$ of the matrices $A_i = D_i^T D_i$, or equivalently of all $S_{ij} = \frac{1}{2}(A_i A_j^{-1} + A_j A_i^{-1})$, $i \neq j$:

$$\begin{aligned} S &\equiv \frac{1}{N(N-1)} \sum_{i=1}^{N} \sum_{j>i}^{N} (A_i A_j^{-1} + A_j A_i^{-1}) \\ &= \frac{2}{N(N-1)} \sum_{i=1}^{N} \sum_{j>i}^{N} S_{ij}, \\ SV &= V\Lambda, \\ V &\equiv (v_1 \ \ldots \ v_n), \quad \Lambda = \mathrm{diag}(\lambda_k), \end{aligned} \quad (2)$$

with $\|v_k\| = 1$. We prove that $S$ is nondefective, i.e., $S$ has $n$ independent eigenvectors, and that its eigenvectors $V$ and eigenvalues $\Lambda$ are real (Theorem 1). We prove that the eigenvalues of $S$ satisfy $\lambda_k \geq 1$ (Theorem 2).

Given $V$, we compute matrices $B_i$ by solving $N$ linear systems:

$$\begin{aligned} VB_i^T &= D_i^T, \\ B_i &\equiv (b_{i,1} \ \ldots \ b_{i,n}), \quad i = 1, \ldots, N, \end{aligned} \quad (3)$$

and we construct $\Sigma_i$ and $U_i = (u_{i,1} \ \ldots \ u_{i,n})$ by normalizing the columns of $B_i$:

$$\begin{aligned} \sigma_{i,k} &= \|b_{i,k}\|, \\ \Sigma_i &= \text{diag}(\sigma_{i,k}), \\ B_i &= U_i \Sigma_i. \end{aligned} \quad (4)$$

HO GSVD Interpretation

In this construction, the rows of each of the $N$ matrices $D_i$ are superpositions of the same right basis vectors, the columns of $V$ (Figures 37 and 38 and Section 1 in Appendix C). As in our GSVD comparison of two matrices, we interpret the $k$th diagonals of $\Sigma_i$, the "higher-order generalized singular value set" $\{\sigma_{i,k}\}$, as indicating the significance of the $k$th right basis vector $v_k$ in the matrices $D_i$, and reflecting the overall information that $v_k$ captures in each $D_i$ respectively. The ratio $\sigma_{i,k}/\sigma_{j,k}$ indicates the significance of $v_k$ in $D_i$ relative to its significance in $D_j$. A ratio of $\sigma_{i,k}/\sigma_{j,k} = 1$ for all $i$ and $j$ corresponds to a right basis vector $v_k$ of equal significance in all $N$ matrices $D_i$. GSVD comparisons of two matrices showed that right basis vectors of approximately equal significance in the two matrices reflect themes that are common to both matrices under comparison [7]. A ratio of $\sigma_{i,k}/\sigma_{j,k} \ll 1$ indicates a basis vector $v_k$ of almost negligible significance in $D_i$ relative to its significance in $D_j$. GSVD comparisons of two matrices showed that right basis vectors of negligible significance in one matrix reflect themes that are exclusive to the other matrix.

We prove that an eigenvalue of $S$ satisfies $\lambda_k = 1$ if and only if the corresponding eigenvector $v_k$ is a right basis vector of equal significance in all $D_i$ and $D_j$, that is, $\sigma_{i,k}/\sigma_{j,k} = 1$ for all $i$ and $j$, and the corresponding left basis vector $u_{i,k}$ is orthonormal to all other vectors in $U_i$ for all $i$. We therefore mathematically define, in analogy with the GSVD, the "common HO GSVD subspace" of the $N \geq 2$ matrices to be the subspace spanned by the right basis vectors $\{v_k\}$ corresponding to the eigenvalues of $S$ that satisfy $\lambda_k = 1$ (Theorem 3).

It follows that each of the right basis vectors $\{v_k\}$ that span the common HO GSVD subspace is a generalized singular vector of all pairwise GSVD factorizations of the matrices $D_i$ and $D_j$ with equal corresponding generalized singular values for all $i$ and $j$ (Corollary 1). Since the GSVD can be computed in a stable way [6], we note that the common HO GSVD subspace can also be computed in a stable way by computing all pairwise GSVD factorizations of the matrices $D_i$ and $D_j$. This also suggests that it may be possible to formulate the HO GSVD as a solution to an optimization problem, in analogy with existing variational formulations of the GSVD [33]. Such a formulation may lead to a stable numerical algorithm for computing the HO GSVD, and possibly also to a higher-order general Gauss-Markov linear statistical model [34–36].

We show, in a comparison of $N = 3$ matrices, that the approximately common HO GSVD subspace of these three matrices reflects a theme that is common to the three matrices under comparison (Section 2).

HO GSVD Mathematical Properties

Theorem 1. *$S$ is nondefective (it has $n$ independent eigenvectors) and its eigensystem is real.*

*Proof.* From Equation (2) it follows that $$S = \frac{1}{N(N-1)}(H - NI),$$
$$H = \left(\sum_{i=1}^{N} A_i\right)\left(\sum_{j=1}^{N} A_j^{-1}\right), \qquad (5)$$

and the eigenvectors of $S$ equal the eigenvectors of $H$.

Let the SVD of the matrices $D_i$ appended along the $n$-columns axis be $$\begin{bmatrix} D_1 \\ \vdots \\ D_N \end{bmatrix} = \begin{bmatrix} \hat{U}_1 \\ \vdots \\ \hat{U}_N \end{bmatrix} \hat{\Sigma} \hat{V}^T,$$
$$\sum_{i=1}^{N} \hat{U}_i^T \hat{U}_i = I. \qquad (6)$$

Since the matrices $D_i$ are real and with full column rank, it follows from the SVD of $\hat{U}_i$ that the symmetric matrices $\hat{U}_i^T \hat{U}_i$ are real and positive definite, and their inverses exist. It then follows from Equations (5) and (6) that $H$ is similar to $\hat{H}$, $$H = \hat{V}\hat{\Sigma}\hat{H}\hat{\Sigma}^{-1}\hat{V}^T,$$
$$\hat{H} = \sum_{j=1}^{N} (\hat{U}_j^T \hat{U}_j)^{-1}, \qquad (7)$$

and the eigenvalues of $H$ equal the eigenvalues of $\hat{H}$.

A sum of real, symmetric and positive definite matrices, $\hat{H}$ is also real, symmetric and positive definite; therefore, its eigensystem $$\hat{Y}^T \hat{H} \hat{Y} = \text{diag}(\mu_k) \qquad (8)$$

is real with $\hat{Y}$ orthogonal and $\mu_k > 0$. Without loss of generality let $\hat{Y}$ be orthonormal, such that $\|\hat{y}_k\| = 1$. It follows from the similarity of $H$ with $\hat{H}$ that the eigensystem of $H$ can be written as $V^{-1}HV = \text{diag}(\mu_k)$, with the real and nonsingular $V = (\hat{V}\hat{\Sigma}\hat{Y})\hat{W}^{-1}$, where $\hat{W} = \text{diag}(\hat{w}_k)$ and $\hat{w}_k = \|\hat{V}\hat{\Sigma}\hat{y}_k\|$ such that $\|v_k\| = 1$ for all $k$.

Thus, from Equation (5), $S$ is nondefective with real eigenvectors $V$. Also, the eigenvalues of $S$ satisfy $$\lambda_k = \frac{1}{N(N-1)}(\mu_k - N), \qquad (9)$$

where $\mu_k > 0$ are the eigenvalues of $H$ and $\hat{H}$. Thus, the eigenvalues of $S$ are real. □

Theorem 2. *The eigenvalues of $S$ satisfy $\lambda_k \geq 1$.*

*Proof.* Following Equation (9), asserting that the eigenvalues of $S$ satisfy $\lambda_k \geq 1$ is equivalent to asserting that the eigenvalues of $\hat{H}$ satisfy $\mu_k \geq N^2$.

From Equations (6) and (7), the eigenvalues of $\hat{H}$ satisfy $$\mu_k \geq \min_x \sum_{j=1}^{N} [x^T (\hat{U}_j^T \hat{U}_j) x]^{-1}, \qquad (10)$$

under the constraint that $$\sum_{j=1}^{N} x^T(\hat{U}_j^T \hat{U}_j)x = 1, \qquad (11)$$

where $x$ is a real unit vector, and where it follows from the Cauchy-Schwarz inequality [37] (see also [4,34,38]) for the real nonzero vectors $(\hat{U}_j^T \hat{U}_j)x$ and $(\hat{U}_j^T \hat{U}_j)^{-1}x$ that for all $j$ $$x^T(\hat{U}_j^T \hat{U}_j)^{-1}x \geq [x^T(\hat{U}_j^T \hat{U}_j)x]^{-1}. \qquad (12)$$

With the constraint of Equation (11), which requires the sum of the $N$ positive numbers $x^T(\hat{U}_j^T \hat{U}_j)^{-1}x$ to equal one, the lower bound on the eigenvalues of $\hat{H}$ in Equation (10) is at its minimum when the sum of the inverses of these numbers is at its minimum, that is, when the numbers equal $$x^T(\hat{U}_i^T \hat{U}_i)x = x^T(\hat{U}_j^T \hat{U}_j)x = N^{-1} \qquad (13)$$

for all $i$ and $j$. Thus, the eigenvalues of $\hat{H}$ satisfy $\mu_k \geq N^2$. □

Theorem 3. *The common HO GSVD subspace.* An eigenvalue of $S$ satisfies $\lambda_k = 1$ if and only if the corresponding eigenvector $v_k$ is a right basis vector of equal significance in all $D_i$ and $D_j$, that is, $\sigma_{i,k}/\sigma_{j,k} = 1$ for all $i$ and $j$, and the corresponding left basis vector $u_{i,k}$ is orthonormal to all other vectors in $U_i$ for all $i$. The "common HO GSVD subspace" of the $N \geq 2$ matrices is, therefore, the subspace spanned by the right basis vectors $\{v_k\}$ corresponding to the eigenvalues of $S$ that satisfy $\lambda_k = 1$.

*Proof.* Without loss of generality, let $k = n$. From Equation (12) and the Cauchy-Schwarz inequality, an eigenvalue of $\hat{H}$ equals its minimum lower bound $\mu_n = N^2$ if and only if the corresponding eigenvector $\hat{y}_n$ is also an eigenvector of $\hat{U}_i^T \hat{U}_i$ for all $i$ [37], where, from Equation (13), the corresponding eigenvalue equals $N^{-1}$, $$(\hat{U}_i^T \hat{U}_i)\hat{Y} = [(\hat{U}_i^T \hat{U}_i)\hat{y}_1 \quad (\hat{U}_i^T \hat{U}_i)\hat{y}_2 \quad \ldots \quad N^{-1}\hat{y}_n]. \qquad (14)$$

Given the eigenvectors $V = (\hat{V}\hat{\Sigma}\hat{Y})\hat{W}^{-1}$ of $S$, we solve Equation (3) for each $D_i = \hat{U}_i \hat{\Sigma} \hat{V}^T$ of Equation (6), and obtain $$\begin{aligned} U_i \Sigma_i = B_i &= D_i V^{-T} \\ &= \hat{U}_i \hat{Y} \hat{W}. \end{aligned} \qquad (15)$$

Following Equations (14) and (15), where $v_n = \hat{w}_n^{-1} \hat{V} \hat{\Sigma} \hat{y}_n$ corresponds to a minimum eigenvalue $\lambda_n = 1$, and since $\hat{Y}$ is orthonormal, we obtain $$\hat{W}^{-1}\Sigma_i(U_i^T U_i)\Sigma_i \hat{W}^{-1} = \hat{Y}^T(\hat{U}_i^T \hat{U}_i)\hat{Y}$$
$$= \begin{bmatrix} \hat{y}_1^T(\hat{U}_i^T \hat{U}_i)\hat{y}_1 & \hat{y}_2^T(\hat{U}_i^T \hat{U}_i)\hat{y}_1 & \ldots & 0 \\ \hat{y}_1^T(\hat{U}_i^T \hat{U}_i)\hat{y}_2 & \hat{y}_2^T(\hat{U}_i^T \hat{U}_i)\hat{y}_2 & \ldots & 0 \\ \vdots & \vdots & \ddots & \vdots \\ 0 & 0 & \ldots & N^{-1} \end{bmatrix}, \qquad (16)$$

with zeroes in the $n$th row and the $n$th column of the matrix above everywhere except for the diagonal element. Thus, an eigenvalue of $S$ satisfies $\lambda_n = 1$ if and only if the corresponding left basis vectors $u_{i,n}$ are orthonormal to all other vectors in $U_i$.

The corresponding higher-order generalized singular values are $\sigma_{i,n} = N^{-1/2}\hat{w}_n > 0$. Thus $\sigma_{i,n}/\sigma_{j,n} = 1$ for all $i$ and $j$, and the corresponding right basis vector $v_n$ is of equal significance in all matrices $D_i$ and $D_j$. □

Corollary 1. *An eigenvalue of $S$ satisfies $\lambda_k = 1$ if and only if the corresponding right basis vector $v_k$ is a generalized singular vector of all pairwise GSVD factorizations of the matrices $D_i$ and $D_j$ with equal corresponding generalized singular values for all $i$ and $j$.*

*Proof.* From Equations (12) and (13), and since the pairwise quotients $A_i A_j^{-1}$ are similar to $(U_i^T U_i)(U_j^T U_j)^{-1}$ with the similarity transformation of $\hat{V}\hat{\Sigma}$ for all $i$ and $j$, it follows that an eigenvalue of $S$ satisfies $\lambda_k = 1$ if and only if the corresponding right basis vector $v_k = \hat{w}_k^{-1} \hat{V} \hat{\Sigma} \hat{y}_k$ is also an eigenvector of each of the pairwise quotients $A_i A_j^{-1}$ of the matrices $A_i = D_i^T D_i$ with equal corresponding eigenvalues, or equivalently of all $S_{ij}$ with all eigenvalues at their minimum of one, $$S_{ij} v_k = \frac{1}{2}(A_i A_j^{-1} + A_i A_j^{-1}) v_k = v_k. \tag{17}$$

We prove (Supplementary Theorems S1–S5 in Appendix C) that in the case of $N = 2$ matrices our definition of $V$ by using the eigensystem of $S_{ij}$ leads algebraically to the GSVD, where an eigenvalue of $S_{ij}$ equals its minimum of one if and only if the two corresponding generalized singular values are equal, such that the corresponding generalized singular vector $v_k$ is of equal significance in both matrices $D_i$ and $D_j$. Thus, it follows that each of the right basis vectors $\{v_k\}$ that span the common HO GSVD subspace is a generalized singular vector of all pairwise GSVD factorizations of the matrices $D_i$ and $D_j$ with equal corresponding generalized singular values for all $i$ and $j$.  □

Note that since the GSVD can be computed in a stable way [6], the common HO GSVD subspace we define (Theorem 3) can also be computed in a stable way by computing all pairwise GSVD factorizations of the matrices $D_i$ and $D_j$ (Corollary 1). It may also be possible to formulate the HO GSVD as a solution to an optimization problem, in analogy with existing variational formulations of the GSVD [33]. Such a formulation may lead to a stable numerical algorithm for computing the HO GSVD, and possibly also to a higher-order general Gauss-Markov linear statistical model [34–36].

Results

HO GSVD Comparison of Global mRNA Expression from Three Organisms

Consider now the HO GSVD comparative analysis of global mRNA expression datasets from the $N = 3$ organisms *S. pombe*, *S. cerevisiae* and human (Supplementary Section 2.1 in Appendix C, Mathematica Notebooks S1 and S2, and Datasets S1–S3). The datasets are tabulated as matrices of $n = 17$ columns each, corresponding to DNA microarray-measured mRNA expression from each organism at 17 time points equally spaced during approximately two cell-cycle periods. The underlying assumption is that there exists a one-to-one mapping among the 17 columns of the three matrices but not necessarily among their rows, which correspond to either $m_1 = 3167$-*S. pombe* genes, $m_2 = 4772$-*S. cerevisiae* genes or $m_3 = 13,068$-human genes. The HO GSVD of Equation (1) transforms the datasets from the organism-specific genes × 17-arrays spaces to the reduced spaces of the 17-"arraylets," i.e., left basis vectors × 17-"genelets," i.e., right basis vectors, where the datasets $D_i$ are represented by the diagonal nonnegative matrices $\Sigma_i$, by using the organism-specific genes × 17-arraylets transformation matrices $U_i$ and the one shared 17-genelets × 17-arrays transformation matrix $V^T$ (Figure 11).

Following Theorem 3, the approximately common HO GSVD subspace of the three datasets is spanned by the five genelets $k = 13, \ldots, 17$ that correspond to $1 \lesssim \lambda_k \lesssim 2$. We find that these five genelets are approximately equally significant with $\sigma_{1,k} : \sigma_{2,k} : \sigma_{3,k} \sim 1 : 1 : 1$ in the *S. pombe*, *S. cerevisiae* and human datasets, respectively (Figure 12 *a* and *b*). The five corresponding arraylets in each dataset are $\epsilon = 0.33$-orthonormal to all other arraylets (Figure 15).

Common HO GSVD Subspace Represents Similar Cell-Cycle Oscillations

The expression variations across time of the five genelets that span the approximately common HO GSVD subspace fit normalized cosine functions of two periods, superimposed on time-invariant expression (Figure 12 c and d). Consistently, the corresponding organism-specific arraylets are enriched [39] in overexpressed or underexpressed organism-specific cell cycle-regulated genes, with 24 of the 30 P-values $< 10^{-8}$ (Table 1 and Supplementary Section 2.2 in Appendix C). For example, the three 17th arraylets, which correspond to the 0-phase 17th genelet, are enriched in overexpressed G2 *S. pombe* genes, G2/M and M/G1 *S. cerevisiae* genes and S and G2 human genes, respectively, representing the cell-cycle checkpoints in which the three cultures are initially synchronized.

Simultaneous sequence-independent reconstruction and classification of the three datasets in the common subspace outline cell-cycle progression in time and across the genes in the three organisms (Supplementary Sections 2.3 and 2.4 in Appendix C). Projecting the expression of the 17 arrays of either organism from the corresponding five-dimensional arraylets subspace onto the two-dimensional subspace that approximates it (Figure 16), $\geq 50\%$ of the contributions of the arraylets add up, rather than cancel out (Figure 13 a–c). In these two-dimensional subspaces, the angular order of the arrays of either organism describes cell-cycle progression in time through approximately two cell-cycle periods, from the initial cell-cycle phase and back to that initial phase twice. Projecting the expression of the genes, $\geq 50\%$ of the contributions of the five genelets add up in the overall expression of 343 of the 380 *S. pombe* genes classified as cell cycle-regulated, 554 of the 641 *S. cerevisiae* cell-cycle genes, and 632 of the 787 human cell-cycle genes (Figure 13 d–f). Simultaneous classification of the genes of either organism into cell-cycle phases according to their angular order in these two-dimensional subspaces is consistent with the classification of the arrays, and is in good agreement with the previous classifications of the genes (Figure 13 g–i). With all 3167 *S. pombe*, 4772 *S. cerevisiae* and 13,068 human genes sorted, the expression variations of the five arraylets from each organism approximately fit one-period cosines, with the initial phase of each arraylet (Figures 17-19) similar to that of its corresponding genelet (Figure 12). The global mRNA expression of each organism, reconstructed in the common HO GSVD subspace, approximately fits a traveling wave, oscillating across time and across the genes.

Figures 12A, 12B, 12C:
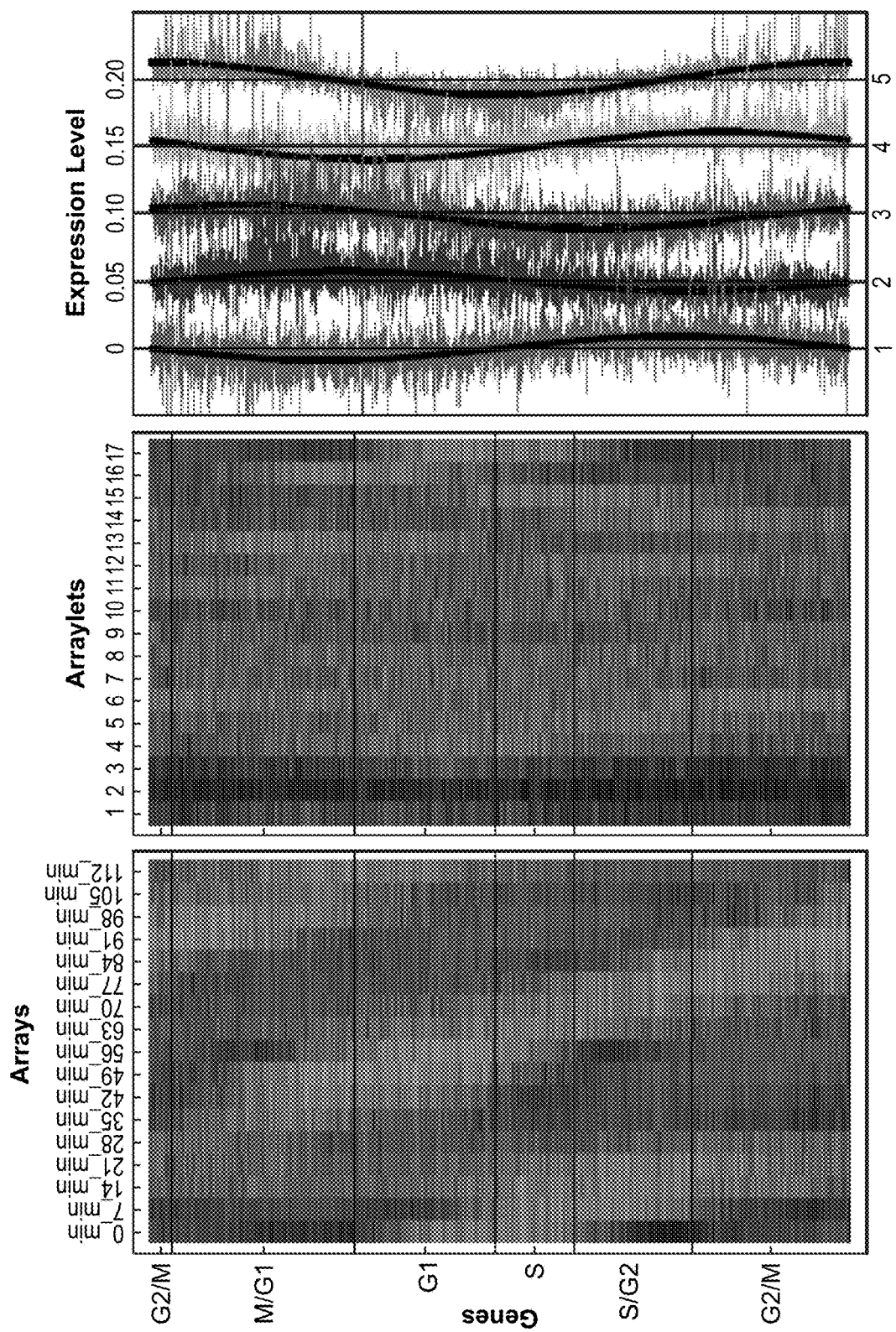
FIG. 12 is a diagram illustrating an example of S. cerevisiae global mRNA expression reconstructed in the five-dimensional approximately common HO GSVD subspace, according to some embodiments.

Note also that simultaneous reconstruction in the common HO GSVD subspace removes the experimental artifacts and batch effects, which are dissimilar, from the three datasets. Consider, for example, the second genelet. With $\sigma_{1,2} : \sigma_{2,2} : \sigma_{3,2} \sim 1 : 8 : 3$ in the *S. pombe*, *S. cerevisiae* and human datasets, respectively, this genelet is almost exclusive to the *S. cerevisiae* dataset. This genelet is anticorrelated with a time decaying pattern of expression (Figure 12a). Consistently, the corresponding *S. cerevisiae*-specific arraylet is enriched in underexpressed *S. cerevisiae* genes that were classified as up-regulated by the *S. cerevisiae* synchronizing agent, the α-factor pheromone, with the P-value $< 10^{-46}$. Reconstruction in the common subspace effectively removes this *S. cerevisiae*-approximately exclusive pattern of expression variation from the three datasets.

Simultaneous HO GSVD Classification of Homologous Genes of Different Cell-Cycle Peak Times Notably, in the simultaneous sequence-independent classification of the genes of the three organisms in the common subspace, genes of significantly different cell-cycle peak times [19] but highly conserved sequences [20, 21] are correctly classified (Supplementary Section 2.5 in Appendix C).

Figures 14A, 14B, 14C:
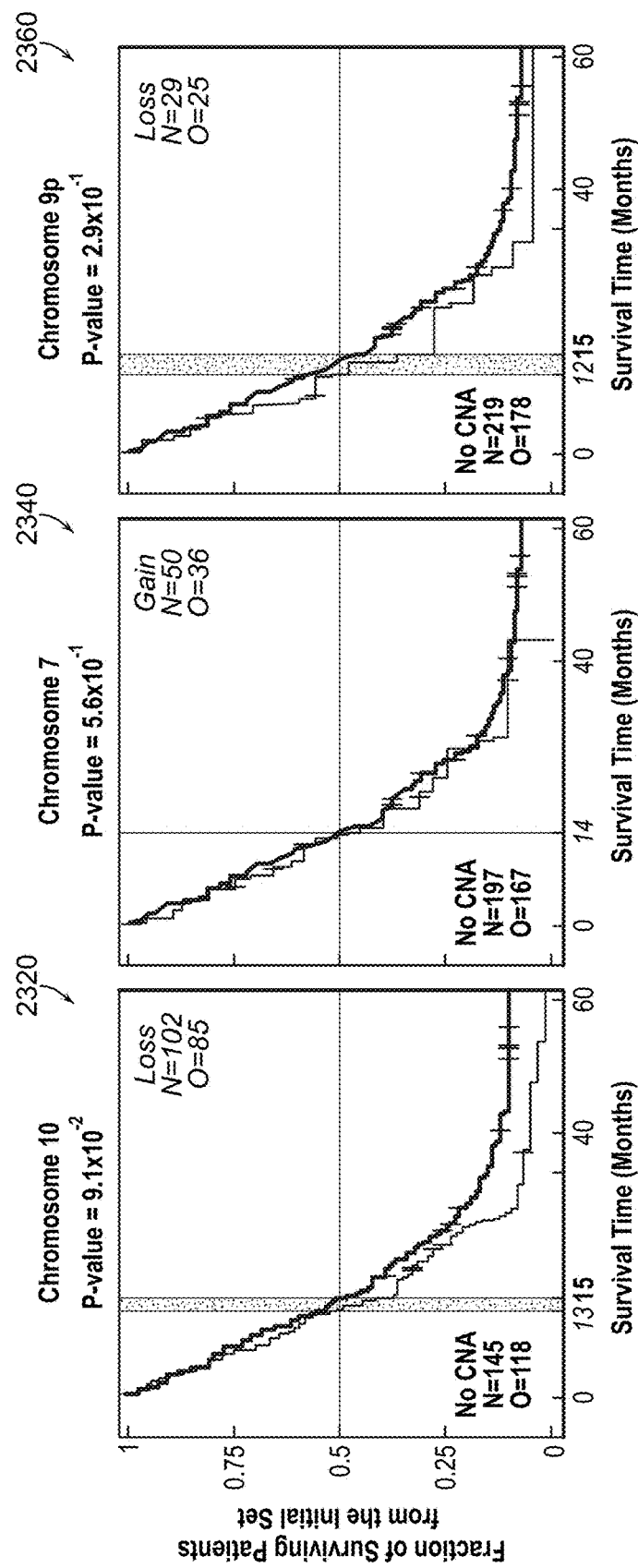
FIG. 14 show diagrams illustrating survival analyses of patients classified GBM-associated chromosome (10, 7, 9p) number changes, according to some embodiments.

For example, consider the G2 *S. pombe* gene *BFR1* (Figure 14a), which belongs to the evolutionarily highly conserved ATP-binding cassette (ABC) transporter superfamily [22]. The closest homologs of *BFR1* in our *S. pombe*, *S. cerevisiae* and human datasets are the *S. cerevisiae* genes *SNQ2*, *PDR5*, *PDR15* and *PDR10* (Supplemental Table S1a in Appendix C). The expression of *SNQ2* and *PDR5* is known to peak at the S/G2 and G2/M cell-cycle phases, respectively [17]. However, sequence similarity does not imply similar cell-cycle peak times, and *PDR15* and *PDR10*, the closest homologs of *PDR5*, are induced during stationary phase [23], which has been hypothesized to occur in G1, before the Cdc28-defined cell-cycle arrest [24]. Consistently, we find *PDR15* and *PDR10* at the M/G1 to G1 transition, antipodal to (i.e., half a cell-cycle period apart from) *SNQ2* and *PDR5*, which are projected onto S/G2 and G2/M, respectively (Figure 14*b*). We also find the transcription factor *PDR1* at S/G2, its known cell-cycle peak time, adjacent to *SNQ2* and *PDR5*, which it positively regulates and might be regulated by, and antipodal to *PDR15*, which it negatively regulates [25–28].

Another example is the *S. cerevisiae* phospholipase B-encoding gene *PLB1* [29], which peaks at the cell-cycle phase M/G1 [30]. Its closest homolog in our *S. cerevisiae* dataset, *PLB3*, also peaks at M/G1 [17] (Figure 14*d*). However, among the closest *S. pombe* and human homologs of *PLB1* (Supplementary Table S1*b* in Appendix C), we find the *S. pombe* genes *SPAC977.09c* and *SPAC1786.02*, which expressions peak at the almost antipodal *S. pombe* cell-cycle phases S and G2, respectively [19] (Figure 14*c*).

As a third example, consider the *S. pombe* G1 B-type cyclin-encoding gene *CIG2* [31,32] (Supplementary Table S1*c* in Appendix C). Its closest *S. pombe* homolog, *CDC13*, peaks at M [19] (Figure 14*e*). The closest human homologs of *CIG2*, the cyclins *CCNA2* and *CCNB2*, peak at G2 and G2/M, respectively (Figure 14*g*). However, while periodicity in mRNA abundance levels through the cell cycle is highly conserved among members of the cyclin family, the cell-cycle peak times are not necessarily conserved [1]: The closest homologs of *CIG2* in our *S. cerevisiae* dataset, are the G2/M promoter-encoding genes *CLB1,2* and *CLB3,4*, which expressions peak at G2/M and S respectively, and *CLB5*, which encodes a DNA synthesis promoter, and peaks at G1 (Figure 14*f*).

Discussion

We mathematically defined a higher-order GSVD (HO GSVD) for two or more large-scale matrices with different row dimensions and the same column dimension. We proved that our new HO GSVD extends to higher orders almost all of the mathematical properties of the GSVD: The eigenvalues of $S$ are always greater than or equal to one, and an eigenvalue of one corresponds to a right basis vector of equal significance in all matrices, and to a left basis vector in each matrix factorization that is orthogonal to all other left basis vectors in that factorization. We therefore mathematically defined, in analogy with the GSVD, the common HO GSVD subspace of the $N \geq 2$ matrices to be the subspace spanned by the right basis vectors that correspond to the eigenvalues of $S$ that equal one.

The only property that does not extend to higher orders in general is the complete column-wise orthogonality of the normalized left basis vectors in each factorization. Recent research showed that several higher-order generalizations are possible for a given matrix decomposition, each preserving some but not all of the properties of the matrix decomposition [12–14]. The HO GSVD has the interesting property of preserving the exactness and diagonality of the matrix GSVD and, in special cases, also partial or even complete column-wise orthogonality. That is, all $N$ matrix factorizations in Equation (1) are exact, all $N$ matrices $\Sigma_i$ are diagonal, and when one or more of the eigenvalues of $S$ equal one, the corresponding left basis vectors in each factorization are orthogonal to all other left basis vectors in that factorization.

The complete column-wise orthogonality of the matrix GSVD [5] enables its stable computation [6]. We showed that each of the right basis vectors that span the common HO GSVD subspace is a generalized singular vector of all pairwise GSVD factorizations of the matrices $D_i$ and $D_j$ with equal corresponding generalized singular values for all $i$ and $j$. Since the GSVD can be computed in a stable way, the common HO GSVD subspace can also be computed in a stable way by computing all pairwise GSVD factorizations of the matrices $D_i$ and $D_j$. That is, the common HO GSVD subspace exists also for $N$ matrices $D_i$ that are not all of full column rank. This also means that the common HO GSVD subspace can be formulated as a solution to an optimization problem, in analogy with existing variational formulations of the GSVD [33].

It would be ideal if our procedure reduced to the stable computation of the matrix GSVD when $N = 2$. To achieve this ideal, we would need to find a procedure that allows a computation of the HO GSVD, not just the common HO GSVD subspace, for $N$ matrices $D_i$ that are not all of full column rank. A formulation of the HO GSVD, not just the common HO GSVD subspace, as a solution to an optimization problem may lead to a stable numerical algorithm for computing the HO GSVD. Such a formulation may also lead to a higher-order general Gauss-Markov linear statistical model [34–36].

It was shown that the GSVD provides a mathematical framework for sequence-independent comparative modeling of DNA microarray data from two organisms, where the mathematical variables and operations represent experimental or biological reality [7, 8]. The variables, subspaces of significant patterns that are common to both or exclusive to either one of the datasets, correlate with cellular programs that are conserved in both or unique to either one of the organisms, respectively. The operation of reconstruction in the subspaces common to both datasets outlines the biological similarity in the regulation of the cellular programs that are conserved across the species. Reconstruction in the common and exclusive subspaces of either dataset outlines the differential regulation of the conserved relative to the unique programs in the corresponding organism. Recent experimental results [9] verify a computationally predicted genome-wide mode of regulation [10, 11], and demonstrate that GSVD modeling of DNA microarray data can be used to correctly predict previously unknown cellular mechanisms.

Here we showed, comparing global cell-cycle mRNA expression from the three disparate organisms *S. pombe*, *S. cerevisiae* and human, that the HO GSVD provides a sequence-independent comparative framework for two or more genomic datasets, where the variables and operations represent biological reality. The approximately common HO GSVD subspace represents the cell-cycle mRNA expression oscillations, which are similar among the datasets. Simultaneous reconstruction in the common subspace removes the experimental artifacts, which are dissimilar, from the datasets. In the simultaneous sequence-independent classification of the genes of the three organisms in this common subspace, genes of highly conserved sequences but significantly different cell-cycle peak times are correctly classified.

Additional possible applications of our HO GSVD in biotechnology include comparison of multiple genomic datasets, each corresponding to: ($i$) the same experiment repeated multiple times using different experimental protocols, to separate the biological signal that is similar in all datasets from the dissimilar experimental artifacts; ($ii$) one of multiple types of genomic information, such as DNA copy number, DNA methylation and mRNA expression, collected from the same set of samples, e.g., tumor samples, to elucidate the molecular composition of the overall biological signal in these samples; ($iii$) one of multiple chromosomes of the same organism, to illustrate the relation, if any, between these chromosomes in terms of their, e.g., mRNA expression in a given set of samples; and ($iv$) one of multiple interacting organisms, e.g., in an ecosystem, to illuminate the exchange of biological information in these interactions.

Supplementary Information

Appendix S1. A PDF format file, readable by Adobe Acrobat Reader.

Mathematica Notebook S1. Higher-order generalized singular value decomposition (HO GSVD) of global mRNA expression datasets from three different organisms. A Mathematica 5.2 code file, executable by Mathematica 5.2 and readable by Mathematica Player, freely available at http://www.wolfram.com/products/player/.

Mathematica Notebook S2. HO GSVD of global mRNA expression datasets from three different organisms. A PDF format file, readable by Adobe Acrobat Reader.

Dataset S1. S. pombe global mRNA expression. A tab-delimited text format file, readable by both Mathematica and Microsoft Excel, reproducing the relative mRNA expression levels of $m_1=3167$ *S. pombe* gene clones at $n=17$ time points during about two cell-cycle periods from Rustici *et al.* [15] with the cell-cycle classifications of Rustici *et al.* or Oliva *et al.* [16].

Dataset S2. S. cerevisiae global mRNA expression. A tab-delimited text format file, readable by both Mathematica and Microsoft Excel, reproducing the relative mRNA expression levels of $m_2=4772$ S. cerevisiae open reading frames (ORFs), or genes, at $n=17$ time points during about two cell-cycle periods, including cell-cycle classifications, from Spellman et al. [17].

Dataset S3. Human global mRNA expression A tab-delimited text format file, readable by both Mathematica and Microsoft Excel, reproducing the relative mRNA expression levels of $m_3=13,068$ human genes at $n=17$ time points during about two cell-cycle periods, including cell-cycle classifications, from Whitfield et al. [18].

Acknowledgements

We thank GH Golub for introducing us to matrix and tensor computations, and the American Institute of Mathematics in Palo Alto and Stanford University for hosting the 2004 Workshop on Tensor Decompositions and the 2006 Workshop on Algorithms for Modern Massive Data Sets, respectively, where some of this work was done. We also thank CH Lee for technical assistance, RA Horn for helpful discussions of matrix analysis and careful reading of the manuscript, and L De Lathauwer and A Goffeau for helpful comments.

References

1. Jensen LJ, Jensen TS, de Lichtenberg U, Brunak S, Bork P (2006) Co-evolution of transcriptional and post-translational cell-cycle regulation. Nature 443: 594-597.

2. Lu Y, Huggins P, Bar-Joseph Z (2009) Cross species analysis of microarray expression data. Bioinformatics 25: 1476-1483.

3. Mushegian AR, Koonin EV (1996) A minimal gene set for cellular life derived by comparison of complete bacterial genomes. Proc Natl Acad Sci USA 93: 10268-10273.

4. Golub GH, Van Loan CF (1996) Matrix Computations. Baltimore: Johns Hopkins University Press, third edition, 694 p.

5. Van Loan CF (1976) Generalizing the singular value decomposition. SIAM J Numer Anal 13: 76-83.

6. Paige CC, Saunders MA (1981) Towards a generalized singular value decomposition. SIAM J Numer Anal 18: 398-405.

7. Alter O, Brown PO, Botstein D (2003) Generalized singular value decomposition for comparative analysis of genome-scale expression data sets of two different organisms. Proc Natl Acad Sci USA 100: 3351-3356.

8. Alter O (2006) Discovery of principles of nature from mathematical modeling of DNA microarray data. Proc Natl Acad Sci USA 103: 16063-16064.

9. Omberg L, Meyerson JR, Kobayashi K, Drury LS, Diffley JF, et al (2009) Global effects of DNA replication and DNA replication origin activity on eukaryotic gene expression. Mol Syst Biol 5: 312.

10. Alter O, Golub GH (2004) Integrative analysis of genome-scale data by using pseudoinverse projection predicts novel correlation between DNA replication and RNA transcription. Proc Natl Acad Sci USA 101: 16577-16582.

11. Omberg L, Golub GH, Alter O (2007) A tensor higher-order singular value decomposition for integrative analysis of DNA microarray data from different studies. Proc Natl Acad Sci USA 104: 18371-18376.

12. De Lathauwer L, De Moor B, Vandewalle J (2000) A multilinear singular value decomposition. SIAM J Matrix Anal Appl 21: 1253-1278.

13. Vandewalle J, De Lathauwer L, Comon P (2003) The generalized higher order singular value decomposition and the oriented signal-to-signal ratios of pairs of signal tensors and their use in signal processing. In: Proc ECCTD'03 - European Conf on Circuit Theory and Design. pp. I-389-I-392.

14. Alter O, Golub GH (2005) Reconstructing the pathways of a cellular system from genome-scale signals using matrix and tensor computations. Proc Natl Acad Sci USA 102: 17559-17564.

15. Rustici G, Mata J, Kivinen K, Lió P, Penkett CJ, et al (2004) Periodic gene expression program of the fission yeast cell cycle. Nat Genet 36: 809-817.

16. Oliva A, Rosebrock A, Ferrezuelo F, Pyne S, Chen H, et al (2005) The cell cycle-regulated genes of Schizosaccharomyces pombe. PLoS Biol 3: e225.

17. Spellman PT, Sherlock G, Zhang MQ, Iyer VR, Anders K, et al (1998) Comprehensive identification of cell cycle-regulated genes of the yeast *Saccharomyces cerevisiae* by microarray hybridization. Mol Biol Cell 9: 3273-3297.

18. Whitfield ML, Sherlock G, Saldanha A, Murray JI, Ball CA, et al (2002) Identification of genes periodically expressed in the human cell cycle and their expression in tumors. Mol Biol Cell 13: 1977-2000.

19. Gauthier NP, Larsen ME, Wernersson R, Brunak S, Jensen TS (2010) Cyclebase.org: version 2.0, an updated comprehensive, multi-species repository of cell cycle experiments and derived analysis results. Nucleic Acids Res 38: D699-D702.

20. Altschul SF, Gish W, Miller W, Myers EW, Lipman DJ (1990) Basic local alignment search tool. J Mol Biol 215: 403-410.

21. Pruitt KD, Tatusova T, Maglott DR (2007) NCBI reference sequences (RefSeq): a curated non-redundant sequence database of genomes, transcripts and proteins. Nucleic Acids Res 35: D61-D65.

22. Decottignies A, Goffeau A (1997) Complete inventory of the yeast ABC proteins. Nat Genet 15: 137-145.

23. Mamnun YM, Schüller C, Kuchler K (2004) Expression regulation of the yeast PDR5 ATP-binding cassette (ABC) transporter suggests a role in cellular detoxification during the exponential growth phase. FEBS Lett 559: 111-117.

24. Werner-Washburne M, Braun E, Johnston GC, Singer RA (1993) Stationary phase in the yeast Saccharomyces cerevisiae. Microbiol Rev 57: 383-401.

25. Meyers S, Schauer W, Balzi E, Wagner M, Goffeau A, et al (1992) Interaction of the yeast pleiotropic drug resistance genes PDR1 and PDR5. Curr Genet 21: 431-436.

26. Mahé Y, Parle-McDermott A, Nourani A, Delahodde A, Lamprecht A, et al (1996) The ATP-binding cassette multidrug transporter Snq2 of Saccharomyces cerevisiae: a novel target for the transcription factors Pdr1 and Pdr3. Mol Microbiol 20: 109-117.

27. Wolfger H, Mahé Y, Parle-McDermott A, Delahodde A, Kuchler K (1997) The yeast ATP binding cassette (ABC) protein genes PDR10 and PDR15 are novel targets for the Pdr1 and Pdr3 transcriptional regulators. FEBS Lett 418: 269-274.

28. Hlaváček O, Kučerová H, Harant K, Palková Z, Váchová L (2009) Putative role for ABC multidrug exporters in yeast quorum sensing. FEBS Lett 583: 1107-1113.

29. Lee KS, Patton JL, Fido M, Hines LK, Kohlwein SD, et al (1994) The Saccharomyces cerevisiae PLB1 gene encodes a protein required for lysophospholipase and phospholipase B activity. J Biol Chem 269: 19725-19730.

30. Cho RJ, Campbell MJ, Winzeler EA, Steinmetz L, Conway A, et al (1998) A genome-wide transcriptional analysis of the mitotic cell cycle. Mol Cell 2: 65-73.

31. Martin-Castellanos C, Labib K, Moreno S (1996) B-type cyclins regulate G1 progression in fission yeast in opposition to the p25rum1 cdk inhibitor. EMBO J 15: 839-849.

32. Fisher DL, Nurse P (1996) A single fission yeast mitotic cyclin B p34$^{cdc2}$ kinase promotes both S-phase and mitosis in the absence of G1 cyclins. EMBO J 15: 850-860.

33. Chu MT, Funderlic RE, Golub GH (1997) On a variational formulation of the generalized singular value decomposition. SIAM J Matrix Anal Appl 18: 1082-1092.

34. Rao CR (1973) Linear Statistical Inference and Its Applications. New York, NY: John Wiley & Sons, second edition, 656 p.

35. Rao CR (1984) Optimization of functions of matrices with applications to statistical problems. In: Rao PSRS, Sedransk J, editors, W.G. Cochran's Impact on Statistics, New York, NY: John Wiley & Sons. pp. 191-202.

36. Paige CC (1985) The general linear model and the generalized singular value decomposition. Linear Algebra Appl 70: 269-284.

37. Marshall AW, Olkin L (1990) Matrix versions of the Cauchy and Kantorovich inequalities. Aequationes Mathematicae 40: 89-93.

38. Horn RA, Johnson CR (1985) Matrix Analysis. Cambridge, UK: Cambridge University Press, 575 p.

39. Tavazoie S, Hughes JD, Campbell MJ, Cho RJ, Church GM (1999) Systematic determination of genetic network architecture. Nat Genet 22: 281-285.

Table 1. Arraylets or left basis vectors.

| Dataset | Arraylet | Overexpression | | Underexpression | |
|---|---|---|---|---|---|
| | | Annotation | $P$-value | Annotation | $P$-value |
| *S. pombe* | 13 | G2 | $2.4 \times 10^{-10}$ | G1 | $1.0 \times 10^{-15}$ |
| | 14 | M | $2.2 \times 10^{-21}$ | G2 | $1.3 \times 10^{-9}$ |
| | 15 | M | $4.1 \times 10^{-13}$ | S | $1.6 \times 10^{-17}$ |
| | 16 | G2 | $5.2 \times 10^{-18}$ | G1 | $1.2 \times 10^{-26}$ |
| | 17 | G2 | $2.4 \times 10^{-10}$ | S | $5.3 \times 10^{-35}$ |
| *S. cerevisiae* | 13 | S/G2 | $4.3 \times 10^{-15}$ | M/G1 | $1.4 \times 10^{-9}$ |
| | 14 | M/G1 | $4.9 \times 10^{-26}$ | G2/M | $2.2 \times 10^{-12}$ |
| | 15 | G1 | $7.7 \times 10^{-17}$ | S | $1.3 \times 10^{-8}$ |
| | 16 | G2/M | $2.3 \times 10^{-38}$ | G1 | $2.0 \times 10^{-32}$ |
| | 17 | G2/M | $2.3 \times 10^{-41}$ | G1 | $2.6 \times 10^{-40}$ |
| Human | 13 | G1/S | $1.1 \times 10^{-33}$ | G2 | $2.4 \times 10^{-44}$ |
| | 14 | M/G1 | $5.7 \times 10^{-3}$ | G2 | $4.7 \times 10^{-2}$ |
| | 15 | G2 | $9.8 \times 10^{-24}$ | None | $1.4 \times 10^{-1}$ |
| | 16 | G1/S | $9.8 \times 10^{-13}$ | G2 | $4.1 \times 10^{-4}$ |
| | 17 | G2 | $9.3 \times 10^{-33}$ | M/G1 | $2.7 \times 10^{-2}$ |

Probabilistic significance of the enrichment of the arraylets, i.e., HO GSVD patterns of expression variation across the *S. pombe*, *S. cerevisiae* and human genes, that span the common HO GSVD subspace in each dataset, in over- or underexpressed cell cycle-regulated genes. The $P$-value of each enrichment is calculated as described [39] (Supplementary Section 2.2) assuming hypergeometric distribution of the annotations (Supplementary Datasets S1–S3) among the genes, including the $m=100$ genes most over- or underexpressed in each arraylet.

Appendix C

Ponnapalli, Saunders, Van Loan & Alter (2011)  A-1  alterlab.org/HO_GSVD/

1. Mathematical Framework: HO GSVD

Comparative analyses of large-scale datasets promise to enhance our fundamental understanding of the data by distinguishing the similar from the dissimilar among these data. For example, comparative analyses of global mRNA expression from multiple model organisms promise to enhance fundamental understanding of the universality and specialization of molecular biological mechanisms, and may prove useful in medical diagnosis, treatment and drug design [1]. Existing algorithms limit analyses to subsets of homologous genes among the different organisms, effectively introducing into the analysis the assumption that sequence and functional similarities are equivalent [2]. For sequence-independent comparisons [3], mathematical frameworks are required that can distinguish the similar from the dissimilar among multiple large-scale datasets tabulated as matrices with the same column dimension and different row dimensions, corresponding to the different sets of genes of the different organisms. The only such framework to date, that of the generalized singular value decomposition (GSVD) [4–6] is limited to two matrices.

Recently we showed that the GSVD provides a comparative mathematical framework for global mRNA expression datasets from two different organisms, tabulated as two matrices with the same column dimension and different row dimensions, where the mathematical variables and operations represent biological reality [7]. In this application, one matrix tabulates DNA microarray-measured genome-scale mRNA expression from the yeast *S. cerevisiae*, sampled at $n$ time points at equal time intervals during the cell-cycle program. This matrix is of size $m_1$-*S. cerevisiae* genes × $n$-DNA microarrays. The second matrix tabulates data from the HeLa human cell line, sampled at the same number of time points, also at equal time intervals, and is of size $m_2$-human genes × $n$-arrays. The underlying assumption of the GSVD as a comparative mathematical framework for the two matrices is that there exists a one-to-one mapping among the columns of the matrices, but not necessarily among their rows. The GSVD factors each matrix into a product of an organism-specific matrix of size $m_1$-*S. cerevisiae* genes or $m_2$-human genes × $n$-"arraylets," i.e., left basis vectors, an organism-specific diagonal matrix of size $n$-arraylets × $n$-"genelets," i.e., right basis vectors, and a shared matrix of size $n$-genelets × $n$-arrays.

We showed that the mathematical variables of the GSVD, i.e., the patterns of the genelets and the two sets of arraylets, represent either the similar or the dissimilar among the biological programs that compose the *S. cerevisiae* and human datasets. Genelets of common significance in both datasets, and the corresponding arraylets, represent cell-cycle checkpoints that are common to *S. cerevisiae* and human. Simultaneous reconstruction and classification of both the *S. cerevisiae* and human data in the common subspace that these patterns span outlines the biological similarity in the regulation of their cell-cycle programs. Patterns almost exclusive to either dataset correlate with either the *S. cerevisiae* or the human exclusive synchronization responses. Reconstruction of either dataset in the subspaces of the common vs. exclusive patterns represents differential gene expression in the *S. cerevisiae* and human conserved cell-cycle programs vs. their unique synchronization-response programs, respectively. Notably, relations such as these between the expression profiles of the *S. cerevisiae* genes *KAR4* and *CIK1*, which are known to be correlated in response to the synchronizing agent, the α-factor pheromone, yet anticorrelated during cell division, are correctly depicted.

We now define a higher-order GSVD (HO GSVD) of $N \geq 2$ datasets, tabulated as $N$ real matrices $D_i$ with the same column dimension and, in general, different row dimensions. In our form of the HO GSVD, each data matrix $D_i$ is assumed to have full column rank and is factored as the product $D_i = U_i \Sigma_i V^T$, where $U_i$ is the same shape as $D_i$ (rectangular), $\Sigma_i$ is diagonal and positive definite, and $V$ is square and nonsingular. The columns of $U_i$ have unit length; we call them the "left basis vectors" for $D_i$ (a different set for each $i$). The columns of $V$ also have unit length; we call them "right basis vectors," and they are the same in all factorizations. In the application of the HO GSVD to a comparison of global mRNA expression from $N \geq 2$ organisms, the right basis vectors are the genelets and the $N$ sets of left basis vectors are the $N$ sets of arraylets. We use the notation:

$$U_i \equiv (u_{i,1} \ \ldots \ u_{i,n}), \qquad \|u_{i,k}\| = 1, \quad (1)$$
$$\Sigma_i \equiv \mathrm{diag}(\sigma_{i,k}), \qquad \sigma_{i,k} > 0, \quad (2)$$
$$V \equiv (v_1 \ \ldots \ v_n), \qquad \|v_k\| = 1. \quad (3)$$

We call $\{\sigma_{i,k}\}$ the "higher-order generalized singular value set." They are weights in the following sums of rank-one matrices of unit norm:

$$D_i = U_i \Sigma_i V^T = \sum_k \sigma_{i,k} u_{i,k} v_k^T, \quad \|u_{i,k} v_k^T\| = 1. \quad (4)$$

Hence we regard the $k$th values $\sigma_{i,k}$ as indicating the significance of the $k$th right basis vector $v_k$ in the matrices $D_i$ (reflecting the overall information that $v_k$ captures in each $D_i$ in turn). To obtain the factorizations, we work with the matrices $A_i = D_i^T D_i$ and the matrix sum $S$, defined as the arithmetic mean of all pairwise quotients $A_i A_j^{-1}$, or equivalently of all $S_{ij} = \frac{1}{2}(A_i A_j^{-1} + A_j A_i^{-1})$, $i \neq j$. The eigensystem $SV = V\Lambda$ is used to define $V$, and the factors $U_i$ and $\Sigma_i$ are computed from $D_i$ and $V$.

To clarify our choice of $S$, we note that in the GSVD, defined by Van Loan [4], the matrix $V$ can be formed from the eigenvectors of the unbalanced quotient $A_1 A_2^{-1}$ (Supplementary Section 1.1). We observe that this $V$ can also be formed from the eigenvectors of the balanced arithmetic mean $S_{12} = \frac{1}{2}(A_1 A_2^{-1} + A_2 A_1^{-1})$. We prove that in the case of $N = 2$, our definition of $V$ by using the eigensystem of $S = S_{12} = \frac{1}{2}(A_1 A_2^{-1} + A_2 A_1^{-1})$ leads algebraically to the GSVD and therefore, as Paige and Saunders showed [5], can be computed in a stable way. We also note that in the GSVD, the matrix $V$ is invariant under the exchange of the two matrices $D_1$ and $D_2$.

Therefore, we define our HO GSVD for $N \geq 2$ matrices by using the balanced arithmetic mean $S$ of all pairwise arithmetic means $S_{ij}$, each of which defines the GSVD of the corresponding pair of matrices $D_i$ and $D_j$, noting that $S$ is invariant under the exchange of any two matrices $D_i$ and $D_j$.

We also show that the existing SVD and GSVD decompositions are in some sense special cases of our HO GSVD (Supplementary Section 1.2). Finally, we conjecture a role for our exact HO GSVD in iterative approximation algorithms (Supplementary Section 1.3).

1.1. The Matrix GSVD

1.1.1. Construction of the matrix GSVD.
Suppose we have two real matrices $D_1 \in \mathbb{R}^{m_1 \times n}$ and $D_2 \in \mathbb{R}^{m_2 \times n}$ each with full column rank. Van Loan [4] defined the GSVD of $D_1$ and $D_2$ as $$U_1^T D_1 X \equiv \Sigma_1,$$
$$U_2^T D_2 X \equiv \Sigma_2, \quad (5)$$

where each $U_i \in \mathbb{R}^{m_i \times n}$ has orthonormal columns, $X \in \mathbb{R}^{n \times n}$ is nonsingular, and the $\Sigma_i = \text{diag}(\sigma_{i,k}) \in \mathbb{R}^{n \times n}$ are diagonal with $\sigma_{i,k} > 0$ ($i = 1, 2$). Paige and Saunders [5] showed that the GSVD can be computed in a stable way by orthogonal transformations. In the full column-rank case it takes the form $$D_1 \equiv U_1 \Sigma_1 V^T,$$
$$D_2 \equiv U_2 \Sigma_2 V^T, \quad (6)$$

where $U_1$, $U_2$ and $\begin{bmatrix} \Sigma_1 \\ \Sigma_2 \end{bmatrix}$ have orthonormal columns [6], and $V$ is square and nonsingular.

We work with the form of Supplementary Equation (6), but we find it useful and more similar to the standard SVD [6] if we assume that the columns of $V$ are scaled to have unit length, with the columns of $\Sigma_i$ scaled accordingly. Note that the ratios $\sigma_{1,k}/\sigma_{2,k}$ are not altered by the scaling.

In place of the methods of Van Loan [4] and Paige and Saunders [5], we construct the GSVD of Supplementary Equation (6) as follows. We obtain $V$ from the eigensystem of $S$, the arithmetic mean of the quotients $A_1 A_2^{-1}$ and $A_2 A_1^{-1}$ of the matrices $A_1 = D_1^T D_1$ and $A_2 = D_2^T D_2$:

$$S \equiv S_{12} = \tfrac{1}{2}(A_1 A_2^{-1} + A_2 A_1^{-1}),$$
$$SV = V\Lambda,$$
$$V \equiv (v_1 \ldots v_n), \quad \Lambda = \text{diag}(\lambda_k), \quad (7)$$

with $\|v_k\| = 1$. Given $V$, we compute matrices $B_i$ by solving two linear systems $$VB_i^T = D_i^T,$$
$$B_i \equiv (b_{i,1} \ldots b_{i,n}), \quad i = 1,2, \quad (8)$$

and we construct $\Sigma_i$ and $U_i = (u_{i,1} \ldots u_{i,n})$ by normalizing the columns of $B_i$:

$$\sigma_{i,k} = \|b_{i,k}\|,$$
$$\Sigma_i = \text{diag}(\sigma_{i,k}),$$
$$B_i = U_i \Sigma_i. \quad (9)$$

We prove below that $S$ is nondefective (it has $n$ independent eigenvectors) and its eigensystem is real.

From Supplementary Equations (8) and (9) we have $D_i = B_i V^T = U_i \Sigma_i V^T$ as in Supplementary Equation (6). We see that the rows of both $D_1$ and $D_2$ are superpositions of the same right basis vectors, the columns of $V$ (Figure 37). This is the construction that we generalize in Equations (1)–(4) to compute our HO GSVD.

1.1.2. Interpretation of the GSVD construction.
In our GSVD comparison of two matrices, we interpreted the $k$th diagonals of $\Sigma_1$ and $\Sigma_2$, i.e., the "generalized singular value pair" $(\sigma_{1,k}, \sigma_{2,k})$, as indicating the significance of the $k$th right basis vector $v_k$ in the matrices $D_1$ and $D_2$, and reflecting the overall information that $v_k$ captures in $D_1$ and $D_2$ respectively [7]. The ratio $\sigma_{1,k}/\sigma_{2,k}$ indicates the significance of $v_k$ in $D_1$ relative to its significance in $D_2$.

A ratio of $\sigma_{1,k}/\sigma_{2,k} = 1$ corresponds to a basis vector $v_k$ of equal significance in $D_1$ and $D_2$. GSVD comparisons of two matrices showed that right basis vectors of approximately equal significance in both matrices reflect themes that are common to the two matrices under comparison [7].

A ratio of $\sigma_{1,k}/\sigma_{2,k} \gg 1$ corresponds to a basis vector $v_k$ of almost negligible significance in $D_2$ relative to its significance in $D_1$. Likewise, a ratio of $\sigma_{1,k}/\sigma_{2,k} \ll 1$ indicates a basis vector $v_k$ of almost negligible significance in $D_1$ relative to its significance in $D_2$. GSVD comparisons of two matrices showed that right basis vectors of negligible significance in one matrix reflect themes that are exclusive to the other matrix.

1.1.3. Mathematical properties of $\Lambda$ and $V$ in the GSVD construction.
Note that our GSVD construction in Supplementary Equations (7)–(9) is well defined for any square nonsingular $V$. We now show that our particular $V$ leads algebraically to the GSVD of Supplementary Equation (6), ignoring the rescaled columns of $\Sigma_i$ and $V$. Recall that $A_i = D_i^T D_i$ and $D_i = U_i \Sigma_i V^T$ with $\Sigma_i$ diagonal.

In practice we would prefer not to form $A_i$ or $S$ directly. Instead we may work with the QR factorizations $D_i = Q_i R_i$, where $Q_i^T Q_i = I$ and $R_i$ is upper triangular and nonsingular. Define another triangular matrix $R$ and its SVD to be $$R \equiv R_1 R_2^{-1} = \widetilde{U} \widetilde{\Sigma} \widetilde{V}^T, \quad (10)$$

where $\widetilde{U}$ and $\widetilde{V}$ are square and orthogonal, and $\widetilde{\Sigma} =$ $\mathrm{diag}(\tilde{\sigma}_k)$, $\tilde{\sigma}_k > 0$. We then have $$\begin{aligned}
S &= \tfrac{1}{2}[(R_1^T R_1)(R_2^T R_2)^{-1} + (R_2^T R_2)(R_1^T R_1)^{-1}], \\
R_1^{-T} S R_1^T &= \tfrac{1}{2}[R_1(R_2^T R_2)^{-1} R_1^T + R_1^{-T}(R_2^T R_2) R_1^{-1}] \\
&= \tfrac{1}{2}[RR^T + (RR^T)^{-1}] \\
&= \tilde{U}\Lambda\tilde{U}^T, \quad\quad\quad\quad\quad\quad\quad\quad (11)
\end{aligned}$$

where $\Lambda \equiv \tfrac{1}{2}(\tilde{\Sigma}^2 + \tilde{\Sigma}^{-2}) \equiv \mathrm{diag}(\lambda_k)$. Thus $$S(R_1^T \tilde{U}) = (R_1^T \tilde{U})\Lambda, \quad\quad\quad\quad (12)$$
$$SV = V\Lambda, \quad\quad V \equiv R_1^T \tilde{U} D, \quad (13)$$

where the diagonal matrix $D$ normalizes $R_1^T \tilde{U}$ so that $V$ has columns of unit length.

Supplementary Theorem S1. *The matrices $U_1$ and $U_2$ constructed in Supplementary Equation (9) have orthonormal columns ($U_1^T U_1 = U_2^T U_2 = I$).*

*Proof.* From Supplementary Equation (8) we have $V B_i^T B_i V^T = D_i^T D_i$, so that $$\begin{aligned}
(R_1^T \tilde{U} D) B_i^T B_i (D \tilde{U}^T R_1) &= R_i^T R_i \\
\Rightarrow DB_1^T B_1 D &= I, \\
DB_2^T B_2 D &= \tilde{U}^T R_1^{-T}(R_2^T R_2) R_1^{-1}\tilde{U} = \tilde{\Sigma}^{-2},
\end{aligned}$$

with help from Supplementary Equations (10), (12) and (13). We see that both $B_i^T B_i$ are diagonal, and the quantities in Supplementary Equation (9) must be $$U_1 = B_1 D, \quad\quad \Sigma_1 = D^{-1}, \quad\quad\quad (14)$$
$$U_2 = B_2 D\tilde{\Sigma}, \quad\quad \Sigma_2 = \tilde{\Sigma}^{-1} D^{-1}, \quad (15)$$

with $U_i$ column-wise orthonormal. □

Supplementary Theorem S2. *The eigenvalues of $S$ satisfy $\lambda_k \geq 1$, and $S$ has a full set of $n$ eigenvectors (it is nondefective). Also, the eigenvectors are real.*

*Proof.* The equivalence transformation of Supplementary Equation (11) shows that $S$ has the same eigenvalues as $\tilde{U}\Lambda\tilde{U}^T$, namely $\Lambda$. From the definition of $\Lambda$ and $\tilde{\Sigma}$, the eigenvalues are $\lambda_k = \tfrac{1}{2}(\tilde{\sigma}_k^2 + 1/\tilde{\sigma}_k^2) \geq 1$. Also, in the eigensystem of $S$ in Supplementary Equation (13), $V = R_1^T \tilde{U} D$ is a product of real nonsingular matrices and hence is real and nonsingular. □

Supplementary Theorem S3. *An eigenvalue $\lambda_k = 1$ corresponds to a right basis vector $v_k$ of equal significance in both matrices $D_1$ and $D_2$. That is, $\sigma_{1,k}/\sigma_{2,k} = 1$.*

*Proof.* From the orthonormality of $U_1$ and $U_2$ of Equations (14) and (15), and our GSVD construction of Equations (7)–(9), we have $\lambda_k = (\sigma_{1,k}^2/\sigma_{2,k}^2 + \sigma_{2,k}^2/\sigma_{1,k}^2)/2$. Therefore, $\lambda_k = 1$ can occur only if $\sigma_{1,k}/\sigma_{2,k} = 1$. In other words, $\lambda_k = 1$ if the $k$th right basis vector $v_k$ is equally significant in $D_1$ and $D_2$. □

Note that the GSVD is a generalization of the SVD in that if one of the matrices is the identity matrix, the GSVD reduces to the SVD of the other matrix.

In Equations (1)–(4), we now define a HO GSVD and in Theorems 1–3 and Corollary 1 we show that this new decomposition extends to higher orders all of the mathematical properties of the GSVD except for complete column-wise orthogonality of the left basis vectors that form the matrices $U_i$ for all $i$. We proceed in the same way as in Supplementary Equations (7)–(9).

1.2. The Matrix GSVD and SVD as Special Cases

Let us now show that the GSVD and the standard SVD are special cases of our HO GSVD.

Supplementary Theorem S4. *Suppose matrices $D$ and $D_j$ are real and have full column rank. The HO GSVD of $N$ matrices satisfying $D_i = D$ for all $i \neq j$ reduces to the GSVD of the two matrices $D$ and $D_j$.*

*Proof.* Substituting $D_i = D$ for all $i \neq j$ in Equation (2), we obtain the matrix sum $S = \tfrac{1}{N}[AA_j^{-1} + A_j A^{-1} + (N-2)I]$, with $A = D^T D$. The eigenvectors of $S$ are the same as the eigenvectors $V$ of $\tfrac{1}{2}(AA_j^{-1} + A_j A^{-1})$, and Supplementary Theorem S2 shows that $V$ exists. Solving two linear systems for $B$ and $B_j$ and normalizing the solutions, $$VB^T = D_i^T = D^T, \quad\quad B = U\Sigma,$$
$$VB_j^T = D_j^T, \quad\quad\quad\quad B_j = U_j \Sigma_j,$$

reduces the HO GSVD of Equation (1) to the GSVD of $D$ and $D_j$ of Supplementary Equation (6):

$$D_i = D = U\Sigma V^T, \quad i \neq j,$$
$$D_j = U_j \Sigma_j V^T.$$

Supplementary Theorem S1 shows that the columns of $U$ and $U_j$ are orthonormal. □

Supplementary Theorem S5. *Suppose the matrix $D_j$ is real and has full column rank. The HO GSVD of $N$ matrices satisfying $D_i = I$ for all $i \neq j$ reduces to the SVD of $D_j$.*

*Proof.* Substituting $D_i = I$ for all $i \neq j$ in Supplementary Equation (2), we obtain the matrix sum $S = \tfrac{1}{N}[A_j + A_j^{-1} + (N-2)I]$. The symmetry of $S$ implies that its eigenvectors $V$ exist and are orthonormal. Computing the matrix $B_j$ from $$VB_j^T = D_j^T, \quad\quad B_j = U_j \Sigma_j,$$

gives $D_j = U_j \Sigma_j V^T$, and Supplementary Theorem S1 shows that the columns of $U_j$ are orthonormal. Hence the factorization must be the SVD of $D_j$ [6]. □

1.3. Role in Approximation Algorithms

Recent research showed that several higher-order generalizations are possible for a given matrix decomposition, each preserving only some but not all of the properties of the matrix decomposition [12, 13].

Our HO GSVD preserves the exactness as well as the diagonality of the matrix GSVD, i.e., all $N$ matrix factorizations in Equation (1) are exact and all $N$ matrices $\Sigma_i$ are diagonal. In general, our HO GSVD does not preserve the orthogonality of the matrix GSVD, i.e., the matrices $U_i$ in Equation (1) are not necessarily columnwise orthonormal. For some applications, however, one might want to preserve the orthogonality instead of the exactness of the matrix GSVD. An iterative approximation algorithm might be used to compute for a set of $N > 2$ real matrices $D_i \in {}^{m_i \times n}$, each with full column rank, an approximate decomposition $$D_1 \approx U_1 \Sigma_1 V^T,$$
$$D_2 \approx U_2 \Sigma_2 V^T,$$
$$\vdots$$
$$D_N \approx U_N \Sigma_N V^T, \qquad (16)$$

where each $U_i \in {}^{m_i \times n}$ is composed of orthonormal columns, each $\Sigma_i = \text{diag}(\sigma_{i,k}) \in {}^{n \times n}$ is diagonal with $\sigma_{i,k} > 0$, and $V$ is identical in all $N$ matrix factorizations.

If there exist an exact decomposition of Equation (1) where the matrices $U_i$ are column-wise orthonormal, then it is reasonable to expect that the iterative approximation algorithm will converge to that exact decomposition. More than that, when the iterative approximation algorithm is initialized with the exact decomposition, it is reasonable to expect convergence in just one iteration. We show below that if there exist an exact decomposition of Equation (1) in which the matrices $U_i$ are column-wise orthonormal, our HO GSVD leads algebraically to that exact decomposition.

Supplementary Theorem S6. *If there exist an exact HO GSVD of Equation (1) where the matrices $U_i$ are column-wise orthonormal, then our particular $V$ leads algebraically to the exact decomposition.*

*Proof.* If there exist an exact decomposition with columnwise orthonormal $U_i$ for all $i$, then $A_i = D_i^T D_i = V \Sigma_i^2 V^T$ and the right basis vectors, i.e., the columns of $V$, simultaneously diagonalize all pairwise quotients $A_i A_j^{-1} V = V \Sigma_i^2 \Sigma_j^{-2}$ as well as their arithmetic mean $SV = V\Lambda$.

Therefore, the $V$ of the eigensystem of $S$ in Equation (2) is equivalent to the $V$ of the HO GSVD of Equation (1) with column-wise orthonormal $U_i$ for all $i$. □

We conjecture, therefore, the following role for our exact HO GSVD in iterative approximation algorithms.

Supplementary Conjecture S1. *An iterative approximation algorithm will converge to the optimal approximate decomposition of Supplementary Equation (16) in a significantly reduced number of iterations when initialized with our exact HO GSVD, rather than with random $U_i$, $\Sigma_i$ and $V$.*

2. Biological Application: Comparison of Global mRNA Expression Datasets from Three Different Organisms

2.1. *S. pombe*, *S. cerevisiae* and Human Datasets

Rustici et al. [15] monitored mRNA levels in the yeast *Schizosaccharomyces pombe* over about two cell-cycle periods, in a culture synchronized initially by the *cdc25-22* block-release late in the cell-cycle phase $G_2$, relative to reference mRNA from an asynchronous culture, at 15min intervals for 240min. The *S. pombe* dataset we analyze (Supplementary Dataset S1) tabulates the ratios of gene expression levels for the $m_1 = 3167$ gene clones with no missing data in at least 14 of the $n=17$ arrays. Of these, the mRNA expression of 380 gene clones was classified as cell cycle-regulated by Rustici et al. or Oliva et al. [16].

Spellman et al. [17] monitored mRNA expression in the yeast *Saccharomyces cerevisiae* over about two cell-cycle periods, in a culture synchronized initially by the $\alpha$-factor pheromone in the cell-cycle phase $M/G_1$, relative to reference mRNA from an asynchronous culture, at 7min intervals for 112min. The *S. cerevisiae* dataset we analyze (Supplementary Dataset S2) tabulates the ratios of gene expression levels for the $m_2 = 4772$ open reading frames (ORFs), or genes, with no missing data in at least 14 of the $n=17$ arrays. Of these, the mRNA expression of 641 ORFs was traditionally or microarray-classified as cell cycle-regulated.

Whitfield et al. [18] monitored mRNA levels in the human HeLa cell line over about two cell-cycle periods, in a culture synchronized initially by a double thymidine-block in S-phase, relative to reference mRNA from an asynchronous culture, at 2hr intervals for 34hr. The human dataset we analyze (Supplementary Dataset S3) tabulates the ratios of gene expression levels for the $m_3 = 13,068$ gene clones with no missing data in at least 14 of the $n=17$ arrays. Of these, the mRNA expression of 787 gene clones was classified as cell cycle-regulated.

Of the 53,839, 81,124 and 222,156 elements in the *S. pombe*, *S. cerevisiae* and human data matrices, 2420, 2936 and 14,680 elements, respectively, i.e., ~5%, are missing valid data. SVD [6] is used to estimate the missing data as described [7]. In each of the data matrices, SVD of the expression patterns of the genes with no missing data uncovered 17 orthogonal patterns of gene expression, i.e., "eigengenes." The five most significant of these patterns, in terms of the fraction of the mRNA expression that they capture, are used to estimate the missing data in the remaining genes. For each of the three data matrices, the five most significant eigengenes and their corresponding fractions are almost identical to those computed after the missing data are estimated, with the corresponding correlations >0.95 (Supplementary Mathematica Notebooks S1 and S2). This suggests that the five most significant eigengenes, as computed for the genes with no missing data, are valid patterns for estimation of missing data. This also indicates that this SVD estimation of missing data is robust to variations in the data selection cutoffs.

We compute the HO GSVD of the three data matrices after missing data estimation by using Equations (1)–(4). Following Theorem 3, we find that the approximately common HO GSVD subspace of the three datasets is spanned by the five genelets $v_k$ $k = 13, \ldots, 17$ (Figures 12 and 15).

2.2. Common Subspace Interpretation

In analogy with the GSVD [7], a common HO GSVD genelet and the $N = 3$ corresponding arraylets, which are approximately orthonormal to all other arraylets in the corresponding datasets (Theorem 3), are inferred to represent a biological process common to the three organisms and the corresponding cellular states when a consistent biological or experimental theme is reflected in the interpretations of the patterns of the genelet and the arraylets.

A genelet $v_k$ is associated with a biological process or an experimental artifact when its pattern of expression variation across the arrays, i.e., across time, is interpretable. An arraylet $u_{i,k}$ is parallel- and antiparallel-associated with the most likely parallel and antiparallel cellular states according to the annotations of the two groups of $m$ genes each, with largest and smallest levels of expression in this arraylet among all $m_i$ genes, respectively. The $P$-value of a given association, i.e., $P(y; m, m_i, z)$, is calculated assuming hypergeometric probability distribution of the $z$ annotations among the $m_i$ genes, and of the subset of $y \subseteq z$ annotations among the subset of $m$ genes, as described [39], $$P(y; m, m_i, z) = \binom{m_i}{m}^{-1} \sum_{x=y}^{m} \binom{z}{x}\binom{m_i - z}{m - x}. \quad (17)$$

We find that the approximately common HO GSVD subspace represents cell-cycle mRNA expression in the three disparate organisms (Figure 12 and Table 1).

2.3. HO GSVD Data Reconstruction

The decoupling of the HO GSVD genelets and $N$ sets of arraylets, i.e., the diagonality of the matrices $\Sigma_i$ in Equation (1), allows simultaneous reconstruction of the $N = 3$ datasets in the common HO GSVD subspace without eliminating genes or arrays.

In analogy with the GSVD [7], given a common HO GSVD subspace that is spanned by the $K$ genelets $\{v_k\}$ where $k = n - K + 1, \ldots, n$, we reconstruct each dataset in terms of only these genelets and the corresponding $\{u_{i,k}\}$ arraylets, $$\begin{aligned} D_i = U_i \Sigma_i V^T &= \sum_{k=1}^{n} \sigma_{i,k} u_{i,k} v_k^T \\ &\rightarrow \sum_{k=n-K+1}^{n} \sigma_{i,k} u_{i,k} v_k^T. \end{aligned} \quad (18)$$

Note that this reconstruction is mathematically equivalent to setting to zero the higher-order generalized singular values $\{\sigma_{i,k}\}$ in $\Sigma_i$ for all $k \neq n - K + 1, \ldots, n$, and then multiplying the matrices $U_i \Sigma_i V^T$ to obtain the reconstructed $D_i$.

2.4. Simultaneous HO GSVD Classification

Identifying the subset of genelets and the corresponding arraylets that span the approximately common HO GSVD subspace allows simultaneous classification of the genes and arrays of the three datasets by similarity in their expression of these genelets or corresponding arraylets, respectively, rather than by their overall expression, as described [7].

We least squares-approximate the $K=5$-dimensional subspace spanned by the five genelets $v_k$ with $k = 13, \ldots, 17$, with the two-dimensional space spanned by two of the three orthonormal vectors $x$, $y$ and $z \in \mathbb{R}^n$ that maximize the norm $\sum_{k=n-K+1}^{n}(\|v_k^T x\|^2 + \|v_k^T y\|^2 + \|v_k^T z\|^2)$ (Supplementary Figure 16). Since the common HO GSVD subspace represents cell-cycle mRNA expression, the two vectors that we select to approximate the common subspace, $x$ and $y$, describe expression oscillations of two periods in the three time courses.

We plot the projection of each gene of the dataset $D_i$ from the $K$-genelets subspace onto $y$, i.e., $e_m^T \sum_{k=n-K+1}^{n}(\sigma_{i,k} u_{i,k} v_k^T) y / a_m$ where $e_{m_i}$ is a unit $m_i$-vector, along the $y$-axis vs. that onto $x$ along the $x$-axis, normalized by its ideal amplitude $a_m$, where the contribution of each genelet to the overall projected expression of the gene adds up rather than cancels out, $a_m^2 = \sum_k \sum_j |\sigma_{i,k}\sigma_{i,j}(e_{m_i}^T u_{i,k} u_{i,j}^T e_{m_i}) v_k^T (xx^T + yy^T) v_j|$. In this plot, the distance of each gene from the origin is the amplitude of its normalized projection. A unit amplitude indicates that the genelets add up; a zero amplitude indicates that they cancel out. The angular distance of each gene from the $x$-axis is its phase in the progression of expression across the genes from $x$ to $y$ and back to $x$, going through the projection of each genelet $v_k$ in this subspace, i.e., $(xx^T + yy^T) v_k$. Sorting the genes according to these angular distances gives the angular order, or classification, of the genes.

Similarly, we plot the projection of each array from the $K$-arraylets subspace onto $\sum_{k=n-K+1}^{n}(u_{i,k} v_k^T) y$, i.e., $y^T \sum_{k=n-K+1}^{n}(\sigma_{i,k} v_k v_k^T) e_n$ where $e_n$ is a unit $n$-vector, along the $y$-axis vs. that onto $\sum_{k=n-K+1}^{n}(u_{i,k} v_k^T) x$ along the $x$-axis, normalized by its ideal amplitude $a_n$, where the contribution of each arraylet to the overall projected expression of the array adds up rather than cancels out, $a_n^2 = \sum_k \sum_j |\sigma_{i,k}\sigma_{i,j}(e_n^T v_k v_j^T e_n) v_k^T (xx^T + yy^T) v_j|$. We sort the arrays according to their angular distances from the $x$-axis.

For classification, we set to zero the arithmetic mean of each genelet across the arrays, i.e., time, and that of each arraylet across the genes, such that the expression of each gene and array is centered at its time- or gene-invariant level, respectively.

With all 3167 *S. pombe*, 4772 *S. cerevisiae* and 13,068 human genes sorted, the expression variations of the five $k = 13, \ldots, 17$ arraylets from each organism approximately fit one period cosines, with the initial phase of each arraylet similar to that of its corresponding genelet. The global mRNA expression of each organism, reconstructed in the common HO GSVD subspace, approximately fits a traveling wave, oscillating across time and across the genes (Figures 17-19).

2.5. Sequence-Independence of the Classification

Our new HO GSVD provides a comparative mathematical framework for $N \geq 2$ large-scale DNA microarray datasets from $N$ organisms tabulated as $N$ matrices that does not require a one-to-one mapping between the genes of the different organisms. The HO GSVD, therefore, can be used to identify genes of common function across different organisms independently of the sequence similarity among these genes, and to study, e.g., nonorthologous gene displacement [3]. The HO GSVD can also be used to identify homologous genes, of similar DNA or protein sequences in one organism or across multiple organisms, that have different cellular functions.

We examine, for example, the HO GSVD classifications of genes of significantly different cell-cycle peak times [19] but highly conserved sequences [20, 21]. We consider three subsets of genes, the closest S. pombe, S. cerevisiae and human homologs of (i) the S. pombe gene BFR1, which belongs to the evolutionarily highly conserved ATP-binding cassette (ABC) transporter superfamily [22–28], (ii) the S. cerevisiae phospholipase B-encoding gene PLB1 [29, 30], and (iii) the S. pombe strongly regulated S-phase cyclin-encoding gene CIG2 [31, 32] (Supplementary Table S1). We find, notably, that these genes are correctly classified (Figure 14).

| | Query Gene | Gene | Organism | RefSeq ID | Bit Score | $E$-value |
|---|---|---|---|---|---|---|
| (a) | Bfr1 | Snq2 | S. cerevisiae | NP_010294.1 | 1149 | 0 |
| | S. pombe | Pdr5 | S. cerevisiae | NP_014796.1 | 1103 | 0 |
| | NP_587932.3 | Pdr18 | S. cerevisiae | NP_014468.1 | 1097 | 0 |
| | | Pdr15 | S. cerevisiae | NP_010694.1 | 1093 | 0 |
| | | Pdr12 | S. cerevisiae | NP_015267.1 | 1070 | 0 |
| | | Pdr10 | S. cerevisiae | NP_014973.1 | 1029 | 0 |
| (b) | Plb1 | Plb2 | S. cerevisiae | NP_013719.1 | 825 | 0 |
| | S. cerevisiae | Plb3 | S. cerevisiae | NP_014632.1 | 813 | 0 |
| | NP_013721.1 | SPAC977.09c | S. pombe | NP_592772.1 | 385 | $7 \times 10^{-107}$ |
| | | SPAC1A6.03c | S. pombe | NP_593194.1 | 372 | $7 \times 10^{-103}$ |
| | | SPCC1450.09c | S. pombe | NP_588308.1 | 369 | $8 \times 10^{-102}$ |
| | | SPAC1786.02 | S. pombe | NP_594024.1 | 355 | $1 \times 10^{-97}$ |
| (c) | Cig2 | Cdc13 | S. pombe | NP_595171.1 | 346 | $3 \times 10^{-95}$ |
| | S. pombe | Clb2 | S. cerevisiae | NP_015444.1 | 248 | $1 \times 10^{-65}$ |
| | NP_593889.1 | Cig1 | S. pombe | NP_588110.2 | 241 | $1 \times 10^{-63}$ |
| | | Clb1 | S. cerevisiae | NP_011622.1 | 234 | $2 \times 10^{-61}$ |
| | | Clb4 | S. cerevisiae | NP_013311.1 | 222 | $5 \times 10^{-58}$ |
| | | Clb3 | S. cerevisiae | NP_010126.1 | 221 | $2 \times 10^{-57}$ |
| | | Ccnb2 | Human | NP_004692.1 | 202 | $5 \times 10^{-52}$ |
| | | Clb6 | S. cerevisiae | NP_011623.1 | 183 | $4 \times 10^{-46}$ |
| | | Clb5 | S. cerevisiae | NP_015445.1 | 179 | $5 \times 10^{-45}$ |
| | | Ccnb1 | Human | NP_114172.1 | 174 | $1 \times 10^{-43}$ |
| | | Rem1 | S. pombe | NP_595798.1 | 160 | $2 \times 10^{-39}$ |
| | | Ccna1 (isoform c) | Human | NP_001104516.1 | 159 | $7 \times 10^{-39}$ |
| | | Ccna1 (isoform a) | Human | NP_003905.1 | 158 | $1 \times 10^{-38}$ |
| | | Ccna1 (isoform b) | Human | NP_001104515.1 | 157 | $1 \times 10^{-38}$ |
| | | Ccna2 | Human | NP_001228.1 | 145 | $6 \times 10^{-35}$ |

Supplementary Table S1. The closest S. pombe, S. cerevisiae and human homologs of (a) the S. pombe gene BFR1, (b) the S. cerevisiae gene PLB1, and (c) the S. pombe gene CIG2, as determined by an NCBI BLAST [20] of the Ponnapalli, Saunders, Van Loan & Alter (2011)  dx.doi.org/10.1371/journal.pone.0028072 | A-7 protein sequence that corresponds to each gene against the NCBI RefSeq database [21].

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10202643B2). An electronic copy of the "Sequence Listing" will also be available from the USPTO upon request and payment of the fee set forth in 37 CFR 1.19(b)(3).

What is claimed is:

1. A method of diagnosing and treating a glioma with increased responsiveness to temozolomide in a patient, the method comprising:
    a) obtaining a sample comprising at least one cell of the glioma from the patient;
    b) measuring the copy number of a genetic segment encompassing Tlk2 and Mettl2a in the at least one cell of the glioma from the patient and comparing the copy number of the genetic segment encompassing Tlk2 and Mettl2a to the copy number of the genetic segment encompassing Tlk2 and Mettl2a of a normal cell;
    c) diagnosing the patient with glioma with increased responsiveness to temozolomide when the copy number of the genetic segment encompassing Tlk2 and Mettl2a from the at least one cell of the glioma from the patient is increased compared to the copy number of the genetic segment encompassing Tlk2 and Mettl2a from the normal cell; and
    d) administering temozolomide to the patient diagnosed with increased responsiveness to temozolomide.

2. The method of claim 1, wherein the patient has further been identified as having an increased copy number of at least one other nucleotide sequence from the at least one cell of the glioma from the patient, the at least one other nucleotide sequence having at least 90 percent sequence identity to at least one of, respectively, SEQ ID NO:7 or 8; SEQ ID NO:9 or 10; SEQ ID NO:11; SEQ ID NO:12, 13, 14, 15,16, 17, or 18; SEQ ID NO: 19, 20, or 21; SEQ ID NO: 22, 23, or 24; SEQ ID NO: 25, 26, or 27; SEQ ID NO: 28; SEQ ID NO: 29, 30, or 31; SEQ ID NO: 32 or 33; SEQ ID NO: 34, 35, 36, or 37; SEQ ID NO: 38; SEQ ID NO: 39; SEQ ID NO: 40; SEQ ID NO: 41; SEQ ID NO: 42; SEQ ID NO: 43; or SEQ ID NO: 44-45.

3. The method of claim 1, wherein the glioma comprises an astrocytoma.

4. The method of claim 1, wherein the glioma comprises a glioblastoma multiforme.

5. The method of claim 1, wherein the increased copy number was determined by a technique selected from the group consisting of: fluorescent in-situ hybridization, complementary genomic hybridization, array complementary genomic hybridization, fluorescence microscopy, oligonucleotide genotyping, sequencing, southern blotting, dynamic allele-specific hybridization (DASH), paralogue ratio rest (PRT), multiple amplicon quantification (MAO), quantitative polymerase chain reaction (QPCR), multiplex ligation dependent probe amplification (MLPA), multiplex amplification and probe hybridization (MAPH), quantitative multiplex PCR of short fluorescent fragment (QMPSF), dynamic allele-specific hybridization, fluorescence in situ hybridization (FISH), semiquantitative fluorescence in situ hybridization (SQ-FISH), and any combination thereof.

6. The method of claim 1, wherein the administering is further based on at least one of the patient's age, sex or ethnicity.

* * * * *

UNITED STATES PATENT AND TRADEMARK OFFICE
CERTIFICATE OF CORRECTION

PATENT NO. : 10,202,643 B2
APPLICATION NO. : 14/354543
DATED : February 12, 2019
INVENTOR(S) : Orly Alter Page 1 of 1

It is certified that error appears in the above-identified patent and that said Letters Patent is hereby corrected as shown below:

In the Specification

Column 1 Line 15 delete the following:
"This invention was made with government support under grant number R01 HG004302 awarded by National Institutes of Health. The government has certain rights in this invention."

And replace it with:
--This invention was made with government support under grant nos. HG004302 and CA202144 awarded by the National Institutes of Health and grant no. DMS0847173 awarded by the National Science Foundation. The government has certain rights in the invention.--

Signed and Sealed this
Twelfth Day of November, 2019

Andrei Iancu
*Director of the United States Patent and Trademark Office*